(12) United States Patent
Perez et al.

(10) Patent No.: US 11,793,834 B2
(45) Date of Patent: Oct. 24, 2023

(54) CHIMERIC ANTIGEN AND T CELL RECEPTORS AND METHODS OF USE

(71) Applicant: Kite Pharma, Inc., Santa Monica, CA (US)

(72) Inventors: Arianne Perez, Woodland Hills, CA (US); Stuart A. Sievers, Van Nuys, CA (US); Ruben Alvarez Rodriguez, Los Angeles, CA (US); Jonathan Belk, Lebanon, NH (US); Jed Wiltzius, Woodland Hills, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 300 days.

(21) Appl. No.: 16/711,180

(22) Filed: Dec. 11, 2019

(65) Prior Publication Data
US 2020/0246382 A1 Aug. 6, 2020

Related U.S. Application Data

(60) Provisional application No. 62/778,893, filed on Dec. 12, 2018.

(51) Int. Cl.
| | |
|---|---|
| *C07K 16/28* | (2006.01) |
| *C12N 5/10* | (2006.01) |
| *C12N 15/63* | (2006.01) |
| *A61K 35/17* | (2015.01) |
| *A61P 35/00* | (2006.01) |

(52) U.S. Cl.
CPC .............. *A61K 35/17* (2013.01); *A61P 35/00* (2018.01); *C07K 16/2803* (2013.01); *C07K 16/2887* (2013.01); *C07K 16/2896* (2013.01); *C12N 5/10* (2013.01); *C12N 15/63* (2013.01); *C07K 2317/24* (2013.01); *C07K 2317/56* (2013.01); *C07K 2317/565* (2013.01); *C07K 2317/622* (2013.01); *C07K 2317/73* (2013.01); *C07K 2317/76* (2013.01)

(58) Field of Classification Search
CPC .......... C07K 14/70596; C07K 16/2887; C07K 16/28; C07K 16/2896; C07K 2317/24; C07K 2317/56; C07K 2317/565; C07K 2317/76; C07K 2319/00; C12N 15/63; C12N 5/10; C12N 5/12
IPC ....................... C07K 16/2803; A62K 39/39558
See application file for complete search history.

(56) References Cited

U.S. PATENT DOCUMENTS

| | | | |
|---|---|---|---|
| 4,946,778 A | 8/1990 | Ladner et al. | |
| 5,091,513 A | 2/1992 | Huston et al. | |
| 5,132,405 A | 7/1992 | Huston et al. | |
| 5,545,806 A | 8/1996 | Lonberg et al. | |
| 5,545,807 A | 8/1996 | Surani et al. | |
| 5,569,825 A | 10/1996 | Longberg et al. | |
| 5,625,126 A | 4/1997 | Longberg et al. | |
| 5,633,425 A | 5/1997 | Longberg et al. | |
| 5,661,016 A | 8/1997 | Lonberg et al. | |
| 5,728,388 A | 3/1998 | Terman | |
| 5,827,642 A | 10/1998 | Riddell et al. | |
| 5,830,462 A | 11/1998 | Crabtree et al. | |
| 5,834,266 A | 11/1998 | Crabtree et al. | |
| 5,869,337 A | 2/1999 | Crabtree et al. | |
| 6,040,177 A | 3/2000 | Riddell et al. | |
| 6,165,787 A | 12/2000 | Crabtree et al. | |
| 6,319,494 B1 | 11/2001 | Capon et al. | |
| 6,410,319 B1 | 6/2002 | Raubitschek et al. | |
| 6,797,514 B2 | 9/2004 | Berenson et al. | |
| 6,867,041 B2 | 3/2005 | Berenson et al. | |
| 6,905,874 B2 | 6/2005 | Berenson et al. | |
| 7,709,226 B2 | 5/2010 | Foote | |
| 7,741,465 B1 | 6/2010 | Eshhar et al. | |
| 8,211,422 B2 | 7/2012 | Eshhar et al. | |
| 8,486,693 B2 | 7/2013 | Park et al. | |
| 8,679,492 B2 | 3/2014 | Blein et al. | |

(Continued)

FOREIGN PATENT DOCUMENTS

| | | |
|---|---|---|
| CN | 103820393 | 5/2014 |
| CN | 103820393 | 5/2017 |

(Continued)

OTHER PUBLICATIONS

Lippow et al., "Computational design of antibody-affinity improvement beyond in vivo maturation," Nature Biotechnology, 25(10) pp. 1171-1176. (Year: 2007).*

(Continued)

*Primary Examiner* — Bridget E Bunner
(74) *Attorney, Agent, or Firm* — Sheppard Mullin Richter & Hampton LLP

(57) ABSTRACT

Provided is a chimeric antigen receptor (CAR) or a T cell receptor (TCR) comprising one or more of the antigen binding motifs disclosed herein. Aspects of the disclosure relate to a polynucleotide encoding a chimeric antigen receptor (CAR) or a T cell receptor (TCR) comprising one or more of the antigen binding motifs. Provided are antibodies and antigen binding systems that comprise a binding motif that binds CD20 and optionally a binding motif that binds CD19, and methods of producing and using the same. Antibodies and antigen binding systems of the present disclosure comprise CARs that comprise an anti-CD20 binding motif and an anti-CD19 binding motif. Provided are compositions, such as antibodies and CARs that are or comprise an anti-CD20/anti-CD19 antigen binding system of the present disclosure, and cell therapies comprising the same, are useful, e.g., in the treatment of cancer.

17 Claims, No Drawings
Specification includes a Sequence Listing.

(56) References Cited

U.S. PATENT DOCUMENTS

| | | | |
|---|---|---|---|
| 9,834,590 B2 | 12/2017 | Campana et al. | |
| 10,221,245 B2 | 3/2019 | Brogdon et al. | |
| 10,287,350 B2 | 5/2019 | Kochenderfer | |
| 10,493,139 B2 | 12/2019 | Wu et al. | |
| 2002/0006409 A1 | 1/2002 | Wood | |
| 2007/0014720 A1* | 1/2007 | Gazit-Bornstein | A61P 37/02 536/23.53 |
| 2010/0104509 A1 | 4/2010 | King et al. | |
| 2011/0286980 A1 | 11/2011 | Brenner | |
| 2012/0093842 A1 | 4/2012 | Eshhar et al. | |
| 2012/0130076 A1 | 5/2012 | Holt et al. | |
| 2012/0213783 A1 | 8/2012 | Rosenberg et al. | |
| 2013/0266551 A1 | 10/2013 | Campana et al. | |
| 2013/0287748 A1 | 10/2013 | June et al. | |
| 2014/0050708 A1 | 2/2014 | Powell et al. | |
| 2014/0099309 A1 | 4/2014 | Powell, Jr. et al. | |
| 2014/0134195 A1 | 5/2014 | Russell | |
| 2014/0154228 A1 | 6/2014 | Volk et al. | |
| 2014/0171649 A1 | 6/2014 | Li et al. | |
| 2014/0227237 A1 | 8/2014 | June et al. | |
| 2014/0271635 A1 | 9/2014 | Brogdon et al. | |
| 2014/0286934 A1 | 9/2014 | Blein et al. | |
| 2014/0286987 A1 | 9/2014 | Spencer et al. | |
| 2015/0038684 A1 | 2/2015 | Jensen | |
| 2015/0202286 A1 | 7/2015 | June et al. | |
| 2015/0266973 A1 | 9/2015 | Jarjour et al. | |
| 2016/0009813 A1 | 1/2016 | Themeli et al. | |
| 2016/0046700 A1 | 2/2016 | Foster et al. | |
| 2017/0173080 A1 | 6/2017 | Lee et al. | |
| 2018/0355052 A1* | 12/2018 | Orentas | C07K 14/70517 |
| 2019/0119638 A1 | 4/2019 | Sadelain et al. | |
| 2019/0359697 A1 | 11/2019 | Young et al. | |
| 2020/0002400 A1 | 1/2020 | Yao et al. | |

FOREIGN PATENT DOCUMENTS

| | | |
|---|---|---|
| CN | 106701827 | 5/2017 |
| WO | WO-199715669 A1 | 5/1997 |
| WO | WO-2007002223 A2 | 1/2007 |
| WO | WO-2006130458 A3 | 2/2007 |
| WO | WO-2008081035 A1 | 7/2008 |
| WO | WO-2009091826 A2 | 7/2009 |
| WO | WO-2009054863 A3 | 9/2009 |
| WO | WO-2010095031 A2 | 8/2010 |
| WO | WO-2012033885 A1 | 3/2012 |
| WO | WO-2012079000 A1 | 6/2012 |
| WO | WO-2012129514 A1 | 9/2012 |
| WO | WO-2012138475 | 10/2012 |
| WO | WO-2013123061 A1 | 8/2013 |
| WO | WO-2013154760 A1 | 10/2013 |
| WO | WO-2014055657 A1 | 4/2014 |
| WO | WO-2014127261 A1 | 8/2014 |
| WO | WO-2014153270 A1 | 9/2014 |
| WO | WO-2014184744 | 11/2014 |
| WO | WO-2014186469 A2 | 11/2014 |
| WO | WO-2015075468 A1 | 5/2015 |
| WO | WO-2015080981 A1 | 6/2015 |
| WO | WO-2015090229 A1 | 6/2015 |
| WO | WO-2015123642 A1 | 8/2015 |
| WO | WO-2015142675 A2 | 9/2015 |
| WO | WO-2015187528 A1 | 12/2015 |
| WO | WO-2016033570 A1 | 3/2016 |
| WO | WO-2016044745 A1 | 3/2016 |
| WO | WO-2016069282 | 5/2016 |
| WO | WO-2016090369 A1 | 6/2016 |
| WO | WO-2016100232 | 6/2016 |
| WO | WO-2016164731 A2 | 10/2016 |
| WO | WO-201 6201389 | 12/2016 |
| WO | WO-2016210293 A1 | 12/2016 |
| WO | WO-201 7025038 | 2/2017 |
| WO | WO-2017015783 A1 | 2/2017 |
| WO | WO-2017161353 A1 | 9/2017 |
| WO | WO-2017189959 A1 | 11/2017 |
| WO | WO-2018067992 A1 | 4/2018 |
| WO | WO-2018145648 | 8/2018 |
| WO | WO-2018145648 A1 | 8/2018 |
| WO | WO-2018161017 A1 | 9/2018 |
| WO | WO-2018213337 A1 | 11/2018 |
| WO | WO-201 9079564 | 4/2019 |

OTHER PUBLICATIONS

Klein et al., "Epitope interactions of monoclonal antibodies targeting CD20 and their relationship to functional properties," mAbs 5:1, pp. 22-33 (Year: 2013).*

Ramos et al., "CAR-T Cell Therapy for Lymphoma," Annu. Rev. Med. 67, pp. 165-183 (Year: 2016).*

Akbar et al., "A compact vocabulary of paratope-epitope interactions enables predictability of antibody-antigen binding," Cell Reports, 34 pp. 1-21 (Year: 2021).*

Wong et al., "Ab-Ligity: identifying sequence-dissimilar antibodies that bind to the same epitope," MABS, vol. 13, No. 1 pp. 1-8 (Year: 2021).*

Lo et al., "Conformational epitope matching and prediction," BMC Genomics, 22(Suppl 2) pp. 1-16 (Year: 2021).*

First Examination Report dated Sep. 2, 2021 in GCC Appl. No. GC 2019-38820.

Office Action, issued in TW Application No. 108145595, dated Jan. 13, 2021.

Albanza et al., "Function of Novel Anti-CD19 Chimeric Antigen Receptors with Human Variable Regions Is Affected by Hinge and Transmembrane Domains," Mol. Ther., 25 (11 ), 2452-2465 (Epub Jul. 27, 2017).

Al-Lazikani et al., "Standard conformations for the canonical structures of immunoglobulins" J Mol Bioi 273: 927-948 (1997).

Arnon et al., "Monoclonal Antibodies and Cancer Therapy", pp. 243-256, Alan R. Liss, Inc. (1985).

Barbas et al., "Recombinant human Fab fragments neutralize human type 1 immunodeficiency virus in vitro", Proc.Natl. Acad. Sci. USA, 89(19): 9339-43 (1992).

Beatty et al., "Mesothelin-specific chimeric antigen receptor mRNA-engineered T cells induce anti-tumor activity in solid malignancies," Cancer Immunologv Research, 2 (2), 112-120 (2014).

Brentjens et al., "CD19-targeted T cells rapidly induce molecular remissions in adults with chemotherapy-refractory acute lymphoblastic leukemia," ScienceTranslational Medicine, 5 (177), 177ra38 (2013), 19 pages, Author Manuscript.

Brentjens et al., "Eradication of systemic B-cell tumors by genetically targeted human T lymphocytes co-stimulated by COBO and interleukin-15," Nature Medicine, 9 (3), 279-286 (2003).

Brentjens et al., "Genetically targeted T cells eradicate systemic acute lymphoblastic leukemia xenografls," Clinical Cancer Research, 13 (18), 5426-5435 (2007).

Brentjens et al., "Novel cellular therapies for leukemia: CAR-modified T cells targeted to the CD19 antigen," Hematology. American Society of Hematology. Education Program, 2012, 143-151 (2012).

Brentjens et al., "Safety and persistence of adoptively transferred autologous CD19-targeted T cells in patients with relapsed or chemotherapy refractory B-cell leukemias," Blood, 118 (18), 4817-4828 (2011).

Brudno et al., "Toxicities of Chimeric Antigen Receptor T Cells: Recognition and Management," Blood, May 20, 2016 (online), pp. 3321-3330, vol. 127, No. 26.

Brudno et al., "Clinical anti-lymphoma activity and toxicity of T cells expressing a novel anti-CD19 chimeric antigen receptor with fully-human variable regions," ASCO Meeting Library, abstract cited in J Clin Oncol., 36, 2018 (suppl; abstr3052).

Burns et al., "Vesicular stomatitis virus G glycoprotein pseudotyped retroviral vectors: concentration to very high titer and efficient gene transfer into mammalian and nonmammalian cells," Proc. Natl. Acad. Sci., USA, 90 (17), 8033-8037 (1993).

Champe et al., "Monoclonal Antibodies That Block the Activity of Leukocyte Function-associated Antigen 1 Recognize Three Discrete Epitopes in the Inserted Domain of CD11a", J Bioi Chern, 270(3): 1388-94 (1995).

(56) References Cited

OTHER PUBLICATIONS

Chayen, "The role of oil in macromolecular crystallization", Structure, 5(10): 1269-1274 (1997).
Cheadle et al., "Natural expression of the CD19 antigen impacts the long-term engraftment but not antitumor activity of CD19-specific engineered T cells," Journal of Immunology, 184 (4), 1885-1896 (2010).
Cheung et al., "Epitope-specific antibody response to the surface antigen of duck hepatitis B virus in infected ducks", Virology, 176(2): 546-552 (1990).
Chothia et al., "Canonical structures for the hypervariable regions of immunoglobulins", J Mol Biol, 196: 901-917 (1987).
Chothia et al., "Structural repertoire of the human VH segments" J Mol Bio1, 227: 799-817 (1992).
Cole et al., In: "Monoclonal Antibodies and Cancer Therapy", Alan R. Liss, Inc., pp. 77-96 (1985).
Cooper et al., "T-cell clones can be rendered specific for CD19: toward the selective augmentation of the graft-versus-B-lineage leukemia effect," Blood, 101(4), 1637-1644 (2003).
Cote et al., Generation of human monoclonal antibodies reactive with cellular antigens, Proc Natl Acad Sci USA, 80 (7): 2026-2030 (1983).
Cunningham et al., "High-resolution epitope mapping of hGH-receptor interactions by alanine-scanning mutagenesis", Science 244(4908): 1081-85 (1989).
Dayhoff et al., "Atlas of Protein Sequence and Structure: A Model of Evolutionary Change in Proteins", 5: 345-352 (1978).
Devereux et al., "A comprehensive set of sequence analysis programs for the VAX", Nucl. Acid Res., 12: 387-395 (1984).
Eshhar et al., "Tumor-specific T-bodies: towards clinical application", Cancer ImmunolImmunotherapy, 45(3-4):131-136 (1997).
Fegan et al. "Chemically controlled protein assembly: techniques and applications", Chern. Rev., 110(6): 3315-3336 (2010).
Finney et al., "Chimeric receptors providing both primary and costimulatory signaling in T cells from a single gene product", Journal of Immunology, 161(6): 2791-2797 (1998).
Fishwild et al., "High-avidity human IgG kappa monoclonal antibodies from a novel strain of minilocus transgenic mice.", Nature Biotechnology, 14(7): 845 51 (1996).
Giege et al., "Crystallogenesis of biological macromolecules: facts and perspectives", Acta Crystallogr D Biol Crystallogr, 50(Pt 4): 339-350 (1994).
Gen Bank Accession No. ADM64594.1, published Jun. 11, 2012.
Gross et al., "Therapeutic Potential of T Cell Chimeric Antigen Receptors (CARs) in Cancer Treatment: Counteracting Off-Tumor Toxicities for Safe CART Cell Therapy", Annu. Rev. Pharmacol. Toxicol., 56: 59-83 (2016).
Grupp et al., "Chimeric antigen receptor-modified T cells for acute lymphoid leukemia," New England Journal of Medicine, 368 (16), 1509-1518 (2013).
Hellstrom et al., "Antibodies For Drug Delivery", in Controlled Drug Delivery (2nd Ed.), Robinson et al. (eds.), Marcel Dekker, Inc., 623-53 (1987).
Henikoff et al., "Amino acid substitution matrices from protein blocks", Proc. Natl. Acad. Sci. U.S.A., 89(22): 10915-10919 (1992).
Hermans et al., "The vital assay: a versatile fluorometric technique for assessing CTL- and NKT-mediated cytotoxicity against multiple targets in vitro and in vivo," Journal of Immunological Methods, 285 (1), 25-40 (2004).
Hornbach et al., "Costimulation by chimeric antigen receptors revisited the T cell antitumor response benefits from combined CD28-OX40 signalling," International Journal of Cancer, 129 (12), 2935-2944 (2011).
Hoogenboom et al., "By-passing immunisation. Human antibodies from synthetic repertoires of germline VH gene segments rearranged in vitro", J. Mol. Bio1., 227(2): 381-8 (1991).
Huston et al., "Protein engineering of antibody binding sites: recovery of specific activity in an anti-digoxin single-chain Fv analogue produced in *Escherichia coli*", Proc Nat Acad Sci USA 85(16):5879-5883 (1988).

Kabat et al., "Attempts to locate complementarity-determining residues in the variable positions of light and heavy chains", Ann NY Acad Sci, 190: 382-391 (1971).
Kalos et al., "T cells with chimeric antigen receptors have potent antitumor effects and can establish memory inatients with advanced leukemia", Sci. Transl. Med., 3(95): 95ra73 (2011).
Kirkland, et al., "Analysis of the fine specificity and cross-reactivity of monoclonal anti-lipid A antibodies", J. Immunol. 137(11): 3614-3619 (1986).
Jensen et al., "Antitransgene rejection responses contribute to attenuated persistence of adoptively transferred CD20/CD19-specific chimeric antigen receptor redirected T cells in humans," Biology of Blood and MarrowTransplantation, 16 (9), 1245-1256 (2010).
Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor", J. Clinical Oncology, pp. 540-549, vol. 33, No. 6 (2015).
Kochenderfer et al., "B-cell depletion and remissions of malignancy along with cytokine-associated toxicity in a clinical trial of anti-CD19 chimeric-antigenreceptor-transduced T cells," Blood, 119 (12), 2709-2720 (2012).
Kochenderfer et al., "Construction and Pre-clinical Evaluation of an Anti-CD19 Chimeric Antigen Receptor", J Immunother., 32(7): 689-702 (2009).
Kochenderfer et al., "Eradication of B-lineage cells and regression of lymphoma in a patient treated with autologous T cells genetically engineered to recognize CD19," Blood, 116 (20), 4099-4102 (2010).
Kochenderfer et al., "Treating B-cell cancers with T cells expressing anti CD19 chimeric antigen receptors," Nature Reviews. Clinical Oncology, 10(5), 267-276 (2013).
Kozbor et al., "The production of monoclonal antibodies from human lymphocytes", Immunol Today, 4(3): 72-9 (1983).
Krause et al., "Antigen-dependent CD28 Signaling Selectively Enhances Survival and Proliferation in Genetically Modified Activated Human Primary T Lymphocytes", J. Exp. Med., 188(4): 619-626 (1998).
Larners et al., "Immune responses to transgene and retroviral vector in patients treated with ex vvo-engineered T cells," Blood, 117 (1), 72-82 (2011).
Latza et al., "The human OX40 homolog: cDNA structure, expression and chromosomal assignment of the ACT35 antigen," European Journal of Immunology, 24 (3), 677-683 (1994).
Ling et al., "Advances in cancer immunotherapy based on chimeric antigen receptor," Translational Med. J., 4 (3), 97-104 (2015).
Locke, Frederick et al., "Phase 1 Results of ZUMA-1: A Multicenter Study of KTE-C19 Anti-CD19 CART Cell Therapy in Refractory Aggressive Lymphoma", Molecular Therapy, pp. 285-295, vol. 25, No. 1 (2017).
Lonberg et al., "Antigen-specific human antibodies from mice comprising four distinct genetic modifications", Nature, 368(6474): 856 859 (1994).
Lonberg, et al. "Human antibodies from transgenic mice", Intern. Rev. Immunol., 13(1) 65 93 (1995).
Lu et al., "A Rapid Cell Expansion Process for Production of Engineered Autologous CAR-T Cell Therapies", Human Gene Therapy Methods, pp. 209-218, vol. 27, No. 6. (2016).
Mannering et al., "A sensitive method for detecting proliferation of rare autoantigen-specific human T cells," Journal of Immunological Methods, 283 (1-2),173-183 (2003).
Marks et al., "By-passing immunization: building high affinity human antibodies by chain shuffling", BioTechnology, 10 (7), 779 783 (1992).
Marks et al., "By-passing immunization. Human antibodies from V-gene libraries displayed on phage", J. Mol. Biol.,22(3):581-97 (1991).
McPherson, "Crystallization of Proteins from Polyethylene Glycol", J Bio1 Chern, 251(20): 6300-6303 (1976).
McPherson, "Current approaches to macromolecular crystallization", Eur J Biochem, 189: 1-23 (1990).

(56) References Cited

OTHER PUBLICATIONS

Moldenhauer et al., "Identity of HML-1 antigen on intestinal intraepithelial T cells and of B-ly7 antigen on hairy cell eukaemia", Scand. J. Immunol., 32(2): 77-82 (1990).

Moran et al., "The TNFRs OX40, 4-1 BB, and CD40 as targets for cancer immunotherapy," Current Opinion in Immunology, 25 (2), 230-237 (2013).

Morel et al., "Monoclonal antibodies to bovine serum albumin: affinity and specificity determinations", Melee. Immunol., 25(1): 7-15 (1988).

Morrison, "Success in specification", Nature, 368, 812 13 (1994).

Nadler et al., "84, a human B lymphocyte-associated antigen expressed on normal, mitogen-activated, and malignant B lymphocytes," Journal of Immunology,131 (1 ), 244-250 (1983).

Neuberger, "Generating high-avidity human Mabs in mice", Nature Biotechnology, 14: 826 (1996).

Neelapu et al., "Axicabtagene Ciloleucel CART-Cell Therapy in Refractory Large B-Cell Lymphoma", The New England Journal of Medicine, pp. 2531-2544, vol. 377, No. 26 (2017).

Nicholson et al., "Construction and characterisation of a functional CD19 specific single chain Fv fragment for immunotherapy of B lineage leukemia and lymphoma," Molecular Immunology, 34 (16-17), 1157-1165 (1997).

Ochi et al., "Functional immunoglobulin M production after transfection of cloned immunoglobulin heavy and light chain genes into lymphoid cells," Proceedings ofthe National Academy of Sciences ofthe United States of America, 80 (20), 6351-6355 (1983).

Pinchera et al. (eds.), "Analysis, Results, And Future Prospective Of The Therapeutic Use Of Radiolabeled Antibody In Cancer Therapy", in Monoclonal Antibodies For Cancer Detection And Therapy, pp. 475-506 (1985).

Porter et al., "Chimeric antigen receptor-modified T cells in chronic lymphoid leukemia", N. Engl. J. Med., 365(8)725-33 (2011).

Porter et al., "Comparison of efficiency of infection of human gene therapy target cells via four different retroviral receptors," Human Gene Therapy, 7 (8),913-919 (1996).

Rosenberg et al., "Adoptive cell transfer as personalized immunotherapy for human cancer", Cancer Immunology and Immunotherapy, 348: 62-68 (2015).

Rubio et al., "Ex vivo identification, isolation and analysis of tumor-cytolytic T cells," Nature Medicine, 9 (11), 1377-1382 (2003).

Ruella et al., "Chimeric Antigen Receptor T cells for B Cell Neoplasms: Choose the Right CAR for You", Curr Hematol Malig Rep, 11: 368-384 (2016).

Sadelain et al., "Targeting Tumors with Genetically Enhanced T Lymphocytes", Nature Rev. Cancer, 3: 35-45 (2003).

Sadelain, et al., "The Basic Principles of Chimeric Antigen Receptor Design", Cancer Discovery, 3: 388-398 (2013).

Savoldo et al., "CD28 costimulation improves expansion and persistence of chimeric antigen receptor-modified T cells in lymphoma patients," Journal of Clinical Investigation, 121 (5), 1822-1826 (2011).

Sommermeyer et al., "Fully human CD19-specific chimeric antigen receptors forTcell therapy", Leukemia 31(10): 2191-2199 (2017).

Song et al., "CD27 costimulation augments the survival and antitumor activity of redirected human T cells in vivo", Blood, 119(3): 696-706 (2012).

Stahli et al., "Distinction of epitopes by monoclonal antibodies", Methods in Enzymology, 92: 242-253 (1983).

Thorpe et al., "The preparation and cytotoxic properties of antibodytoxin conjugates", Immunol. Rev., 62: 119-58 (1982).

Thorpe et al., "Monoclonal Antibodies '84: Biological and Clinical Applications", Proceedings ofthe International Sympposium on Monoclonal Antibodies '84 held in Florence, Italy, Oct. 16-19, 1984.

Tramontano et al., "Framework residue 71 is a major determinant of the position and conformation of the second hypervariable region in the VH domains of immunoglobulins" J Mol Biol, 215(1): 175-82 (1990).

Uniprot KB-P01732 (CD8A Human) (14 pages) Jul. 21, 1986.

Watkins et al., "CD19-targeted Immunotherapies for Treatment of Patients with non-Hodgkin B-cell Lymphomas", Expert Opinion on Investigational Drugs, pp. 601-611, vol. 27, No. 7 (2018).

Weinberg et al., "Science gone translational: the OX40 agonist story," Immunological Reviews, 244 (1), 218-231 (2011), Author Manuscript.

Wu et al., "Remote control of therapeutic T cells through a small molecule-gated chimeric receptor", Science, 350:6258 (2014).

Yang et al., "A simplified method for the clinical-scale generation of central memory-like CDS+ T cells after transduction with lentiviral vectors encoding antitumor antigen T-cell receptors," Journal of Immunotherapy, 33 (6), 648-658 (2010).

Zebedee et al., "Human combinatorial antibody libraries to hepatitis B surface antigen", Proc. Natl. Acad. Sci. USA, 89(8): 3175-79 (1992).

Cartellieri et al., Chimeric Antigen Receptor-Engineered T Cells for Immunotherapy of Cancer. Journal of Biomedicine and Biotechnology 2010, XP055206629, doi:10.1155/2010/956304. 13 pages.

Chen et al., Discovery of Small-Molecule Inhibitors of HCV NS3-4A Protease as Potential Therapeutic Agents against HCV Infection. Current Medicinal Chemistry 2005, vol. 12, No. 20, doi:10.2174/0929867054864769, pp. 2317-2342, XP009110972.

Gust et al., Endothelial Activation and Blood-Brain Barrier Disruption in Neurotoxicity after Adoptive Immunotherapy with CD19 Car-T Cells. Cancer Discovery 2017, 7(12), pp. 1404-1419.

International Search Report and Written Opinion for International Application No. PCT/US2019/065776 dated Jun. 24, 2020. 21 pages.

Jena et al., Redirecting T-cell specificity by introducing a tumorspecific chimeric antigen receptor. Blood 2010; vol. 116, No. 7, pp. 1035-1044, XP055021403.

Locke et al., Abstract CT019: Primary results from ZUMA-1: a pivotal trial of axicabtagene ciloleucel (axicel; KTE-C19) in patients with refractory aggressive non-Hodgkin lymphoma (NHL). AACR Annual Meeting 2017. 4 pages.

Park et al., Adoptive Transfer of Chimeric Antigen Receptor Redirected Cytolytic T Lymphocyte Clones in Patients with Neuroblastoma. Molecular Therapy 2007, vol. 15, No. 4, pp. 825-833.

Patel et al., T-cell killing of heterogenous tumor or viral targets with bispecific chimeric immune receptors. Cancer Gene Therapy 2000, vol. 7, No. 8, pp. 1127-1134, XP055259929.

Raboisson et al., Structure-activity relationship study on a novel series of cyclopentane-containing macrocyclic inhibitors of the hepatitis C virus NS3/4A protease leading to the discovery of TMC435350. Bioorganic & Medicinal Chemistry Letters 2008, vol. 18, No. 17, doi:10.1016/J.BMCL.2008.07.088, pp. 4853-4858, XP024100116.

Schneider et al., Minimizing leukemia escape: implementing a dual anti-CD20- and CD19-scFv-based chimeric antigen receptor (CAR). Journal for ImmunoTherapy of Cancer 2015, vol. 3, No. 2, doi:10.1186/2051-1426-3-S2-P122, XP021235172. 1 page.

Urbanska et al., Targeted cancer immunotherapy via combination of designer bispecific antibody and novel gene-engineered T cells. Journal of Translational Medicine 2014, vol. 12, No. 1, XP021207565. 12 pages.

Venkatraman et al., Macrocyclic inhibitors of HCV NS3 protease. Expert Opinion on Therapeutic Patents 2009, vol. 19, No. 9, doi: 10.1517/13543770903044994, pp. 1277-1303, XP055084885.

Ando et al., A Safeguard System for Induced Pluripotent Stem Cell-Derived Rejuvenated T Cell Therapy, Stem Cell Reports 2015, vol. 5, pp. 597-608.

Examiner Requisition for Canadian Application No. 3,122,762 dated Jul. 29, 2022. 4 pages.

Galon et al., Characterization of anti-CD19 chimeric antigen receptor (CAR) T cell-mediated tumor microenvironment immune gene profile in a multicenter trial (ZUMA-1) with axicabtagene ciloleucel (axi-cel, KTE-C19). J. Clin Oncol. 2017;35(15), Abstract 3025. 4 pages.

Lee et al., Current concepts in the diagnosis and management of cytokine release syndrome, Blood 2014, 124(2): pp. 188-195.

Littman et al., The isolation and sequence of the gene encoding T8: A molecule defining functional classes of T lymphocytes, Cell 1985, vol. 40, pp. 237-246.

(56) References Cited

OTHER PUBLICATIONS

Locke et al., Updated Phase 1 Results from ZUMA-1: Molecular Therapy, vol. 24, Supplement 1, (Year: 2016). 1 page.
Office Action for Japanese Application No. 2021-533159 dated Jan. 10, 2023. 4 pages.
Office Action for Japanese Application No. 2021-533159 dated Jul. 5, 2022. 10 pages.
Ren et al., Multiplex Genome Editing to Generate Universal CAR T Cells Resistant to PD1 Inhibition, Clin Cancer Res; 23(9); 2255-2266. 2016.
Tammana et al., 4-1BB and CD28 Signaling Plays a Synergistic Role in Redirecting Umbilical Cord Blood T Cells Against B-Cell Malignancies, Human Gene Therapy 2010, 21, pp. 75-86.
Examination Report for Australian Application No. 2019397033 dated Mar. 9, 2023. 5 pages.

* cited by examiner

SEQUENCE LISTING

```
<160> NUMBER OF SEQ ID NOS: 314

<210> SEQ ID NO 1
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Gly Ser Trp Tyr Ser Asn Trp Phe Asp Pro Trp Gly Gln
            100                 105                 110

Gly Thr Met Val Thr Val Ser Ser
        115                 120

<210> SEQ ID NO 2
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
```

-continued

<400> SEQUENCE: 2

```
caggtgcagc tacagcagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattgggaa atcgaccata gtggaagcac caactacaac   180
ccgtccctca agagtcgagt caccatatca gtagacacgt ccaagaacca gttctccctg   240
aagctgagct ctgtgaccgc cgcggacacg gcggtgtact actgcgccag aggtggagga   300
agttggtaca gcaactggtt cgacccatgg ggacaggta caatggtcac cgtctcctca   360
```

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Gly Gly Ser Phe Ser Gly Tyr Tyr
1               5
```

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Gly Tyr Tyr Trp Ser
1               5
```

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Gly Gly Ser Phe Ser Gly
1               5
```

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Ile Asp His Ser Gly Ser Thr
1               5
```

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Ile Asp His Ser Gly Ser Thr Asn Tyr Asn Pro Ser Leu Lys Ser
1               5                   10                  15

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp His Ser Gly Ser
1               5

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Arg Gly Gly Gly Ser Trp Tyr Ser Asn Trp Phe Asp Pro
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Ser Trp Tyr Ser Asn Trp Phe Asp Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Ser Trp Tyr Ser Asn Trp Phe Asp Pro
1               5                   10

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45
Tyr Asp Ala Ser Ser Leu Glu Ser Gly Val Pro Ser Arg Phe Ser Gly
 50                  55                  60
Ser Gly Ser Gly Thr Glu Phe Thr Leu Thr Ile Ser Ser Leu Gln Pro
 65                  70                  75                  80
Asp Asp Phe Ala Thr Tyr Tyr Cys Gln Gln Asp Arg Ser Leu Pro Pro
                 85                  90                  95
Thr Phe Gly Gly Gly Thr Lys Val Glu Ile Lys
            100                 105

<210> SEQ ID NO 13
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gacatccaga tgacccagtc tccttccacc ctgtctgcat ctgtaggaga cagagtcacc        60
atcacttgcc gggccagtca gagtattagt agctggttgg cctggtatca gcagaaacca       120
gggaaagccc ctaagctcct gatctatgat gcctccagtt tggaaagtgg ggtcccatca       180
aggttcagcg gcagtggatc tgggacagaa ttcactctca ccatcagcag cctgcagcct       240
gatgattttg caacttatta ctgccagcag gaccgaagtc tccctcctac ttttggcgga       300
gggaccaagg ttgagatcaa a                                                 321

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ala Ser Gln Ser Ile Ser Ser Trp Leu Ala
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ala Ser Gln Ser Ile Ser Ser Trp Leu Ala
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ala Ser Gln Ser Ile Ser Ser Trp Leu Ala
 1               5                  10

```
<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Ala Ser Ser Leu Glu Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Ala Ser Ser Leu Glu Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Ala Ser Ser Leu Glu Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Asp Arg Ser Leu Pro Pro Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gln Asp Arg Ser Leu Pro Pro Thr
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 22

Gln Gln Asp Arg Ser Leu Pro Pro Thr
1               5

<210> SEQ ID NO 23
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Ser Phe Ser Gly Ile
            20                  25                  30

His Trp Asn Trp Ile Arg Gln Pro Pro Gly Lys Gly Leu Glu Trp Ile
        35                  40                  45

Gly Asp Ile Asp Thr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Gly Gln Glu Ser Ala Thr Tyr Leu Gly Met Asp Val Trp Gly
            100                 105                 110

Gln Gly Thr Thr Val Thr Val Ser Ser
        115                 120

<210> SEQ ID NO 24
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
caggtgcagc tacagcagtg gggcgcagga ctgttgaagc cttcggagac cctgtccctc      60
acctgcgctg tctatggtgg gtccttcagt ggtatccact ggaactggat ccgccagccc     120
ccagggaagg gctggagtg gattggggac atcgacacaa gtggaagcac caactacaac     180
ccgtccctca agagtcgagt caccatatcc gtagacacgt ccaagaacca gttctccctg     240
aagctgagtt ctgtgaccgc cgcagacacg gcggtgtact actgcgccag attgggacag     300
gagtcagcca cctatctcgg aatggacgta tggggccagg aacaactgt caccgtctcc     360 tca                                                                    363

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Ser Phe Ser Gly Ile His
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ile His Trp Asn
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Ser Phe Ser Gly
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Asp Thr Ser Gly Ser Thr
1               5

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Ile Asp Thr Ser Gly Ser Thr Asn Tyr Asn Pro Ser Leu Lys Ser
1               5                   10                  15

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Thr Ser Gly Ser
1               5

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 31

Ala Arg Leu Gly Gln Glu Ser Ala Thr Tyr Leu Gly Met Asp Val
1               5                   10                  15

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Gly Gln Glu Ser Ala Thr Tyr Leu Gly Met Asp Val
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Gly Gln Glu Ser Ala Thr Tyr Leu Gly Met Asp Val
1               5                   10

<210> SEQ ID NO 34
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Leu Tyr Thr Tyr Pro Phe Thr Phe Gly Gly Gly Thr Lys Val Glu Ile
            100                 105                 110

Lys

<210> SEQ ID NO 35
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
gacatcgtga tgacccagtc tccagactcc ctggctgtgt ctctgggcga gagggccacc      60
atcaactgca agtccagcca gagtgtttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcagct ctacacctac     300
cctttcactt ttggcggagg gaccaaggtt gagatcaaa                            339
```

```
<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Ser Ser Gln Ser Val Leu Tyr Ser Ser Asn Asn Lys Asn Tyr Leu
1               5                   10                  15

Ala

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Ser Ser Gln Ser Val Leu Tyr Ser Ser Asn Asn Lys Asn Tyr Leu
1               5                   10                  15

Ala

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Ser Ser Gln Ser Val Leu Tyr Ser Ser Asn Asn Lys Asn Tyr Leu
1               5                   10                  15

Ala

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Trp Ala Ser Thr Arg Glu Ser
1               5

<210> SEQ ID NO 40
<211> LENGTH: 7
<212> TYPE: PRT
<213> ORGANISM: Artificial Sequence
```

```
-continued

<220> FEATURE:
<223> OTHER INFORMATION: Description of Artificial Sequence: Synthetic
      peptide

<400> SEQUENCE: 40

Trp Ala Ser Thr Arg Glu Ser
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Trp Ala Ser Thr Arg Glu Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Gln Leu Tyr Thr Tyr Pro Phe Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Gln Leu Tyr Thr Tyr Pro Phe Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gln Leu Tyr Thr Tyr Pro Phe Thr
1               5

<210> SEQ ID NO 45
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Leu Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Thr Asp Tyr Ser Ser Gly Met Gly Tyr Gly Met Asp
            100                 105                 110

Val Trp Gly Gln Gly Thr Thr Val Thr Val Ser Ser
        115                 120

<210> SEQ ID NO 46
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag ggaaggggct ggagtggatt gggagtatct attatagtgg gagcacctac     180
tacaacccgt ccctcaagag tcgagtcacc atatccgtag acacgtccaa gaaccagttc     240
tccctgaagc tgagttctgt gaccgccgca gacacggcgg tgtactactg cgccagagag     300
actgactaca gcagcggaat gggatacgga atggacgtat ggggccaggg aacaactgtc     360
accgtctcct ca                                                         372

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gly Ser Ile Ser Ser Ser Ser Tyr Tyr
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Ser Ser Tyr Tyr Trp Gly
1               5

<210> SEQ ID NO 49
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 49

Gly Gly Ser Ile Ser Ser Ser Ser
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Tyr Tyr Ser Gly Ser Thr
1               5

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Ile Tyr Tyr Ser Gly Ser Thr Tyr Tyr Asn Pro Ser Leu Lys Ser
1               5                   10                  15

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Tyr Tyr Ser Gly Ser
1               5

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Arg Glu Thr Asp Tyr Ser Ser Gly Met Gly Tyr Gly Met Asp Val
1               5                   10                  15

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Thr Asp Tyr Ser Ser Gly Met Gly Tyr Gly Met Asp Val
1               5                   10
```

```
<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Thr Asp Tyr Ser Ser Gly Met Gly Tyr Gly Met Asp Val
1               5                   10

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Ala Asp Pro Phe
                85                  90                  95

Thr Phe Gly Gly Gly Thr Lys Val Glu Ile Lys
            100                 105

<210> SEQ ID NO 57
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gacatccaga tgacccagtc tccatcctcc ctgtctgcat ctgtaggaga cagagtcacc      60
atcacttgcc gggcaagtca gagcattaac agctatttaa attggtatca gcagaaacca     120
gggaaagccc ctaagctcct gatctatgct gcatccagtt tgcaaagtgg ggtcccatca     180
aggttcagtg gcagtggatc tgggacagat tcactctca ccatcagcag tctgcaacct      240
gaagattttg caacttacta ctgccagcaa agcctcgccg acccttttca ttttggcgga     300
gggaccaagg ttgagatcaa a                                               321

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58
```

Arg Ala Ser Gln Ser Ile Asn Ser Tyr Leu Asn
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Ala Ser Gln Ser Ile Asn Ser Tyr Leu Asn
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Ala Ser Gln Ser Ile Asn Ser Tyr Leu Asn
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Ala Ser Ser Leu Gln Ser
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Ala Ser Ser Leu Gln Ser
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Ala Ser Ser Leu Gln Ser
1               5

<210> SEQ ID NO 64
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 64

Gln Gln Ser Leu Ala Asp Pro Phe Thr
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Gln Ser Leu Ala Asp Pro Phe Thr
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Gln Ser Leu Ala Asp Pro Phe Thr
1               5

<210> SEQ ID NO 67
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Glu Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Ser Gly His Thr Tyr Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Gly Pro His Tyr Asp Asp Trp Ser Gly Phe Ile Ile Trp Phe
            100                 105                 110

Asp Pro Trp Gly Gln Gly Thr Leu Val Thr Val Ser Ser
        115                 120                 125

<210> SEQ ID NO 68
<211> LENGTH: 375
<212> TYPE: DNA
<213> ORGANISM: Artificial Sequence
<220> FEATURE:
<223> OTHER INFORMATION: Description of Artificial Sequence: Synthetic
```

-continued polynucleotide

<400> SEQUENCE: 68

```
caggttcagc tggtgcagtc tggagctgag gtgaagaagc ctggggcctc agtgaaggtc      60
tcctgcaagg cttctggtta cacctttaaa gaatatggta tcagctgggt gcgacaggcc     120
cctggacaag ggcttgagtg gatgggatgg atcagcgctt acagtggtca cacatactat     180
gcacagaagc tccagggcag agtcaccatg accacagaca catccacgag cacagcctac     240
atggagctga ggagcctgag atctgacgac acggcggtgt actactgcgc cagagggcct     300
cactacgacg actggagcgg atttatcata tggttcgacc catggggaca gggtacattg     360
gtcaccgtct cctca                                                       375
```

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Gly Tyr Thr Phe Lys Glu Tyr Gly
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Glu Tyr Gly Ile Ser
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Gly Tyr Thr Phe Lys Glu
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Ile Ser Ala Tyr Ser Gly His Thr
1               5

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Trp Ile Ser Ala Tyr Ser Gly His Thr Tyr Tyr Ala Gln Lys Leu Gln
1               5                   10                  15

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Ala Tyr Ser Gly
1               5

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Arg Gly Pro His Tyr Asp Asp Trp Ser Gly Phe Ile Ile Trp Phe
1               5                   10                  15

Asp Pro

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Pro His Tyr Asp Asp Trp Ser Gly Phe Ile Ile Trp Phe Asp Pro
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Pro His Tyr Asp Asp Trp Ser Gly Phe Ile Ile Trp Phe Asp Pro
1               5                   10                  15

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Gln Met Thr Gln Ser Pro Ser Ser Leu Ser Ala Ser Val Gly

```
1               5                  10                 15
Asp Arg Val Thr Ile Thr Cys Arg Ala Ser Gln Ser Ile Ser Ser Tyr
                20                 25                 30

Leu Asn Trp Tyr Gln Gln Lys Pro Gly Lys Ala Pro Lys Leu Leu Ile
            35                 40                 45

Tyr Ala Ala Ser Ser Leu Gln Ser Gly Val Pro Ser Arg Phe Ser Gly
        50                 55                 60

Ser Gly Ser Gly Thr Asp Phe Thr Leu Thr Ile Ser Ser Leu Gln Pro
65                  70                 75                 80

Glu Asp Phe Ala Thr Tyr Tyr Cys Gln Gln Ser Tyr Arg Phe Pro Pro
                85                 90                 95

Thr Phe Gly Gln Gly Thr Lys Val Glu Ile Lys
            100                105
```

```
<210> SEQ ID NO 79
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccttca    180
aggttcagtg gcagtggatc tgggacagat ttcactctca ccatcagcag tctgcaacct    240
gaagattttg caacttacta ctgtcaacag agttacaggt tcctcctac ctttggccaa     300 gggaccaagg ttgagatcaa a                                               321
```

```
<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Ala Ser Gln Ser Ile Ser Ser Tyr Leu Asn
1               5                   10
```

```
<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Ala Ser Gln Ser Ile Ser Ser Tyr Leu Asn
1               5                   10
```

```
<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 82

Arg Ala Ser Gln Ser Ile Ser Ser Tyr Leu Asn
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Ala Ser Ser Leu Gln Ser
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Ala Ser Ser Leu Gln Ser
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Ala Ser Ser Leu Gln Ser
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Gln Ser Tyr Arg Phe Pro Pro Thr
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Gln Ser Tyr Arg Phe Pro Pro Thr
1               5

<210> SEQ ID NO 88
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Gln Ser Tyr Arg Phe Pro Pro Thr
1               5

<210> SEQ ID NO 89
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Pro
            20                  25                  30

Asp His Tyr Trp Gly Trp Ile Arg Gln Pro Pro Gly Lys Gly Leu Glu
        35                  40                  45

Trp Ile Gly Ser Ile Tyr Ala Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Thr Asp Tyr Ser Ser Gly Met Gly Tyr Gly Met Asp
            100                 105                 110

Val Trp Gly Gln Gly Thr Thr Val Thr Val Ser Ser
        115                 120

<210> SEQ ID NO 90
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
caggtgcagc tgcaggagtc gggcccagga ctggtgaagc cttcggagac cctgtccctc      60
acctgcactg tctctggtgg ctccatcagc agtcccgacc actactgggg ctggatccgc     120
cagcccccag ggaaggggct ggagtggatt gggtccatct acgccagtgg gagcaccttc     180
tacaacccgt ccctcaagag tcgagtcacc atatccgtag acacgtccaa gaaccagttc     240
tccctgaagc tgagctctgt gaccgccgcg gacacggcgg tgtactactg cgccagagag     300
actgactaca gcagcggaat gggatacgga atggacgtat ggggccaggg aacaactgtc     360
accgtctcct ca                                                        372

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 91

Gly Gly Ser Ile Ser Ser Pro Asp His Tyr
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Pro Asp His Tyr Trp Gly
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Gly Ser Ile Ser Ser Pro Asp
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ile Tyr Ala Ser Gly Ser Thr
1               5

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Ile Tyr Ala Ser Gly Ser Thr Phe Tyr Asn Pro Ser Leu Lys Ser
1               5                   10                  15

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Ala Ser Gly Ser
1               5

<210> SEQ ID NO 97
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Arg Glu Thr Asp Tyr Ser Ser Gly Met Gly Tyr Gly Met Asp Val
1               5                   10                  15

<210> SEQ ID NO 98
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Glu Thr Asp Tyr Ser Ser Gly Met Gly Tyr Gly Met Asp Val
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Glu Thr Asp Tyr Ser Ser Gly Met Gly Tyr Gly Met Asp Val
1               5                   10

<210> SEQ ID NO 100
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Ala Asp Pro Phe
                85                  90                  95

Thr Phe Gly Gly Gly Thr Lys Val Glu Ile Lys
            100                 105

<210> SEQ ID NO 101
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 101

```
gacatccaga tgacccagtc tccatcctcc ctgtctgcat ctgtaggaga cagagtcacc    60
atcacttgcc gggcaagtca gagcattaac agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgccagcaa agcctcgccg acccttt cac ttttggcgga   300 gggaccaagg ttgagatcaa a                                             321
```

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Ala Ser Gln Ser Ile Asn Ser Tyr Leu Asn
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Ala Ser Gln Ser Ile Asn Ser Tyr Leu Asn
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Ala Ser Gln Ser Ile Asn Ser Tyr Leu Asn
1               5                   10

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Ala Ser Ser Leu Gln Ser
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 106

Ala Ala Ser Ser Leu Gln Ser
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Ala Ser Ser Leu Gln Ser
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gln Gln Ser Leu Ala Asp Pro Phe Thr
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Gln Ser Leu Ala Asp Pro Phe Thr
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Gln Ser Leu Ala Asp Pro Phe Thr
1               5

<210> SEQ ID NO 111
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asp Thr Glu
                20                  25                  30
```

Gly Val Gly Val Gly Trp Ile Arg Gln Pro Pro Gly Lys Ala Leu Glu
            35                  40                  45

Trp Leu Ala Leu Ile Tyr Phe Asn Asp Gln Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Val Tyr Tyr
                 85                  90                  95

Cys Ala Arg Asp Thr Gly Tyr Ser Arg Trp Tyr Tyr Gly Met Asp Val
            100                 105                 110

Trp Gly Gln Gly Thr Thr Val Thr Val Ser Ser
        115                 120

<210> SEQ ID NO 112
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
cagatcacct tgaaggagtc tggtcctacg ctggtgaaac ccacacagac cctcacgctg      60
acctgcacct tctctgggtt ctcactcgac actgaaggag tgggtgtggg ctggatccgt     120
cagcccccag gaaaggccct ggagtggctt gcactcattt atttcaatga tcaaaagcgc     180
tacagcccat ctctgaagag caggctcacc atcaccaagg acacctccaa aaaccaggtg     240
gtccttacaa tgaccaacat ggaccctgtg gacacggcgg tgtactactg cgccagagac     300
acgggataca gccgatggta ctacggcatg gatgtatggg gccagggaac aactgtcacc     360
gtctcctca                                                            369

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Phe Ser Leu Asp Thr Glu Gly Val Gly
 1               5                  10

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Glu Gly Val Gly Val Gly
 1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 115

Gly Phe Ser Leu Asp Thr Glu Gly
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ile Tyr Phe Asn Asp Gln Lys
1               5

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Leu Ile Tyr Phe Asn Asp Gln Lys Arg Tyr Ser Pro Ser Leu Lys Ser
1               5                   10                  15

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Tyr Phe Asn Asp Gln
1               5

<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Arg Asp Thr Gly Tyr Ser Arg Trp Tyr Tyr Gly Met Asp Val
1               5                   10                  15

<210> SEQ ID NO 120
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asp Thr Gly Tyr Ser Arg Trp Tyr Tyr Gly Met Asp Val
1               5                   10

<210> SEQ ID NO 121
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Thr Gly Tyr Ser Arg Trp Tyr Tyr Gly Met Asp Val
1               5                   10

<210> SEQ ID NO 122
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ala Tyr Pro Ile
                85                  90                  95

Thr Phe Gly Gly Gly Thr Lys Val Glu Ile Lys
            100                 105

<210> SEQ ID NO 123
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat tcactctcac ccatcagcag cctgcagcct     240
gaagattttg caacttatta ctgtcagcag gcatacgcct accctatcac ttttggcgga     300
gggaccaagg ttgagatcaa a                                                321

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Ala Ser Gln Gly Ile Ser Ser Trp Leu Ala
1               5                   10
```

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Ala Ser Gln Gly Ile Ser Ser Trp Leu Ala
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Arg Ala Ser Gln Gly Ile Ser Ser Trp Leu Ala
1               5                   10

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ala Ala Ser Ser Leu Gln Ser
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Ala Ser Ser Leu Gln Ser
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Ala Ser Ser Leu Gln Ser
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 130

Gln Gln Ala Tyr Ala Tyr Pro Ile Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gln Gln Ala Tyr Ala Tyr Pro Ile Thr
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Gln Ala Tyr Ala Tyr Pro Ile Thr
1               5

<210> SEQ ID NO 133
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Glu Lys Tyr
            20                  25                  30

Tyr Trp Ser Trp Ile Arg Gln Pro Pro Gly Lys Gly Leu Glu Trp Ile
        35                  40                  45

Gly Glu Ile Tyr His Ser Gly Leu Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Arg Tyr Asp Ser Ser Asp Ser Tyr Tyr Tyr Ser Tyr Asp Tyr
            100                 105                 110

Gly Met Asp Val Trp Gly Gln Gly Thr Thr Val Thr Val Ser Ser
        115                 120                 125

<210> SEQ ID NO 134
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134

```
caggtgcagc tacagcagtg gggcgcagga ctgttgaagc cttcggagac cctgtccctc      60
acctgcgctg tctatggtgg gtccttcgaa aaatactact ggagctggat ccgccagccc     120
ccagggaagg ggctggagtg gattggggaa atctaccata gtggactcac caactacaac     180
ccgtccctca gagtcgagt caccatatca gtagacacgt ccaagaacca gttctccctg      240
aagctgagct ctgtgaccgc cgcggacacg gcggtgtact actgcgccag ggtcagatac     300
gacagcagcg actcctacta ctatagctac gattatggaa tggacgtatg gggccaggga    360
acaactgtca ccgtctcctc a                                              381
```

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Gly Ser Phe Glu Lys Tyr Tyr
1               5

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Lys Tyr Tyr Trp Ser
1               5

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Gly Ser Phe Glu Lys
1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ile Tyr His Ser Gly Leu Thr
1               5

<210> SEQ ID NO 139
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Glu Ile Tyr His Ser Gly Leu Thr Asn Tyr Asn Pro Ser Leu Lys Ser
1               5                   10                  15

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Tyr His Ser Gly Leu
1               5

<210> SEQ ID NO 141
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ala Arg Val Arg Tyr Asp Ser Ser Asp Ser Tyr Tyr Tyr Ser Tyr Asp
1               5                   10                  15

Tyr Gly Met Asp Val
            20

<210> SEQ ID NO 142
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Val Arg Tyr Asp Ser Ser Asp Ser Tyr Tyr Tyr Ser Tyr Asp Tyr Gly
1               5                   10                  15

Met Asp Val

<210> SEQ ID NO 143
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Val Arg Tyr Asp Ser Ser Asp Ser Tyr Tyr Tyr Ser Tyr Asp Tyr Gly
1               5                   10                  15

Met Asp Val

<210> SEQ ID NO 144
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

```
Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Phe Pro Trp Thr Phe Gly Gly Gly Thr Lys Val Glu Ile
            100                 105                 110

Lys
```

```
<210> SEQ ID NO 145
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
gacatcgtgc tgacccagtc tccagactcc ctggctgtgt ctctgggcga gagggccacc      60
atcaactgca agtccagcca gagtgtttta tacagctcca acaataagaa ctacttagct     120
tggtaccagc agaaaccagg acagcctcct aagctgctca tttactgggc atctagccgg     180
gaatccgggg tccctgaccg attcagtggc agcgggtctg ggacagattt cactctcacc     240
atcagcagcc tgcaggctga agatgtggca gtttattact gtcagcagtc ctactccttc     300
ccttggactt ttggcggagg gaccaaggtt gagatcaaa                            339
```

```
<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Lys Ser Ser Gln Ser Val Leu Tyr Ser Ser Asn Asn Lys Asn Tyr Leu
1               5                   10                  15

Ala
```

```
<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Lys Ser Ser Gln Ser Val Leu Tyr Ser Ser Asn Asn Lys Asn Tyr Leu
1               5                   10                  15

Ala
```

```
<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Lys Ser Ser Gln Ser Val Leu Tyr Ser Ser Asn Asn Lys Asn Tyr Leu
1               5                   10                  15

Ala

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Trp Ala Ser Ser Arg Glu Ser
1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Trp Ala Ser Ser Arg Glu Ser
1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Trp Ala Ser Ser Arg Glu Ser
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gln Gln Ser Tyr Ser Phe Pro Trp Thr
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 153

Gln Gln Ser Tyr Ser Phe Pro Trp Thr
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gln Gln Ser Tyr Ser Phe Pro Trp Thr
1               5

<210> SEQ ID NO 155
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Arg Tyr
            20                  25                  30

Val Trp Ser Trp Ile Arg Gln Pro Pro Gly Lys Gly Leu Glu Trp Ile
        35                  40                  45

Gly Glu Ile Asp Ser Ser Gly Lys Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Arg Tyr Asp Ser Ser Asp Ser Tyr Tyr Ser Tyr Asp Tyr
            100                 105                 110

Gly Met Asp Val Trp Gly Gln Gly Thr Thr Val Thr Val Ser Ser
        115                 120                 125

<210> SEQ ID NO 156
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
caggtgcagc tacagcagtg gggcgcagga ctgttgaagc cttcggagac cctgtccctc        60
acctgcgctg tctatggtgg gtccttcagt cgatacgtat ggagctggat ccgccagccc       120
ccagggaagg ggctggagtg gattggggaa atcgactcca gtggaaaaac caactacaac       180
ccgtccctca gagtcgagt caccatatca gtagacacgt ccaagaacca gttctccctg        240
aagctgagct ctgtgaccgc cgcggacacg gcggtgtact actgcgccag gtcagatac        300 gacagcagcg actcctacta ctatagctac gattatggaa tggacgtatg gggccaggga       360

-continued acaactgtca ccgtctcctc a                                               381

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Gly Ser Phe Ser Arg Tyr Val
1               5

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Arg Tyr Val Trp Ser
1               5

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Gly Ser Phe Ser Arg
1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ile Asp Ser Ser Gly Lys Thr
1               5

<210> SEQ ID NO 161
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Glu Ile Asp Ser Ser Gly Lys Thr Asn Tyr Asn Pro Ser Leu Lys Ser
1               5                   10                  15

<210> SEQ ID NO 162
<211> LENGTH: 5
<212> TYPE: PRT
<213> ORGANISM: Artificial Sequence
<220> FEATURE:
<223> OTHER INFORMATION: Description of Artificial Sequence: Synthetic

```
                                  peptide

<400> SEQUENCE: 162

Asp Ser Ser Gly Lys
1               5

<210> SEQ ID NO 163
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ala Arg Val Arg Tyr Asp Ser Ser Asp Ser Tyr Tyr Tyr Ser Tyr Asp
1               5                   10                  15

Tyr Gly Met Asp Val
            20

<210> SEQ ID NO 164
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Val Arg Tyr Asp Ser Ser Asp Ser Tyr Tyr Tyr Ser Tyr Asp Tyr Gly
1               5                   10                  15

Met Asp Val

<210> SEQ ID NO 165
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Val Arg Tyr Asp Ser Ser Asp Ser Tyr Tyr Tyr Ser Tyr Asp Tyr Gly
1               5                   10                  15

Met Asp Val

<210> SEQ ID NO 166
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Ser Arg Glu Ser Gly Val
    50                  55                  60
```

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Phe Pro Trp Thr Phe Gly Gly Gly Thr Lys Val Glu Ile
            100                 105                 110

Lys

<210> SEQ ID NO 167
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167
gacatcgtgc tgacccagtc tccagactcc ctggctgtgt ctctgggcga gagggccacc        60
atcaactgca gtccagccca gagtgtttta tacagctcca acaataagaa ctacttagct       120
tggtaccagc agaaaccagg acagcctcct aagctgctca tttactgggc atctagccgg       180
gaatccgggg tccctgaccg attcagtggc agcgggtctg ggacagattt cactctcacc       240
atcagcagcc tgcaggctga agatgtggca gtttattact gtcagcagtc ctactccttc       300
ccttggactt ttggcggagg gaccaaggtt gagatcaaa                              339

<210> SEQ ID NO 168
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Lys Ser Ser Gln Ser Val Leu Tyr Ser Ser Asn Asn Lys Asn Tyr Leu
1               5                   10                  15

Ala

<210> SEQ ID NO 169
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Lys Ser Ser Gln Ser Val Leu Tyr Ser Ser Asn Asn Lys Asn Tyr Leu
1               5                   10                  15

Ala

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Lys Ser Ser Gln Ser Val Leu Tyr Ser Ser Asn Asn Lys Asn Tyr Leu
1               5                   10                  15

Ala

```
<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Trp Ala Ser Ser Arg Glu Ser
1               5

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Trp Ala Ser Ser Arg Glu Ser
1               5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Trp Ala Ser Ser Arg Glu Ser
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gln Gln Ser Tyr Ser Phe Pro Trp Thr
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gln Gln Ser Tyr Ser Phe Pro Trp Thr
1               5

<210> SEQ ID NO 176
<211> LENGTH: 9
<212> TYPE: PRT
<213> ORGANISM: Artificial Sequence
<220> FEATURE:
```

<223> OTHER INFORMATION: Description of Artificial Sequence: Synthetic
peptide

<400> SEQUENCE: 176

Gln Gln Ser Tyr Ser Phe Pro Trp Thr
1               5

<210> SEQ ID NO 177
<211> LENGTH: 127
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 177

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Ala Trp Ser Trp Ile Arg Gln Pro Pro Gly Lys Gly Leu Glu Trp Ile
        35                  40                  45

Gly Glu Ile Asp His Arg Gly Phe Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Arg Tyr Asp Ser Ser Asp Ser Tyr Tyr Tyr Ser Tyr Asp Tyr
            100                 105                 110

Gly Met Asp Val Trp Gly Gln Gly Thr Thr Val Thr Val Ser Ser
        115                 120                 125

<210> SEQ ID NO 178
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 178
caggtgcagc tacagcagtg gggcgcagga ctgttgaagc cttcggagac cctgtccctc      60
acctgcgctg tctatggtgg gtccttctcc ggttacgcat ggagctggat ccgccagccc    120
ccagggaagg gctggagtg gattggggaa atcgaccatc gaggattcac caactacaac     180
ccgtccctca agagtcgagt caccatatca gtagacacgt ccaagaacca gttctccctg    240
aagctgagct ctgtgaccgc cgcggacacg gcggtgtact actgcgccag ggtcagatac    300
gacagcagcg actcctacta ctatagctac gattatggaa tggacgtatg gggccaggga    360
acaactgtca ccgtctcctc a                                              381

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 179

```
Gly Gly Ser Phe Ser Gly Tyr Ala
1               5

<210> SEQ ID NO 180
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Tyr Ala Trp Ser
1               5

<210> SEQ ID NO 181
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Gly Ser Phe Ser Gly
1               5

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ile Asp His Arg Gly Phe Thr
1               5

<210> SEQ ID NO 183
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Glu Ile Asp His Arg Gly Phe Thr Asn Tyr Asn Pro Ser Leu Lys Ser
1               5                   10                  15

<210> SEQ ID NO 184
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Asp His Arg Gly Phe
1               5

<210> SEQ ID NO 185
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 185

Ala Arg Val Arg Tyr Asp Ser Ser Asp Ser Tyr Tyr Ser Tyr Asp
1               5                   10                  15

Tyr Gly Met Asp Val
            20

<210> SEQ ID NO 186
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Val Arg Tyr Asp Ser Ser Asp Ser Tyr Tyr Ser Tyr Asp Tyr Gly
1               5                   10                  15

Met Asp Val

<210> SEQ ID NO 187
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Val Arg Tyr Asp Ser Ser Asp Ser Tyr Tyr Ser Tyr Asp Tyr Gly
1               5                   10                  15

Met Asp Val

<210> SEQ ID NO 188
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Phe Pro Trp Thr Phe Gly Gly Gly Thr Lys Val Glu Ile
                100                 105                 110

Lys

<210> SEQ ID NO 189
```

```
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 189
gacatcgtgc tgacccagtc tccagactcc ctggctgtgt ctctgggcga gagggccacc    60
atcaactgca gtccagcca gagtgtttta tacagctcca acaataagaa ctacttagct   120
tggtaccagc agaaaccagg acagcctcct aagctgctca tttactgggc atctagccgg   180
gaatccgggg tccctgaccg attcagtggc agcgggtctg ggacagattt cactctcacc   240
atcagcagcc tgcaggctga agatgtggca gtttattact gtcagcagtc ctactccttc   300
ccttggactt ttggcggagg gaccaaggtt gagatcaaa                          339

<210> SEQ ID NO 190
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Lys Ser Ser Gln Ser Val Leu Tyr Ser Ser Asn Asn Lys Asn Tyr Leu
1               5                   10                  15

Ala

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Lys Ser Ser Gln Ser Val Leu Tyr Ser Ser Asn Asn Lys Asn Tyr Leu
1               5                   10                  15

Ala

<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Lys Ser Ser Gln Ser Val Leu Tyr Ser Ser Asn Asn Lys Asn Tyr Leu
1               5                   10                  15

Ala

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193
```

```
Trp Ala Ser Ser Arg Glu Ser
1               5

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Trp Ala Ser Ser Arg Glu Ser
1               5

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Trp Ala Ser Ser Arg Glu Ser
1               5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gln Gln Ser Tyr Ser Phe Pro Trp Thr
1               5

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gln Gln Ser Tyr Ser Phe Pro Trp Thr
1               5

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gln Gln Ser Tyr Ser Phe Pro Trp Thr
1               5

<210> SEQ ID NO 199
<211> LENGTH: 123
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 199

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Gln Lys Tyr
            20                  25                  30

Tyr Trp Ser Trp Ile Arg Gln Pro Pro Gly Lys Gly Leu Glu Trp Ile
        35                  40                  45

Gly Glu Ile Asp Thr Ser Gly Phe Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Gly Arg Tyr Ser Tyr Gly Tyr Tyr Ile Thr Ala Phe Asp Ile
            100                 105                 110

Trp Gly Gln Gly Thr Thr Val Thr Val Ser Ser
        115                 120

<210> SEQ ID NO 200
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200
caggtgcagc tacagcagtg gggcgcagga ctgttgaagc cttcggagac cctgtccctc      60
acctgcgctg tctatggtgg gtccttccaa aaatactact ggagctggat ccgccagccc     120
ccagggaagg ggctggagtg gattgggaa atcgacacca gtggattcac caactacaac     180
ccgtccctca agagtcgagt caccatatca gtagacacgt ccaagaacca gttctccctg     240
aagctgagct ctgtgaccgc cgcggacacg gcggtgtact actgcgccag agtgggaagg     300
tacagctacg gatactatat caccgcattc gacatatggg gtcagggtac aactgtcacc     360
gtctcctca                                                            369

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Gly Ser Phe Gln Lys Tyr Tyr
1               5

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

```
Lys Tyr Tyr Trp Ser
1               5

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Gly Ser Phe Gln Lys
1               5

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ile Asp Thr Ser Gly Phe Thr
1               5

<210> SEQ ID NO 205
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Glu Ile Asp Thr Ser Gly Phe Thr Asn Tyr Asn Pro Ser Leu Lys Ser
1               5                   10                  15

<210> SEQ ID NO 206
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Asp Thr Ser Gly Phe
1               5

<210> SEQ ID NO 207
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ala Arg Val Gly Arg Tyr Ser Tyr Gly Tyr Tyr Ile Thr Ala Phe Asp
1               5                   10                  15

Ile

<210> SEQ ID NO 208
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Val Gly Arg Tyr Ser Tyr Gly Tyr Tyr Ile Thr Ala Phe Asp Ile
1               5                   10                  15

<210> SEQ ID NO 209
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Val Gly Arg Tyr Ser Tyr Gly Tyr Tyr Ile Thr Ala Phe Asp Ile
1               5                   10                  15

<210> SEQ ID NO 210
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Phe Pro Phe Thr Phe Gly Gly Gly Thr Lys Val Glu Ile
            100                 105                 110

Lys

<210> SEQ ID NO 211
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211
gacatcgtga tgacccagtc tccagactcc ctggctgtgt ctctgggcga gagggccacc      60
atcaactgca agtccagcca gagtgtttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcagca ctactccttc     300
```
cctttcactt ttggcggagg gaccaaggtt gagatcaaa         339

<210> SEQ ID NO 212
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Lys Ser Ser Gln Ser Val Leu Tyr Ser Ser Asn Asn Lys Asn Tyr Leu
1               5                   10                  15

Ala

<210> SEQ ID NO 213
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Lys Ser Ser Gln Ser Val Leu Tyr Ser Ser Asn Asn Lys Asn Tyr Leu
1               5                   10                  15

Ala

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Lys Ser Ser Gln Ser Val Leu Tyr Ser Ser Asn Asn Lys Asn Tyr Leu
1               5                   10                  15

Ala

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Trp Ala Ser Thr Arg Glu Ser
1               5

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Trp Ala Ser Thr Arg Glu Ser
1               5

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Trp Ala Ser Thr Arg Glu Ser
1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gln Gln His Tyr Ser Phe Pro Phe Thr
1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gln Gln His Tyr Ser Phe Pro Phe Thr
1               5

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gln Gln His Tyr Ser Phe Pro Phe Thr
1               5

<210> SEQ ID NO 221
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 222
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222
gaggtgaaac tgcaggagtc aggacctggc ctggtggcgc cctcacagag cctgtccgtc      60
acatgcactg tctcagggt ctcattaccc gactatggtg taagctggat tcgccagcct     120
ccacgaaagg gtctggagtg gctgggagta atatggggta gtgaaaccac atactataat    180
tcagctctca aatccagact gaccatcatc aaggacaact ccaagagcca agttttctta    240
aaaatgaaca gtctgcaaac tgatgacaca gccatttact actgtgccaa acattattac    300
tacggtggta gctatgctat ggactactgg ggtcaaggaa cctcagtcac cgtctcctca    360

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Val Ser Leu Pro Asp Tyr Gly
1               5

<210> SEQ ID NO 224
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Asp Tyr Gly Val Ser
1               5

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Val Ser Leu Pro Asp Tyr
1               5

<210> SEQ ID NO 226

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ile Trp Gly Ser Glu Thr Thr
1               5

<210> SEQ ID NO 227
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Val Ile Trp Gly Ser Glu Thr Thr Tyr Tyr Asn Ser Ala Leu Lys Ser
1               5                   10                  15

<210> SEQ ID NO 228
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Trp Gly Ser Glu Thr
1               5

<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ala Lys His Tyr Tyr Tyr Gly Gly Ser Tyr Ala Met Asp Tyr
1               5                   10

<210> SEQ ID NO 230
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

His Tyr Tyr Tyr Gly Gly Ser Tyr Ala Met Asp Tyr
1               5                   10

<210> SEQ ID NO 231
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231
```

```
His Tyr Tyr Tyr Gly Gly Ser Tyr Ala Met Asp Tyr
1               5                   10
```

<210> SEQ ID NO 232
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105
```

<210> SEQ ID NO 233
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233

```
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat tacactcagg agtcccatca   180
aggttcagtg gcagtgggtc tggaacagat tattctctca ccattagcaa cctggagcaa   240
gaagatattg ccacttactt ttgccaacag ggtaatacgc ttccgtacac gttcggaggg   300
gggactaagt tggaaataac a                                              321
```

<210> SEQ ID NO 234
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

```
Arg Ala Ser Gln Asp Ile Ser Lys Tyr Leu Asn
1               5                   10
```

<210> SEQ ID NO 235
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 235

Arg Ala Ser Gln Asp Ile Ser Lys Tyr Leu Asn
1               5                   10

<210> SEQ ID NO 236
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Arg Ala Ser Gln Asp Ile Ser Lys Tyr Leu Asn
1               5                   10

<210> SEQ ID NO 237
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

His Thr Ser Arg Leu His Ser
1               5

<210> SEQ ID NO 238
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

His Thr Ser Arg Leu His Ser
1               5

<210> SEQ ID NO 239
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

His Thr Ser Arg Leu His Ser
1               5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gln Gln Gly Asn Thr Leu Pro Tyr Thr
1               5

<210> SEQ ID NO 241

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gln Gln Gly Asn Thr Leu Pro Tyr Thr
1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gln Gln Gly Asn Thr Leu Pro Tyr Thr
1               5

<210> SEQ ID NO 243
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220
```

Tyr Tyr Gly Gly Ser Tyr Ala Met Asp Tyr Trp Gly Gln Gly Thr Ser
225                 230                 235                 240

Val Thr Val Ser Ser
            245

<210> SEQ ID NO 244
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 244
gacatccaga tgacacagac tacatcctcc ctgtctgcct ctctgggaga cagagtcacc      60
atcagttgca gggcaagtca ggacattagt aaatatttaa attggtatca gcagaaacca     120
gatggaactg ttaaactcct gatctaccat acatcaagat tacactcagg agtcccatca     180
aggttcagtg gcagtgggtc tggaacagat tattctctca ccattagcaa cctggagcaa     240
gaagatattg ccacttactt ttgccaacag gtaatacgc ttccgtacac gttcggaggg      300
gggactaagt tggaaataac aggctccacc tctggatccg gcaagcccgg atctggcgag     360
ggatccacca agggcgaggt gaaactgcag gagtcaggac ctggcctggt ggcgccctca     420
cagagcctgt ccgtcacatg cactgtctca ggggtctcat tacccgacta tggtgtaagc     480
tggattcgcc agcctccacg aaagggtctg gagtggctgg agtaatatg gggtagtgaa      540 accacatact ataattcagc tctcaaatcc agactgacca tcatcaagga caactccaag     600
agccaagttt tcttaaaaat gaacagtctg caaactgatg acacagccat ttactactgt     660
gccaaacatt attactacgg tggtagctat gctatggact actggggtca aggaaccctca    720 gtcaccgtct cctca                                                      735

<210> SEQ ID NO 245
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 246
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
atgcttctcc tggtgacaag ccttctgctc tgtgagttac cacacccagc attcctcctg      60
atccca                                                                66

<210> SEQ ID NO 247
<211> LENGTH: 18
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 247

Gly Ser Thr Ser Gly Ser Gly Lys Pro Gly Ser Gly Glu Gly Ser Thr
1               5                   10                  15

Lys Gly

<210> SEQ ID NO 248
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
ggctccacct ctggatccgg caagcccgga tctggcgagg gatccaccaa gggc         54

<210> SEQ ID NO 249
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Met Glu Trp Thr Trp Val Phe Leu Phe Leu Leu Ser Val Thr Ala Gly
1               5                   10                  15

Val His Ser

<210> SEQ ID NO 250
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Met Ala Leu Pro Val Thr Ala Leu Leu Leu Pro Leu Ala Leu Leu Leu
1               5                   10                  15

His Ala Ala Arg Pro
            20

<210> SEQ ID NO 251
<211> LENGTH: 813
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251 ggtaccccg  ggcccatggc tcttcctgtg acagctcttc tgctgcccct ggccctgctt    60
ctgcatgctg ctagacctca ggttcagttg cagcaatggg gagctggcct gttaaagccc   120
agcgaaaccc tgtccctcac ctgcgctgtg tatggcggaa gcttcagcgg ctattactgg   180
agctggatcc ggcagcctcc tggaaaagga ttagaatgga tcggcgagat agaccacagc   240
gggagcacaa actacaaccc cagcctgaaa tcgcgggtta caatctctgt ggacacaagc   300
```

| | | |
|---|---|---|
| aagaatcagt tctccctgaa gctgagcagc gttactgccg ccgacacagc tgtgtactat | 360 | |
| tgcgccagag gcggaggctc ctggtacagc aactggttcg atccttgggg ccaaggcacc | 420 | |
| atggtgaccg tttccagcgg ctctacaagc ggcagcggga aacctggttc tggagagggc | 480 | |
| agcacaaagg gcgacatcca gatgacacag agccccagca cccttagcgc ctctgtggga | 540 | |
| gatagggtta ccattacctg cagggcttcc cagagcatca gcagctggct ggcatggtat | 600 | |
| caacagaagc ctggcaaggc tcccaagctg ctcatctatg acgcctccag cctgaaagc | 660 | |
| ggggttccct ccagatttag cggctcaggc tccggaacag agttcaccct taccatctct | 720 | |
| agcctgcaac ccgacgactt cgctacttat tactgtcaac agacagaag cttgccccc | 780 | |
| acattcggcg gagggaccaa ggttgagatc aag | 813 | |

```
<210> SEQ ID NO 252
<211> LENGTH: 834
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252
```

| | | |
|---|---|---|
| ggtaccccg ggcccatggc tcttcctgtg acagctcttc tgctgcccct ggccctgctt | 60 | |
| ctgcatgctg ctagacctca ggttcagttg cagcaatggg gagctggcct gttaaagccc | 120 | |
| agcgaaaccc tgtccctcac ctgcgctgtg tatggcggaa gcttcagcgg catccactgg | 180 | |
| aactggatcc ggcagcctcc tggcaaaggc cttgaatgga tcggcgatat cgacaccagc | 240 | |
| ggctccacca actacaaccc cagcctgaaa tcgaggggtta caatctctgt ggacacaagc | 300 | |
| aagaatcagt tctccctgaa gctgagcagc gttactgccg ccgacacagc tgtgtactat | 360 | |
| tgcgccagac tgggccagga aagcgctacc taccttggca tggatgtgtg ggggcagggc | 420 | |
| accaccgtta ctgttagctc tggctcaaca agcggcagcg gcaagcctgg ctcaggagaa | 480 | |
| ggaagcacaa agggcgacat tgtaatgact cagagccccg acagcctggc cgttagctta | 540 | |
| ggcgaaaggg ctacaatcaa ttgcaagagc agccagagcg ttctgtacag cagcaacaac | 600 | |
| aagaactacc tcgcatggta tcaacagaag ccaggccagc ctcccaagct gctcatctac | 660 | |
| tgggcttcca ccagagagag cggggttccc gatagattct ccggctccgg ttctggaaca | 720 | |
| gatttcacgc tcacaatcag cagcttacag gccgaggatg tggctgtcta ctattgtcag | 780 | |
| cagttgtaca cctaccccct cacattcggc ggaggcacca aggttgagat caag | 834 | |

```
<210> SEQ ID NO 253
<211> LENGTH: 825
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 253
```

| | | |
|---|---|---|
| ggtaccccg ggcccatggc tcttcctgtg acagctcttc tgctgcccct ggccctgctt | 60 | |
| ctgcatgctg ctagacctca gcttcagctc aagagagcg gacctggctt agtgaagccc | 120 | |
| agcgaaaccc tgtccctcac ctgcaccgtt tctggcggaa gcatcagcag ctccagctat | 180 | |
| tactggggat ggatcaggca gcccctggc aagggtttag aatggatcgg ctcgatatat | 240 | |
| tactccggca gcacctacta taaccccagc ttgaagagcc gggttaccat ttctgtggac | 300 | |
| acatcaaaga accagttcag cctgaagctg agctctgtga ctgccgccga cacagctgtg | 360 | |

```
tactactgtg ccagagagac agactactcc agcggcatgg gctacggcat ggatgtgtgg      420
ggacaaggaa ccaccgttac tgtgagcagc ggttccacca cggctcagg caagcctggc       480 tcaggagaag gaagcaccaa gggggatata cagatgacac agagcccctc agcctgtcc       540 gccagcgttg gcgatcgtgt aacgatcacc tgccgggcct ctcagagcat caactcctac      600
ctcaattggt atcaacagaa gccaggcaag ccccccaaat tactcatcta cgccgccagc      660
agcttacaga gcggggttcc ctctagattc tccggctccg gttctggaac agatttcacc      720
ctcactatct ccagcttgca gcccgaggat ttcgccactt attactgtca gcagagcctg      780 gccgaccct tcacattcgg cggaggcaca aaggttgaga tcaag                       825

<210> SEQ ID NO 254
<211> LENGTH: 828
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254 ggtaccccg ggcccatggc tcttcctgtg acagctcttc tgctgcccct ggccctgctt        60
ctgcatgctg ctagacctca ggttcagctt gtgcagagcg gagctgaagt taagaagcct      120
ggcgcctctg tgaaggttag ctgcaaggcc agcggctaca cattcaagga atatggcatc      180
tcctgggtta ggcaggctcc cggccaaggc ttagaatgga tgggctggat ctccgcctac      240
tccggccaca cctactacgc ccagaagctt cagggcaggg ttaccatgac caccgacacc      300
agcacctcta ccgcctatat ggagctgagg agcctgagat cggacgacac agctgtgtat      360
tactgcgcca gaggccccca ctacgacgac tggtctggat ttatcatctg gttcgacccc      420
tgggggcagg gcaccctggt cacagtttct tctggctcca ccagcggaag cggcaagcca      480
ggctcaggcg aaggatctac aaaaggcgac atccaaatga cacagagccc cagcagcttg      540
agcgcctccg ttggcgacag agttacaatc acctgcaggg cctctcagag catcagcagc      600
tatttgaatt ggtatcaaca gaagccagga aaggccccta agctgctcat ctacgctgcc      660
agctcgctcc aatctggcgt tcctagcaga tttagcggct ccggcagcgg cacagacttt      720
actcttacca ttagctccct gcagcccgag gacttcgcta cctactattg ccagcaaagc      780
tacagattcc ctcccacctt tggccagggc acaaaggttg agatcaag                   828

<210> SEQ ID NO 255
<211> LENGTH: 825
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 255 ggtaccccg ggcccatggc tcttcctgtg acagctcttc tgctgcccct ggccctgctt        60
ctgcatgctg ctagacctca ggttcagtta caagagagcg gacctggctt agtgaagccc      120
agcgaaaccc tgtccctcac ctgcaccgtt tctggcggaa gcatcagctc tcccgaccat      180
tactggggat ggatcaggca gcccccctggc aagggtttgg aatggatcgg cagcatctac      240
gccagcggca gcacattcta caaccccctcg ctcaaaagca gggttactat ttctgtggac      300
acaagcaaaa atcagttcag cctgaagctg agctctgtga ctgccgccga cacagctgtg      360
```

| | |
|---|---|
| tactactgtg ccagagagac agactactcc agcgggatgg gctacggcat ggatgtgtgg | 420 |
| ggacaaggaa ccaccgttac tgtgagcagc ggctccacaa gcggctcagg caagcctggc | 480 |
| tcaggagaag gaagcaccaa gggggacatt caaatgaccc aaagcccctc cagcctgtcc | 540 |
| gccagcgttg gcgatagggt taccattacc tgcagggcca gccaaagcat caactcctac | 600 |
| ctaaattggt atcaacagaa gccaggcaag gcccccaaac tactcattta cgccgccagc | 660 |
| agcttacaga gcggggttcc ctctagattc tccggcagcg gttctggaac agatttcact | 720 |
| ctcacaatat cttcgctgca gcccgaggat ttcgctacct actattgcca gcaatccctg | 780 |
| gccgacccct tcacattcgg cggaggcaca aaggttgaga tcaag | 825 |

<210> SEQ ID NO 256
<211> LENGTH: 822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 256

| | |
|---|---|
| ggtaccccg ggcccatggc tcttcctgtg acagctcttc tgctgcccct ggccctgctt | 60 |
| ctgcatgctg ctagacctca gatcacatta aaagagagcg acctacact ggtgaagccc | 120 |
| acccaaacgc ttaccctcac ctgcaccttt agcgggttca gctggacac agagggcgtt | 180 |
| ggcgttggat ggatcaggca gcctcctggc aaagccctcg aatggcttgc cctcatctac | 240 |
| ttcaacgacc agaagagata cagccccctcc ttaaaatctc ggctcacaat caccaaagac | 300 |
| acaagcaaaa atcaggttgt gctcaccatg accaacatgg accctgtgga caccgctgtg | 360 |
| tactactgtg ccagagacac cggctacagc agatggtact acgggatgga cgtttggggc | 420 |
| caaggcacca ctgtgaccgt ttccagcggc tctacaagcg gcagcgggaa acctggttct | 480 |
| ggagagggca gcacaaaggg cgacatccag atgacgcaat cccccagctc tgtgagcgcc | 540 |
| tctgtgggag acagagttac aatcacatgc cgggcctccc agggcatcag ctcttggctg | 600 |
| gcatggtatc aacagaagcc tggcaaggct cccaagctgc tcatctatgc cgcctcctcc | 660 |
| ttacaatctg gagttccctc caggttcagc gggagcggct caggaacaga cttcacccctt | 720 |
| accatctcta gcctgcaacc cgaggacttc gctacttatt actgtcagca ggcctacgcc | 780 |
| taccccatca cattcggcgg aggaacaaag gttgagatca ag | 822 |

<210> SEQ ID NO 257
<211> LENGTH: 852
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 257

| | |
|---|---|
| ggtaccccg ggcccatggc tcttcctgtg acagctcttc tgctgcccct ggccctgctt | 60 |
| ctgcatgctg ctagacctca ggttcagttg cagcaatggg gagctggcct gttaaagccc | 120 |
| agcgaaaccc tgtccctcac ctgcgctgtg tatggcggaa gcttcgagaa atactactgg | 180 |
| agctggatcc ggcagcctcc cggcaaaggc ttagaatgga tcggcgagat ttatcacagc | 240 |
| gggctcacca actacaaccc cagcctgaaa tctcgagtta caatctctgt ggacacaagc | 300 |
| aagaatcagt tctcccctgaa gctgagcagc gttactgccg ccgacacagc tgtgtactat | 360 |
| tgcgccagag ttagatacga cagcagcgac agctattact acagctatga ctacggcatg | 420 |

```
gatgtgtggg ggcagggcac caccgttact gtctcctctg gatctaccag cggcagcggc    480
aagcctggat ctggcgaagg aagcacaaag ggcgacattg tgctcaccca gagccccgac    540
agcctggctg tgtctttagg cgaaagggct accatcaact gcaagagcag ccagagcgtt    600
ctgtacagca gcaacaacaa gaactacctt gcttggtatc aacagaagcc tggccagccc    660
cctaagctgc tcatctactg ggcctctagc agagagagcg gggttcccga tcggtttagc    720
ggctccggct caggaaccga tttcaccctc actatctcca gcctccaggc cgaggatgtg    780
gctgtctact attgtcagca gagctatagc ttcccctgga cattcggcgg aggcaccaag    840
gttgagatca ag                                                       852
```

<210> SEQ ID NO 258
<211> LENGTH: 852
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 258

```
ggtaccccg ggcccatggc tcttcctgtg acagctcttc tgctgcccct ggccctgctt     60
ctgcatgctg ctagacctca ggttcagtta caacaatggg gagctggcct gttaaagccc    120
agcgaaaccc tgtccctcac ctgcgctgtg tatggcggaa gcttcagccg ctatgtgtgg    180
agctggatcc ggcagcctcc tggcaaaggc cttgaatgga tcggagagat agacagcagc    240
ggcaagacca actacaaccc cagcctgaaa tcacgcgtta caatctctgt ggacacaagc    300
aagaatcagt tctcccctgaa gctgagcagc gttactgccg ccgacacagc tgtgtactat    360
tgcgccagag ttagatacga cagctccgac agctattact acagctatga ctacggcatg    420
gatgtgtggg ggcagggcac caccgttaca gttagctctg gaagcaccag cggctccggc    480
aagcctggat ctggtgaagg aagcacaaag ggcgacattg tgctcaccca gagccccgac    540
agcctggctg tgtctttagg cgaaagggct accatcaact gcaagagcag ccagagcgtt    600
ctgtacagca gcaacaacaa gaactacctt gcatggtatc aacagaagcc tggccagcct    660
cccaagctgc tcatctactg ggcctctagc agagagagcg gggttcccga tcgctttagc    720
ggcagcggtt ctggcaccga tttcactctt acaatcagca gcttacaggc cgaggatgtg    780
gctgtctact attgtcagca gagctatagc ttcccctgga cattcggcgg aggcaccaag    840
gttgagatca ag                                                       852
```

<210> SEQ ID NO 259
<211> LENGTH: 852
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259

```
ggtaccccg ggcccatggc tcttcctgtg acagctcttc tgctgcccct ggccctgctt     60
ctgcatgctg ctagacctca ggttcagtta caacaatggg gagctggcct gttaaagccc    120
agcgaaaccc tgtccctcac ctgcgctgtg tatggcggaa gcttcagcgg ctacgcttgg    180
agctggatta gacagcctcc tggcaaagga ctagaatgga tcggagagat cgaccacaga    240
ggcttcacca actacaaccc cagcctgaaa tccagagtta caatctctgt ggacacaagc    300
```

```
aagaatcagt tctccctgaa gctgagcagc gttactgccg ccgacacagc tgtgtactat    360
tgcgccaggg ttagatacga cagcagcgac agctattact acagctatga ctacggcatg    420
gatgtgtggg ggcagggcac caccgttacg gttagctctg gatctaccag cggcagcggc    480
aagcctggct caggagaagg aagcacaaag ggcgacattg tgctcaccca gagccccgac    540
agcctggccg tttctttagg cgaaagggct accatcaact gcaagagcag ccagagcgtt    600
ctgtacagca gcaacaacaa gaactacctt gcatggtatc aacagaagcc aggccagcct    660
cccaagctgc tcatctactg ggcctctagc agagagagcg gggttcccga tagattttcg    720
ggatcaggct ccggcaccga tttcactctt acgatcagca gcttacaggc cgaggatgtg    780
gctgtctact attgtcagca gagctatagc ttcccctgga cattcggcgg aggcaccaag    840
gttgagatca ag                                                        852
```

<210> SEQ ID NO 260
<211> LENGTH: 840
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 260

```
ggtaccccg ggcccatggc tcttcctgtg acagctcttc tgctgcccct ggccctgctt    60
ctgcatgctg ctagacctca ggttcagtta caacaatggg gagctggcct gttaaagccc    120
agcgaaaccc tgtccctcac ctgcgctgtg tatggcggaa gcttccagaa atactactgg    180
agctggatcc ggcagcctcc cggcaaaggc ttagaatgga tcggagagat agacaccagc    240
ggcttcacca actacaaccc cagcctgaaa tctagggtta caatctctgt ggacacaagc    300
aagaatcagt tctccctgaa gctgagcagc gttactgccg ccgacacagc tgtgtactat    360
tgcgccagag ttggcagata cagctacggc tactacatca ccgccttcga catttgggc    420 caaggcacca ctgtgaccgt ttccagcgga agcactagcg gcagcgggaa acctggttct    480
ggagagggct caaccaaggg cgacatcgtg atgacacaga gccccgactc tctggctgtg    540
tccctgggag agagagccac catcaactgc aagagcagcc agagcgttct gtacagcagc    600
aacaacaaga actacctggc atggtatcaa cagaagcctg gccagccccc taagctgctc    660
atctactggg cttccaccag agaatcaggc gttccagaca ggttctccgg ctcgggttca    720
ggcacagact tcacccttac catctcttcc ctgcaggccg aagatgtggc cgtttactac    780
tgtcagcagc actacagctt ccctttcaca ttcggcggag gcaccaaggt tgagatcaag    840
```

<210> SEQ ID NO 261
<211> LENGTH: 258
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 261

```
gcagctgctt tcgtgcctgt gttcctgcct gctaagccca ccaccactcc tgctccaaga    60
cctcctaccc ccgctcctac aatcgccagc caacctctga gcctgagacc ggaggcatgc    120
agacctgcgg caggggagc agttcacaca agaggcttgg acttcgcttg cgacatctac    180
atctgggccc tctgccggg cacatgcgga gttcttcttc ttagcctggt gatcaccctg    240
tactgcaacc acagaaac                                                  258
```

<210> SEQ ID NO 262
<211> LENGTH: 180
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 262
gctgctgcat tggataatga aaaatcgaac ggcacaatca ttcatgtgaa gggcaaacac      60
ctgtgtccca gccccttgtt cccaggacct agcaagcctt tttgggttct cgtggtggtg     120
ggcggcgttc tggcttgcta ctctctactt gtaactgtcg catttattat attctgggtt     180

<210> SEQ ID NO 263
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 263
ggaggaggag gatctctgga taacgagaaa agcaacggga ccatcattca tgtgaaggga      60
aaacatctgt gtcccagccc cttgttcccc ggacctagca agccgttttg ggttctcgtg     120
gtggtgggcg gcgttctggc ttgctactct ctgcttgtga ccgttgcctt cattatcttc     180
tgggtt                                                                186

<210> SEQ ID NO 264
<211> LENGTH: 201
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 264
ggaggaggag gatctggtgg aggaggttct ctggacaatg agaaatcaaa tggaacgatc      60
atccatgtga aggggaagca cctctgcccc tctcccctgt ttcctggtcc tagcaagccc     120
ttctgggttt tggtggtcgt gggcggcgtt ctggcttgct acagcctgtt agtgaccgtt     180
gcatttatca tattttgggt t                                               201

<210> SEQ ID NO 265
<211> LENGTH: 201
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 265
ggaggaggag gatctggtgg aggaggttct ctggacaatg agaaatcgaa tggacaatc       60 atccatgtga aggggaagca cctgagcccc tctcccctgt ttcctggtcc tagcaagccc     120
ttctgggttt tggtggtcgt gggcggcgtt ctggccgttt acagcctgtt agtgaccgtt     180
gcttttatca tattttgggt t                                               201

<210> SEQ ID NO 266
<211> LENGTH: 201
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 266

```
ggaggaggag gatctggtgg aggaggttct ctggacaatg aaaagagcaa tggcacaatc    60
atccatgtga aggggaagca cctgaacggc tccgccctgt ttcctggtcc tagcaagcca   120
ttttgggttc tcgtggtggt gggcggcgtt ctggccgttt acagcctgtt agtgaccgtt   180
gcgttcataa tcttctgggt t                                             201
```

<210> SEQ ID NO 267
<211> LENGTH: 216
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 267

```
ggaggaggag gatctggtgg aggaggttct ggaggaggcg gctctctcga caacgaaaag    60
agcaatggca ccattattca cgttaaaggc aagcatctgt gcccctcccc cctgttcccc   120
ggaccttcaa aacctttttg ggttctcgtg gtggtgggcg gcgttctggc ctgctattct   180
ttgctggtaa ctgtagcctt cattatcttc tgggtt                             216
```

<210> SEQ ID NO 268
<211> LENGTH: 771
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 268

```
gagagcaagt acggacctcc ttgtcctcca tgtcctgctc ccgagttcga gggcggacct    60
tcagtgttcc tgttccccccc taaacccaag gatactctta tgatcagccg gacccccgag   120
gtcacctgtg tggtggtaga tgttagccag gaggatcccg aggtgcagtt caactggtac   180
gtcgacggcg tcgaggtaca caacgccaag accaagccta gggaggagca gttccagtcc   240
acctataggg tcgtgagcgt gcttaccgtg ctgcaccagg actggttgaa cggcaaggag   300
tacaagtgca aggtgtccaa caagggcctc cccagcagca tcgagaagac cattagcaag   360
gcaaagggac agcccaggga gccccaggtg tacacattac ctccttccca ggaagagatg   420
accaagaacc aggtgtcgct tacctgcctg gtcaagggct cctacccctc cgacattgca   480
gttgaatggg agtcaaacgg ccagccgagg aacaattaca gaccaccccc cccagtcttg   540
gacagcgacg gctcttttctt cctctactcg cggcttactg tagataaaag tcgttggcag   600
gagggaaacg tgttcagctg ctctgtgatg cacgaggccc tccataacca ctacacccag   660
aagagcctct ccctgtctct gggcaagatg ttctgggtgc tggtcgtggt gggcggagtt   720
cttgcttgct actccctgct cgtgaccgtc gctttcatta tattctgggt c            771
```

<210> SEQ ID NO 269
<211> LENGTH: 795
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 269

```
gagagaaagt gttgtgttga gtgtcctcct tgtcctccct gccctgctcc cgagttactt      60
ggcggacctt cagtgttcct gttccccccc aagcccaagg atactctcat gatcagccgg     120
accccccgagg tcacctgtgt ggtggtagat gttagccacg aggaccctga ggtcaagttc    180
aactggtacg tcgacggcgt cgaggtgcac aacgccaaga ccaagcctcg tgaagaacag    240
taccagtcca cctacagagt tgtgagcgtg cttaccgtgc tgcaccagga ctggctgaac    300
ggcaaggagt acaagtgcaa ggtgtccaac aaggccctcc ccgctcccat cgagaagaca    360
atcagcaagg ccaagcccctg tccagcccct gagctcttag gaggacctag cgttttcctt    420
ttccctccca agcctaagga cactcttatg atctccagaa caccagaggt tacctgcgtc    480
gtggtggacg tgtcccatga ggacccagaa gtcaaattca attggtatgt agatggggtc    540
gaggtccaca acgctaagac aaagcccccgc gaggagcagt acaactctac ctacagggtc    600
gtgtccgtgc tcacagtgct gcatcaggat tggctcaacg ggaaggagta taagtgcaaa    660
gtgtccaata aggcccttcc cgcccctatc gagaaaacca tctctaaggc caaattctgg    720
gtgctggtgg ttgtgggcgg cgtgcttgct tgttactccc tgctggtcac tgtagctttc    780
atcatatttt gggtg                                                      795
```

<210> SEQ ID NO 270
<211> LENGTH: 494
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 270

```
agattcagcg ttgtgaagag aggccggaag aagctgctgt acatcttcaa gcagcccttc      60
atgagacctg tgcagaccac acaggaggaa gacggctgca gctgtagatt ccccgaggaa    120
gaggagggcg gctgtgagct gagagttaag ttcagcagga gcgccgacgc ccctgcctac    180
cagcaaggac agaatcaact gtacaacgag ctgaacctgg gcagacggga ggaatacgat    240
gtgctggaca gaggagagg cagagacccc gagatgggcg gcaaacctag aagaaagaac    300
ccccaggagg gcctgtataa cgagctccag aaggacaaga tggccgaggc ctacagcgag    360
atcggcatga agggcgaaag aagaagaggc aagggccacg acggcctcta ccagggctta    420
agcacagcta caaaggacac ctacgacgcc ctgcacatgc aggccctgcc ccctagatga    480
ttaattaaat cgat                                                       494
```

<210> SEQ ID NO 271
<211> LENGTH: 1577
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 271

```
ggtaccccccg ggcccatggc tcttcctgtg acagctcttc tgctgcccct ggccctgctt     60
ctgcatgctg ctagacctca gcttcagctc caagagagcg acctggctt agtgaagccc    120
agcgaaaccc tgtccctcac ctgcaccgtt tctggcggaa gcatcagcag ctccagctat    180
tactggggat ggatcaggca gcccccctggc aagggtttag aatggatcgg ctcgatatat    240
```

```
tactccggca gcacctacta taaccccagc ttgaagagcc gggttaccat ttctgtggac    300
acatcaaaga accagttcag cctgaagctg agctctgtga ctgccgccga cacagctgtg    360
tactactgtg ccagagagac agactactcc agcggcatgg gctacggcat ggatgtgtgg    420
ggacaaggaa ccaccgttac tgtgagcagc ggttccacca gcggctcagg caagcctggc    480
tcaggagaag gaagcaccaa gggggatata cagatgacac agagcccctc cagcctgtcc    540
gccagcgttg gcgatcgtgt aacgatcacc tgccgggcct ctcagagcat caactcctac    600
ctcaattggt atcaacagaa gccaggcaag gcccccaaat tactcatcta cgccgccagc    660
agcttacaga gcggggttcc ctctagattc tccggctccg gttctggaac agatttcacc    720
ctcactatct ccagcttgca gcccgaggat ttcgccactt attactgtca gcagagcctg    780
gccgaccect tcacattcgg cggaggcaca aaggttgaga tcaaggcagc tgctttcgtg    840
cctgtgttcc tgcctgctaa gcccaccacc actcctgctc aagacctcc taccccgct     900
cctacaatcg ccagccaacc tctgagcctg agaccggagg catgcagacc tgcggcaggg    960
ggagcagttc acacaagagg cttggacttc gcttgcgaca tctacatctg ggcccctctg   1020
gccggcacat gcggagttct tcttcttagc ctggtgatca ccctgtactg caaccacaga   1080
aacagattca gcgttgtgaa gagaggccgg aagaagctgc tgtacatctt caagcagccc   1140
ttcatgagac ctgtgcagac cacacaggag gaagacggct gcagctgtag attccccgag   1200
gaagaggagg gcggctgtga gctgagagtt aagttcagca ggagcgccga cgcccctgcc   1260
taccagcaag gacagaatca actgtacaac gagctgaacc tgggcagacg ggaggaatac   1320
gatgtgctgg acaagaggag aggcagagac cccgagatgg gcggcaaacc tagaagaaag   1380
aacccccagg agggcctgta taacgagctc cagaaggaca gatggccga ggcctacagc    1440
gagatcggca tgaagggcga aagaagaaga ggcaagggcc acgacggcct ctaccagggc   1500
ttaagcacag ctacaaagga cacctacgac gccctgcaca tgcaggccct gccccctaga   1560
tgattaatta aatcgat                                                  1577

<210> SEQ ID NO 272
<211> LENGTH: 1577
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 272 ggtaccccg ggcccatggc tcttcctgtg acagctcttc tgctgcccct ggccctgctt      60
ctgcatgctg ctagacctca ggttcagtta caagagagcg acctggctt agtgaagccc     120
agcgaaaccc tgtccctcac ctgcaccgtt tctggcggaa gcatcagctc tcccgaccat    180
tactggggat ggatcaggca gccccctggc aagggtttgg aatggatcgg cagcatctac    240
gccagcggca gcacattcta caaccctcg ctcaaaagca gggttactat ttctgtggac     300
acaagcaaaa atcagttcag cctgaagctg agctctgtga ctgccgccga cacagctgtg    360
tactactgtg ccagagagac agactactcc agcgggatgg gctacggcat ggatgtgtgg    420
ggacaaggaa ccaccgttac tgtgagcagc ggctccacaa gcggctcagg caagcctggc    480
tcaggagaag gaagcaccaa ggggacatt caaatgaccc aaagccccctc cagcctgtcc    540
gccagcgttg gcgatagggt taccattacc tgcagggcca gccaaagcat caactcctac    600
ctaaattggt atcaacagaa gccaggcaag gcccccaaac tactcatttta cgccgccagc    660
```

| | |
|---|---|
| agcttacaga gcggggttcc ctctagattc tccggcagcg gttctggaac agatttcact | 720 |
| ctcacaatat cttcgctgca gcccgaggat ttcgctacct actattgcca gcaatccctg | 780 |
| gccgacccct tcacattcgg cggaggcaca aaggttgaga tcaaggcagc tgctttcgtg | 840 |
| cctgtgttcc tgcctgctaa gcccaccacc actcctgctc caagacctcc tacccccgct | 900 |
| cctacaatcg ccagccaacc tctgagcctg agaccggagg catgcagacc tgcggcaggg | 960 |
| ggagcagttc acacaagagg cttggacttc gcttgcgaca tctacatctg gcccctctg | 1020 |
| gccggcacat gcggagttct tcttcttagc ctggtgatca ccctgtactg caaccacaga | 1080 |
| aacagattca gcgttgtgaa gagaggccgg aagaagctgc tgtacatctt caagcagccc | 1140 |
| ttcatgagac ctgtgcagac cacacaggag gaagacggct gcagctgtag attccccgag | 1200 |
| gaagaggagg gcggctgtga gctgagagtt aagttcagca ggagcgccga cgcccctgcc | 1260 |
| taccagcaag gacagaatca actgtacaac gagctgaacc tgggcagacg ggaggaatac | 1320 |
| gatgtgctgg acaagaggag aggcagagac cccgagatgg gcggcaaacc tagaagaaag | 1380 |
| aaccccagg agggcctgta taacgagctc cagaaggaca gatggccga ggcctacagc | 1440 |
| gagatcggca tgaagggcga aagaagaaga ggcaagggcc acgacggcct ctaccagggc | 1500 |
| ttaagcacag ctacaaagga cacctacgac gccctgcaca tgcaggccct gccccctaga | 1560 |
| tgattaatta aatcgat | 1577 |

<210> SEQ ID NO 273
<211> LENGTH: 1574
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 273

| | |
|---|---|
| ggtaccccg ggcccatggc tcttcctgtg acagctcttc tgctgcccct ggccctgctt | 60 |
| ctgcatgctg ctagacctca gatcacatta aaagagagcg acctacact ggtgaagccc | 120 |
| acccaaacgc ttaccctcac ctgcaccttt agcgggttca gcctggacac agagggcgtt | 180 |
| ggcgttggat ggatcaggca gcctcctggc aaagccctcg aatggcttgc cctcatctac | 240 |
| ttcaacgacc agaagagata cagccccctcc ttaaaatctc ggctcacaat caccaaagac | 300 |
| acaagcaaaa atcaggttgt gctcaccatg accaacatgg accctgtgga caccgctgtg | 360 |
| tactactgtg ccagagacac cggctacagc agatggtact acgggatgga cgtttggggc | 420 |
| caaggcacca ctgtgaccgt ttccagcggc tctacaagcg gcagcgggaa acctggttct | 480 |
| ggagagggca gcacaaaggg cgacatccag atgacgcaat cccccagctc tgtgagcgcc | 540 |
| tctgtgggag acagagttac aatcacatgc cgggcctccc agggcatcag ctcttggctg | 600 |
| gcatggtatc aacagaagcc tggcaaggct cccaagctgc tcatctatgc cgcctcctcc | 660 |
| ttacaatctg gagttccctc caggttcagc gggagcggct caggaacaga cttcacccctt | 720 |
| accatctcta gcctgcaacc cgaggacttc gctacttatt actgtcagca ggcctacgcc | 780 |
| taccccatca cattcggcgg aggaacaaag gttgagatca aggcagctgc tttcgtgcct | 840 |
| gtgttcctgc ctgctaagcc caccaccact cctgctccaa gacctcctac ccccgctcct | 900 |
| acaatcgcca gccaacctct gagcctgaga ccggaggcat gcagacctgc ggcaggggga | 960 |
| gcagttcaca caagaggctt ggacttcgct tgcgacatct acatctgggc ccctctggcc | 1020 |
| ggcacatgcg gagttcttct tcttagcctg gtgatcaccc tgtactgcaa ccacagaaac | 1080 |

| | |
|---|---|
| agattcagcg ttgtgaagag aggccggaag aagctgctgt acatcttcaa gcagcccttc | 1140 |
| atgagacctg tgcagaccac acaggaggaa gacggctgca gctgtagatt ccccgaggaa | 1200 |
| gaggagggcg gctgtgagct gagagttaag ttcagcagga gcgccgacgc ccctgcctac | 1260 |
| cagcaaggac agaatcaact gtacaacgag ctgaacctgg gcagacggga ggaatacgat | 1320 |
| gtgctggaca gaggagagg cagagacccc gagatgggcg gcaaacctag aagaaagaac | 1380 |
| ccccaggagg gcctgtataa cgagctccag aaggacaaga tggccgaggc ctacagcgag | 1440 |
| atcggcatga agggcgaaag aagaagaggc aagggccacg acggcctcta ccagggctta | 1500 |
| agcacagcta caaaggacac ctacgacgcc ctgcacatgc aggccctgcc ccctagatga | 1560 |
| ttaattaaat cgat | 1574 |

<210> SEQ ID NO 274
<211> LENGTH: 1592
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 274

| | |
|---|---|
| ggtaccccg ggcccatggc tcttcctgtg acagctcttc tgctgcccct ggccctgctt | 60 |
| ctgcatgctg ctagacctca ggttcagtta caacaatggg gagctggcct gttaaagccc | 120 |
| agcgaaaccc tgtccctcac ctgcgctgtg tatggcggaa gcttccagaa atactactgg | 180 |
| agctggatcc ggcagcctcc cggcaaaggc ttagaatgga tcggagagat agacaccagc | 240 |
| ggcttcacca actacaaccc cagcctgaaa tctagggtta caatctctgt ggacacaagc | 300 |
| aagaatcagt tctccctgaa gctgagcagc gttactgccg ccgacacagc tgtgtactat | 360 |
| tgcgccagag ttggcagata cagctacggc tactacatca ccgccttcga catttgggc | 420 |
| caaggcacca ctgtgaccgt ttccagcgga agcactagcg gcagcgggaa acctggttct | 480 |
| ggagagggct caaccaaggg cgacatcgtg atgacacaga gccccgactc tctggctgtg | 540 |
| tccctgggag agagagccac catcaactgc aagagcagcc agagcgttct gtacagcagc | 600 |
| aacaacaaga actacctggc atggtatcaa cagaagcctg gccagccccc taagctgctc | 660 |
| atctactggg cttccaccag agaatcaggc gttccagaca ggttctccgg ctcgggttca | 720 |
| ggcacagact caccccttac catctcttcc ctgcaggccg aagatgtggc cgtttactac | 780 |
| tgtcagcagc actacagctt cccctttcaca ttcggcggag caccaaggt tgagatcaag | 840 |
| gcagctgctt tcgtgcctgt gttcctgcct gctaagccca ccaccactcc tgctccaaga | 900 |
| cctcctaccc ccgctcctac aatcgccagc caacctctga gcctgagacc ggaggcatgc | 960 |
| agacctgcgg caggggagc agttcacaca agaggcttgg acttcgcttg cgacatctac | 1020 |
| atctgggccc ctctggccgg cacatgcgga gttcttcttc ttagcctggt gatcaccctg | 1080 |
| tactgcaacc acagaaacag attcagcgtt gtgaagagag ccggaagaa gctgctgtac | 1140 |
| atcttcaagc agcccttcat gagacctgtg cagaccacac aggaggaaga cggctgcagc | 1200 |
| tgtagattcc ccgaggaaga ggagggcggc tgtgagctga gagttaagtt cagcaggagc | 1260 |
| gccgacgccc tgcctacca gcaaggacag aatcaactgt acaacgagct gaacctgggc | 1320 |
| agacgggagg aatacgatgt gctggacaag aggagaggca gagaccccga gatgggcggc | 1380 |
| aaacctagaa gaaagaaccc ccaggagggc ctgtataacg agctccagaa ggacaagatg | 1440 |
| gccgaggcct acagcgagat cggcatgaag ggcgaaagaa gaagaggcaa gggccacgac | 1500 |

-continued

| | |
|---|---|
| ggcctctacc agggcttaag cacagctaca aaggacacct acgacgccct gcacatgcag | 1560 |
| gccctgcccc ctagatgatt aattaaatcg at | 1592 |

<210> SEQ ID NO 275
<211> LENGTH: 1604
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 275

| | |
|---|---|
| ggtaccccg ggcccatggc tcttcctgtg acagctcttc tgctgcccct ggccctgctt | 60 |
| ctgcatgctg ctagacctca ggttcagttg cagcaatggg gagctggcct gttaaagccc | 120 |
| agcgaaaccc tgtccctcac ctgcgctgtg tatggcggaa gcttcgagaa atactactgg | 180 |
| agctggatcc ggcagcctcc cggcaaaggc ttagaatgga tcggcgagat ttatcacagc | 240 |
| gggctcacca actacaaccc cagcctgaaa tctcgagtta caatctctgt ggacacaagc | 300 |
| aagaatcagt tctcccctgaa gctgagcagc gttactgccg ccgacacagc tgtgtactat | 360 |
| tgcgccagag ttagatacga cagcagcgac agctattact acagctatga ctacggcatg | 420 |
| gatgtgtggg ggcagggcac caccgttact gtctcctctg gatctaccag cggcagcggc | 480 |
| aagcctggat ctggcgaagg aagcacaaag ggcgacattg tgctcaccca gagccccgac | 540 |
| agcctggctg tgtctttagg cgaaagggct accatcaact gcaagagcag ccagagcgtt | 600 |
| ctgtacagca gcaacaacaa gaactacctt gcttggtatc aacagaagcc tggccagccc | 660 |
| cctaagctgc tcatctactg ggcctctagc agagagagcg gggttcccga tcggtttagc | 720 |
| ggctccggct caggaaccga tttcacccctc actatctcca gcctccaggc cgaggatgtg | 780 |
| gctgtctact attgtcagca gagctatagc ttcccctgga cattcggcgg aggcaccaag | 840 |
| gttgagatca aggcagctgc tttcgtgcct gtgttcctgc tgctaagcc caccaccact | 900 |
| cctgctccaa gacctcctac ccccgctcct acaatcgcca gccaacctct gagcctgaga | 960 |
| ccggaggcat gcagacctgc ggcaggggga gcagttcaca caagaggctt ggacttcgct | 1020 |
| tgcgacatct acatctgggc ccctctggcc ggcacatgcg gagttcttct tcttagcctg | 1080 |
| gtgatcaccc tgtactgcaa ccacagaaac agattcagcg ttgtgaagag aggccggaag | 1140 |
| aagctgctgt acatcttcaa gcagcccttc atgagacctg tgcagaccac acaggaggaa | 1200 |
| gacggctgca gctgtagatt ccccgaggaa gaggagggcg gctgtgagct gagagttaag | 1260 |
| ttcagcagga gcgccgacgc ccctgcctac cagcaaggac agaatcaact gtacaacgag | 1320 |
| ctgaacctgg gcagacggga ggaatacgat gtgctggaca agaggagagg cagagaccccc | 1380 |
| gagatgggcg gcaaacctag aagaaagaac ccccaggagg gcctgtataa cgagctccag | 1440 |
| aaggacaaga tggccgaggc ctacagcgag atcggcatga gggcgaaag aagaagaggc | 1500 |
| aagggccacg acggctcta ccagggctta agcacagcta caaggacac ctacgacgcc | 1560 |
| ctgcacatgc aggccctgcc cctagatga ttaattaaat cgat | 1604 |

<210> SEQ ID NO 276
<211> LENGTH: 1604
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 276

```
ggtaccccg ggcccatggc tcttcctgtg acagctcttc tgctgcccct ggccctgctt      60
ctgcatgctg ctagacctca ggttcagtta caacaatggg gagctggcct gttaaagccc     120
agcgaaaccc tgtccctcac ctgcgctgtg tatggcggaa gcttcagccg ctatgtgtgg     180
agctggatcc ggcagcctcc tggcaaaggc cttgaatgga tcggagagat agacagcagc     240
ggcaagacca actacaaccc cagcctgaaa tcacgcgtta caatctctgt ggacacaagc     300
aagaatcagt tctccctgaa gctgagcagc gttactgccg ccgacacagc tgtgtactat     360
tgcgccagag ttagatacga cagctccgac agctattact acagctatga ctacggcatg     420
gatgtgtggg gcagggcac caccgttaca gttagctctg gaagcaccag cggctccggc      480
aagcctggat ctggtgaagg aagcacaaag ggcgacattg tgctcaccca gagccccgac     540
agcctggctg tgtctttagg cgaaagggct accatcaact gcaagagcag ccagagcgtt     600
ctgtacagca gcaacaacaa gaactacctt gcatggtatc aacagaagcc tggccagcct     660
cccaagctgc tcatctactg ggcctctagc agagagagcg gggttcccga tcgctttagc     720
ggcagcggtt ctggcaccga tttcactctt acaatcagca gcttacaggc cgaggatgtg     780
gctgtctact attgtcagca gagctatagc ttccccctgga cattcggcgg aggcaccaag     840
gttgagatca aggcagctgc tttcgtgcct gtgttcctgc ctgctaagcc caccaccact     900
cctgctccaa gacctcctac ccccgctcct acaatgccca gccaacctct gagcctgaga     960
ccggaggcat gcagacctgc ggcaggggga gcagttcaca agaggcttg gacttcgct    1020 tgcgacatct acatctgggc ccctctggcc ggcacatgcg gagttcttct tcttagcctg    1080
gtgatcaccc tgtactgcaa ccacagaaac agattcagcg ttgtgaagag aggccggaag    1140
aagctgctgt acatcttcaa gcagcccttc atgagacctg gcagaccac acaggaggaa    1200 gacggctgca gctgtagatt ccccgaggaa gaggagggcg gctgtgagct gagagttaag    1260
ttcagcagga gcgccgacgc ccctgcctac cagcaaggac agaatcaact gtacaacgag    1320
ctgaacctgg gcagacggga ggaatacgat gtgctggaca gaggagagg cagagacccc    1380 gagatgggcg gcaaacctag aagaaagaac ccccaggagg gcctgtataa cgagctccag    1440
aaggacaaga tggccgaggc ctacagcgag atcggcatga agggcgaaag aagaagaggc    1500
aagggccacg acggcctcta ccagggctta agcacagcta caaaggacac ctacgacgcc    1560
ctgcacatgc aggccctgcc ccctagatga ttaattaaat cgat                     1604
```

<210> SEQ ID NO 277
<211> LENGTH: 1604
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 277

```
ggtaccccg ggcccatggc tcttcctgtg acagctcttc tgctgcccct ggccctgctt       60
ctgcatgctg ctagacctca ggttcagtta caacaatggg gagctggcct gttaaagccc     120
agcgaaaccc tgtccctcac ctgcgctgtg tatggcggaa gcttcagcgg ctacgcttgg     180
agctggatta gacagcctcc tggcaaagga ctagaatgga tcggagagat cgaccacaga     240
ggcttcacca actacaaccc cagcctgaaa tccagagtta caatctctgt ggacacaagc     300
aagaatcagt tctccctgaa gctgagcagc gttactgccg ccgacacagc tgtgtactat     360
tgcgccaggg ttagatacga cagcagcgac agctattact acagctatga ctacggcatg     420
```

```
gatgtgtggg ggcagggcac caccgttacg gttagctctg gatctaccag cggcagcggc    480
aagcctggct caggagaagg aagcacaaag ggcgacattg tgctcaccca gagccccgac    540
agcctggccg tttctttagg cgaaagggct accatcaact gcaagagcag ccagagcgtt    600
ctgtacagca gcaacaacaa gaactacctt gcatggtatc aacagaagcc aggccagcct    660
cccaagctgc tcatctactg ggcctctagc agagagagcg gggttcccga tagattttcg    720
ggatcaggct ccggcaccga tttcactctt acgatcagca gcttacaggc cgaggatgtg    780
gctgtctact attgtcagca gagctatagc ttcccctgga cattcggcgg aggcaccaag    840
gttgagatca aggcagctgc tttcgtgcct gtgttcctgc ctgctaagcc caccaccact    900
cctgctccaa gacctcctac ccccgctcct acaatcgcca gccaacctct gagcctgaga    960
ccggaggcat gcagacctgc ggcaggggga gcagttcaca caagaggctt ggacttcgct   1020
tgcgacatct acatctgggc ccctctggcc ggcacatgcg gagttcttct tcttagcctg   1080
gtgatcaccc tgtactgcaa ccacagaaac agattcagcg ttgtgaagag aggccggaag   1140
aagctgctgt acatcttcaa gcagcccttc atgagacctg tgcagaccac acaggaggaa   1200
gacggctgca gctgtagatt ccccgaggaa gaggagggcg gctgtgagct gagagttaag   1260
ttcagcagga gcgccgacgc ccctgcctac cagcaaggac agaatcaact gtacaacgag   1320
ctgaacctgg gcagacggga ggaatacgat gtgctggaca gaggagagg cagagacccc   1380 gagatgggcg gcaaacctag aagaaagaac ccccaggagg gcctgtataa cgagctccag   1440
aaggacaaga tggccgaggc ctacagcgag atcggcatga agggcgaaag aagaagaggc   1500
aagggccacg acggcctcta ccagggctta agcacagcta caaaggacac ctacgacgcc   1560
ctgcacatgc aggccctgcc ccctagatga ttaattaaat cgat                   1604
```

<210> SEQ ID NO 278
<211> LENGTH: 1565
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 278

```
ggtaccccccg ggcccatggc tcttcctgtg acagctcttc tgctgcccct ggccctgctt     60
ctgcatgctg ctagacctca ggttcagttg cagcaatggg gagctggcct gttaaagccc    120
agcgaaaccc tgtccctcac ctgcgctgtg tatggcggaa gcttcagcgg ctattactgg    180
agctggatcc ggcagcctcc tggaaaagga ttagaatgga tcggcgagat agaccacagc    240
gggagcacaa actacaaccc cagcctgaaa tcgcgggtta caatctctgt ggacacaagc    300
aagaatcagt tctccctgaa gctgagcagc gttactgccg ccgacacagc tgtgtactat    360
tgcgccagag gcggaggctc ctggtacagc aactggttcg atccttgggg ccaaggcacc    420
atggtgaccg tttccagcgg ctctacaagc ggcagcggga aacctggttc tggagagggc    480
agcacaaagg gcgacatcca gatgacacag agccccagca cccttagcgc ctctgtggga    540
gatagggtta ccattacctg cagggcttcc cagagcatca gcagctggct ggcatggtat    600
caacagaagc ctggcaaggc tcccaagctg ctcatctatg acgcctccag cctggaaagc    660
ggggttccct ccagatttag cggctcaggc tccggaacag agttcaccct taccatctct    720
agcctgcaac ccgacgactt cgctacttat tactgtcaac aagacagaag cttgccccca    780
acattcggcg gagggaccaa ggttgagatc aaggcagctg cttttcgtgcc tgtgttcctg    840
```

```
cctgctaagc ccaccaccac tcctgctcca agacctccta cccccgctcc tacaatcgcc     900
agccaacctc tgagcctgag accggaggca tgcagacctg cggcaggggg agcagttcac     960
acaagaggct tggacttcgc ttgcgacatc tacatctggg cccctctggc cggcacatgc    1020
ggagttcttc ttcttagcct ggtgatcacc ctgtactgca accacagaaa cagattcagc    1080
gttgtgaaga gaggccggaa gaagctgctg tacatcttca gcagcccttt catgagacct    1140
gtgcagacca cacaggagga agacggctgc agctgtagat tccccgagga agaggagggc    1200
ggctgtgagc tgagagttaa gttcagcagg agcgccgacg ccctgcctta ccagcaagga    1260
cagaatcaac tgtacaacga gctgaacctg ggcagacggg aggaatacga tgtgctggac    1320
aagaggagag gcagagaccc cgagatgggc ggcaaaccta agaaagaa ccccaggag      1380 ggcctgtata cgagctcca gaaggacaag atggccgagg cctacagcga gatcggcatg    1440
aagggcgaaa gaagaagagg caagggccac gacggcctct accagggctt aagcacagct    1500
acaaaggaca cctacgacgc cctgcacatg caggccctgc ccctagatg attaattaaa    1560 tcgat                                                               1565
```

<210> SEQ ID NO 279
<211> LENGTH: 1580
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279

```
ggtaccccg ggcccatggc tcttcctgtg acagctcttc tgctgcccct ggccctgctt       60
ctgcatgctg ctagacctca ggttcagctt gtgcagagcg gagctgaagt taagaagcct      120
ggcgcctctg tgaaggttag ctgcaaggcc agcggctaca cattcaagga atatggcatc     180
tcctgggtta ggcaggctcc cggccaaggc ttagaatgga tgggctggat ctccgcctac     240
tccggccaca cctactacgc ccagaagctt cagggcaggg ttaccatgac caccgacacc     300
agcacctcta ccgcctatat ggagctgagg agcctgagat cggacgacac agctgtgtat     360
tactgcgcca gaggcccca ctacgacgac tggtctggat ttatcatctg gttcgacccc      420 tggggcagg gcaccctggt cacagtttct tctggctcca ccagcggaag cggcaagcca    480
ggctcaggcg aaggatctac aaaaggcgac atccaaatga cacagagccc cagcagcttg     540
agcgcctccg ttggcgacag agttacaatc acctgcaggg cctctcagag catcagcagc    600
tatttgaatt ggtatcaaca gaagccagga aaggcccta agctgctcat ctacgctgcc     660
agctcgctcc aatctggcgt tcctagcaga tttagcggct ccggcagcgg cacagacttt    720
actcttacca ttagctccct gcagcccgag gacttcgcta cctactattg ccagcaaagc     780
tacagattcc ctcccacctt tggccagggc acaaaggttg agatcaaggc agctgctttc    840
gtgcctgtgt tcctgcctgc taagcccacc accactcctg ctccaagacc tcctaccccc    900
gctcctacaa tcgccagcca acctctgagc ctgagaccgg aggcatgcag acctgcggca    960
gggggagcag ttcacacaag aggcttggac ttcgcttgcg acatctacat ctgggcccct   1020
ctggccggca catgcggagt tcttcttctt agcctggtga tcaccctgta ctgcaaccac    1080
agaaacagat cagcgttgt gaagagaggc cggaagaagc tgctgtacat cttcaagcag    1140
cccttcatga gacctgtgca gaccacacag gaggaagacg gctgcagctg tagattcccc    1200
gaggaagagg agggcggctg tgagctgaga gttaagttca gcaggagcgc cgacgccct   1260
```

```
gcctaccagc aaggacagaa tcaactgtac aacgagctga acctgggcag acggaggaa    1320 tacgatgtgc tggacaagag gagaggcaga gaccccgaga tgggcggcaa acctagaaga    1380
aagaaccccc aggagggcct gtataacgag ctccagaagg acaagatggc cgaggcctac    1440
agcgagatcg gcatgaaggg cgaaagaaga gaggcaagg gccacgacgg cctctaccag     1500
ggcttaagca cagctacaaa ggacacctac gacgccctgc acatgcaggc cctgccccct    1560
agatgattaa ttaaatcgat                                                1580
```

<210> SEQ ID NO 280
<211> LENGTH: 1586
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 280

```
ggtaccccg  ggcccatggc tcttcctgtg acagctcttc tgctgcccct ggccctgctt     60
ctgcatgctg ctagacctca ggttcagttg cagcaatggg gagctggcct gttaaagccc    120
agcgaaaccc tgtccctcac ctgcgctgtg tatggcggaa gcttcagcgg catccactgg    180
aactggatcc ggcagcctcc tggcaaaggc cttgaatgga tcggcgatat cgacaccagc    240
ggctccacca actacaaccc cagcctgaaa tcgagggtta caatctctgt ggacacaagc    300
aagaatcagt tctcccctga agctgagcag gttactgccg ccgacacagc tgtgtactat    360
tgcgccagac tgggccagga aagcgctacc taccttggca tggatgtgtg ggggcagggc    420
accaccgtta ctgttagctc tggctcaaca agcggcagcg gcaagcctgg ctcaggagaa    480
ggaagcacaa agggcgacat tgtaatgact cagagcccg acagcctggc cgttagctta    540
ggcgaaaggg ctacaatcaa ttgcaagagc agccagagcg ttctgtacag cagcaacaac    600
aagaactacc tcgcatggta tcaacagaag ccaggccagc ctcccaagct gctcatctac    660
tgggcttcca ccagagagag cggggttccc gatagattct ccggctccgg ttctggaaca    720
gatttcacgc tcacaatcag cagcttacag gccgaggatg tggctgtcta ctattgtcag    780
cagttgtaca cctaccccTT cacattcggc ggaggcacca aggttgagat caaggcagct    840
gctttcgtgc ctgtgttcct gcctgctaag cccaccacca ctcctgctcc aagacctcct    900 accccgctc  ctacaatcgc cagccaacct ctgagcctga ccggaggc   atgcagacct    960 gcggcagggg gagcagttca cacaagaggc ttggacttcg cttgcgacat ctacatctgg    1020
gccccTctgg ccggcacatg cggagttctt cttcttagcc tggtgatcac cctgtactgc    1080
aaccacagaa acagattcag cgttgtgaag agaggccgga gaagctgct  gtacatcttc    1140 aagcagccct tcatgagacc tgtgcagacc acacaggagg aagacggctg cagctgtaga    1200
ttccccgagg aagaggaggg cggctgtgag ctgagagtta agttcagcag gagcgccgac    1260
gcccctgcct accagcaagg acagaatcaa ctgtacaacg agctgaacct gggcagacgg    1320
gaggaatacg atgtgctgga caagaggaga ggcagagacc ccgagatggg cggcaaacct    1380
agaagaaaga accccagga gggcctgtat aacgagctcc agaaggacaa gatggccgag    1440
gcctacagcg agatcggcat gaagggcgaa agaagaagag caagggcca cgacggcctc    1500 taccagggct taagcacagc tacaaaggac acctacgacg ccctgcacat gcaggccctg    1560
ccccctagat gattaattaa atcgat                                          1586
```

-continued

<210> SEQ ID NO 281
<211> LENGTH: 1499
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281

| | |
|---|---|
| ggtaccccg ggcccatggc tcttcctgtg acagctcttc tgctgcccct ggccctgctt | 60 |
| ctgcatgctg ctagacctca gcttcagctc aagagagcg acctggctt agtgaagccc | 120 |
| agcgaaaccc tgtccctcac ctgcaccgtt tctggcggaa gcatcagcag ctccagctat | 180 |
| tactggggat ggatcaggca gccccctggc aagggtttag aatggatcgg ctcgatatat | 240 |
| tactccggca gcacctacta taaccccagc ttgaagagcc gggttaccat ttctgtggac | 300 |
| acatcaaaga accagttcag cctgaagctg agctctgtga ctgccgccga cacagctgtg | 360 |
| tactactgtg ccagagagac agactactcc agcggcatgg gctacggcat ggatgtgtgg | 420 |
| ggacaaggaa ccaccgttac tgtgagcagc ggttccacca gcggctcagg caagcctggc | 480 |
| tcaggagaag gaagcaccaa gggggatata cagatgacac agagcccctc cagcctgtcc | 540 |
| gccagcgttg gcgatcgtgt aacgatcacc tgccgggcct ctcagagcat caactcctac | 600 |
| ctcaattggt atcaacagaa gccaggcaag gcccccaaat tactcatcta cgccgccagc | 660 |
| agcttacaga gcggggttcc ctctagattc tccggctccg ttctggaaac agatttcacc | 720 |
| ctcactatct ccagcttgca gcccgaggat ttcgccactt attactgtca gcagagcctg | 780 |
| gccgaccct tcacattcgg cggaggcaca aaggttgaga tcaaggctgc tgcattggat | 840 |
| aatgaaaaat cgaacggcac aatcattcat gtgaagggca acacctgtg tcccagcccc | 900 |
| tgttcccag gacctagcaa gccttttggg gttctcgtgg tggtgggcgg cgttctggct | 960 |
| tgctactctc tacttgtaac tgtcgcattt attatattct gggttagatt cagcgttgtg | 1020 |
| aagagaggcc ggaagaagct gctgtacatc ttcaagcagc ccttcatgag acctgtgcag | 1080 |
| accacacagg aggaagacgg ctgcagctgt agattccccg aggaagagga gggcggctgt | 1140 |
| gagctgagag ttaagttcag caggagcgcc gacgcccctg cctaccagca aggacagaat | 1200 |
| caactgtaca acgagctgaa cctgggcaga cgggaggaat acgatgtgct ggacaagagg | 1260 |
| agaggcagag accccgagat gggcggcaaa cctagaagaa agaaccccca ggagggcctg | 1320 |
| tataacgagc tccagaagga caagatggcc gaggcctaca gcgagatcgg catgaagggc | 1380 |
| gaaagaagaa gaggcaaggg ccacgacggc ctctaccagg gcttaagcac agctacaaag | 1440 |
| gacacctacg acgccctgca catgcaggcc ctgccccta gatgattaat taaatcgat | 1499 |

<210> SEQ ID NO 282
<211> LENGTH: 1499
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 282

| | |
|---|---|
| ggtaccccg ggcccatggc tcttcctgtg acagctcttc tgctgcccct ggccctgctt | 60 |
| ctgcatgctg ctagacctca ggttcagtta aagagagcg acctggctt agtgaagccc | 120 |
| agcgaaaccc tgtccctcac ctgcaccgtt tctggcggaa gcatcagctc tcccgaccat | 180 |
| tactggggat ggatcaggca gccccctggc aagggtttgg aatggatcgg cagcatctac | 240 |

```
gccagcggca gcacattcta caaccccctcg ctcaaaagca gggttactat ttctgtggac    300
acaagcaaaa atcagttcag cctgaagctg agctctgtga ctgccgccga cacagctgtg    360
tactactgtg ccagagagac agactactcc agcgggatgg gctacggcat ggatgtgtgg    420
ggacaaggaa ccaccgttac tgtgagcagc ggctccacaa gcggctcagg caagcctggc    480
tcaggagaag gaagcaccaa ggggacatt caaatgaccc aaagcccctc cagcctgtcc      540
gccagcgttg gcgatagggt taccattacc tgcagggcca gccaaagcat caactcctac    600
ctaaattggt atcaacagaa gccaggcaag gcccccaaac tactcattta cgccgccagc    660
agcttacaga gcggggttcc ctctagattc tccggcagcg gttctggaac agatttcact    720
ctcacaatat cttcgctgca gcccgaggat ttcgctacct actattgcca gcaatccctg    780
gccgacccct tcacattcgg cggaggcaca aaggttgaga tcaaggctgc tgcattggat    840
aatgaaaaat cgaacggcac aatcattcat gtgaagggca acacctgtg tcccagcccc     900 ttgttcccag gacctagcaa gccttttttgg gttctcgtgg tggtgggcgg cgttctggct   960
tgctactctc tacttgtaac tgtcgcattt attatattct gggttagatt cagcgttgtg   1020
aagagaggcc ggaagaagct gctgtacatc ttcaagcagc ccttcatgag acctgtgcag   1080
accacacagg aggaagacgg ctgcagctgt agattccccg aggaagagga gggcggctgt   1140
gagctgagag ttaagttcag caggagcgcc gacgccccctg cctaccagca aggacagaat   1200
caactgtaca cgagctgaa cctgggcaga cgggaggaat acgatgtgct ggacaagagg    1260
agaggcagag accccgagat gggcggcaaa cctagaagaa agaaccccca ggagggcctg   1320
tataacgagc tccagaagga caagatggcc gaggcctaca gcgagatcgg catgaagggc   1380
gaaagaagaa gaggcaaggg ccacgacggc ctctaccagg gcttaagcac agctacaaag   1440
gacacctacg acgccctgca catgcaggcc ctgccccta gatgattaat taaatcgat    1499
```

<210> SEQ ID NO 283
<211> LENGTH: 1496
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 283

```
ggtaccccg ggcccatggc tcttcctgtg acagctcttc tgctgcccct ggccctgctt      60
ctgcatgctg ctagacctca gatcacatta aaagagagcg gacctacact ggtgaagccc    120
acccaaacgc ttaccctcac ctgcaccttt agcgggttca gctggacac agagggcgtt    180 ggcgttggat ggatcaggca gcctcctggc aaagccctcg aatggcttgc cctcatctac    240
ttcaacgacc agaagagata cagccccctcc ttaaaatctc ggctcacaat caccaaagac    300
acaagcaaaa atcaggttgt gctcaccatg accaacatgg accctgtgga caccgctgtg   360
tactactgtg ccagagacac cggctacagc agatggtact acgggatgga cgtttggggc   420
caaggcacca ctgtgaccgt ttccagcggc tctacaagcg gcagcgggaa acctggttct    480
ggagagggca gcacaaaggg cgacatccag atgacgcaat cccccagctc tgtgagcgcc   540
tctgtgggag acagagttac aatcacatgc cgggcctccc agggcatcag ctcttggctg    600
gcatggtatc aacagaagcc tggcaaggct cccaagctgc tcatctatgc cgcctcctcc    660
ttacaatctg gagttccctc caggttcagc gggagcggcc aggaacaga cttcaccctt    720 accatctcta gcctgcaacc cgaggacttc gctacttatt actgtcagca ggcctacgcc    780
```

-continued

| | |
|---|---|
| taccccatca cattcggcgg aggaacaaag gttgagatca aggctgctgc attggataat | 840 |
| gaaaaatcga acggcacaat cattcatgtg aagggcaaac acctgtgtcc cagccccttg | 900 |
| ttcccaggac ctagcaagcc ttttggtt ctcgtggtgg tgggcggcgt tctggcttgc | 960 |
| tactctctac ttgtaactgt cgcatttatt atattctggg ttagattcag cgttgtgaag | 1020 |
| agaggccgga agaagctgct gtacatcttc aagcagccct tcatgagacc tgtgcagacc | 1080 |
| acacaggagg aagacggctg cagctgtaga ttccccgagg aagaggaggg cggctgtgag | 1140 |
| ctgagagtta agttcagcag gagcgccgac gcccctgcct accagcaagg acagaatcaa | 1200 |
| ctgtacaacg agctgaacct gggcagacgg gaggaatacg atgtgctgga caagaggaga | 1260 |
| ggcagagacc ccgagatggg cggcaaacct agaagaaaga accccagga gggcctgtat | 1320 |
| aacgagctcc agaaggacaa gatggccgag gcctacagcg agatcggcat gaagggcgaa | 1380 |
| agaagaagag gcaagggcca cgacggcctc taccagggct aagcacagc tacaaaggac | 1440 |
| acctacgacg ccctgcacat gcaggccctg cccctagat gattaattaa atcgat | 1496 |

<210> SEQ ID NO 284
<211> LENGTH: 1514
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 284

| | |
|---|---|
| ggtaccccg ggcccatggc tcttcctgtg acagctcttc tgctgcccct ggccctgctt | 60 |
| ctgcatgctg ctagacctca ggttcagtta caacaatggg gagctggcct gttaaagccc | 120 |
| agcgaaaccc tgtccctcac ctgcgctgtg tatggcggaa gcttccagaa atactactgg | 180 |
| agctggatcc ggcagcctcc cggcaaaggc ttagaatgga tcggagagat agacaccagc | 240 |
| ggcttcacca actacaaccc cagcctgaaa tctagggtta caatctctgt ggacacaagc | 300 |
| aagaatcagt tctccctgaa gctgagcagc gttactgccg ccgacacagc tgtgtactat | 360 |
| tgcgccagag ttggcagata cagctacggc tactacatca ccgccttcga catttgggc | 420 |
| caaggcacca ctgtgaccgt tccagcgga agcactagcg cagcgggaa acctggttct | 480 |
| ggagagggct caaccaaggg cgacatcgtg atgacacaga gccccgactc tctggctgtg | 540 |
| tccctgggag agagagccac catcaactgc aagagcagcc agagcgttct gtacagcagc | 600 |
| aacaacaaga actacctggc atggtatcaa cagaagcctg gccagccccc taagctgctc | 660 |
| atctactggg cttccaccag agaatcaggc gttccagaca ggttctccgg ctcgggttca | 720 |
| ggcacagact tcacccttac catctcttcc ctgcaggccg aagatgtggc cgtttactac | 780 |
| tgtcagcagc actacagctt ccctttcaca ttcggcggag caccaaggt tgagatcaag | 840 |
| gctgctgcat tggataatga aaaatcgaac ggcacaatca ttcatgtgaa gggcaaacac | 900 |
| ctgtgtccca gccccttgtt cccaggacct agcaagcctt ttggggttct cgtggtggtg | 960 |
| ggcggcgttc tggcttgcta ctctctactt gtaactgtcg catttattat attctgggtt | 1020 |
| agattcagcg ttgtgaagag aggccggaag aagctgctgt acatcttcaa gcagccctc | 1080 |
| atgagacctg tgcagaccac acaggaggaa gacggctgca gctgtagatt ccccgaggaa | 1140 |
| gaggagggcg gctgtgagct gagagttaag ttcagcagga gcgccgacgc ccctgcctac | 1200 |
| cagcaaggac agaatcaact gtacaacgag ctgaacctgg gcagacggga ggaatacgat | 1260 |
| gtgctggaca gaggagagg cagagacccc gagatgggcg gcaaacctag aagaaagaac | 1320 |

```
cccccaggagg gcctgtataa cgagctccag aaggacaaga tggccgaggc ctacagcgag    1380
atcggcatga agggcgaaag aagaagaggc aagggccacg acggcctcta ccagggctta    1440
agcacagcta caaaggacac ctacgacgcc ctgcacatgc aggccctgcc ccctagatga    1500
ttaattaaat cgat                                                      1514
```

<210> SEQ ID NO 285
<211> LENGTH: 1526
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 285

```
ggtaccccg ggcccatggc tcttcctgtg acagctcttc tgctgcccct ggccctgctt     60
ctgcatgctg ctagacctca ggttcagttg cagcaatggg gagctggcct gttaaagccc    120
agcgaaaccc tgtccctcac ctgcgctgtg tatggcggaa gcttcgagaa atactactgg    180
agctggatcc ggcagcctcc cggcaaaggc ttagaatgga tcggcgagat ttatcacagc    240
gggctcacca actacaaccc cagcctgaaa tctcgagtta caatctctgt ggacacaagc    300
aagaatcagt tctccctgaa gctgagcagc gttactgccg ccgacacagc tgtgtactat    360
tgcgccagag ttagatacga cagcagcgac agctattact acagctatga ctacggcatg    420
gatgtgtggg ggcagggcac caccgttact gtctcctctg gatctaccag cggcagcggc    480
aagcctggat ctggcgaagg aagcacaaag ggcgacattg tgctcaccca gagccccgac    540
agcctggctg tgtctttagg cgaaagggct accatcaact gcaagagcag ccagagcgtt    600
ctgtacagca gcaacaacaa gaactacctt gcttggtatc aacagaagcc tggccagccc    660
cctaagctgc tcatctactg ggcctctagc agagagagcg gggttcccga tcggtttagc    720
ggctccggct caggaaccga tttcacccct actatctcca gcctccaggc cgaggatgtg    780
gctgtctact attgtcagca gagctatagc ttccctgga cattcggcgg aggcaccaag    840
gttgagatca aggctgctgc attggataat gaaaaatcga acggcacaat cattcatgtg    900
aagggcaaac acctgtgtcc cagcccccttg ttcccaggac ctagcaagcc ttttgggtt     960 ctcgtggtgg tgggcggcgt tctggcttgc tactctctac ttgtaactgt cgcatttatt    1020
atattctggg ttagattcag cgttgtgaag agaggccgga gaagctgct gtacatcttc    1080 aagcagccct tcatgagacc tgtgcagacc acacaggagg aagacggctg cagctgtaga    1140
ttccccgagg aagaggaggg cggctgtgag ctgagagtta agttcagcag gagcgccgac    1200
gcccctgcct accagcaagg acagaatcaa ctgtacaacg agctgaacct gggcagacgg    1260
gaggaatacg atgtgctgga caagaggaga ggcagagacc ccgagatggg cggcaaacct    1320
agaagaaaga accccccagga gggcctgtat aacgagctcc agaaggacaa gatggccgag    1380
gcctacagcg agatcggcat gaagggcgaa agaagaagag gcaagggcca cgacggcctc    1440
taccagggct taagcacagc tacaaaggac acctacgacg ccctgcacat gcaggccctg    1500 cccccctagat gattaattaa atcgat                                        1526
```

<210> SEQ ID NO 286
<211> LENGTH: 1526
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 286

```
ggtaccccg ggcccatggc tcttcctgtg acagctcttc tgctgcccct ggccctgctt        60
ctgcatgctg ctagacctca ggttcagtta caacaatggg gagctggcct gttaaagccc      120
agcgaaaccc tgtccctcac ctgcgctgtg tatggcggaa gcttcagccg ctatgtgtgg      180
agctggatcc ggcagcctcc tggcaaaggc cttgaatgga tcggagagat agacagcagc      240
ggcaagacca actacaaccc cagcctgaaa tcacgcgtta caatctctgt ggacacaagc      300
aagaatcagt tctcctgaa gctgagcagc gttactgccg ccgacacagc tgtgtactat       360
tgcgccagag ttagatacga cagctccgac agctattact acagctatga ctacggcatg      420
gatgtgtggg gcagggcac caccgttaca gttagctctg aagcaccag cggctccggc        480
aagcctggat ctggtgaagg aagcacaaag gcgacattg tgctcaccca gagccccgac       540
agcctggctg tgtctttagg cgaaagggct accatcaact gcaagagcag ccagagcgtt      600
ctgtacagca gcaacaacaa gaactacctt gcatggtatc aacagaagcc tggccagcct      660
cccaagctgc tcatctactg ggcctctagc agagagagcg gggttcccga tcgctttagc      720
ggcagcggtt ctggcaccga tttcactctt acaatcagca gcttacaggc cgaggatgtg      780
gctgtctact attgtcagca gagctatagc ttcccctgga cattcggcgg aggcaccaag      840
gttgagatca aggctgctgc attggataat gaaaaatcga acggcacaat cattcatgtg      900
aagggcaaac acctgtgtcc cagccccttg ttcccaggac ctagcaagcc ttttgggtt       960
ctcgtggtgg tgggcggcgt tctggcttgc tactctctac ttgtaactgt cgcatttatt     1020
atattctggg ttagattcag cgttgtgaag agaggccgga agaagctgct gtacatcttc     1080
aagcagccct tcatgagacc tgtgcagacc acacaggagg aagacggctg cagctgtaga     1140
ttccccgagg aagaggaggg cggctgtgag ctgagagtta agttcagcag gagcgccgac     1200
gcccctgcct accagcaagg acagaatcaa ctgtacaacg agctgaacct gggcagacgg     1260
gaggaatacg atgtgctgga caagaggaga ggcagagacc ccgagatggg cggcaaacct     1320
agaagaaaga ccccccagga gggcctgtat aacgagctcc agaaggacaa gatggccgag     1380
gcctacagcg agatcggcat gaaggcgaa agaagaagg gcaagggcca cgacggcctc       1440
taccagggct aagcacagc tacaaaggac acctacgacg ccctgcacat gcaggccctg     1500
ccccctagat gattaattaa atcgat                                          1526
```

<210> SEQ ID NO 287
<211> LENGTH: 1526
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 287

```
ggtaccccg ggcccatggc tcttcctgtg acagctcttc tgctgcccct ggccctgctt        60
ctgcatgctg ctagacctca ggttcagtta caacaatggg gagctggcct gttaaagccc      120
agcgaaaccc tgtccctcac ctgcgctgtg tatggcggaa gcttcagcgg ctacgcttgg      180
agctggatta gacagcctcc tggcaaagga ctagaatgga tcggagagat cgaccacaga      240
ggcttcacca actacaaccc cagcctgaaa tccagagtta caatctctgt ggacacaagc      300
aagaatcagt tctcctgaa gctgagcagc gttactgccg ccgacacagc tgtgtactat       360
tgcgccaggg ttagatacga cagcagcgac agctattact acagctatga ctacggcatg      420
```

```
gatgtgtggg ggcagggcac caccgttacg gttagctctg gatctaccag cggcagcggc    480
aagcctggct caggagaagg aagcacaaag ggcgacattg tgctcaccca gagccccgac    540
agcctggccg tttctttagg cgaaagggct accatcaact gcaagagcag ccagagcgtt    600
ctgtacagca gcaacaacaa gaactacctt gcatggtatc aacagaagcc aggccagcct    660
cccaagctgc tcatctactg ggcctctagc agagagagcg gggttcccga tagattttcg    720
ggatcaggct ccggcaccga tttcactctt acgatcagca gcttacaggc cgaggatgtg    780
gctgtctact attgtcagca gagctatagc ttcccctgga cattcggcgg aggcaccaag    840
gttgagatca aggctgctgc attggataat gaaaaatcga acggcacaat cattcatgtg    900
aagggcaaac acctgtgtcc cagccccttg ttcccaggac ctagcaagcc ttttgggtt    960 ctcgtggtgg tgggcggcgt tctggcttgc tactctctac ttgtaactgt cgcatttatt   1020
atattctggg ttagattcag cgttgtgaag agaggccgga agaagctgct gtacatcttc   1080
aagcagccct tcatgagacc tgtgcagacc acacaggagg aagacggctg cagctgtaga   1140
ttccccgagg aagaggaggg cggctgtgag ctgagagtta agttcagcag gagcgccgac   1200
gcccctgcct accagcaagg acagaatcaa ctgtacaacg agctgaacct gggcagacgg   1260
gaggaatacg atgtgctgga caagaggaga ggcagagacc ccgagatggg cggcaaacct   1320
agaagaaaga accccagga gggcctgtat aacgagctcc agaaggacaa gatggccgag   1380
gcctacagcg agatcggcat gaagggcgaa agaagaagag gcaagggcca cgacggcctc   1440
taccagggct taagcacagc tacaaaggac acctacgacg ccctgcacat gcaggccctg   1500 cccccctagat gattaattaa atcgat                                       1526

<210> SEQ ID NO 288
<211> LENGTH: 1487
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 288 ggtaccccg ggcccatggc tcttcctgtg acagctcttc tgctgcccct ggccctgctt     60
ctgcatgctg ctagacctca ggttcagttg cagcaatggg gagctggcct gttaaagccc    120
agcgaaaccc tgtccctcac ctgcgctgtg tatggcggaa gcttcagcgg ctattactgg    180
agctggatcc ggcagcctcc tggaaaagga ttagaatgga tcggcgagat agaccacagc    240
gggagcacaa actacaaccc cagcctgaaa tcgcgggtta caatctctgt ggacacaagc    300
aagaatcagt tctccctgaa gctgagcagc gttactgccg ccgacacagc tgtgtactat    360
tgcgccagag gcggaggctc ctggtacagc aactggttcg atccttgggg ccaaggcacc    420
atggtgaccg tttccagcgg ctctacaagc ggcagcggga aacctggttc tggagagggc    480
agcacaaagg gcgacatcca gatgacacag agccccagca cccttagcgc ctctgtggga    540
gatagggtta ccattacctg cagggcttcc cagagcatca gcagctggct ggcatggtat    600
caacagaagc ctggcaaggc tcccaagctg ctcatctatg acgcctccag cctgaaaagc    660
ggggttccct ccagatttag cggctcaggc tccggaacag agttcaccct taccatctct    720
agcctgcaac ccgacgactt cgctacttat tactgtcaac aagacagaag cttgccccc    780 acattcggcg gagggaccaa ggttgagatc aaggctgctg cattggataa tgaaaaatcg    840
aacggcacaa tcattcatgt gaagggcaaa cacctgtgtc ccagccccct tgttcccagga   900
```

```
cctagcaagc cttttgggt  tctcgtggtg gtgggcggcg ttctggcttg ctactctcta   960
cttgtaactg tcgcatttat tatattctgg gttagattca gcgttgtgaa gagaggccgg  1020
aagaagctgc tgtacatctt caagcagccc ttcatgagac ctgtgcagac cacacaggag  1080
gaagacggct gcagctgtag attccccgag aagaggagg  gcggctgtga gctgagagtt  1140
aagttcagca ggagcgccga cgccctgcc  taccagcaag acagaatca  actgtacaac  1200 gagctgaacc tgggcagacg gaggaatac  gatgtgctgg acaagaggag aggcagagac  1260
cccgagatgg gcggcaaacc tagaagaaag aaccccagg  agggcctgta taacgagctc  1320
cagaaggaca agatggccga ggcctacagc gagatcggca tgaagggcga agaagaaga   1380 ggcaagggcc acgacggcct ctaccagggc ttaagcacag ctacaaagga cacctacgac  1440
gccctgcaca tgcaggccct gccccctaga tgattaatta aatcgat              1487
```

<210> SEQ ID NO 289
<211> LENGTH: 1502
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 289

```
ggtaccccg  ggcccatggc tcttcctgtg acagctcttc tgctgcccct ggccctgctt    60
ctgcatgctg ctagacctca ggttcagctt gtgcagagcg gagctgaagt taagaagcct   120
ggcgcctctg tgaaggttag ctgcaaggcc agcggctaca cattcaagga atatggcatc   180
tcctgggtta ggcaggctcc cggccaaggc ttagaatgga tgggctggat ctccgcctac   240 tccgccaca  cctactacgc ccagaagctt cagggcaggg ttaccatgac caccgacacc   300
agcacctcta ccgcctatat ggagctgagg agcctgagat cggacgacac agctgtgtat   360
tactgcgcca gaggccccca ctacgacgac tggtctggat ttatcatctg gttcgacccc   420
tggggccagg gcaccctggt cacagtttct tctggctcca ccagcggaag cggcaagcca   480
ggctcaggcg aaggatctac aaaaggcgac atccaaatga cacagagccc cagcagcttg   540
agcgcctccg ttggcgacag agttacaatc acctgcaggg cctctcagag catcagcagc   600
tatttgaatt ggtatcaaca gaagccagga aaggccccta gctgctcat  ctacgctgcc   660 agctcgctcc aatctggcgt tcctagcaga tttagcggct ccggcagcgg cacagacttt   720
actcttacca ttagctccct gcagcccgag gacttcgcta cctactattg ccagcaaagc   780
tacagattcc ctcccacctt tggccagggc acaaaggttg agatcaaggc tgctgcattg   840
gataatgaaa aatcgaacgg cacaatcatt catgtgaagg gcaaacacct gtgtcccagc   900
cccttgttcc caggacctag caagccttt  tgggttctcg tggtggtggg cggcgttctg   960
gcttgctact ctctacttgt aactgtcgca tttattatat tctgggttag attcagcgtt  1020
gtgaagagag gccggaagaa gctgctgtac atcttcaagc agcccttcat gagacctgtg  1080
cagaccacac aggaggaaga cggctgcagc tgtagattcc ccgaggaaga ggagggcggc  1140
tgtgagctga gagttaagtt cagcaggagc gccgacgccc tgcctacca  gcaaggacag  1200 aatcaactgt acaacgagct gaacctgggc agacggagg  aatacgatgt gctggacaag  1260
aggagaggca gagacccga  gatgggcggc aaacctagaa gaagaaccc  caggagggc   1320 ctgtataacg agctccagaa ggacaagatg gccgaggcct acagcgagat cggcatgaag  1380
ggcgaaagaa gaagaggcaa gggccacgac ggcctctacc agggcttaag cacagctaca  1440
```

```
aaggacacct acgacgccct gcacatgcag gccctgcccc ctagatgatt aattaaatcg    1500
at                                                                   1502

<210> SEQ ID NO 290
<211> LENGTH: 1508
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 290 ggtaccccg  ggcccatggc tcttcctgtg acagctcttc tgctgcccct ggccctgctt      60
ctgcatgctg ctagacctca ggttcagttg cagcaatggg gagctggcct gttaaagccc     120
agcgaaaccc tgtccctcac ctgcgctgtg tatggcggaa gcttcagcgg catccactgg     180
aactggatcc ggcagcctcc tggcaaaggc cttgaatgga tcggcgatat cgacaccagc     240
ggctccacca actacaaccc cagcctgaaa tcgagggtta caatctctgt ggacacaagc     300
aagaatcagt tctccctgaa gctgagcagc gttactgccg ccgacacagc tgtgtactat     360
tgcgccagac tgggccagga aagcgctacc taccttggca tggatgtgtg ggggcagggc     420
accaccgtta ctgttagctc tggctcaaca agcggcagcg gcaagcctgg ctcaggagaa     480
ggaagcacaa agggcgacat tgtaatgact cagagccccg acagcctggc cgttagctta     540
ggcgaaaggg ctacaatcaa ttgcaagagc agccagagcg ttctgtacag cagcaacaac     600
aagaactacc tcgcatggta tcaacagaag ccaggccagc ctcccaagct gctcatctac     660
tgggcttcca ccagagagag cggggttccc gatagattct ccggctccgg ttctggaaca     720
gatttcacgc tcacaatcag cagcttacag gccgaggatg tggctgtcta ctattgtcag     780
cagttgtaca cctacccctt cacattcggc ggaggcacca aggttgagat caaggctgct     840
gcattggata tgaaaaatc gaacggcaca atcattcatg tgaagggcaa acacctgtgt     900
cccagcccct tgttcccagg acctagcaag ccttttgggt tctcgtggt ggtgggcggc     960 gttctggctt gctactctct acttgtaact gtcgcattta ttatattctg ggttagattc    1020
agcgttgtga agagaggccg gaagaagctg ctgtacatct tcaagcagcc cttcatgaga    1080
cctgtgcaga ccacacagga ggaagacggc tgcagctgta gattccccga ggaagaggag    1140
ggcggctgtg agctgagagt taagttcagc aggagcgccg acgcccctgc ctaccagcaa    1200
ggacagaatc aactgtacaa cgagctgaac ctgggcagac gggaggaata cgatgtgctg    1260
gacaagagga gaggcagaga ccccgagatg ggcggcaaac ctagaagaaa gaaccccag    1320 gagggcctgt ataacgagct ccagaaggac aagatggccg aggcctacag cgagatcggc    1380
atgaagggcg aaagaagaag aggcaagggc cacgacggcc tctaccaggg cttaagcaca    1440
gctacaaagg acacctacga cgccctgcac atgcaggccc tgccctag atgattaatt    1500 aaatcgat                                                             1508

<210> SEQ ID NO 291
<211> LENGTH: 3057
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 291
```

```
atgctgctgc tggtgacatc tctgctgctt tgcgagctgc cccaccctgc cttcctgctt      60
atccccgaca ttcagatgac ccagaccacc agcagcctga cgccagctt aggagataga      120
gttaccatca gctgcagagc cagccaggac atcagcaaat acctgaactg gtatcagcag     180
aagcccgacg gcactgtgaa actgcttatt taccacacct ccagactgca cagcggcgtt     240
cccagcagat tctctggcag cggatctgga accgactaca gcctcaccat ctccaacctg     300
gagcaggagg acatcgccac ctacttctgc cagcagggca acacactgcc ctacaccttc     360
ggaggaggaa ccaagctgga gatcaccggg ggaggaggct ctggaggcgg cggatcagga     420
ggagggggat ctgaggttaa gctgcaggag agcggccctg gcctggtggc tcctagccaa     480
tctttatctg tgacctgcac tgtgtccggc gttagcctgc ccgattatgg cgtttcctgg     540
atcagacagc cccccagaaa gggcctggaa tggctgggcg ttatctgggg cagcgagacc     600
acatactaca acagcgccct gaagagcaga cttacgatta tcaaggacaa cagcaagagc     660
caggttttcc tgaagatgaa cagcctgcag accgacgaca ccgccatcta ctactgcgct     720
aagcactact actacggcgg cagctacgcc atggactact ggggccaggg aacaagcgtt     780
accgttagca gcgctgctgc actggacaac gagaagagca acggcaccat catccacgtt     840
aagggcaagc acctgtgccc cagccctctg ttccctggac cttctaagcc tttctgggtt     900
ctggtggtgg tcggcggcgt tttagcctgt tacagccttc tggtgactgt ggccttcatc     960
atcttttggg ttagaagcaa gagaagcaga ctgctccaca cgactacat gaacatgacc      1020
cccagacggc ctggccccac cagaaagcat taccagccct acgctcctcc cagagacttc     1080
gccgcctaca ggagcagagt taaattcagc agatccgccg atgcccccgc ttaccaacag     1140
ggacaaaacc agctgtacaa tgagctcaac ctggggagaa gagaagaata cgacgttctg     1200
gataagagaa ggggcagaga tcccgaaatg ggggcaagc ccagacgcaa gaaccctcag      1260
gaggggcttt acaacgaact gcagaaggat aagatggctg aggcttactc ggagattggg     1320
atgaagggg agagaaggcg gggcaaggga cacgatggct taccagggg gctgagcacc       1380
gccaccaagg acacatacga cgctcttcat atgcaggctc tgcccccaag aagggctaag     1440
agatctggct ctggcgaggg cagaggcagc ttgcttacat gtggcgatgt ggaggagaac     1500
cccgggccca tggctcttcc tgtgacagct cttctgctgc ccctggccct gcttctgcat     1560
gctgctagac ctcagcttca gctccaagag agcggacctg gcttagtgaa gcccagcgaa     1620
accctgtccc tcacctgcac cgtttctggc ggaagcatca gcagctccag ctattactgg     1680
ggatggatca ggcagccccc tggcaagggt ttagaatgga tcggctcgat atattactcc     1740
ggcagcacct actataaccc cagcttgaag agccgggtta ccatttctgt ggacacatca     1800
aagaaccagt tcagcctgaa gctgagctct gtgactgccg ccgacacagc tgtgtactac     1860
tgtgccagag agacagacta ctccagcggc atgggctacg gcatggatgt gtggggacaa     1920
ggaaccaccg ttactgtgag cagcggttcc accagcggct caggcaagcc tggctcagga     1980
gaaggaagca ccaaggggga tatacagatg acacagagcc cctccagcct gtccgccagc     2040
gttggcgatc gtgtaacgat cacctgccgg gcctctcaga gcatcaactc ctacctcaat     2100
tggtatcaac agaagccagg caaggccccc aaaattactca tctacgccgc cagcagctta    2160
cagagcgggg ttccctctag attctccggc tccggttctg gaacagattt caccctcact     2220
atctccagct tgcagcccga ggatttcgcc acttattact gtcagcagag cctggccgac     2280
cccttcacat tcggcggagg cacaaaggtt gagatcaagg cagctgcttt cgtgcctgtg     2340
ttcctgcctg ctaagcccac caccactcct gctccaagac ctcctacccc cgctcctaca     2400
```

-continued

```
atcgccagcc aacctctgag cctgagaccg gaggcatgca gacctgcggc agggggagca      2460
gttcacacaa gaggcttgga cttcgcttgc gacatctaca tctgggcccc tctggccggc      2520
acatgcggag ttcttcttct tagcctggtg atcaccctgt actgcaacca cagaaacaga      2580
ttcagcgttg tgaagagagg ccggaagaag ctgctgtaca tcttcaagca gcccttcatg      2640
agacctgtgc agaccacaca ggaggaagac ggctgcagct gtagattccc cgaggaagag      2700
gagggcggct gtgagctgag agttaagttc agcaggagcg ccgacgcccc tgcctaccag      2760
caaggacaga tcaactgta caacgagctg aacctgggca gacgggagga atacgatgtg      2820
ctggacaaga ggagaggcag agaccccgag atgggcggca aacctagaag aaagaacccc      2880
caggagggcc tgtataacga gctccagaag gacaagatgg ccgaggccta cagcgagatc      2940
ggcatgaagg gcgaaagaag aagaggcaag ggccacgacg gcctctacca gggcttaagc      3000
acagctacaa aggacaccta cgacgccctg cacatgcagg ccctgccccc tagatga        3057
```

<210> SEQ ID NO 292
<211> LENGTH: 1018
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240
```

-continued

```
Lys His Tyr Tyr Tyr Gly Gly Ser Tyr Ala Met Asp Tyr Trp Gly Gln
                245                 250                 255

Gly Thr Ser Val Thr Val Ser Ser Ala Ala Ala Leu Asp Asn Glu Lys
            260                 265                 270

Ser Asn Gly Thr Ile Ile His Val Lys Gly Lys His Leu Cys Pro Ser
        275                 280                 285

Pro Leu Phe Pro Gly Pro Ser Lys Pro Phe Trp Val Leu Val Val Val
    290                 295                 300

Gly Gly Val Leu Ala Cys Tyr Ser Leu Leu Val Thr Val Ala Phe Ile
305                 310                 315                 320

Ile Phe Trp Val Arg Ser Lys Arg Ser Arg Leu Leu His Ser Asp Tyr
                325                 330                 335

Met Asn Met Thr Pro Arg Arg Pro Gly Pro Thr Arg Lys His Tyr Gln
            340                 345                 350

Pro Tyr Ala Pro Pro Arg Asp Phe Ala Ala Tyr Arg Ser Arg Val Lys
        355                 360                 365

Phe Ser Arg Ser Ala Asp Ala Pro Ala Tyr Gln Gln Gly Gln Asn Gln
    370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg
                405                 410                 415

Lys Asn Pro Gln Glu Gly Leu Tyr Asn Glu Leu Gln Lys Asp Lys Met
            420                 425                 430

Ala Glu Ala Tyr Ser Glu Ile Gly Met Lys Gly Glu Arg Arg Arg Gly
        435                 440                 445

Lys Gly His Asp Gly Leu Tyr Gln Gly Leu Ser Thr Ala Thr Lys Asp
    450                 455                 460

Thr Tyr Asp Ala Leu His Met Gln Ala Leu Pro Pro Arg Arg Ala Lys
465                 470                 475                 480

Arg Ser Gly Ser Gly Glu Gly Arg Gly Ser Leu Leu Thr Cys Gly Asp
                485                 490                 495

Val Glu Glu Asn Pro Gly Pro Met Ala Leu Pro Val Thr Ala Leu Leu
            500                 505                 510

Leu Pro Leu Ala Leu Leu Leu His Ala Ala Arg Pro Gln Leu Gln Leu
        515                 520                 525

Gln Glu Ser Gly Pro Gly Leu Val Lys Pro Ser Glu Thr Leu Ser Leu
    530                 535                 540

Thr Cys Thr Val Ser Gly Gly Ser Ile Ser Ser Ser Tyr Tyr Trp
545                 550                 555                 560

Gly Trp Ile Arg Gln Pro Pro Gly Lys Gly Leu Glu Trp Ile Gly Ser
                565                 570                 575

Ile Tyr Tyr Ser Gly Ser Thr Tyr Tyr Asn Pro Ser Leu Lys Ser Arg
            580                 585                 590

Val Thr Ile Ser Val Asp Thr Ser Lys Asn Gln Phe Ser Leu Lys Leu
        595                 600                 605

Ser Ser Val Thr Ala Ala Asp Thr Ala Val Tyr Tyr Cys Ala Arg Glu
    610                 615                 620

Thr Asp Tyr Ser Ser Gly Met Gly Tyr Gly Met Asp Val Trp Gly Gln
625                 630                 635                 640

Gly Thr Thr Val Thr Val Ser Ser Gly Ser Thr Ser Gly Ser Gly Lys
                645                 650                 655

Pro Gly Ser Gly Glu Gly Ser Thr Lys Gly Asp Ile Gln Met Thr Gln
```

```
                    660                 665                 670
Ser Pro Ser Ser Leu Ser Ala Ser Val Gly Asp Arg Val Thr Ile Thr
            675                 680                 685

Cys Arg Ala Ser Gln Ser Ile Asn Ser Tyr Leu Asn Trp Tyr Gln Gln
        690                 695                 700

Lys Pro Gly Lys Ala Pro Lys Leu Leu Ile Tyr Ala Ala Ser Ser Leu
705                 710                 715                 720

Gln Ser Gly Val Pro Ser Arg Phe Ser Gly Ser Gly Ser Gly Thr Asp
                725                 730                 735

Phe Thr Leu Thr Ile Ser Ser Leu Gln Pro Glu Asp Phe Ala Thr Tyr
            740                 745                 750

Tyr Cys Gln Gln Ser Leu Ala Asp Pro Phe Thr Phe Gly Gly Gly Thr
        755                 760                 765

Lys Val Glu Ile Lys Ala Ala Phe Val Pro Val Phe Leu Pro Ala
770                 775                 780

Lys Pro Thr Thr Thr Pro Ala Pro Arg Pro Pro Thr Pro Ala Pro Thr
785                 790                 795                 800

Ile Ala Ser Gln Pro Leu Ser Leu Arg Pro Glu Ala Cys Arg Pro Ala
                805                 810                 815

Ala Gly Gly Ala Val His Thr Arg Gly Leu Asp Phe Ala Cys Asp Ile
                820                 825                 830

Tyr Ile Trp Ala Pro Leu Ala Gly Thr Cys Gly Val Leu Leu Leu Ser
            835                 840                 845

Leu Val Ile Thr Leu Tyr Cys Asn His Arg Asn Arg Phe Ser Val Val
        850                 855                 860

Lys Arg Gly Arg Lys Lys Leu Leu Tyr Ile Phe Lys Gln Pro Phe Met
865                 870                 875                 880

Arg Pro Val Gln Thr Thr Gln Glu Glu Asp Gly Cys Ser Cys Arg Phe
                885                 890                 895

Pro Glu Glu Glu Glu Gly Gly Cys Glu Leu Arg Val Lys Phe Ser Arg
            900                 905                 910

Ser Ala Asp Ala Pro Ala Tyr Gln Gln Gly Gln Asn Gln Leu Tyr Asn
        915                 920                 925

Glu Leu Asn Leu Gly Arg Arg Glu Glu Tyr Asp Val Leu Asp Lys Arg
930                 935                 940

Arg Gly Arg Asp Pro Glu Met Gly Gly Lys Pro Arg Arg Lys Asn Pro
945                 950                 955                 960

Gln Glu Gly Leu Tyr Asn Glu Leu Gln Lys Asp Lys Met Ala Glu Ala
                965                 970                 975

Tyr Ser Glu Ile Gly Met Lys Gly Glu Arg Arg Arg Gly Lys Gly His
            980                 985                 990

Asp Gly Leu Tyr Gln Gly Leu Ser  Thr Ala Thr Lys Asp  Thr Tyr Asp
        995                 1000                1005

Ala Leu  His Met Gln Ala Leu  Pro Pro Arg
    1010                1015

<210> SEQ ID NO 293
<211> LENGTH: 2202
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 293
```

| | |
|---|---|
| atgcttctcc tggtgacaag ccttctgctc tgtgagttac cacacccagc attcctcctg | 60 |
| atcccagaca tccagatgac ccagtctcca tcctccctgt ctgcatctgt aggagacaga | 120 |
| gtcaccatca cttgccgggc aagtcagagc attaacagct atttaaattg gtatcagcag | 180 |
| aaaccaggga aagcccctaa gctcctgatc tatgctgcat ccagtttgca aagtggggtc | 240 |
| ccatcaaggt tcagtggcag tggatctggg acagatttca ctctcaccat cagcagtctg | 300 |
| caacctgaag attttgcaac ttactactgc cagcaaagcc tcgccgaccc tttcactttt | 360 |
| ggcggaggga ccaaggttga gatcaaaggg ggggtggaa gtgggaagcc tggcagcggc | 420 |
| gagggcggca gtcagctgca gctgcaggag tcgggcccag gactggtgaa gccttcggag | 480 |
| accctgtccc tcacctgcac tgtctctggt ggctccatca gcagtagtag ttactactgg | 540 |
| ggctggatcc gccagccccc agggaagggg ctggagtgga ttgggagtat ctattatagt | 600 |
| gggagcacct actacaaccc gtccctcaag agtcgagtca ccatatccgt agacacgtcc | 660 |
| aagaaccagt tctccctgaa gctgagttct gtgaccgccg cagacacggc ggtgtactac | 720 |
| tgcgccagag agactgacta cagcagcgga atgggatacg gaatggacgt atggggccag | 780 |
| ggaacaactg tcaccgtctc ctcaggcggt ggcggcagtg gaagcctgg cagcgatatt | 840 |
| caaatgaccc agtccccgtc ctccctgagt gcctccgtcg gtgaccgtgt tacgattacc | 900 |
| tgccgtgcga gccaagacat tctaaatac ctgaactggt atcagcaaaa accggatcag | 960 |
| gcaccgaaac tgctgatcaa acatacctca cgtctgcact cgggtgtgcc gagccgcttt | 1020 |
| agtggttccg gctcaggtac cgattacacc ctgacgatca gctctctgca gccggaagac | 1080 |
| tttgccacgt attactgcca gcaaggtaat accctgccgt atacgttcgg ccaaggtacc | 1140 |
| aaactggaaa tcaaaggggg gggtggaagt ggggcggtg gcagcggcgg tggcggcagt | 1200 |
| gaagtgcagc tggttgaaag cggtggtggt ctggttcaac cgggtcgttc cctgcgtctg | 1260 |
| tcatgtacgg cgagtggtgt ctccctgccg gactatggcg tgtcctggat tcgtcagccg | 1320 |
| ccgggtaaag gcctgaatg gattggtgtc atctggggca gtgaaaccac gtattacaac | 1380 |
| tcggccctga aaagccgttt caccatctct cgcgataaca gtaaaaatac gctgtacctg | 1440 |
| cagatgaata gcctgcgcgc ggaagacacc gccgtttact actgcgcaaa acattactac | 1500 |
| tacggtggca gctatgctat ggattactgg ggtcaaggca cgctggtcac cgtttcgtca | 1560 |
| gccgctgccc tagacaatga aagagcaat ggaaccatta tccatgtgaa agggaaacac | 1620 |
| ctttgtccaa gtcccctatt tcccggacct tctaagccct tttgggtgct ggtggtggtt | 1680 |
| gggggagtcc tggcttgcta tagcttgcta gtaacagtgg cctttattat tttctgggtg | 1740 |
| aggagtaaga ggagcaggct cctgcacagt gactacatga acatgactcc ccgccgcccc | 1800 |
| gggcccaccc gcaagcatta ccagccctat gccccaccac gcgacttcgc agcctatcgc | 1860 |
| tccagagtga agttcagcag gagcgcagac gccccgcgt accagcaggg ccagaaccag | 1920 |
| ctctataacg agctcaatct aggacgaaga gaggagtacg atgttttgga caagagacgt | 1980 |
| ggccgggacc ctgagatggg gggaaagccg agaaggaaga accctcagga aggcctgtac | 2040 |
| aatgaactgc agaaagataa gatggcggag gcctacagtg agattgggat gaaaggcgag | 2100 |
| cgccggaggg gcaaggggca cgatggcctt taccagggtc tcagtacagc caccaaggac | 2160 |
| acctacgacg cccttcacat gcaggccctg ccccctcgat ga | 2202 |

<210> SEQ ID NO 294
<211> LENGTH: 733
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Ser Ile Asn Ser Tyr Leu Asn Trp Tyr Gln Gln Lys Pro Gly Lys
        50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Ser Leu Ala Asp Pro Phe Thr Phe Gly Gly Gly Thr Lys Val Glu Ile
            115                 120                 125

Lys Gly Gly Gly Gly Ser Gly Lys Pro Gly Ser Gly Glu Gly Gly Ser
    130                 135                 140

Gln Leu Gln Leu Gln Glu Ser Gly Pro Gly Leu Val Lys Pro Ser Glu
145                 150                 155                 160

Thr Leu Ser Leu Thr Cys Thr Val Ser Gly Gly Ser Ile Ser Ser Ser
                165                 170                 175

Ser Tyr Tyr Trp Gly Trp Ile Arg Gln Pro Pro Gly Lys Gly Leu Glu
                180                 185                 190

Trp Ile Gly Ser Ile Tyr Tyr Ser Gly Ser Thr Tyr Tyr Asn Pro Ser
            195                 200                 205

Leu Lys Ser Arg Val Thr Ile Ser Val Asp Thr Ser Lys Asn Gln Phe
        210                 215                 220

Ser Leu Lys Leu Ser Ser Val Thr Ala Ala Asp Thr Ala Val Tyr Tyr
225                 230                 235                 240

Cys Ala Arg Glu Thr Asp Tyr Ser Ser Gly Met Gly Tyr Gly Met Asp
                245                 250                 255

Val Trp Gly Gln Gly Thr Thr Val Thr Val Ser Ser Gly Gly Gly Gly
                260                 265                 270

Ser Gly Lys Pro Gly Ser Asp Ile Gln Met Thr Gln Ser Pro Ser Ser
            275                 280                 285

Leu Ser Ala Ser Val Gly Asp Arg Val Thr Ile Thr Cys Arg Ala Ser
        290                 295                 300

Gln Asp Ile Ser Lys Tyr Leu Asn Trp Tyr Gln Gln Lys Pro Asp Gln
305                 310                 315                 320

Ala Pro Lys Leu Leu Ile Lys His Thr Ser Arg Leu His Ser Gly Val
                325                 330                 335

Pro Ser Arg Phe Ser Gly Ser Gly Ser Gly Thr Asp Tyr Thr Leu Thr
                340                 345                 350

Ile Ser Ser Leu Gln Pro Glu Asp Phe Ala Thr Tyr Tyr Cys Gln Gln
            355                 360                 365

Gly Asn Thr Leu Pro Tyr Thr Phe Gly Gln Gly Thr Lys Leu Glu Ile
        370                 375                 380

Lys Gly Gly Gly Gly Ser Gly Gly Gly Gly Ser Gly Gly Gly Gly Ser
```

-continued

```
            385                 390                 395                 400
        Glu Val Gln Leu Val Glu Ser Gly Gly Gly Leu Val Gln Pro Gly Arg
                            405                 410                 415

Ser Leu Arg Leu Ser Cys Thr Ala Ser Gly Val Ser Leu Pro Asp Tyr
                            420                 425                 430

Gly Val Ser Trp Ile Arg Gln Pro Pro Gly Lys Gly Leu Glu Trp Ile
                            435                 440                 445

Gly Val Ile Trp Gly Ser Glu Thr Thr Tyr Tyr Asn Ser Ala Leu Lys
                            450                 455                 460

Ser Arg Phe Thr Ile Ser Arg Asp Asn Ser Lys Asn Thr Leu Tyr Leu
        465                 470                 475                 480

Gln Met Asn Ser Leu Arg Ala Glu Asp Thr Ala Val Tyr Tyr Cys Ala
                            485                 490                 495

Lys His Tyr Tyr Tyr Gly Gly Ser Tyr Ala Met Asp Tyr Trp Gly Gln
                            500                 505                 510

Gly Thr Leu Val Thr Val Ser Ser Ala Ala Leu Asp Asn Glu Lys
                            515                 520                 525

Ser Asn Gly Thr Ile Ile His Val Lys Gly Lys His Leu Cys Pro Ser
                            530                 535                 540

Pro Leu Phe Pro Gly Pro Ser Lys Pro Phe Trp Val Leu Val Val Val
        545                 550                 555                 560

Gly Gly Val Leu Ala Cys Tyr Ser Leu Leu Val Thr Val Ala Phe Ile
                            565                 570                 575

Ile Phe Trp Val Arg Ser Lys Arg Ser Arg Leu Leu His Ser Asp Tyr
                            580                 585                 590

Met Asn Met Thr Pro Arg Arg Pro Gly Pro Thr Arg Lys His Tyr Gln
                            595                 600                 605

Pro Tyr Ala Pro Pro Arg Asp Phe Ala Ala Tyr Arg Ser Arg Val Lys
                            610                 615                 620

Phe Ser Arg Ser Ala Asp Ala Pro Ala Tyr Gln Gln Gly Gln Asn Gln
        625                 630                 635                 640

Leu Tyr Asn Glu Leu Asn Leu Gly Arg Arg Glu Glu Tyr Asp Val Leu
                            645                 650                 655

Asp Lys Arg Arg Gly Arg Asp Pro Glu Met Gly Gly Lys Pro Arg Arg
                            660                 665                 670

Lys Asn Pro Gln Glu Gly Leu Tyr Asn Glu Leu Gln Lys Asp Lys Met
                            675                 680                 685

Ala Glu Ala Tyr Ser Glu Ile Gly Met Lys Gly Glu Arg Arg Arg Gly
                            690                 695                 700

Lys Gly His Asp Gly Leu Tyr Gln Gly Leu Ser Thr Ala Thr Lys Asp
        705                 710                 715                 720

Thr Tyr Asp Ala Leu His Met Gln Ala Leu Pro Pro Arg
                            725                 730

<210> SEQ ID NO 295
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Met Leu Leu Leu Val Thr Ser Leu Leu Leu Cys Glu Leu Pro His Pro
1               5                   10                  15
```

Ala Phe Leu Leu Ile Pro
            20

<210> SEQ ID NO 296
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Ala Asp Pro Phe
                85                  90                  95

Thr Phe Gly Gly Gly Thr Lys Val Glu Ile Lys
            100                 105

<210> SEQ ID NO 297
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gly Gly Gly Gly Ser Gly Lys Pro Gly Ser Gly Glu Gly Gly Ser
1               5                   10                  15

<210> SEQ ID NO 298
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Thr Asp Tyr Ser Ser Gly Met Gly Tyr Gly Met Asp

```
                    100                 105                 110
Val Trp Gly Gln Gly Thr Thr Val Thr Val Ser Ser
            115                 120

<210> SEQ ID NO 299
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gly Gly Gly Gly Ser Gly Lys Pro Gly Ser
1               5                   10

<210> SEQ ID NO 300
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Asp Gln Ala Pro Lys Leu Leu Ile
        35                  40                  45

Lys His Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gln Gly Thr Lys Leu Glu Ile Lys
            100                 105

<210> SEQ ID NO 301
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Gly Gly Gly Gly Ser Gly Gly Gly Gly Ser Gly Gly Gly Gly Ser
1               5                   10                  15

<210> SEQ ID NO 302
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Glu Val Gln Leu Val Glu Ser Gly Gly Gly Leu Val Gln Pro Gly Arg
1               5                   10                  15
```

```
Ser Leu Arg Leu Ser Cys Thr Ala Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 303
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro
            20                  25                  30

<210> SEQ ID NO 304
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 305
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 306
<211> LENGTH: 112
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 306

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 307
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 307

```
Gly Gly Gly Gly Ser
1               5
```

<210> SEQ ID NO 308
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

```
Gly Gly Gly Gly Ser Gly Gly Gly Gly Ser
1               5                   10
```

<210> SEQ ID NO 309
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 309

```
Gly Gly Gly Gly Ser Gly Gly Gly Gly Ser Gly Gly Gly Gly Ser
1               5                   10                  15
```

<210> SEQ ID NO 310
<211> LENGTH: 20
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 310

Gly Gly Gly Gly Ser Gly Gly Gly Ser Gly Gly Gly Ser Gly
1               5                   10                  15

Gly Gly Gly Ser
            20

<210> SEQ ID NO 311
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Pro Ser Thr Pro Pro Thr Pro Ser Pro Ser Thr Pro Pro Thr Pro Ser
1               5                   10                  15

Pro Ser

<210> SEQ ID NO 312
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Pro Ala Pro
      Ala Pro" repeating units

<400> SEQUENCE: 312

Pro Ala Pro Ala Pro Pro Ala Pro Ala Pro Pro Ala Pro Ala Pro Pro
1               5                   10                  15

Ala Pro Ala Pro Pro Ala Pro Ala Pro Pro Ala Pro Ala Pro Pro Ala
            20                  25                  30

Pro Ala Pro Pro Ala Pro Ala Pro Pro Ala Pro Ala Pro Pro Ala Pro
        35                  40                  45

Ala Pro
    50

<210> SEQ ID NO 313
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Glu Ala Ala
      Ala Lys" repeating units

<400> SEQUENCE: 313

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
            20                  25                  30

Ala Ala Lys Glu Ala Ala Ala Lys Glu Ala Ala Ala Lys Glu Ala Ala
        35                  40                  45

Ala Lys
    50
```

```
<210> SEQ ID NO 314
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (4)..(4)
<223> OTHER INFORMATION: Any amino acid

<400> SEQUENCE: 314

Asp Xaa Glu Xaa Asn Pro Gly Pro
1               5
```

CHIMERIC ANTIGEN AND T CELL RECEPTORS AND METHODS OF USE

CROSS-REFERENCE TO RELATED APPLICATIONS

The present application claims the priority benefit of U.S. Provisional Application No. 62/778,893, filed Dec. 12, 2018, which is hereby incorporated by reference in its entirety.

BACKGROUND OF THE DISCLOSURE

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Current therapies T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) and engineered T cell receptors (TCRs), which comprise binding domains capable of interacting with a particular tumor antigen, allow T cells to target and kill cancer cells that express the particular tumor antigen. A need exists for CARs and TCRs for targeting and killing cancer cells.

SUMMARY

In at least a first aspect, the present disclosure comprises an antigen binding system, antibody, or antigen binding fragment thereof comprising an anti-CD20 binding motif, wherein the anti-CD20 binding motif comprises sequences of three heavy chain complementarity determining regions (HCDRs) of any one heavy chain variable region (HCVR) selected from the group consisting of SEQ ID NOs: 1, 23, 45, 67, 89, 111, 133, 155, 177, and 199, and sequences of three light chain CDRs (LCDRs) of any one light chain variable region (LCVR) selected from the group consisting of SEQ ID NOs: 12, 34, 56, 78, 100, 122, 144, 166, 188, and 210. In some embodiments, the anti-CD20 binding motif comprises a first domain comprising three heavy chain complementarity determining regions (HCDR1, HCDR2 and HCDR3) and a second domain comprising three light chain complementarity determining regions (LCDR1, LCDR2 and LCDR3), wherein (i) the HCDR1 has a sequence according to any one of SEQ ID NOs: 3-5, 25-27, 47-49, 69-71, 91-93, 113-115, 135-137, 157-159, 179-181; and 201-203; (ii) the HCDR2 has a sequence according to any one of SEQ ID NOs: 6-8, 28-30, 50-52, 72-74, 94-96, 116-118, 138-140, 160-162, 182-184, and 204-206; (iii) the HCDR3 has a sequence according to any one of SEQ ID NOs: 9-11, 31-33, 53-55, 75-77, 97-99, 119-121, 141-143, 163-165, 185-187, and 207-209; (iv) the LCDR1 has a sequence according to any one of SEQ ID NOs: 14-16, 36-38, 58-60, 80-82, 102-104, 124-126, 146-148, 168-170, 190-192, and 212-214; (v) the LCDR2 has a sequence according to any one of SEQ ID NOs: 17-19, 39-41, 61-63, 83-85, 105-107, 127-129, 149-151, 171-173, 193-195; and 215-217; and (vi) the LCDR3 has a sequence according to any one of SEQ ID NOs: 20-22, 42-44, 64-66, 86-88, 108-110, 130-132, 152-154, 174-176, 196-198, and 218-220. In some embodiments, the HCDRs comprise: (i) an HCDR1 according to any of SEQ ID NOs: 3-5; an HCDR2 according to any of SEQ ID NOs: 6-8; an HCDR3 according to any one of SEQ ID NOs: 9-11; (ii) an HCDR1 according to any of SEQ ID NOs: 25-27; an HCDR2 according to any of SEQ ID NOs: 28-30; an HCDR3 according to any one of SEQ ID NOs: 31-33; (iii) an HCDR1 according to any of SEQ ID NOs: 47-49; an HCDR2 according to any of SEQ ID NOs: 50-52; an HCDR3 according to any one of SEQ ID NOs: 53-55; (iv) an HCDR1 according to any of SEQ ID NOs: 69-71; an HCDR2 according to any of SEQ ID NOs: 72-74; an HCDR3 according to any one of SEQ ID NOs: 75-77; (v) an HCDR1 according to any of SEQ ID NOs: 91-93; an HCDR2 according to any of SEQ ID NOs: 94-96; an HCDR3 according to any one of SEQ ID NOs: 97-99; (vi) an HCDR1 according to any of SEQ ID NOs: 113-115; an HCDR2 according to any of SEQ ID NOs: 116-118; an HCDR3 according to any one of SEQ ID NOs: 119-121; (vii) an HCDR1 according to any of SEQ ID NOs: 135-137; an HCDR2 according to any of SEQ ID NOs: 138-140; an HCDR3 according to any one of SEQ ID NOs: 141-143; (viii) an HCDR1 according to any of SEQ ID NOs: 157-159; an HCDR2 according to any of SEQ ID NOs: 160-162; an HCDR3 according to any one of SEQ ID NOs: 163-165; (ix) an HCDR1 according to any of SEQ ID NOs: 179-181; an HCDR2 according to any of SEQ ID NOs: 182-184; an HCDR3 according to any one of SEQ ID NOs: 185-187; or (x) an HCDR1 according to any of SEQ ID NOs: 201-203; an HCDR2 according to any of SEQ ID NOs: 204-206; an HCDR3 according to any one of SEQ ID NOs: 207-209; and the LCDRs comprise: (i) an LCDR1 according to any of SEQ ID NOs: 14-16; an LCDR2 according to any of SEQ ID NOs: 17-19; an LCDR3 according to any one of SEQ ID NOs: 20-22; (ii) an LCDR1 according to any of SEQ ID NOs: 36-38; an LCDR2 according to any of SEQ ID NOs: 39-41; an LCDR3 according to any one of SEQ ID NOs: 42-44; (iii) an LCDR1 according to any of SEQ ID NOs: 58-60; an LCDR2 according to any of SEQ ID NOs: 61-63; an LCDR3 according to any one of SEQ ID NOs: 64-66; (iv) an LCDR1 according to any of SEQ ID NOs: 80-82; an LCDR2 according to any of SEQ ID NOs: 83-85; an LCDR3 according to any one of SEQ ID NOs: 86-88; (v) an LCDR1 according to any of SEQ ID NOs: 102-104; an LCDR2 according to any of SEQ ID NOs: 105-107; an LCDR3 according to any one of SEQ ID NOs: 108-110; (vi) an LCDR1 according to any of SEQ ID NOs: 124-126; an LCDR2 according to any of SEQ ID NOs: 127-129; an LCDR3 according to any one of SEQ ID NOs: 130-132; (vii) an LCDR1 according to any of SEQ ID NOs: 146-148; an LCDR2 according to any of SEQ ID NOs: 149-151; an LCDR3 according to any one of SEQ ID NOs: 152-154; (viii) an LCDR1 according to any of SEQ ID NOs: 168-170; an LCDR2 according to any of SEQ ID NOs: 171-173; an LCDR3 according to any one of SEQ ID NOs: 174-176; (ix) an LCDR1 according to any of SEQ ID NOs: 190-192; an LCDR2 according to any of SEQ ID NOs: 193-195; an LCDR3 according to any one of SEQ ID NOs: 196-198; or (x) an LCDR1 according to any of SEQ ID NOs: 212-214; an LCDR2 according to any of SEQ ID NOs: 215-217; an LCDR3 according to any one of SEQ ID NOs: 218-220.

In various embodiments, an antigen binding system, antibody, or antigen binding fragment thereof of the present disclosure comprises a first domain comprising three heavy chain complementarity determining regions (HCDRs) and a second domain comprising three light chain complementarity determining regions (LCDRs), wherein: the HCDRs and LCDRs comprise: (i) an HCDR1 according to any of SEQ ID NOs: 3-5; an HCDR2 according to any of SEQ ID NOs: 6-8; an HCDR3 according to any one of SEQ ID NOs: 9-11; an LCDR1 according to any of SEQ ID NOs: 14-16; an LCDR2 according to any of SEQ ID NOs: 17-19; an LCDR3 according to any one of SEQ ID NOs: 20-22; (ii) an HCDR1 according to any of SEQ ID NOs: 25-27; an HCDR2 according to any of SEQ ID NOs: 28-30; an HCDR3 according to any one of SEQ ID NOs: 31-33; an LCDR1 according to any of SEQ ID NOs: 36-38; an LCDR2 according to any of SEQ ID NOs: 39-41; an LCDR3 according to any one of SEQ ID NOs: 42-44; (iii) an HCDR1 according to any of SEQ ID NOs: 47-49; an HCDR2 according to any of SEQ ID NOs: 50-52; an HCDR3 according to any one of SEQ ID NOs: 53-55; an LCDR1 according to any of SEQ ID NOs: 58-60; an LCDR2 according to any of SEQ ID NOs: 61-63; an LCDR3 according to any one of SEQ ID NOs: 64-66; (iv) an HCDR1 according to any of SEQ ID NOs: 69-71; an HCDR2 according to any of SEQ ID NOs: 72-74; an HCDR3 according to any one of SEQ ID NOs: 75-77; an LCDR1 according to any of SEQ ID NOs: 80-82; an LCDR2 according to any of SEQ ID NOs: 83-85; an LCDR3 according to any one of SEQ ID NOs: 86-88; (v) an HCDR1 according to any of SEQ ID NOs: 91-93; an HCDR2 according to any of SEQ ID NOs: 94-96; an HCDR3 according to any one of SEQ ID NOs: 97-99; an LCDR1 according to any of SEQ ID NOs: 102-104; an LCDR2 according to any of SEQ ID NOs: 105-107; an LCDR3 according to any one of SEQ ID NOs: 108-110; (vi) an HCDR1 according to any of SEQ ID NOs: 113-115; an HCDR2 according to any of SEQ ID NOs: 116-118; an HCDR3 according to any one of SEQ ID NOs: 119-121; an LCDR1 according to any of SEQ ID NOs: 124-126; an LCDR2 according to any of SEQ ID NOs: 127-129; an LCDR3 according to any one of SEQ ID NOs: 130-132; (vii) an HCDR1 according to any of SEQ ID NOs: 135-137; an HCDR2 according to any of SEQ ID NOs: 138-140; an HCDR3 according to any one of SEQ ID NOs: 141-143; an LCDR1 according to any of SEQ ID NOs: 146-148; an LCDR2 according to any of SEQ ID NOs: 149-151; an LCDR3 according to any one of SEQ ID NOs: 152-154; (viii) an HCDR1 according to any of SEQ ID NOs: 157-159; an HCDR2 according to any of SEQ ID NOs: 160-162; an HCDR3 according to any one of SEQ ID NOs: 163-165; an LCDR1 according to any of SEQ ID NOs: 168-170; an LCDR2 according to any of SEQ ID NOs: 171-173; an LCDR3 according to any one of SEQ ID NOs: 174-176; (ix) an HCDR1 according to any of SEQ ID NOs: 179-181; an HCDR2 according to any of SEQ ID NOs: 182-184; an HCDR3 according to any one of SEQ ID NOs: 185-187; an LCDR1 according to any of SEQ ID NOs: 190-192; an LCDR2 according to any of SEQ ID NOs: 193-195; an LCDR3 according to any one of SEQ ID NOs: 196-198; or (x) an HCDR1 according to any of SEQ ID NOs: 201-203; an HCDR2 according to any of SEQ ID NOs: 204-206; an HCDR3 according to any one of SEQ ID NOs: 207-209; an LCDR1 according to any of SEQ ID NOs: 212-214; an LCDR2 according to any of SEQ ID NOs: 215-217; an LCDR3 according to any one of SEQ ID NOs: 218-220. In some embodiments, the antigen binding system, antibody, or antigen binding fragment thereof comprises a first heavy chain variable domain comprising the three HCDRs and a light chain variable domain comprising the three LCDRs, wherein: (i) the heavy chain variable domain is at least 80% identical to SEQ ID NO: 1, SEQ ID NO: 23, SEQ ID NO: 45, SEQ ID NO: 67, SEQ ID NO: 89, SEQ ID NO: 111, SEQ ID NO: 133, SEQ ID NO: 155, SEQ ID NO: 177, or SEQ ID NO: 199; and (ii) the light chain variable domain is at least 80% identical to SEQ ID NO: 12, SEQ ID NO: 34, SEQ ID NO: 56, SEQ ID NO: 78, SEQ ID NO: 100, SEQ ID NO: 122, SEQ ID NO: 144, SEQ ID NO: 166, SEQ ID NO: 188, or SEQ ID NO: 210. In some embodiments, the antigen binding system, antibody, or antigen binding fragment thereof comprises a first heavy chain variable domain comprising the three HCDRs and a light chain variable domain comprising the three LCDRs, wherein: (i) the heavy chain variable domain is at least 80% identical to SEQ ID NO: 1 and the light chain variable domain is at least 80% identical to SEQ ID NO: 12; (ii) the heavy chain variable domain is at least 80% identical to SEQ ID NO: 23 and the light chain variable domain is at least 80% identical to SEQ ID NO: 34; (iii) the heavy chain variable domain is at least 80% identical to SEQ ID NO: 45 and the light chain variable domain is at least 80% identical to SEQ ID NO: 56; (iv) the heavy chain variable domain is at least 80% identical to SEQ ID NO: 67 and the light chain variable domain is at least 80% identical to SEQ ID NO: 78; (v) the heavy chain variable domain is at least 80% identical to SEQ ID NO: 89 and the light chain variable domain is at least 80% identical to SEQ ID NO: 100; (vi) the heavy chain variable domain is at least 80% identical to SEQ ID NO: 111 and the light chain variable domain is at least 80% identical to SEQ ID NO: 122; (vii) the heavy chain variable domain is at least 80% identical to SEQ ID NO: 133 and the light chain variable domain is at least 80% identical to SEQ ID NO: 144; (viii) the heavy chain variable domain is at least 80% identical to SEQ ID NO: 155 and the light chain variable domain is at least 80% identical to SEQ ID NO: 166; (ix) the heavy chain variable domain is at least 80% identical to SEQ ID NO: 177 and the light chain variable domain is at least 80% identical to SEQ ID NO: 188; or (x) the heavy chain variable domain is at least 80% identical to SEQ ID NO: 199 and the light chain variable domain is at least 80% identical to SEQ ID NO: 210.

In some embodiments of the present disclosure comprising the three HCDRs and the three LCDRs, the three HCDRs and the three LCDRs are comprised by a single polypeptide. In some embodiments of the present disclosure comprising the three HCDRs and the three LCDRs, the three HCDRs are comprised by a first polypeptide and the three LCDRs are comprised by a second polypeptide. In some embodiments, the first polypeptide is an antibody heavy chain and the second polypeptide is an antibody light chain.

In some embodiments, the antigen binding system, antibody, or antigen binding fragment thereof further comprises: (i) a binding motif that binds an antigen selected from the group consisting of 5T4, alphafetoprotein, B cell maturation antigen (BCMA), B cell receptor, CA-125, carcinoembryonic antigen, CD19, CD20, CD22, CD23, CD30, CD33, CD40, CD56, CD79, CD78, CD123, CD138, c-Met, CSPG4, IgM, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gp120, IL-11Ralpha, kappa chain, lambda chain, melanoma-associated antigen, mesothelin, MUC-1, mutated p53, mutated ras, prostate-specific antigen, ROR1, VEGFR2, EphA3 (EPH receptor A3), BAFFR (B-cell activating factor receptor), and combinations thereof; and/or (ii) a binding motif that binds an antigen that is characteristic of B-cells, optionally wherein the antigen that is characteristic of B-cells is not CD19 or CD20. In some embodiments, the antigen binding system, antibody, or antigen binding fragment thereof further comprises an anti-CD19 binding motif. In some embodiments, the anti-CD19 binding motif comprises a first domain comprising three HCDRs and a second domain comprising three LCDRs, wherein: the three HCDRs of the anti-CD19 binding motif comprise an HCDR1, an HCDR2, and an HCDR3; the three LCDRs of the anti-CD19 binding motif comprise an LCDR1, an LCDR2, and an LCDR3; and the HCDRs and LCDRs of the anti-CD19 binding motif comprise an HCDR1 according to any of SEQ ID NOs: 223-225; an HCDR2 according to any of SEQ ID NOs: 226-228; an HCDR3 according to any one of SEQ ID NOs: 229-231; an LCDR1 according to any of SEQ ID NOs: 234-236; an LCDR2 according to any of SEQ ID NOs: 237-239; an LCDR3 according to any one of SEQ ID NOs: 240-242. In some embodiments, the anti-CD19 binding motif comprises a first heavy chain variable domain comprising the three HCDRs of the anti-CD19 binding motif and a light chain variable domain comprising the three LCDRs of the anti-CD19 binding motif, wherein the heavy chain variable domain of the anti-CD19 binding motif is at least 80% identical to SEQ ID NO: 221 and the light chain variable domain of the anti-CD19 binding motif is at least 80% identical to SEQ ID NO: 232. In some embodiments, the three HCDRs of the anti-CD19 binding motif and the three LCDRs of the anti-CD19 binding motif are comprised by a single polypeptide. In some embodiments, the three HCDRs of the anti-CD20 binding motif, the three LCDRs of the anti-CD20 binding motif, the three HCDRs of the anti-CD19 binding motif, and the three LCDRs of the anti-CD19 binding motif are together comprised by a single polypeptide.

In various embodiments, the antigen binding system, antibody, or antigen binding fragment thereof is, or is comprised by, a chimeric antigen receptor. In some embodiments, the antigen binding system, antibody, or antigen binding fragment thereof is a single polypeptide that is, or is comprised by, a chimeric antigen receptor, which chimeric antigen receptor is a bispecific chimeric antigen receptor. In some embodiments, the chimeric antigen receptor comprises a transmembrane domain that is a transmembrane domain of 4-1BB/CD137, an alpha chain of a T cell receptor, a beta chain of a T cell receptor, CD3 epsilon, CD4, CD5, CD8 alpha, CD9, CD16, CD19, CD22, CD28, CD33, CD37, CD45, CD64, CD80, CD86, CD134, CD137, CD154, or a zeta chain of a T cell receptor, or any combination thereof. In some embodiments, (i) the three HCDRs of the anti-CD20 binding motif and the three LCDRs of the anti-CD20 binding motif are present in a first polypeptide and (ii) the three HCDRs of the anti-CD19 binding motif and the three LCDRs of the anti-CD19 binding motif are together comprised by a second different polypeptide. In some embodiments, the first polypeptide is, or is comprised by, a first chimeric antigen receptor. In some embodiments, the second polypeptide is, or is comprised by, a second chimeric antigen receptor.

In various embodiments, the present disclosure comprises a nucleic acid encoding at least one polypeptide of the present disclosure and/or a vector comprising such a nucleic acid. The present disclosure further comprises a method of generating an engineered cell, the method comprising transfecting or transducing a cell with a nucleic acid encoding at least one polypeptide of the present disclosure. Further provided herein is a cell encoding or expressing an antigen binding system, antibody, or antigen binding fragment provided herein, optionally wherein the cell is an immune cell, optionally wherein the cell is a T cell.

The present disclosure further comprises a method of treating cancer in a subject in need thereof, the method comprising administering to the subject a cell therapy composition comprising one or more cells that encode or comprise an antigen binding system, antibody, or antigen binding fragment thereof of the present disclosure. Also provided herein is a method of inducing an immune response in a subject or immunizing a subject against a cancer, the method comprising administering to the subject a cell therapy composition comprising one or more cells that encode or comprise an antigen binding system, antibody, or antigen binding fragment thereof of the present disclosure. In some embodiments, the cells are CAR-T cells. In various embodiments, the cancer is acute lymphoblastic leukemia (ALL) (including non T cell ALL), acute myeloid leukemia, B cell prolymphocytic leukemia, B cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia, chronic or acute leukemia, diffuse large B cell lymphoma (DLBCL), follicular lymphoma (FL), hairy cell leukemia, Hodgkin's Disease, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome, non-Hodgkin's lymphoma (NHL), plasma cell proliferative disorder (including asymptomatic myeloma (smoldering multiple myeloma or indolent myeloma), plasmablastic lymphoma, plasmacytoid dendritic cell neoplasm, plasmacytomas (including plasma cell dyscrasia; solitary myeloma; solitary plasmacytoma; extramedullary plasmacytoma; and multiple plasmacytoma), POEMS syndrome (also known as Crow-Fukase syndrome; Takatsuki disease; and PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, or Waldenstrom macroglobulinemia, Mantle cell lymphoma (MCL), Transformed follicular lymphoma (TFL), Primary mediastinal B cell lymphoma (PMBCL), Multiple myeloma, Hairy cell lymphoma/leukemia, or a combination thereof. In some embodiments, cell therapy is an allogeneic cell therapy or an autologous cell therapy.

At least one aspect of the present disclosure includes a chimeric antigen receptor comprising an anti-CD20 binding motif, the anti-CD20 binding motif comprising three heavy chain complementarity determining regions (HCDRs) contained within any one of the heavy chain variable region (HCVR) sequences selected from the group consisting of SEQ ID NOs: 1, 23, 45, 67, 89, 111, 133, 155, 177, and 199, and three light chain CDRs (LCDRs) contained within any one of the light chain variable region (LCVR) sequences selected from the group consisting of SEQ ID NOs: 12, 34, 56, 78, 100, 122, 144, 166, 188, and 210. In some embodiments, a first domain comprising the three heavy chain complementarity determining regions (HCDRs) and a second domain comprising the three light chain complementarity determining regions (LCDRs), wherein (i) the HCDR1 has a sequence according to any one of SEQ ID NOs: 3-5, 25-27, 47-49, 69-71, 91-93, 113-115, 135-137, 157-159, 179-181; and 201-203; (ii) the HCDR2 has a sequence according to any one of SEQ ID NOs: 6-8, 28-30, 50-52, 72-74, 94-96, 116-118, 138-140, 160-162, 182-184; and 204-206; (iii) the HCDR3 has a sequence according to any one of SEQ ID NOs: 9-11, 31-33, 53-55, 75-77, 97-99, 119-121, 141-143, 163-165, 185-187; and 207-209; (iv) the LCDR1 has a sequence according to any one of SEQ ID NOs: 14-16, 36-38, 58-60, 80-82, 102-104, 124-126, 146-148, 168-170, 190-192; and 212-214; (v) the LCDR2 has a sequence according to any one of SEQ ID NOs: 17-19, 39-41, 61-63, 83-85, 105-107, 127-129, 149-151, 171-173, 193-195; and 215-217; and (vi) the LCDR3 has a sequence according to any one of SEQ ID NOs: 20-22, 42-44, 64-66, 86-88, 108-110, 130-132, 152-154, 174-176, 196-198; and 218-220. In some embodiments, the HCDRs comprise: (i) an HCDR1 according to any of SEQ ID NOs: 3-5; an HCDR2 according to any of SEQ ID NOs: 6-8; an HCDR3 according to any one of SEQ ID NOs: 9-11; (ii) an HCDR1 according to any of SEQ ID NOs: 25-27; an HCDR2 according to any of SEQ ID NOs: 28-30; an HCDR3 according to any one of SEQ ID NOs: 31-33; (iii) an HCDR1 according to any of SEQ ID NOs: 47-49; an HCDR2 according to any of SEQ ID NOs: 50-52; an HCDR3 according to any one of SEQ ID NOs: 53-55; (iv) an HCDR1 according to any of SEQ ID NOs: 69-71; an HCDR2 according to any of SEQ ID NOs: 72-74; an HCDR3 according to any one of SEQ ID NOs: 75-77; (v) an HCDR1 according to any of SEQ ID NOs: 91-93; an HCDR2 according to any of SEQ ID NOs: 94-96; an HCDR3 according to any one of SEQ ID NOs: 97-99; (vi) an HCDR1 according to any of SEQ ID NOs: 113-115; an HCDR2 according to any of SEQ ID NOs: 116-118; an HCDR3 according to any one of SEQ ID NOs: 119-121; (vii) an HCDR1 according to any of SEQ ID NOs: 135-137; an HCDR2 according to any of SEQ ID NOs: 138-140; an HCDR3 according to any one of SEQ ID NOs: 141-143; (viii) an HCDR1 according to any of SEQ ID NOs: 157-159; an HCDR2 according to any of SEQ ID NOs: 160-162; an HCDR3 according to any one of SEQ ID NOs: 163-165; (ix) an HCDR1 according to any of SEQ ID NOs: 179-181; an HCDR2 according to any of SEQ ID NOs: 182-184; an HCDR3 according to any one of SEQ ID NOs: 185-187; or (x) an HCDR1 according to any of SEQ ID NOs: 201-203; an HCDR2 according to any of SEQ ID NOs: 204-206; an HCDR3 according to any one of SEQ ID NOs: 207-209; and the LCDRs comprise: (i) an LCDR1 according to any of SEQ ID NOs: 14-16; an LCDR2 according to any of SEQ ID NOs: 17-19; an LCDR3 according to any one of SEQ ID NOs: 20-22; (ii) an LCDR1 according to any of SEQ ID NOs: 36-38; an LCDR2 according to any of SEQ ID NOs: 39-41; an LCDR3 according to any one of SEQ ID NOs: 42-44; (iii) an LCDR1 according to any of SEQ ID NOs: 58-60; an LCDR2 according to any of SEQ ID NOs: 61-63; an LCDR3 according to any one of SEQ ID NOs: 64-66; (iv) an LCDR1 according to any of SEQ ID NOs: 80-82; an LCDR2 according to any of SEQ ID NOs: 83-85; an LCDR3 according to any one of SEQ ID NOs: 86-88; (v) an LCDR1 according to any of SEQ ID NOs: 102-104; an LCDR2 according to any of SEQ ID NOs: 105-107; an LCDR3 according to any one of SEQ ID NOs: 108-110; (vi) an LCDR1 according to any of SEQ ID NOs: 124-126; an LCDR2 according to any of SEQ ID NOs: 127-129; an LCDR3 according to any one of SEQ ID NOs: 130-132; (vii) an LCDR1 according to any of SEQ ID NOs: 146-148; an LCDR2 according to any of SEQ ID NOs: 149-151; an LCDR3 according to any one of SEQ ID NOs: 152-154; (viii) an LCDR1 according to any of SEQ ID NOs: 168-170; an LCDR2 according to any of SEQ ID NOs: 171-173; an LCDR3 according to any one of SEQ ID NOs: 174-176; (ix) an LCDR1 according to any of SEQ ID NOs: 190-192; an LCDR2 according to any of SEQ ID NOs: 193-195; an LCDR3 according to any one of SEQ ID NOs: 196-198; or (x) an LCDR1 according to any of SEQ ID NOs: 212-214; an LCDR2 according to any of SEQ ID NOs: 215-217; an LCDR3 according to any one of SEQ ID NOs: 218-220.

In some embodiments, the chimeric antigen receptor comprises a first domain comprising three heavy chain complementarity determining regions (HCDRs) and a second domain comprising three light chain complementarity determining regions (LCDRs), wherein: the three HCDRs comprise an HCDR1, an HCDR2, and an HCDR3; the three LCDRs comprise an LCDR1, an LCDR2, and an LCDR3; and the HCDRs and LCDRs comprise: (i) an HCDR1 according to any of SEQ ID NOs: 3-5; an HCDR2 according to any of SEQ ID NOs: 6-8; an HCDR3 according to any one of SEQ ID NOs: 9-11; an LCDR1 according to any of SEQ ID NOs: 14-16; an LCDR2 according to any of SEQ ID NOs: 17-19; an LCDR3 according to any one of SEQ ID NOs: 20-22; (ii) an HCDR1 according to any of SEQ ID NOs: 25-27; an HCDR2 according to any of SEQ ID NOs: 28-30; an HCDR3 according to any one of SEQ ID NOs: 31-33; an LCDR1 according to any of SEQ ID NOs: 36-38; an LCDR2 according to any of SEQ ID NOs: 39-41; an LCDR3 according to any one of SEQ ID NOs: 42-44; (iii) an HCDR1 according to any of SEQ ID NOs: 47-49; an HCDR2 according to any of SEQ ID NOs: 50-52; an HCDR3 according to any one of SEQ ID NOs: 53-55; an LCDR1 according to any of SEQ ID NOs: 58-60; an LCDR2 according to any of SEQ ID NOs: 61-63; an LCDR3 according to any one of SEQ ID NOs: 64-66; (iv) an HCDR1 according to any of SEQ ID NOs: 69-71; an HCDR2 according to any of SEQ ID NOs: 72-74; an HCDR3 according to any one of SEQ ID NOs: 75-77; an LCDR1 according to any of SEQ ID NOs: 80-82; an LCDR2 according to any of SEQ ID NOs: 83-85; an LCDR3 according to any one of SEQ ID NOs: 86-88; (v) an HCDR1 according to any of SEQ ID NOs: 91-93; an HCDR2 according to any of SEQ ID NOs: 94-96; an HCDR3 according to any one of SEQ ID NOs: 97-99; an LCDR1 according to any of SEQ ID NOs: 102-104; an LCDR2 according to any of SEQ ID NOs: 105-107; an LCDR3 according to any one of SEQ ID NOs: 108-110; (vi) an HCDR1 according to any of SEQ ID NOs: 113-115; an HCDR2 according to any of SEQ ID NOs: 116-118; an HCDR3 according to any one of SEQ ID NOs: 119-121; an LCDR1 according to any of SEQ ID NOs: 124-126; an LCDR2 according to any of SEQ ID NOs: 127-129; an LCDR3 according to any one of SEQ ID NOs: 130-132; (vii) an HCDR1 according to any of SEQ ID NOs: 135-137; an HCDR2 according to any of SEQ ID NOs: 138-140; an HCDR3 according to any one of SEQ ID NOs: 141-143; an LCDR1 according to any of SEQ ID NOs: 146-148; an LCDR2 according to any of SEQ ID NOs: 149-151; an LCDR3 according to any one of SEQ ID NOs: 152-154; (viii) an HCDR1 according to any of SEQ ID NOs: 157-159; an HCDR2 according to any of SEQ ID NOs: 160-162; an HCDR3 according to any one of SEQ ID NOs: 163-165; an LCDR1 according to any of SEQ ID NOs: 168-170; an LCDR2 according to any of SEQ ID NOs: 171-173; an LCDR3 according to any one of SEQ ID NOs: 174-176; (ix) an HCDR1 according to any of SEQ ID NOs: 179-181; an HCDR2 according to any of SEQ ID NOs: 182-184; an HCDR3 according to any one of SEQ ID NOs: 185-187; an LCDR1 according to any of SEQ ID NOs: 190-192; an LCDR2 according to any of SEQ ID NOs: 193-195; an LCDR3 according to any one of SEQ ID NOs: 196-198; or (x) an HCDR1 according to any of SEQ ID NOs: 201-203;

an HCDR2 according to any of SEQ ID NOs: 204-206; an HCDR3 according to any one of SEQ ID NOs: 207-209; an LCDR1 according to any of SEQ ID NOs: 212-214; an LCDR2 according to any of SEQ ID NOs: 215-217; an LCDR3 according to any one of SEQ ID NOs: 218-220. In various embodiments, the chimeric antigen receptor comprises a first heavy chain variable domain comprising the three HCDRs and a light chain variable domain comprising the three LCDRs, wherein: (i) the heavy chain variable domain is at least 80% identical to SEQ ID NO: 1, SEQ ID NO: 23, SEQ ID NO: 45, SEQ ID NO: 67, SEQ ID NO: 89, SEQ ID NO: 111, SEQ ID NO: 133, SEQ ID NO: 155, SEQ ID NO: 177, or SEQ ID NO: 199; and (ii) the light chain variable domain is at least 80% identical to SEQ ID NO: 12, SEQ ID NO: 34, SEQ ID NO: 56, SEQ ID NO: 78, SEQ ID NO: 100, SEQ ID NO: 122, SEQ ID NO: 144, SEQ ID NO: 166, SEQ ID NO: 188, or SEQ ID NO: 210. In some embodiments, the chimeric antigen receptor comprises a first heavy chain variable domain comprising the three HCDRs and a light chain variable domain comprising the three LCDRs, wherein: (i) the heavy chain variable domain is at least 80% identical to SEQ ID NO: 1 and the light chain variable domain is at least 80% identical to SEQ ID NO: 12; (ii) the heavy chain variable domain is at least 80% identical to SEQ ID NO: 23 and the light chain variable domain is at least 80% identical to SEQ ID NO: 34; (iii) the heavy chain variable domain is at least 80% identical to SEQ ID NO: 45 and the light chain variable domain is at least 80% identical to SEQ ID NO: 56; (iv) the heavy chain variable domain is at least 80% identical to SEQ ID NO: 67 and the light chain variable domain is at least 80% identical to SEQ ID NO: 78; (v) the heavy chain variable domain is at least 80% identical to SEQ ID NO: 89 and the light chain variable domain is at least 80% identical to SEQ ID NO: 100; (vi) the heavy chain variable domain is at least 80% identical to SEQ ID NO: 111 and the light chain variable domain is at least 80% identical to SEQ ID NO: 122; (vii) the heavy chain variable domain is at least 80% identical to SEQ ID NO: 133 and the light chain variable domain is at least 80% identical to SEQ ID NO: 144; (viii) the heavy chain variable domain is at least 80% identical to SEQ ID NO: 155 and the light chain variable domain is at least 80% identical to SEQ ID NO: 166; (ix) the heavy chain variable domain is at least 80% identical to SEQ ID NO: 177 and the light chain variable domain is at least 80% identical to SEQ ID NO: 188; or (x) the heavy chain variable domain is at least 80% identical to SEQ ID NO: 199 and the light chain variable domain is at least 80% identical to SEQ ID NO: 210.

In some embodiments comprising three HCDRs and the three LCDRs, the three HCDRs and the three LCDRs are comprised by a single polypeptide. In some embodiments comprising three HCDRs and the three LCDRs, the three HCDRs are comprised by a first polypeptide and the three LCDRs are comprised by a second polypeptide. In some embodiments, the first polypeptide is an antibody heavy chain and the second polypeptide is an antibody light chain. In some embodiments, the chimeric antigen receptor further comprises: (i) a binding motif that specifically binds an antigen selected from the group consisting of 5T4, alphafetoprotein, B cell maturation antigen (BCMA), B cell receptor, CA-125, carcinoembryonic antigen, CD19, CD20, CD22, CD23, CD30, CD33, CD40, CD56, CD79, CD78, CD123, CD138, c-Met, CSPG4, IgM, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gp120, IL-11Ralpha, kappa chain, lambda chain, melanoma-associated antigen, mesothelin, MUC-1, mutated p53, mutated ras, prostate-specific antigen, ROR1, VEGFR2, EphA3 (EPH receptor A3), BAFFR (B-cell activating factor receptor), and combinations thereof; and/or (ii) a binding motif that specifically binds an antigen that is characteristic of B-cells, optionally wherein the antigen that is characteristic of B-cells is not CD19 or CD20. In some embodiments, the chimeric antigen receptor further comprises an anti-CD19 binding motif.

In some embodiments, the anti-CD19 binding motif comprises a first domain comprising three HCDRs and a second domain comprising three LCDRs, wherein: the three HCDRs of the anti-CD19 binding motif comprise an HCDR1, an HCDR2, and an HCDR3; the three LCDRs of the anti-CD19 binding motif comprise an LCDR1, an LCDR2, and an LCDR3; and the HCDRs and LCDRs of the anti-CD19 binding motif comprise an HCDR1 according to any of SEQ ID NOs: 223-225; an HCDR2 according to any of SEQ ID NOs: 226-228; an HCDR3 according to any one of SEQ ID NOs: 229-231; an LCDR1 according to any of SEQ ID NOs: 234-236; an LCDR2 according to any of SEQ ID NOs: 237-239; an LCDR3 according to any one of SEQ ID NOs: 240-242. In some embodiments, the anti-CD19 binding motif comprises a first heavy chain variable domain comprising the three HCDRs of the anti-CD19 binding motif and a light chain variable domain comprising the three LCDRs of the anti-CD19 binding motif, wherein the heavy chain variable domain of the anti-CD19 binding motif is at least 80% identical to SEQ ID NO: 221 and the light chain variable domain of the anti-CD19 binding motif is at least 80% identical to SEQ ID NO: 232. In some embodiments, the three HCDRs of the anti-CD19 binding motif and the three LCDRs of the anti-CD19 binding motif are comprised by a single polypeptide.

In some embodiments, the three HCDRs of the anti-CD20 binding motif, the three LCDRs of the anti-CD20 binding motif, the three HCDRs of the anti-CD19 binding motif, and the three LCDRs of the anti-CD19 binding motif are together comprised by a single polypeptide. In some embodiments, the chimeric antigen receptor comprises a transmembrane domain that is a transmembrane domain of 4-1BB/CD137, an alpha chain of a T cell receptor, a beta chain of a T cell receptor, CD3 epsilon, CD4, CD5, CD8 alpha, CD9, CD16, CD19, CD22, CD28, CD33, CD37, CD45, CD64, CD80, CD86, CD134, CD137, CD154, or a zeta chain of a T cell receptor, or any combination thereof.

In various embodiments, the present disclosure comprises a bicistronic chimeric antigen receptor comprising a first chimeric antigen receptor of the present disclosure and a second chimeric antigen receptor that comprises a binding motif that specifically binds an antigen selected from the group consisting of 5T4, alphafetoprotein, B cell maturation antigen (BCMA), B cell receptor, CA-125, carcinoembryonic antigen, CD19, CD20, CD22, CD23, CD30, CD33, CD40, CD56, CD79, CD78, CD123, CD138, c-Met, CSPG4, IgM, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gp120, IL-11Ralpha, kappa chain, lambda chain, melanoma-associated antigen, mesothelin, MUC-1, mutated p53, mutated ras, prostate-specific antigen, ROR1, VEGFR2, EphA3 (EPH receptor A3), BAFFR (B-cell activating factor receptor), and combinations thereof; and/or a binding motif that specifically binds an antigen that is characteristic of B-cells, optionally wherein the antigen that is characteristic of B-cells is not CD19 or CD20. In some embodiments, the second chimeric antigen receptor comprises an anti-CD19 binding motif.

The present disclosure further provides a nucleic acid encoding at least one polypeptide of the present disclosure and/or a vector comprising such nucleic acid. The present disclosure also comprises a method of generating an engineered cell, the method comprising transfecting or transducing a cell with a nucleic acid of the present disclosure. In various embodiments, the present disclosure comprises a cell encoding or expressing the chimeric antigen receptor provided herein, optionally wherein the cell is an immune cell, optionally wherein the cell is a T cell.

The present disclosure further provides a method of treating cancer in a subject in need thereof, the method comprising administering to the subject a cell therapy composition comprising one or more cells that encode or comprise an chimeric antigen receptor of the present disclosure. The present disclosure further provides a method of inducing an immune response in a subject or immunizing a subject against a cancer, the method comprising administering to the subject a cell therapy composition comprising one or more cells that encode or comprise an chimeric antigen receptor of the present disclosure. In various embodiments, the cells are CAR-T cells. In various embodiments, the cancer is acute lymphoblastic leukemia (ALL) (including non T cell ALL), acute myeloid leukemia, B cell prolymphocytic leukemia, B cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia, chronic or acute leukemia, diffuse large B cell lymphoma (DLBCL), follicular lymphoma (FL), hairy cell leukemia, Hodgkin's Disease, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome, non-Hodgkin's lymphoma (NHL), plasma cell proliferative disorder (including asymptomatic myeloma (smoldering multiple myeloma or indolent myeloma), plasmablastic lymphoma, plasmacytoid dendritic cell neoplasm, plasmacytomas (including plasma cell dyscrasia; solitary myeloma; solitary plasmacytoma; extramedullary plasmacytoma; and multiple plasmacytoma), POEMS syndrome (also known as Crow-Fukase syndrome; Takatsuki disease; and PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, or Waldenstrom macroglobulinemia, Mantle cell lymphoma (MCL), Transformed follicular lymphoma (TFL), Primary mediastinal B cell lymphoma (PMBCL), Multiple myeloma, Hairy cell lymphoma/leukemia, or a combination thereof. In some embodiments, the cell therapy is an allogeneic cell therapy or an autologous cell therapy.

In at least one aspect, the present disclosure comprises a chimeric antigen receptor comprising an anti-CD20 binding motif and a CD19 binding motif, wherein the anti-CD20 binding motif comprising amino acid sequences selected from the group consisting of SEQ ID NOs: 1, 23, 45, 67, 89, 111, 133, 155, 177, 199, 12, 34, 56, 78, 100, 122, 144, 166, 188, and 210. In some embodiments, the CD19 binding motif comprising amino acid sequences selected from the group consisting of SEQ ID NOs: 221 and 232. In some embodiments, the anti-CD20 binding motif comprising amino acid sequences selected from the group consisting of SEQ ID NOs: 1, 23, 45, 67, 89, 111, 133, 155, 177, 199, 12, 34, 56, 78, 100, 122, 144, 166, 188, and 210; wherein the CD19 binding motif comprising amino acid sequences selected from the group consisting of SEQ ID NOs: 221 and 232. In some embodiments, the anti-CD20 binding motif and the CD19 binding motif are comprised by one polypeptide. In some embodiments, the anti-CD20 binding motif and the CD19 binding motif are comprised by different polypeptides.

In at least one aspect, the present disclosure comprises a polynucleotide encoding amino acid sequences selected from the group consisting of SEQ ID NOs: 1, 23, 45, 67, 89, 111, 133, 155, 177, 199, 12, 34, 56, 78, 100, 122, 144, 166, 188, and 210. In at least one aspect, the present disclosure comprises a pharmaceutical composition comprising a chimeric antigen receptor comprising an anti-CD20 binding motif having amino acid sequences selected from the group consisting of SEQ ID NOs: 1, 23, 45, 67, 89, 111, 133, 155, 177, 199, 12, 34, 56, 78, 100, 122, 144, 166, 188, and 210. In some embodiments, the composition further comprises a CD19 binding motif.

DETAILED DESCRIPTION OF THE DISCLOSURE

The present disclosure relates to novel polypeptides comprising novel antigen binding molecules and polynucleotides encoding the same. Some aspects of the disclosure relate to a polynucleotide encoding a chimeric antigen receptor (CAR) comprising at least one of the heavy chain and light chains disclosed herein (or CDRs thereof). The present disclosure also provides vectors (e.g., viral vectors) comprising such polynucleotides and compositions comprising such vectors. The present disclosure further provides polynucleotides encoding such CARs or TCRs and compositions comprising such polynucleotides. The present disclosure additionally provides engineered cells (e.g., T cells) comprising such polynucleotides and/or transduced with such viral vectors and compositions comprising such engineered cells. The present disclosure provides compositions (e.g., pharmaceutical compositions) including a plurality of engineered T cells. The present disclosure provides methods for manufacturing such engineered T cells and compositions and uses (e.g., in treating a melanoma) of such engineered T cells and compositions. And, the present disclosure provides a method of inducing an immunity against a tumor comprising administering to a subject an effective amount of a cell comprising a polynucleotide, a vector, or a polypeptide of the present disclosure. Other aspects of the disclosure relate to cells comprising the CAR and their use in a T cell therapy for the treatment of a patient suffering from a cancer.

Any aspect or embodiment described herein may be combined with any other aspect or embodiment as disclosed herein. While the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims. The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, dictionaries, documents, manuscripts and scientific literature cited herein are hereby incorporated by reference. Other features and advantages of the disclosure will be apparent from the following Detailed Description, comprising the Examples, and the claims.

Definitions

In order for the present disclosure to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. "About" or "comprising essentially of" can mean a range of up to 10% (i.e., ±10%). Thus, "about" can be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg can include any amount between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", 5$^{th}$ ed., (2013), Academic Press; and "The Oxford Dictionary Of Biochemistry And Molecular Biology", Cammack et al. eds., 2$^{nd}$ ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (Clq) of the classical complement system. In general, human antibodies are approximately 150 kD tetrameric agents composed of two identical heavy (H) chain polypeptides (about 50 kD each) and two identical light (L) chain polypeptides (about 25 kD each) that associate with each other into what is commonly referred to as a "Y-shaped" structure. The heavy and light chains are linked or connected to one another by a single disulfide bond; two other disulfide bonds connect the heavy chain hinge regions to one another, so that the dimers are connected to one another and the tetramer is formed. Naturally-produced antibodies are also glycosylated, e.g., on the CH2 domain.

The term "human antibody" is intended to comprise antibodies having variable and constant domain sequences generated, assembled, or derived from human immunoglobulin sequences, or sequences indistinguishable therefrom. In some embodiments, antibodies (or antibody components) may be considered to be "human" even though their amino acid sequences comprise residues or elements not encoded by human germline immunoglobulin sequences (e.g., variations introduced by in vitro random or site-specific mutagenesis or introduced by in vivo somatic mutation). The term "humanized" is intended to comprise antibodies having a variable domain with a sequence derived from a variable domain of a non-human species (e.g., a mouse), modified to be more similar to a human germline encoded sequence. In some embodiments, a "humanized" antibody comprises one or more framework domains having substantially the amino acid sequence of a human framework domain, and one or more complementary determining regions having substantially the amino acid sequence as that of a non-human antibody. In some embodiments, a humanized antibody comprises at least a portion of an immunoglobulin constant region (Fc), generally that of a human immunoglobulin constant domain. In some embodiments, a humanized antibodies may comprise a $C_H1$, hinge, $C_H2$, $C_H3$, and, optionally, a $C_H4$ region of a human heavy chain constant domain.

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen binding fragments of any of the above. In certain embodiments, antibodies described herein refer to polyclonal antibody populations. Antibodies may also comprise, for example, Fab' fragments, Fd' fragments, Fd fragments, isolated CDRs, single chain Fvs, polypeptide-Fc fusions, single domain antibodies (e.g., shark single domain antibodies such as IgNAR or fragments thereof), camelid antibodies, single chain or Tandem diabodies (TandAb®), Anticalins®, Nanobodies® minibodies, BiTE®s, ankyrin repeat proteins or DARPINs®, Avimers®, DARTs, TCR-like antibodies, Adnectins®, Affilins®, TransBodies®, Affibodies®, TrimerX®, MicroProteins, Fynomers®, Centyrins®, and KALBITOR®s.

An immunoglobulin may derive from any of the commonly known isotypes, including but not limited to IgA, secretory IgA, IgG, IgE and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen binding fragment or an antigen-binding portion of any of the aforementioned immunoglobulins, and includes a monovalent and a divalent fragment or portion, and a single chain Ab.

An "antigen binding molecule," "antigen binding portion," or "antibody fragment" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In certain embodiments, the antigen binding molecule binds to BCMA, CLL-1, or FLT3. In certain embodiments, the antigen binding molecule binds to CD19, CD20, or both. In further embodiments, the antigen binding molecule is an antibody fragment that specifically binds to the antigen, including one or more of the complementarity determining regions (CDRs) thereof In further embodiments, the antigen binding molecule is a single chain variable fragment (scFv). In some embodiments, the antigen binding molecule comprises or consists of avimers.

In some instances, a CDR is substantially identical to one found in a reference antibody (e.g., an antibody of the present disclosure) and/or the sequence of a CDR provided in the present disclosure. In some embodiments, a CDR is substantially identical to a reference CDR (e.g., a CDR provided in the present disclosure) in that it is either identical in sequence or contains between 1, 2, 3, 4, or 5 (e.g. 1-5) amino acid substitutions as compared with the reference CDR. In some embodiments a CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR (e.g., 85-90%, 85-95%, 85-100%, 90-95%, 90-100%, or 95-100%). In some embodiments a CDR is substantially identical to a reference CDR in that it shows at least 96%, 96%, 97%, 98%, 99%, or 100% sequence identity with the reference CDR. In some embodiments a CDR is substantially identical to a reference CDR in that one amino acid within the CDR is deleted, added, or substituted as compared with the reference CDR while the CDR has an amino acid sequence that is otherwise identical with that of the reference CDR. In some embodiments a CDR is substantially identical to a reference CDR in that 2, 3, 4, or 5 (e.g. 2-5) amino acids within the CDR are deleted, added, or substituted as compared with the reference CDR while the CDR has an amino acid sequence that is otherwise identical to the reference CDR. In various embodiments, an antigen binding fragment binds a same antigen as a reference antibody.

An antigen binding fragment may be produced by any means. For example, in some embodiments, an antigen binding fragment may be enzymatically or chemically produced by fragmentation of an intact antibody. In some embodiments, an antigen binding fragment may be recombinantly produced (i.e., by expression of an engineered nucleic acid sequence. In some embodiments, an antigen binding fragment may be wholly or partially synthetically produced. In some embodiments, an antigen binding fragment may have a length of at least about 50, 60, 70, 80, 90, 100, 110, 120, 130, 140, 150, 160, 170, 180, 190 amino acids or more; in some embodiments at least about 200 amino acids (e.g., 50-100, 50-150, 50-200, or 100-200 amino acids).

The term "variable region" or "variable domain" is used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding molecule thereof.

The terms "VH" and "VH domain" are used interchangeably to refer to the heavy chain variable region of an antibody or an antigen-binding molecule thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

CDR Numbering

| Loop | Kabat | AbM | Chothia | Contact |
|---|---|---|---|---|
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B (Kabat Numbering) | H26--H35B | H26--H32 . . . 34 | H30--H35B |
| H1 | H31--H35 (Chothia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Kabat numbering" and like terms are recognized in the art and refer to a system of numbering amino acid residues in the heavy and light chain variable regions of an antibody, or an antigen-binding molecule thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

The terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

The term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

The term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIACORE® or KinExA.

A "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen-binding molecule thereof can be replaced with an amino acid residue with a similar side chain. In general, two sequences are generally considered to be "substantially similar" if they contain a conservative amino acid substitution in corresponding positions. For example, certain amino acids are generally classified as "hydrophobic" or "hydrophilic" amino acids, and/or as having "polar" or "non-polar" side chains. Substitution of one amino acid for another of the same type may be considered a conservative substitution. Exemplary amino acid categorizations are summarized in Tables 2 and 3 below:

TABLE 2

| Amino Acid | 3-Letter | 1-Letter | Property | Property | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 3

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

The term "heterologous" means from any source other than naturally occurring sequences. For example, a heterologous sequence included as a part of a costimulatory protein having the amino acid sequence of SEQ ID NO: 232, e.g., the corresponding human costimulatory protein, is amino acids that do not naturally occur as, i.e., do not align with, the wild type human costimulatory protein. For example, a heterologous nucleotide sequence refers to a nucleotide sequence other than that of the wild type human costimulatory protein-encoding sequence.

An "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody: antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

An antigen binding molecule, an antibody, or an antigen binding molecule thereof "cross-competes" with a reference antibody or an antigen binding molecule thereof if the interaction between an antigen and the first binding molecule, an antibody, or an antigen binding molecule thereof blocks, limits, inhibits, or otherwise reduces the ability of the reference binding molecule, reference antibody, or an antigen binding molecule thereof to interact with the antigen. Cross competition can be complete, e.g., binding of the binding molecule to the antigen completely blocks the ability of the reference binding molecule to bind the antigen, or it can be partial, e.g., binding of the binding molecule to the antigen reduces the ability of the reference binding molecule to bind the antigen. In certain embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope as the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137:3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

The term "binding" generally refers to a non-covalent association between or among two or more entities. Direct binding involves physical contact between entities or moieties. "Indirect" binding involves physical interaction by way of physical contact with one or more intermediate entities. Binding between two or more entities may be assessed in any of a variety of contexts, e.g., where interacting entities or moieties are studied in isolation or in the context of more complex systems (e.g., while covalently or otherwise associated with a carrier entity and/or in a biological system such as a cell).

The terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE®, KinExA 3000 instrument (Sapidyne Instruments, Boise, Id.), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen. Binding may comprise preferential association of a binding motif, antibody, or antigen binding system with a target of the binding motif, antibody, or antigen binding system as compared to association of the binding motif, antibody, or antigen binding system with an entity that is not the target (i.e. non-target). In some embodiments, a binding motif, antibody, or antigen binding system selectively binds a target if binding between the binding motif, antibody, or antigen binding system and the target is greater than 2-fold, greater than 5-fold, greater than 10-fold, 20-fold, 30-fold, 40-fold, 50-fold, 60-fold, 70-fold, 80-fold, 90-fold, or greater than 100-fold as compared with binding of the binding motif, antibody, or antigen binding system and a non-target. In some embodiments, a binding motif, antibody, or antigen binding system selectively binds a target if the binding affinity is less than about $10^{-5}$ M, less than about $10^{-6}$ M, less than about $10^{-7}$ M, less than about $10^{-7}$ M, or less than about $10^{-9}$ M.

In another embodiment, molecules that specifically bind to an antigen bind with a dissociation constant ($K_d$) of about $1\times10^{-7}$ M. In some embodiments, the antigen binding molecule specifically binds an antigen with "high affinity" when the $K_d$ is about $1\times10^{-9}$ M to about $5\times10^{-9}$ M. In some embodiments, the antigen binding molecule specifically binds an antigen with "very high affinity" when the $K_d$ is $1\times10^{-10}$ M to about $5\times10^{-10}$ M. In one embodiment, the antigen binding molecule has a $K_d$ of $10^{-9}$ M. In one embodiment, the off-rate is less than about $1\times10^{-5}$. In other embodiments, the antigen binding molecule binds human BCMA with a $K_d$ of between about $1\times10^{-7}$ M and about $1\times10^{-13}$ M. In yet another embodiment, the antigen binding molecule binds human BCMA with a $K_d$ of about $1\times10^{-10}$ M to about $5\times10^{-10}$ M. In some embodiments, the antigen binding molecule binds human CD19, CD20, or both with a $K_d$ of between about $1\times10^{-7}$ M and about $1\times10^{-13}$ M. In yet another embodiment, the antigen binding molecule binds human CD19, CD20, or both with a $K_d$ of about $1\times10^{-10}$ M to about $5\times10^{-10}$ M.

In a specific embodiment, provided herein is an antibody or an antigen binding molecule thereof that binds to a target human antigen, e.g., human BCMA or human CLL-1, with higher affinity than to another species of the target antigen, e.g., a non-human BCMA or a non-human CLL-1. In some embodiments, provided herein is an antibody or an antigen binding molecule thereof that binds to human CD19, human CD20, or both, with higher affinity than to another species of one or both target antigens, e.g., a non-human CD19, non-human CD20, or both. In certain embodiments, provided herein is an antibody or an antigen binding molecule t thereof that binds to the target human antigen, e.g., human BCMA or human CLL-1, with a 5%, 10%, 15%, 20%, 25%, 30%, 35%, 40%, 45%, 50%, 55%, 60%, 65%, 70% or higher affinity than to another species of the target antigen as measured by, e.g., a radioimmunoassay, surface plasmon resonance, or kinetic exclusion assay. In certain embodiments, provided herein is an antibody or an antigen binding molecule thereof that binds to human CD19, human CD20, or both, with a 5%, 10%, 15%, 20%, 25%, 30%, 35%, 40%, 45%, 50%, 55%, 60%, 65%, 70% or higher affinity than to another species of one or both target antigens as measured by, e.g., a radioimmunoassay, surface plasmon resonance, or kinetic exclusion assay. In a specific embodiment, an antibody or an antigen binding molecule thereof described herein, which binds to a target human antigen, will bind to another species of the target antigen with less than 10%, 15%, or 20% of the binding of the antibody or an antigen binding molecule thereof to the human antigen as measured by, e.g., a radioimmunoassay, surface plasmon resonance, or kinetic exclusion assay.

"Chimeric antigen receptor" or "CAR" refers to a molecule engineered to comprise a binding motif and a means of activating immune cells (for example T cells such as naive T cells, central memory T cells, effector memory T cells or combination thereof) upon antigen binding. CARs are also known as artificial T cell receptors, chimeric T cell receptors or chimeric immunoreceptors. In some embodiments, a CAR comprises a binding motif, an extracellular domain, a transmembrane domain, one or more co-stimulatory domains, and an intracellular signaling domain. A T cell that has been genetically engineered to express a chimeric antigen receptor may be referred to as a CAR T cell. "Extracellular domain" (or "ECD") refers to a portion of a polypeptide that, when the polypeptide is present in a cell membrane, is understood to reside outside of the cell membrane, in the extracellular space.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In one embodiment, antigens are tumor antigens. In one particular embodiment, the antigen is all or a fragment of CD19 or CD20. A "target" is any molecule bound by a binding motif, antigen binding system, or binding agent, e.g., an antibody. In some embodiments, a target is an antigen or epitope of the present disclosure.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

"Transformation" refers to any process by which exogenous DNA is introduced into a host cell. Transformation may occur under natural or artificial conditions using various methods. Transformation may be achieved using any known method for the insertion of foreign nucleic acid sequences into a prokaryotic or eukaryotic host cell. In some embodiments, some transformation methodology is selected based on the host cell being transformed and/or the nucleic acid to be inserted. Methods of transformation may comprise, yet are not limited to, viral infection, electroporation, and lipofection. In some embodiments, a "transformed" cell is stably transformed in that the inserted DNA is capable of replication either as an autonomously replicating plasmid or as part of the host chromosome. In some embodiments, a transformed cell may express introduced nucleic acid.

Term "vector" refers to a recipient nucleic acid molecule modified to comprise or incorporate a provided nucleic acid sequence. One type of vector is a "plasmid," which refers to a circular double stranded DNA molecule into which additional DNA may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) may be integrated into the genome of a host cell upon introduction into the host cell, and thereby are replicated along with the host genome. Moreover, certain vectors comprise sequences that direct expression of inserted genes to which they are operatively linked. Such vectors may be referred to herein as "expression vectors." Standard techniques may be used for engineering of vectors, e.g., as found in Sambrook et al., Molecular Cloning: A Laboratory Manual (2d ed., Cold Spring Harbor Laboratory Press, Cold Spring Harbor, N.Y. (1989)), which is incorporated herein by reference for any purpose.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present disclosure include, but are not limited to, cancers of the immune system including lymphoma, leukemia, myeloma, and other leukocyte malignancies. In some embodiments, the methods of the present disclosure can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In one particular embodiment, the cancer is multiple myeloma. The particular cancer can be responsive to chemo- or radiation therapy or the cancer can be Arefractory. A refractory cancer refers to a cancer that is not amendable to surgical intervention and the cancer is either initially unresponsive to chemo- or radiation therapy or the cancer becomes unresponsive over time. Cancer further includes relapsed or refractory large B-cell lymphoma after two or more lines of systemic therapy, including diffuse large B-cell lymphoma (DLBCL) not otherwise specified, primary mediastinal large B-cell lymphoma after two or more lines of systemic therapy, high grade B-cell lymphoma, and DLBCL arising from follicular lymphoma.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β gamma-induced protein 10 (IP-10), and thymus and activation regulated chemokine (TARC or CCL17).

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory $T_{SCM}$ cells, like naive cells, are CD45RO−, CCR7+, CD45RA+, CD62L+(L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

"Linker" (L) or "linker domain" or "linker region" refers to an oligo- or polypeptide region from about 1 to 100 amino acids in length, which links together any of the domains/regions of the CAR of the invention. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In some embodiments, the linkers include the picornaviral 2A-like linker, CHYSEL sequences of porcine teschovirus (P2A), virus (T2A) or combinations, variants and functional equivalents thereof. In other embodiments, the linker sequences may comprise Asp-Val/Ile-Glu-X-Asn-Pro-Gly.$^{(2,4)}$-Pro.$^{(2B)}$motif (SEQ ID NO: 314), which results in cleavage between the 2A glycine and the 2B proline. Other linkers will be apparent to those of skill in the art and may be used in connection with alternate embodiments of the invention. By way of example, in some examples, a linker may be used to connect or link different antigen binding systems such as two CARs of a bicistronic CAR. A linker may be a portion of a multi-element agent that connects different elements to one another. For example, a polypeptide comprises two or more functional or structural domains may comprise a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. A linker may connect or link together any of the domains/regions of a CAR of the present disclosure. In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length (e.g., 1 to 10, 1 to 20, 1 to 30, 1 to 40, 1 to 50, 1 to 60, 1 to 70, 1 to 80, 1 to 90, 1 to 100, 10 to 20, 10 to 30, 10 to 40, 10 to 50, 10 to 60, 10 to 70, 10 to 80, 10 to 90, or 10 to 100 amino acids in length). In some embodiments, a linker is characterized in that it tends not to adopt a rigid three-dimensional structure, and instead provides flexibility to the polypeptide.

"Single chain variable fragment", "single-chain antibody variable fragments" or "scFv" antibodies refer to forms of antibodies comprising the variable regions of only the heavy and light chains, connected by a linker peptide.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome. Engineering generally comprises manipulation by the hand of man. For example, a polynucleotide is considered to be "engineered" when two or more sequences, that are not linked or connected together in that order in nature, are manipulated by the hand of man to be directly linked or connected to one another in the engineered polynucleotide. In the context of manipulation of cells by techniques of molecular biology, a cell or organism is considered to be "engineered" if it has been manipulated so that its genetic information is altered (e.g., new genetic material not previously present has been introduced, for example by transformation, somatic hybridization, transfection, transduction, or other mechanism, or previously present genetic material is altered or removed, for example by substitution or deletion mutation, or by other protocols). In some embodiments, a binding agent is a modified lymphocyte, e.g., a T cell, may be obtained from a patient or a donor. An engineered cell may be modified to express an exogenous construct, such as, e.g., a chimeric antigen receptor (CAR) or a T cell receptor (TCR), which is incorporated into the cell's genome. Progeny of an engineered polynucleotide or binding agent are generally referred to as "engineered" even though the actual manipulation was performed on a prior entity. In some embodiments, "engineered" refers to an entity that has been designed and produced. The term "designed" refers to an agent (i) whose structure is or was selected by the hand of man; (ii) that is produced by a process requiring the hand of man; and/or (iii) that is distinct from natural substances and other known agents. A "T cell receptor" or "TCR" refers to antigen-recognition molecules present on the surface of T-cells. During normal T-cell development, each of the four TCR genes, α, β, γ, and δ, may rearrange leading to highly diverse TCR proteins.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy.

Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising at least one costimulatory domain and at least one activating domain. The costimulatory domain can be derived from a naturally-occurring costimulatory domain, e.g., having the amino acid sequence of SEQ ID NO: 232, or a variant thereof, e.g., a variant having a truncated hinge domain ("THD"), and the activating domain can be derived from, e.g., CD3-zeta. In certain embodiments, the CAR is designed to have two, three, four, or more costimulatory domains. The CAR scFv can be designed to target, for example, CD19, which is a transmembrane protein expressed by cells in the B cell lineage, including all normal B cells and B cell malignancies, including but not limited to NHL, CLL, and non-T cell ALL. In some embodiments, the CAR is engineered such that the costimulatory domain is expressed as a separate polypeptide chain. Example CART cell therapies and constructs are described in U.S. Patent Publication Nos. 2013/0287748, 2014/0227237, 2014/0099309, and 2014/0050708, and these references are incorporated by reference in their entirety. "Adoptive cell therapy" or "ACT" involves transfer of immune cells with anti-tumor activity into a subject, e.g., a cancer patient. In some embodiments, ACT is a treatment approach that involves the use of lymphocytes (e.g., engineered lymphocytes) with anti-tumor activity.

A "patient" includes any human who is afflicted with a cancer (e.g., a lymphoma or a leukemia). The terms "subject" and "patient" are used interchangeably herein.

The term "in vitro" refers to events occurring in an artificial environment, e.g., in a test tube, reaction vessel, cell culture, etc., rather than within a multi-cellular organism. The term "in vitro cell" refers to any cell which is cultured ex vivo. In particular, an in vitro cell can include a T cell. The term "in vivo" refers to events that occur within a multi-cellular organism, such as a human or a non-human animal.

"Antigen-specific targeting region" (ASTR) refers to the region of the CAR which targets specific antigens. The CARs of the invention comprise at least two targeting regions which target at least two different antigens. In an embodiment, CARs comprise three or more targeting regions which target at least three or more different antigens. The targeting regions on the CAR are extracellular. In some embodiments, the antigen-specific targeting regions comprise an antibody or a functional equivalent thereof or a fragment thereof or a derivative thereof and each of the targeting regions target a different antigen. The targeting regions may comprise full length heavy chain, Fab fragments, single chain Fv (scFv) fragments, divalent single chain antibodies or diabodies, each of which are specific to the target antigen. There are, however, numerous alternatives, such as linked cytokines (which leads to recognition of cells bearing the cytokine receptor), affibodies, ligand binding domains from naturally occurring receptors, soluble protein/peptide ligand for a receptor (for example on a tumor cell), peptides, and vaccines to prompt an immune response, which may each be used in various embodiments of the invention. In fact, almost any molecule that binds a given antigen with high affinity can be used as an antigen-specific targeting region, as will be appreciated by those of skill in the art.

"Antigen presenting cell" or "APC" refers to cells that process and present antigens to T-cells. Exemplary APCs comprise dendritic cells, macrophages, B cells, certain activated epithelial cells, and other cell types capable of TCR stimulation and appropriate T cell costimulation.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody (such as OKT3), an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand" as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CD5, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

The terms "improve," "increase," "inhibit," and "reduce" indicate values that are relative to a baseline or other reference measurement. In some embodiments, an appropriate reference measurement may comprise a measurement in certain system (e.g., in a single individual) under otherwise comparable conditions absent presence of (e.g., prior to and/or after) an agent or treatment, or in presence of an appropriate comparable reference agent. In some embodiments, an appropriate reference measurement may comprise a measurement in comparable system known or expected to respond in a comparable way, in presence of the relevant agent or treatment.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission. In some embodiments, treatment may be of a subject who does not exhibit signs of the relevant disease, disorder and/or condition and/or of a subject who exhibits only early signs of the disease, disorder, and/or condition. In some embodiments, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The term "agent" may refer to a molecule or entity of any class comprising, or a plurality of molecules or entities, any of which may be, for example, a polypeptide, nucleic acid, saccharide, lipid, small molecule, metal, cell, or organism (for example, a fraction or extract thereof) or component thereof. In some embodiments, an agent may be utilized in isolated or pure form. In some embodiments, an agent may be utilized in a crude or impure form. In some embodiments, an agent may be provided as a population, collection, or library, for example that may be screened to identify or characterize members present therein.

Two events or entities are "associated" with one another if the presence, level, and/or form of one is correlated with that of the other. For example, an entity (e.g., polypeptide, genetic signature, metabolite, microbe, etc.) is considered to be associated with a disease, disorder, or condition, if its presence, level, and/or form correlates with incidence of and/or susceptibility to the disease, disorder, or condition (e.g., across a relevant population). For example, two or more entities are physically "associated" with one another if they interact, directly or indirectly, so that they are and/or remain in physical proximity with one another (e.g., bind). In additional examples, two or more entities that are physically associated with one another are covalently linked or connected to one another, or non-covalently associated, for example by means of hydrogen bonds, van der Waals interaction, hydrophobic interactions, magnetism, and combinations thereof.

Term "identity" refers to the overall relatedness between polymeric molecules, e.g., between nucleic acid molecules (e.g., DNA molecules and/or RNA molecules) and/or between polypeptide molecules. Methods for the calculation of a percent identity as between two provided polypeptide sequences are known. Calculation of the percent identity of two nucleic acid or polypeptide sequences, for example, may be performed by aligning the two sequences for optimal comparison purposes (e.g., gaps may be introduced in one or both of a first and a second sequences for optimal alignment and non-identical sequences may be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, optionally taking into account the number of gaps, and the length of each gap, which may need to be introduced for optimal alignment of the two sequences. Comparison or alignment of sequences and determination of percent identity between two sequences may be accomplished using a mathematical algorithm, such as BLAST (basic local alignment search tool). In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical (e.g., 85-90%, 85-95%, 85-100%, 90-95%, 90-100%, or 95-100%).

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm. Other algorithms are also available for comparison of amino acid or nucleic acid sequences, comprising those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs," Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying similar sequences, the programs mentioned above generally provide an indication of the degree of similarity. In some embodiments, two sequences are considered to be substantially similar if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are similar and/or identical over a relevant stretch of residues (e.g., 85-90%, 85-95%, 85-100%, 90-95%, 90-100%, or 95-100%). In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues. Sequences with substantial sequence similarity may be homologs of one another.

"Combination therapy" refers to those situations in which a subject is simultaneously exposed to two or more therapeutic regimens (e.g., two or more therapeutic moieties). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

"Corresponding to" may be used to designate the position/identity of a structural element in a molecule or composition through comparison with an appropriate reference molecule or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, for purposes of simplicity, residues in a polypeptide may be designated using a canonical numbering system based on a reference related polypeptide, so that an amino acid "corresponding to" a residue at position 100, for example, need not actually be the 100th amino acid in an amino acid chain provided it corresponds to the residue found at position 100 in the reference polypeptide. Various sequence alignment strategies are available, comprising software programs such as, for example, BLAST, CS-BLAST, CUDASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that may be utilized, for example, to identify "corresponding" residues in polypeptides and/or nucleic acids in accordance with the present disclosure.

The term "domain" refers to a portion of an entity. In some embodiments, a "domain" is associated with a structural and/or functional feature of the entity, e.g., so that, when the domain is physically separated from the rest of its parent entity, it substantially or entirely retains the structural and/or functional feature. In some embodiments, a domain may comprise a portion of an entity that, when separated from that (parent) entity and linked or connected with a different (recipient) entity, substantially retains and/or imparts on the recipient entity one or more structural and/or functional features, e.g., that characterized it in the parent entity. In some embodiments, a domain is a portion of a molecule (e.g., a small molecule, carbohydrate, lipid, nucleic acid, or polypeptide). In some embodiments, a domain is a section of a polypeptide; in some such embodiments, a domain is characterized by a structural element (e.g., an amino acid sequence or sequence motif, α-helix character, β-sheet character, coiled-coil character, random coil character, etc.), and/or by a functional feature (e.g., binding activity, enzymatic activity, folding activity, signaling activity, etc.).

The term "dosage form" may be used to refer to a physically discrete unit of an active agent (e.g., an antigen binding system or antibody) for administration to a subject. Generally, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population. The total amount of a therapeutic composition or agent administered to a subject is determined by one or more medical practitioners and may involve administration of more than one dosage forms.

The term "dosing regimen" may be used to refer to a set of one or more unit doses that are administered individually to a subject. In some embodiments, a given therapeutic agent has a recommended dosing regimen, which may involve one or more doses. In some embodiments, a dosing regimen comprises a plurality of doses each of which is separated in time from other doses. In some embodiments, a dosing regimen comprises a plurality of doses and consecutive doses are separated from one another by time periods of equal length; in some embodiments, a dosing regimen comprises a plurality of doses and consecutive doses are separated from one another by time periods of at least two different lengths. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen is periodically adjusted to achieve a desired or beneficial outcome.

"Effector function" refers to a biological result of interaction of an antibody Fc region with an Fc receptor or ligand. Effector functions comprise, without limitation, antibody-dependent cell-mediated cytotoxicity (ADCC), antibody-dependent cell-mediated phagocytosis (ADCP), and complement-mediated cytotoxicity (CMC). An effector function may be antigen binding dependent, antigen binding independent, or both. ADCC refers to lysis of antibody-bound target cells by immune effector cells. Without wishing to be bound by any theory, ADCC is generally understood to involve Fc receptor (FcR)-bearing effector cells recognizing and subsequently killing antibody-coated target cells (e.g., cells that express on their surface antigens to which an antibody is bound). Effector cells that mediate ADCC may comprise immune cells, comprising yet not limited to, one or more of natural killer (NK) cells, macrophages, neutrophils, eosinophils.

"Effector cell" refers to a cell of the immune system that expresses one or more Fc receptors and mediates one or more effector functions. In some embodiments, effector cells may comprise, without limitation, one or more of monocytes, macrophages, neutrophils, dendritic cells, eosinophils, mast cells, platelets, large granular lymphocytes, Langerhans' cells, natural killer (NK) cells, T-lymphocytes, and B-lymphocytes. Effector cells may be of any organism comprising, without limitation, humans, mice, rats, rabbits, and monkeys.

The term "excipient" refers to an agent that may be comprised in a composition, for example to provide or contribute to a desired consistency or stabilizing effect. In some embodiments, a suitable excipient may comprise, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or the like.

A "fragment" or "portion" of a material or entity as described herein has a structure that comprises a discrete portion of the whole, e.g., of a physical entity or abstract entity. In some embodiments, a fragment lacks one or more moieties found in the whole. In some embodiments, a fragment consists of or comprises a characteristic structural element, domain or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer (e.g., 85-90%, 85-95%, 85-100%, 90-95%, 90-100%, or 95-100%). The whole material or entity may in some embodiments be referred to as the "parent" of the fragment.

The term "fusion polypeptide" or "fusion protein" generally refers to a polypeptide comprising at least two segments. Generally, a polypeptide containing at least two such segments is considered to be a fusion polypeptide if the two segments are moieties that (1) are not comprised in nature in the same peptide, and/or (2) have not previously been linked or connected to one another in a single polypeptide, and/or (3) have been linked or connected to one another through action of the hand of man.

The term "gene product" or "expression product" generally refers to an RNA transcribed from the gene (pre- and/or post-processing) or a polypeptide (pre- and/or post-modification) encoded by an RNA transcribed from the gene.

The term "isolated" refers to a substance that (1) has been separated from at least some components with which it was associated at an earlier time or with which the substance would otherwise be associated, and/or (2) is present in a composition that comprises a limited or defined amount or concentration of one or more known or unknown contaminants. An isolated substance, in some embodiments, may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% (e.g., 85-90%, 85-95%, 85-100%, 90-95%, 90-100%, or 95-100%) of other non-substance components with which the substance was associated at an earlier time, e.g., other components or contaminants with which the substance was previously or otherwise would be associated. In certain instances, a substance is isolated if it is present in a composition that comprises a limited or reduced amount or concentration of molecules of a same or similar type. For instance, in certain instances, a nucleic acid, DNA, or RNA substance is isolated if it is present in a composition that comprises a limited or reduced amount or concentration of non-substance nucleic acid, DNA, or RNA molecules. For instance, in certain instances, a polypeptide substance is isolated if it is present in a composition that comprises a limited or reduced amount or concentration of non-substance polypeptide molecules. In certain embodiments, an amount may be, e.g., an amount measured relative to the amount of a desired substance present in a composition. In certain embodiments, a limited amount may be an amount that is no more than 100% of the amount of substance in a composition, e.g., no more than 1%, 5%, 10%, 20%, 30%, 40%, 50%, 60%, 70%, 80%, 90%, or 95% of the amount of substance in a composition (e.g., 85-90%, 85-95%, 85-100%, 90-95%, 90-100%, or 95-100%). In certain instances, a composition is pure or substantially pure with respect to a selected substance. In some embodiments, an isolated substance is about 80%, about 85%, about 90%, about 91%, about 92%, about 93%, about 94%, about 95%, about 96%, about 97%, about 98%, about 99%, or more than about 99% pure (e.g., 85-90%, 85-95%, 85-100%, 90-95%, 90-100%, or 95-100%). A substance is "pure" if it is substantially free of other components or of contaminants. In some embodiments, a substance may still be considered "isolated" or even "pure," after having been combined with certain other components such as, for example, one or more carriers or excipients (e.g., buffer, solvent, water, etc.); in such embodiments, percent isolation or purity of the substance is calculated without comprising such carriers or excipients.

"Nucleic acid" refers to any polymeric chain of nucleotides. A nucleic acid may be DNA, RNA, or a combination thereof. In some embodiments, a nucleic acid comprises one or more natural nucleic acid residues. In some embodiments, a nucleic acid comprises of one or more nucleic acid analogs. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long (e.g., 20 to 100, 20 to 500, 20 to 1000, 20 to 2000, or 20 to 5000 or more residues). In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide.

"Operably linked" refers to a juxtaposition where the components described are in a relationship permitting them to function in their intended manner. For example, a control element "operably linked" to a functional element is associated in such a way that expression and/or activity of the functional element is achieved under conditions compatible with the control element.

The term "pharmaceutically acceptable" refers to a molecule or composition that, when administered to a recipient, is not deleterious to the recipient thereof, or that any deleterious effect is outweighed by a benefit to the recipient thereof. With respect to a carrier, diluent, or excipient used to formulate a composition as disclosed herein, a pharmaceutically acceptable carrier, diluent, or excipient must be compatible with the other ingredients of the composition and not deleterious to the recipient thereof, or any deleterious effect must be outweighed by a benefit to the recipient. The term "pharmaceutically acceptable carrier" means a pharmaceutically-acceptable material, composition or vehicle, such as a liquid or solid filler, diluent, excipient, or solvent encapsulating material, involved in carrying or transporting an agent from one portion of the body to another (e.g., from one organ to another). Each carrier present in a pharmaceutical composition must be "acceptable" in the sense of being compatible with the other ingredients of the formulation and not deleterious to the patient, or any deleterious effect must be outweighed by a benefit to the recipient. Some examples of materials which may serve as pharmaceutically acceptable carriers comprise: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "pharmaceutical composition" refers to a composition in which an active agent is formulated together with one or more pharmaceutically acceptable carriers. In some embodiments, the active agent is present in a unit dose amount appropriate for administration in a therapeutic regimen that shows a statistically significant probability of achieving a predetermined therapeutic effect when administered to a relevant subject or population. In some embodiments, a pharmaceutical composition may be formulated for administration in solid or liquid form, comprising, without limitation, a form adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

The term "reference" describes a standard or control relative to which a comparison is performed. For example, in some embodiments, an agent, animal, individual, population, sample, sequence, or value of interest is compared with a reference or control that is an agent, animal, individual, population, sample, sequence, or value. In some embodiments, a reference or control is tested, measured, and/or determined substantially simultaneously with the testing, measuring, or determination of interest. In some embodiments, a reference or control is a historical reference or control, optionally embodied in a tangible medium. Generally, a reference or control is determined or characterized under comparable conditions or circumstances to those under assessment. When sufficient similarities are present to justify reliance on and/or comparison to a selected reference or control.

"Regulatory T cells" ("Treg", "Treg cells", or "Tregs") refer to a lineage of CD4+T lymphocytes that participate in controlling certain immune activities, e.g., autoimmunity, allergy, and response to infection. Regulatory T cells may regulate the activities of T cell populations, and may also influence certain innate immune system cell types. Tregs may be identified by the expression of the biomarkers CD4, CD25 and Foxp3, and low expression of CD127. Naturally occurring Treg cells normally constitute about 5-10% of the peripheral CD4+T lymphocytes. However, Treg cells within a tumor microenvironment (i.e. tumor-infiltrating Treg cells), Treg cells may make up as much as 20-30% of the total CD4+T lymphocyte population.

The term "sample" generally refers to an aliquot of material obtained or derived from a source of interest. In some embodiments, a source of interest is a biological or environmental source. In some embodiments, a source of interest may comprise a cell or an organism, such as a cell population, tissue, or animal (e.g., a human). In some embodiments, a source of interest comprises biological tissue or fluid. In some embodiments, a biological tissue or fluid may comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may comprise an intracellular fluid, an extracellular fluid, an intravascular fluid (blood plasma), an interstitial fluid, a lymphatic fluid, and/or a transcellular fluid. In some embodiments, a biological fluid may comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., brocheoalvealar, ductal, nasal, ocular, oral, uterine, vaginal, or other washing or lavage). In some embodiments, a biological sample comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

The term "stage of cancer" refers to a qualitative or quantitative assessment of the level of advancement of a cancer. In some embodiments, criteria used to determine the stage of a cancer may comprise, without limitation, one or more of where the cancer is located in a body, tumor size, whether the cancer has spread to lymph nodes, whether the cancer has spread to one or more different parts of the body, etc. In some embodiments, cancer may be staged using the so-called TNM System, according to which T refers to the size and extent of the main tumor, usually called the primary tumor; N refers to the number of nearby lymph nodes that have cancer; and M refers to whether the cancer has metastasized. In some embodiments, a cancer may be referred to as Stage 0 (abnormal cells are present without having spread to nearby tissue, also called carcinoma in situ, or CIS; CIS is not cancer, though could become cancer), Stage I-III (cancer is present; the higher the number, the larger the tumor and the more it has spread into nearby tissues), or Stage IV (the cancer has spread to distant parts of the body). In some embodiments, a cancer may be assigned to a stage selected from the group consisting of: in situ; localized (cancer is limited to the place where it started, with no sign that it has spread); regional (cancer has spread to nearby lymph nodes, tissues, or organs): distant (cancer has spread to distant parts of the body); and unknown (there is not enough information to determine the stage).

The phrase "therapeutic agent" may refer to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms or human subjects. In some embodiments, an appropriate population may be defined by various criteria, such as a certain age group, gender, genetic background, preexisting clinical conditions, in accordance with presence or absence of a biomarker, etc. In some embodiments, a therapeutic agent is a substance that may be used to alleviate, ameliorate, relieve, inhibit, prevent, delay onset of, reduce severity of, and/or reduce incidence of one or more symptoms or features of a disease, disorder, and/or condition. In some embodiments, a therapeutic agent is an agent that has been or is required to be approved by a government agency before it may be marketed for administration to humans. In some embodiments, a therapeutic agent is an agent for which a medical prescription is required for administration to humans.

Various aspects of the disclosure are described in further detail in the following subsections. The present disclosure provides antigen binding systems and binding agents comprising at least an anti-CD20 binding motif. Among other things, the present disclosure provides methods and compositions useful for treatment of cancer and/or for initiating or modulating immune responses. In certain embodiments, the present disclosure comprises antigen binding systems and binding agents that are dual-targeted in that they comprise an anti-CD20 binding motif and a second binding motif against a second antigen or epitope. In some instances, the second binding motif selectively binds CD19. In various embodiments, one or more binding motifs is an scFv. Exemplary binding motif amino acid sequences, and nucleic acid sequences encoding the same, are provided herein. In some embodiments, an antigen binding system of the present disclosure is a chimeric antigen receptor. In some embodiments, an antigen binding system of the present disclosure is a bispecific or bicistronic chimeric antigen receptor. In some embodiments, a binding agent of the present disclosure is an engineered T cell receptor.

Various embodiments of the present disclosure provide a vector encoding a binding motif or antigen binding system provided herein, e.g., a vector encoding an anti-CD20/anti-CD19 antigen binding system, such as a bispecific or bicistronic anti-CD20/anti-CD19 chimeric antigen receptor. Various embodiments of the present disclosure provide binding agent that is a cell encoding or expressing an antigen binding system or binding motif provided herein, e.g., a T cell engineered to encode or express an anti-CD20/anti-CD19 chimeric antigen receptor, such as a bispecific or bicistronic anti-CD20/anti-CD19 chimeric antigen receptor. The present disclosure provides binding agents, e.g., comprising binding agents that are immune cells genetically modified with an integrated gene, e.g., a nucleotide sequence of interest (e.g., a constitutive expression construct and/or an inducible expression construct that comprises such nucleotide sequence). In some embodiments, the present disclosure provides methods of treating a subject having a tumor, comprising administering to the subject a binding agent therapy described herein and/or a protein therapeutic described herein. In some embodiments, methods further comprise administration of one or more additional therapies (e.g., a second binding agent (e.g., CAR-T cell, CAR-NK cell, TCR-T cell, TIL cell, allogeneic NK cell, and autologous NK cell), an antibody-drug conjugate, an antibody, a bispecific antibody, a T cell-engaging bispecific antibody, an engineered antibody, and/or a polypeptide described herein).

Other features, objects, and advantages of the present disclosure are apparent in the detailed description that follows. It should be understood, however, that the detailed description, while indicating embodiments of the present disclosure, is given by way of illustration only, not limitation.

An anti-CD20 binding motif of the present disclosure may comprise antigen-binding sequences as found in an antibody described herein. In some instances, an anti-CD20 binding motif of the present disclosure comprises an antigen binding fragment described herein. Unless otherwise indicated, it is to be appreciated the references to CD20 in the present disclosure relate to human CD20. In various embodiments, an anti-CD20 binding motif of the present disclosure comprises at least one heavy chain CDR (HCDR) provided herein, e.g., at least one HCDR disclosed in any one of Tables 4-13. In various embodiments, an anti-CD20 binding motif of the present disclosure comprises two HCDRs provided herein, e.g., at least two HCDRs disclosed in any one of Tables 4-13. In various embodiments, an anti-CD20 binding motif of the present disclosure comprises three HCDRs provided herein, e.g., three HCDRs disclosed in any one of Tables 4-13. In various embodiments, an anti-CD20 binding motif of the present disclosure comprises at least one light chain CDR (LCDR) provided herein, e.g., at least one LCDR disclosed in any one of Tables 4-13. In various embodiments, an anti-CD20 binding motif of the present disclosure comprises two LCDRs provided herein, e.g., at least two LCDRs disclosed in any one of Tables 4-13. In various embodiments, an anti-CD20 binding motif of the present disclosure comprises three LCDRs provided herein, e.g., three LCDRs disclosed in any one of Tables 4-13.

In various embodiments, an anti-CD20 binding motif of the present disclosure comprises at least one HCDR provided herein, e.g., at least one HCDR disclosed in any one of Tables 4-13, and at least one LCDR provided herein, e.g., at least one LCDR disclosed in any one of Tables 4-13. In various embodiments, an anti-CD20 binding motif of the present disclosure comprises one HCDR provided herein, e.g., at least one HCDR disclosed in any one of Tables 4-13, and one LCDR provided herein, e.g., derived from the same Table of Tables 4-13 as the HCDR(s). In various embodiments, an anti-CD20 binding motif of the present disclosure comprises two HCDRs provided herein, e.g., at least two HCDRs disclosed in any one of Tables 4-13, and two LCDRs provided herein, e.g., at least two LCDRs disclosed in any one of Tables 4-13. In various embodiments, an anti-CD20 binding motif of the present disclosure comprises two HCDRs provided herein, e.g., at least two HCDRs disclosed in any one of Tables 4-13, and two LCDRs provided herein, e.g., derived from the same Table of Tables 4-13 as the HCDR(s). In various embodiments, an anti-CD20 binding motif of the present disclosure comprises three HCDRs provided herein, e.g., three HCDRs disclosed in any one of Tables 4-13, and three LCDRs provided herein, e.g., three LCDRs disclosed in any one of Tables 4-13. In various embodiments, an anti-CD20 binding motif of the present disclosure comprises three HCDRs provided herein, e.g., three HCDRs disclosed in any one of Tables 4-13, and three LCDRs derived from the same Table of Tables 4-13 as the HCDR(s).

In various embodiments, an anti-CD20 binding motif of the present disclosure comprises at least one heavy chain framework region (heavy chain FR) of a heavy chain variable domain disclosed herein, e.g., at least one heavy chain FR of a heavy chain variable domain disclosed in any one of Tables 4-13. In various embodiments, an anti-CD20 binding motif of the present disclosure comprises two heavy chain FRs of a heavy chain variable domain disclosed herein, e.g., at least two heavy chain FRs of a heavy chain variable domain disclosed in any one of Tables 4-13. In various embodiments, an anti-CD20 binding motif of the present disclosure comprises three heavy chain FRs of a heavy chain variable domain disclosed herein, e.g., three heavy chain FRs of a heavy chain variable domain disclosed in any one of Tables 4-13.

In various embodiments, an anti-CD20 binding motif of the present disclosure comprises at least one light chain FR of a light chain variable domain disclosed herein, e.g., at least one light chain FR of a light chain variable domain disclosed in any one of Tables 4-13. In various embodiments, an anti-CD20 binding motif of the present disclosure comprises two light chain FRs of a light chain variable domain disclosed herein, e.g., at least two light chain FRs of a light chain variable domain disclosed in any one of Tables 4-13. In various embodiments, an anti-CD20 binding motif of the present disclosure comprises three light chain FRs of a light chain variable domain disclosed herein, e.g., three light chain FRs of a light chain variable domain disclosed in any one of Tables 4-13.

In various embodiments, an anti-CD20 binding motif of the present disclosure comprises at least one heavy chain FR of a heavy chain variable domain disclosed herein, e.g., at least one heavy chain FR of a heavy chain variable domain disclosed in any one of Tables 4-13, and at least one light chain FR of a light chain variable domain disclosed herein, e.g., at least one light chain FR of a light chain variable domain disclosed in any one of Tables 4-13. In various embodiments, an anti-CD20 binding motif of the present disclosure comprises one heavy chain FR of a heavy chain variable domain disclosed herein, e.g., at least one heavy chain FR of a heavy chain variable domain disclosed in any one of Tables 4-13, and one light chain FR of a light chain variable domain disclosed herein, e.g., derived from the same Table of Tables 4-13 as the heavy chain FR(s). In various embodiments, an anti-CD20 binding motif of the present disclosure comprises two heavy chain FRs of a heavy chain variable domain disclosed herein, e.g., at least two heavy chain FRs of a heavy chain variable domain disclosed in any one of Tables 4-13, and two light chain FRs of a light chain variable domain disclosed herein, e.g., at least two light chain FRs of a light chain variable domain disclosed in any one of Tables 4-13. In various embodiments, an anti-CD20 binding motif of the present disclosure comprises two heavy chain FRs of a heavy chain variable domain disclosed herein, e.g., at least two heavy chain FRs of a heavy chain variable domain disclosed in any one of Tables 4-13, and two light chain FRs of a light chain variable domain disclosed herein, e.g., derived from the same Table of Tables 4-13 as the heavy chain FR(s). In various embodiments, an anti-CD20 binding motif of the present disclosure comprises three heavy chain FRs of a heavy chain variable domain disclosed herein, e.g., three heavy chain FRs of a heavy chain variable domain disclosed in any one of Tables 4-13, and three light chain FRs of a light chain variable domain disclosed herein, e.g., three light chain FRs of a light chain variable domain disclosed in any one of Tables 4-13. In various embodiments, an anti-CD20 binding motif of the present disclosure comprises three heavy chain FRs of a heavy chain variable domain disclosed herein, e.g., three light chain FRs of a light chain variable domain disclosed in any one of Tables 4-13, and three light chain FRs derived from the same Table of Tables 4-13 as the heavy chain FR(s).

Exemplary antibody sequences provided in Tables 4-13 are suitable for use in any antibody format, comprising, e.g., a tetrameric antibody, a monospecific antibody, a bispecific antibody, an antigen binding fragment, or a binding motif. Heavy chain variable domains and light chain variable domains and portions thereof provided in Tables 4-13 may be comprised in a binding motif.

In various embodiments, an anti-CD20 binding motif of the present disclosure comprises one, two, or three FRs that together or each individually have at least 75% identity (e.g., at least 75%, at least 80%, at least 90%, at least 95%, or 100%, e.g., 85-90%, 85-95%, 85-100%, 90-95%, 90-100%, or 95-100%) to corresponding FR(s) of a heavy chain variable domain of a heavy chain variable domain disclosed in in any one of Tables 4-13. In various embodiments, an anti-CD20 binding motif of the present disclosure comprises one, two, or three FRs that together or each individually have at least 75% identity (e.g., at least 75%, at least 80%, at least 90%, at least 95%, or 100%) to corresponding FR(s) of a light chain variable domain of a light chain variable domain disclosed in any one of Tables 4-13.

In various embodiments, an anti-CD20 binding motif of the present disclosure comprises at least one heavy chain variable domain having at least 75% sequence identity to a heavy chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%). In various embodiments, an anti-CD20 binding motif of the present disclosure comprises two heavy chain variable domains each having at least 75% sequence identity to a heavy chain variable domain disclosed in Tables 4-13 (e.g., at least 75%, at least 80%, at least 90%, at least 95%, or 100% identity; e.g., 85-90%, 85-95%, 85-100%, 90-95%, 90-100%, or 95-100%), which heavy chain variable domains may be same or different.

In various embodiments, an anti-CD20 binding motif of the present disclosure comprises at least one light chain variable domain having at least 75% sequence identity to a light chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%). In various embodiments, an anti-CD20 binding motif of the present disclosure comprises two light chain variable domains each having at least 75% sequence identity to a light chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%), which light chain variable domains may be same or different.

In various embodiments, an anti-CD20 binding motif of the present disclosure comprises at least one heavy chain variable domain having at least 75% sequence identity to a heavy chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%) and at least one light chain variable domain having at least 75% sequence identity to a light chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-CD20 binding motif of the present disclosure comprises one heavy chain variable domain having at least 75% sequence identity to a heavy chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%) and one light chain variable domain having at least 75% sequence identity to a light chain variable domain disclosed in any one of Tables 4-13 (e.g., at least 75%, at least 80%, at least 90%, at least 95%, or 100% identity; e.g., 85-90%, 85-95%, 85-100%, 90-95%, 90-100%, or 95-100%), where the heavy chain variable domain and light chain variable domain are optionally derived from the same Table of Tables 4-13.

In various embodiments, an anti-CD20 binding motif of the present disclosure comprises two heavy chain variable domains each having at least 75% sequence identity to a heavy chain variable domain disclosed in Tables 4-13 (e.g., at least 75%, at least 80%, at least 90%, at least 95%, or 100% identity; e.g., 85-90%, 85-95%, 85-100%, 90-95%, 90-100%, or 95-100%) and two light chain variable domains each having at least 75% sequence identity to a light chain variable domain disclosed in Tables 4-13 (e.g., at least 75%, at least 80%, at least 90%, at least 95%, or 100% identity; e.g., 85-90%, 85-95%, 85-100%, 90-95%, 90-100%, or 95-100%), where, in various embodiments, (i) each of the heavy chain variable domains may be same or different; (ii) each of the light chain variable domains may be same or different; (iii) at least one heavy chain variable domain and at least one light chain variable domain may be derived from the same Table of Tables 4-13; or (iv) the two heavy chain variable domains and the two light chain variable domains are all derived from the same Table of Tables 4-13. Each of Tables 4-13 represents the heavy chain variable domain and light chain variable domain sequences of an exemplary antibody, comprising (i) the heavy chain variable domain of the exemplary antibody; (ii) a DNA sequence encoding the heavy chain variable domain (iii) three heavy chain variable domain CDRs of the heavy chain variable domain, according to IMGT, Kabat, and Chothia numbering; (iv) the light chain variable domain of the exemplary antibody; (v) a DNA sequence encoding the light chain variable domain; and (vi) three light chain variable domain CDRs of the light chain variable domain, according to IMGT, Kabat, and Chothia numbering. Information provided in each table provides framework amino acid sequences, as well as nucleotide sequences encoding each CDR amino acid sequence and nucleotide sequences encoding corresponding FR amino acid sequence.

In various embodiments a binding motif may comprise a heavy chain variable domain of the present disclosure (e.g., having at least 75% sequence identity to a heavy chain variable domain of any one of Tables 4-13, e.g., at least 80%, 85%, 90%, 95%, or 100% identity; e.g., 85-90%, 85-95%, 85-100%, 90-95%, 90-100%, or 95-100%), a light chain variable domain of the present disclosure (e.g., having at least 75% sequence identity to a light chain variable domain of any one of Tables 4-13, e.g., at least 80%, 85%, 90%, 95%, or 100% identity; e.g., 85-90%, 85-95%, 85-100%, 90-95%, 90-100%, or 95-100%), and a linker (e.g., a linker according to SEQ ID NO: 247 and/or a linker according to any one of SEQ ID NOs: 307-313; see, e.g., Whitlow et al. Protein Eng. 1993 November; 6(8):989-95.). In various embodiments a binding motif may comprise a leader sequence, a heavy chain variable domain of the present disclosure (e.g., having at least 75% sequence identity to a heavy chain variable domain of any one of Tables 4-13, e.g., at least 80%, 85%, 90%, 95%, or 100% identity; e.g., 85-90%, 85-95%, 85-100%, 90-95%, 90-100%, or 95-100%), a light chain variable domain of the present disclosure (e.g., having at least 75% sequence identity to a light chain variable domain of any one of Tables 4-13, e.g., at least 80%, 85%, 90%, 95%, or 100% identity; e.g., 85-90%, 85-95%, 85-100%, 90-95%, 90-100%, or 95-100%), and a linker. If provided with an amino acid or nucleotide sequence of a binding motif comprising a heavy chain variable domain of the present disclosure and a light chain variable domain of the present disclosure, the linker joining the two variable domains will be apparent from the sequence in view of the present disclosure. If provided with an amino acid or nucleotide sequence of a binding motif comprising a heavy chain variable domain of the present disclosure and a light chain variable domain of the present disclosure, the leader sequence will be apparent in view of the present disclosure. For the avoidance of doubt, a heavy chain variable domain and a light chain variable domain of the present disclosure may be present in any orientation, e.g., an orientation in which the heavy chain variable domain is C terminal of the light chain variable domain or in which the heavy chain variable domain is N terminal of the light chain variable domain. In various embodiments a binding motif may comprise a linker according to SEQ ID NO: 247 and/or a linker according to any one of SEQ ID NOs: 307-313 adjacent to one or more additional linkers.

In certain embodiments, an anti-CD20 binding motif of the present disclosure comprises a binding motif that comprises a heavy chain variable domain of the present disclosure, a light chain variable domain of the present disclosure, and a linker having at least 75% sequence identity to SEQ ID NO: 247 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-CD20 binding motif of the present disclosure comprises a binding motif that comprises a linker according to SEQ ID NO: 247 and/or a linker according to any one of SEQ ID NOs: 307-313. In certain embodiments, an anti-CD20 binding motif of the present disclosure comprises a binding motif that comprises a heavy chain variable domain of the present disclosure, a light chain variable domain of the present disclosure, and a leader sequence having at least 75% sequence identity to SEQ ID NO: 245 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-CD20 binding motif of the present disclosure comprises a binding motif that comprises a CSF2RA leader sequence according to SEQ ID NO: 245. In certain embodiments, an anti-CD20 binding motif of the present disclosure comprises a binding motif that comprises a heavy chain variable domain of the present disclosure, a light chain variable domain of the present disclosure, a linker of the present disclosure, and a leader sequence of the present disclosure. Exemplary nucleotide sequences encoding an anti-CD19 binding motif and components thereof are found in SEQ ID NOs: 246, and 248. In various embodiments, a binding motif of the present disclosure has a sequence according to any one of the sequences of Table 53 (SEQ ID NOs: 251-260).

A binding agent of the present disclosure that is based on an exemplary antibody provided herein, such as for example Ab1, may be provided in any fragment or format, comprising a heavy chain variable domain according to the indicated exemplary antibody and a light chain variable domain according to the indicated exemplary antibody.

TABLE 4

Exemplary Antibody Sequences 1 (Ab1)

| SEQ ID NO: | Description | Sequence |
|---|---|---|
| 1 | Heavy Chain Variable Domain | QVQLQQWGAGLLKPSETLSLTCAVYGGSFSGYY WSWIRQPPGKGLEWIGEIDHSGSTNYNPSLKSR VTISVDTSKNQFSLKLSSVTAADTAVYYCARGG GSWYSNWFDPWGQGTMVTVSS |
| 2 | VH (DNA) | CAGGTGCAGCTACAGCAGTGGGGCGCAGGACTG TTGAAGCCTTCGGAGACCCTGTCCCTCACCTGC GCTGTCTATGGTGGGTCCTTCAGTGGTTACTAC TGGAGCTGGATCCGCCAGCCCCCAGGGAAGGGG CTGGAGTGGATTGGGGAAATCGACCATAGTGGA AGCACCAACTACAACCCGTCCCTCAAGAGTCGA GTCACCATATCAGTAGACACGTCCAAGAACCAG TTCTCCCTGAAGCTGAGCTCTGTGACCGCCGCG GACACGGCGGTGTACTACTGCGCCAGAGGTGGA GGAAGTTGGTACAGCAACTGGTTCGACCCATGG GGACAGGGTACAATGGTCACCGTCTCCTCA |
| 3 | CDRH1 IMGT (Prot) | GGSFSGYY |
| 4 | CDRH1 Kabat (Prot) | GYYWS |
| 5 | CDRH1 Chothia (Prot) | GGSFSG |
| 6 | CDRH2 IMGT (Prot) | IDHSGST |
| 7 | CDRH2 Kabat (Prot) | EIDHSGSTNYNPSLKS |
| 8 | CDRH2 Chothia (Prot) | DHSGS |
| 9 | CDRH3 IMGT (Prot) | ARGGGSWYSNWFDP |
| 10 | CDRH3 Kabat (Prot) | GGGSWYSNWFDP |
| 11 | CDRH3 Chothia (Prot) | GGGSWYSNWFDP |

TABLE 4-continued

Exemplary Antibody Sequences 1 (Ab1)

| SEQ ID NO: | Description | Sequence |
|---|---|---|
| 12 | Light Chain Variable Domain | DIQMTQSPSTLSASVGDRVTITCRASQSISSWLAWYQQKPGKAPKLLIYDASSLESGVPSRFSGSGSGTEFTLTISSLQPDDFATYYCQQDRSLPPTFGGGTKVEIK |
| 13 | VL (DNA) | GACATCCAGATGACCCAGTCTCCTTCCACCCTGTCTGCATCTGTAGGAGACAGAGTCACCATCACTTGCCGGGCCAGTCAGAGTATTAGTAGCTGGTTGGCCTGGTATCAGCAGAAACCAGGGAAAGCCCCTAAGCTCCTGATCTATGATGCCTCCAGTTTGGAAAGTGGGGTCCCATCAAGGTTCAGCGGCAGTGGATCTGGGACAGAATTCACTCTCACCATCAGCAGCCTGCAGCCTGATGATTTTGCAACTTATTACTGCCAGCAGGACCGAAGTCTCCCTCCTACTTTTGGCGGAGGGACCAAGGTTGAGATCAAA |
| 14 | CDRL1 IMGT (Prot) | RASQSISSWLA |
| 15 | CDRL1 Kabat (Prot) | RASQSISSWLA |
| 16 | CDRL1 Chothia (Prot) | RASQSISSWLA |
| 17 | CDRL2 IMGT (Prot) | DASSLES |
| 18 | CDRL2 Kabat (Prot) | DASSLES |
| 19 | CDRL2 Chothia (Prot) | DASSLES |
| 20 | CDRL3 IMGT (Prot) | QQDRSLPPT |
| 21 | CDRL3 Kabat (Prot) | QQDRSLPPT |
| 22 | CDRL3 Chothia (Prot) | QQDRSLPPT |

TABLE 5

Exemplary Antibody Sequences 2 (Ab2)

| SEQ ID NO: | Description | Sequence |
|---|---|---|
| 23 | Heavy Chain Variable Domain | QVQLQQWGAGLLKPSETLSLTCAVYGGSFSGIHWNWIRQPPGKGLEWIGDIDTSGSTNYNPSLKSRVTISVDTSKNQFSLKLSSVTAADTAVYYCARLGQESATYLGMDVWGQGTTVTVSS |
| 24 | VH (DNA) | CAGGTGCAGCTACAGCAGTGGGGCGCAGGACTGTTGAAGCCTTCGGAGACCCTGTCCCTCACCTGCGCTGTCTATGGTGGGTCCTTCAGTGGTATCCACTGGAACTGGATCCGCCAGCCCCCAGGGAAGGGGCTGGAGTGGATTGGGGACATCGACACAAGTGGAAGCACCAACTACAACCCGTCCCTCAAGAGTCGAGTCACCATATCCGTAGACACGTCCAAGAACCAGTTCTCCCTGAAGCTGAGTTCTGTGACCGCCGCAGACACGGCGGTGTACTACTGCGCCAGATTGGGACAGGAGTCAGCCACCTATCTCGGAATGGACGTATGGGGCCAGGGAACAACTGTCACCGTCTCCTCA |
| 25 | CDRH1 IMGT (Prot) | GGSFSGIH |
| 26 | CDRH1 Kabat (Prot) | GIHWN |
| 27 | CDRH1 Chothia (Prot) | GGSFSG |
| 28 | CDRH2 IMGT (Prot) | IDTSGST |
| 29 | CDRH2 Kabat (Prot) | DIDTSGSTNYNPSLKS |
| 30 | CDRH2 Chothia (Prot) | DTSGS |
| 31 | CDRH3 IMGT (Prot) | ARLGQESATYLGMDV |
| 32 | CDRH3 Kabat (Prot) | LGQESATYLGMDV |
| 33 | CDRH3 Chothia (Prot) | LGQESATYLGMDV |
| 34 | Light Chain Variable Domain | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQLYTYPFTFGGGTKVEIK |
| 35 | VL (DNA) | GACATCGTGATGACCCAGTCTCCAGACTCCCTGGCTGTGTCTCTGGGCGAGAGGGCCACCATCAACTGCAAGTCCAGCCAGAGTGTTTTATACAGCTCCAACAATAAGAACTACTTAGCTTGGTACCAGCAGAAACCAGGACAGCCTCCTAAGCTGCTCATTTACTGGGCATCTACCCGGGAATCCGGGGTCCCTGACCGATTCAGTGGCAGCGGGTCTGGGACAGATTTCACTCTCACCATCAGCAGCCTGCAGGCTGAAGATGTGGCAGTTTATTACTGTCAGCAGCTCTACACCTACCCTTTCACTTTTGGCGGAGGGACCAAGGTTGAGATCAAA |
| 36 | CDRL1 IMGT (Prot) | KSSQSVLYSSNNKNYLA |
| 37 | CDRL1 Kabat (Prot) | KSSQSVLYSSNNKNYLA |
| 38 | CDRL1 Chothia (Prot) | KSSQSVLYSSNNKNYLA |
| 39 | CDRL2 IMGT (Prot) | WASTRES |
| 40 | CDRL2 Kabat (Prot) | WASTRES |
| 41 | CDRL2 Chothia (Prot) | WASTRES |
| 42 | CDRL3 IMGT (Prot) | QQLYTYPFT |
| 43 | CDRL3 Kabat (Prot) | QQLYTYPFT |
| 44 | CDRL3 Chothia (Prot) | QQLYTYPFT |

TABLE 6

Exemplary Antibody Sequences 3 (Ab3)

| SEQ ID NO: | Description | Sequence |
|---|---|---|
| 45 | Heavy Chain Variable Domain | QLQLQESGPGLVKPSETLSLTCTVSGGSISSSS YYWGWIRQPPGKGLEWIGSIYYSGSTYYNPSLK SRVTISVDTSKNQFSLKLSSVTAADTAVYYCAR ETDYSSGMGYGMDVWGQGTTVTVSS |
| 46 | VH (DNA) | CAGCTGCAGCTGCAGGAGTCGGGCCCAGGACTG GTGAAGCCTTCGGAGACCCTGTCCCTCACCTGC ACTGTCTCTGGTGGCTCCATCAGCAGTAGTAGT TACTACTGGGGCTGGATCCGCCAGCCCCCAGGG AAGGGGCTGGAGTGGATTGGGAGTATCTATTAT AGTGGGAGCACCTACTACAACCCGTCCCTCAAG AGTCGAGTCACCATATCCGTAGACACGTCCAAG AACCAGTTCTCCCTGAAGCTGAGTTCTGTGACC GCCGCAGACACGGCGGTGTACTACTGCGCCAGA GAGACTGACTACAGCAGCGGAATGGGATACGGA ATGGACGTATGGGGCCAGGGAACAACTGTCACC GTCTCCTCA |
| 47 | CDRH1 IMGT (Prot) | GGSISSSSYY |
| 48 | CDRH1 Kabat (Prot) | SSSYYWG |
| 49 | CDRH1 Chothia (Prot) | GGSISSSS |
| 50 | CDRH2 IMGT (Prot) | IYYSGST |
| 51 | CDRH2 Kabat (Prot) | SIYYSGSTYYNPSLKS |
| 52 | CDRH2 Chothia (Prot) | YYSGS |
| 53 | CDRH3 IMGT (Prot) | ARETDYSSGMGYGMDV |
| 54 | CDRH3 Kabat (Prot) | ETDYSSGMGYGMDV |
| 55 | CDRH3 Chothia (Prot) | ETDYSSGMGYGMDV |
| 56 | Light Chain Variable Domain | DIQMTQSPSSLSASVGDRVTITCRASQSINSYL NWYQQKPGKAPKLLIYAASSLQSGVPSRFSGSG SGTDFTLTISSLQPEDFATYYCQQSLADPFTFG GGTKVEIK |
| 57 | VL (DNA) | GACATCCAGATGACCCAGTCTCCATCCTCCCTG TCTGCATCTGTAGGAGACAGAGTCACCATCACT TGCCGGCAAGTCAGAGCATTAACAGCTATTTAA ATTGGTATCAGCAGAAACCAGGGAAAGCCCCTA AGCTCCTGATCTATGCTGCATCCAGTTTGCAAA GTGGGGTCCCATCAAGGTTCAGTGGCAGTGGAT CTGGGACAGATTTCACTCTCACCATCAGCAGTC TGCAACCTGAAGATTTTGCAACTTACTACTGCC AGCAAAGCCTCGCCGACCCTTTCACTTTTGGCG GAGGGACCAAGGTTGAGATCAAA |
| 58 | CDRL1 IMGT (Prot) | RASQSINSYLN |
| 59 | CDRL1 Kabat (Prot) | RASQSINSYLN |
| 60 | CDRL1 Chothia (Prot) | RASQSINSYLN |
| 61 | CDRL2 IMGT (Prot) | AASSLQS |
| 62 | CDRL2 Kabat (Prot) | AASSLQS |
| 63 | CDRL2 Chothia (Prot) | AASSLQS |
| 64 | CDRL3 IMGT (Prot) | QQSLADPFT |
| 65 | CDRL3 Kabat (Prot) | QQSLADPFT |
| 66 | CDRL3 Chothia (Prot) | QQSLADPFT |

TABLE 7

Exemplary Antibody Sequences 4 (Ab4)

| SEQ ID NO: | Description | Sequence |
|---|---|---|
| 67 | Heavy Chain Variable Domain | QVQLVQSGAEVKKPGASVKVSCKASGYTFKEYG ISWVRQAPGQGLEWMGWISAYSGHTYYAQKLQG RVTMTTDTSTSTAYMELRSLRSDDTAVYYCARG PHYDDWSGFIIWFDPWGQGTLVTVSS |
| 68 | VH (DNA) | CAGGTTCAGCTGGTGCAGTCTGGAGCTGAGGTG AAGAAGCCTGGGGCCTCAGTGAAGGTCTCCTGC AAGGCTTCTGGTTACACCTTTAAAGAATATGGT ATCAGCTGGGTGCGACAGGCCCCTGGACAAGGG CTTGAGTGGATGGGATGGATCAGCGCTTACAGT GGTCACACATACTATGCACAGAAGCTCCAGGGC AGAGTCACCATGACCACAGACACATCCACGAGC ACAGCCTACATGGAGCTGAGGAGCCTGAGATCT GACGACACGGCGGTGTACTACTGCGCCAGAGGG CCTCACTACGACGACTGGAGCGGATTTATCATA TGGTTCGACCCATGGGGACAGGGTACATTGGTC ACCGTCTCCTCA |
| 69 | CDRH1 IMGT (Prot) | GYTFKEYG |
| 70 | CDRH1 Kabat (Prot) | EYGIS |
| 71 | CDRH1 Chothia (Prot) | GYTFKE |
| 72 | CDRH2 IMGT (Prot) | ISAYSGHT |
| 73 | CDRH2 Kabat (Prot) | WISAYSGHTYYAQKLQ |
| 74 | CDRH2 Chothia (Prot) | SAYSG |
| 75 | CDRH3 IMGT (Prot) | ARGPHYDDWSGFIIWFDP |
| 76 | CDRH3 Kabat (Prot) | GPHYDDWSGFIIWFDP |
| 77 | CDRH3 Chothia (Prot) | GPHYDDWSGFIIWFDP |

TABLE 7-continued

Exemplary Antibody Sequences 4 (Ab4)

| SEQ ID NO: | Description | Sequence |
|---|---|---|
| 78 | Light Chain Variable Domain | DIQMTQSPSSLSASVGDRVTITCRASQSISSYL NWYQQKPGKAPKLLIYAASSLQSGVPSRFSGSG SGTDFTLTISSLQPEDFATYYCQQSYRFPPTFG QGTKVEIK |
| 79 | VL (DNA) | GACATCCAGATGACCCAGTCTCCATCCTCCCTG TCTGCATCTGTAGGAGACAGAGTCACCATCACT TGCCGGGCAAGTCAGAGCATTAGCAGCTATTTA AATTGGTATCAGCAGAAACCAGGGAAAGCCCCT AAGCTCCTGATCTATGCTGCATCCAGTTTGCAA AGTGGGGTCCCTTCAAGGTTCAGTGGCAGTGGA TCTGGGACAGATTTCACTCTCACCATCAGCAGT CTGCAACCTGAAGATTTTGCAACTTACTACTGT CAACAGAGTTACAGGTTTCCTCCTACCTTTGGC CAAGGGACCAAGGTTGAGATCAAA |
| 80 | CDRL1 IMGT (Prot) | RASQSISSYLN |
| 81 | CDRL1 Kabat (Prot) | RASQSISSYLN |
| 82 | CDRL1 Chothia (Prot) | RASQSISSYLN |
| 83 | CDRL2 IMGT (Prot) | AASSLQS |
| 84 | CDRL2 Kabat (Prot) | AASSLQS |
| 85 | CDRL2 Chothia (Prot) | AASSLQS |
| 86 | CDRL3 IMGT (Prot) | QQSYRFPPT |
| 87 | CDRL3 Kabat (Prot) | QQSYRFPPT |
| 88 | CDRL3 Chothia (Prot) | QQSYRFPPT |

TABLE 8

Exemplary Antibody Sequences 5 (Ab5)

| SEQ ID NO: | Description | Sequence |
|---|---|---|
| 89 | Heavy Chain Variable Domain | QVQLQESGPGLVKPSETLSLTCTVSGGSISS PDHYWGWIRQPPGKGLEWIGSIYASGSTFYN PSLKSRVTISVDTSKNQFSLKLSSVTAADTA VYYCARETDYSSGMGYGMDVWGQGTTVTVSS |
| 90 | VH (DNA) | CAGGTGCAGCTGCAGGAGTCGGGCCCAGGAC TGGTGAAGCCTTCGGAGACCCTGTCCCTCAC CTGCACTGTCTCTGGTGGCTCCATCAGCAGT CCCGACCACTACTGGGGCTGGATCCGCCAGC CCCCAGGGAAGGGGCTGGAGTGGATTGGGTC CATCTACGCCAGTGGGAGCACCTTCTACAAC CCGTCCCTCAAGAGTCGAGTCACCATATCCG TAGACACGTCCAAGAACCAGTTCTCCCTGAA GCTGAGCTCTGTGACCGCCGCGGACACGGCG GTGTACTACTGCGCCAGAGAGACTGACTACA GCAGCGGAATGGGATACGGAATGGACGTATG GGGCCAGGGAACAACTGTCACCGTCTCCTCA |
| 91 | CDRH1 IMGT (Prot) | GGSISSPDHY |
| 92 | CDRH1 Kabat (Prot) | SPDHYWG |
| 93 | CDRH1 Chothia (Prot) | GGSISSPD |
| 94 | CDRH2 IMGT (Prot) | IYASGST |
| 95 | CDRH2 Kabat (Prot) | SIYASGSTFYNPSLKS |
| 96 | CDRH2 Chothia (Prot) | YASGS |
| 97 | CDRH3 IMGT (Prot) | ARETDYSSGMGYGMDV |
| 98 | CDRH3 Kabat (Prot) | ETDYSSGMGYGMDV |
| 99 | CDRH3 Chothia (Prot) | ETDYSSGMGYGMDV |
| 100 | Light Chain Variable Domain | DIQMTQSPSSLSASVGDRVTITCRASQSINS YLNWYQQKPGKAPKLLIYAASSLQSGVPSRF SGSGSGTDFTLTISSLQPEDFATYYCQQSLA DPFTFGGGTKVEIK |
| 101 | VL (DNA) | GACATCCAGATGACCCAGTCTCCATCCTCCC TGTCTGCATCTGTAGGAGACAGAGTCACCAT CACTTGCCGGGCAAGTCAGAGCATTAACAGC TATTTAAATTGGTATCAGCAGAAACCAGGGA AAGCCCCTAAGCTCCTGATCTATGCTGCATC CAGTTTGCAAAGTGGGGTCCCATCAAGGTTC AGTGGCAGTGGATCTGGGACAGATTTCACTC TCACCATCAGCAGTCTGCAACCTGAAGATTT TGCAACTTACTACTGCCAGCAAAGCCTCGCC GACCCTTTCACTTTTGGCGGAGGGACCAAGG TTGAGATCAAA |
| 102 | CDRL1 IMGT (Prot) | RASQSINSYLN |
| 103 | CDRL1 Kabat (Prot) | RASQSINSYLN |
| 104 | CDRL1 Chothia (Prot) | RASQSINSYLN |
| 105 | CDRL2 IMGT (Prot) | AASSLQS |
| 106 | CDRL2 Kabat (Prot) | AASSLQS |
| 107 | CDRL2 Chothia (Prot) | AASSLQS |
| 108 | CDRL3 IMGT (Prot) | QQSLADPFT |
| 109 | CDRL3 Kabat (Prot) | QQSLADPFT |
| 110 | CDRL3 Chothia (Prot) | QQSLADPFT |

TABLE 9

Exemplary Antibody Sequences 6 (Ab6)

| SEQ ID NO: | Description | Sequence |
|---|---|---|
| 111 | Heavy Chain Variable Domain | QITLKESGPTLVKPTQTLTLTCTFSGFSLDTEGVGVGWIRQPPGKALEWLALIYFNDQKRYSPSLKSRLTITKDTSKNQVVLTMTNMDPVDTAVYYCARDTGYSRWYYGMDVWGQGTTVTVSS |
| 112 | VH (DNA) | CAGATCACCTTGAAGGAGTCTGGTCCTACGCTGGTGAAACCCACACAGACCCTCACGCTGACCTGCACCTTCTCTGGGTTCTCACTCGACACTGAAGGAGTGGGTGTGGGCTGGATCCGTCAGCCCCCAGGAAAGGCCCTGGAGTGGCTTGCACTCATTTATTTCAATGATCAAAAGCGCTACAGCCCATCTCTGAAGAGCAGGCTCACCATCACCAAGGACACCTCCAAAAACCAGGTGGTCCTTACAATGACCAACATGGACCCTGTGGACACGGCGGTGTACTACTGCGCCAGAGACACGGGATACAGCCGATGGTACTACGGCATGGATGTATGGGGCCAGGGAACAACTGTCACCGTCTCCTCA |
| 113 | CDRH1 IMGT (Prot) | GFSLDTEGVG |
| 114 | CDRH1 Kabat (Prot) | TEGVGVG |
| 115 | CDRH1 Chothia (Prot) | GFSLDTEG |
| 116 | CDRH2 IMGT (Prot) | IYFNDQK |
| 117 | CDRH2 Kabat (Prot) | LIYFNDQKRYSPSLKS |
| 118 | CDRH2 Chothia (Prot) | YFNDQ |
| 119 | CDRH3 IMGT (Prot) | ARDTGYSRWYYGMDV |
| 120 | CDRH3 Kabat (Prot) | DTGYSRWYYGMDV |
| 121 | CDRH3 Chothia (Prot) | DTGYSRWYYGMDV |
| 122 | Light Chain Variable Domain | DIQMTQSPSSVSASVGDRVTITCRASQGISSWLAWYQQKPGKAPKLLIYAASSLQSGVPSRFSGSGSGTDFTLTISSLQPEDFATYYCQQAYAYPITFGGGTKVEIK |
| 123 | VL (DNA) | GACATCCAGATGACCCAGTCTCCATCTTCCGTGTCTGCATCTGTAGGAGACAGAGTCACCATCACTTGTCGGGCGAGTCAGGGTATTAGCAGCTGGTTAGCCTGGTATCAGCAGAAACCAGGGAAAGCCCCTAAGCTCCTGATCTATGCTGCATCCAGTTTGCAAAGTGGGGTCCCATCAAGGTTCAGCGGCAGTGGATCTGGGACAGATTTCACTCTCACCATCAGCAGCCTGCAGCCTGAAGATTTTGCAACTTATTACTGTCAGCAGGCATACGCCTACCCTATCACTTTTGGCGGAGGGACCAAGGTTGAGATCAAA |
| 124 | CDRL1 IMGT (Prot) | RASQGISSWLA |
| 125 | CDRL1 Kabat (Prot) | RASQGISSWLA |
| 126 | CDRL1 Chothia (Prot) | RASQGISSWLA |
| 127 | CDRL2 IMGT (Prot) | AASSLQS |
| 128 | CDRL2 Kabat (Prot) | AASSLQS |
| 129 | CDRL2 Chothia (Prot) | AASSLQS |
| 130 | CDRL3 IMGT (Prot) | QQAYAYPIT |
| 131 | CDRL3 Kabat (Prot) | QQAYAYPIT |
| 132 | CDRL3 Chothia (Prot) | QQAYAYPIT |

TABLE 10

Exemplary Antibody Sequences 7 (Ab7)

| SEQ ID NO: | Description | Sequence |
|---|---|---|
| 133 | Heavy Chain Variable Domain | QVQLQQWGAGLLKPSETLSLTCAVYGGSFEKYYWSWIRQPPGKGLEWIGEIYHSGLTNYNPSLKSRVTISVDTSKNQFSLKLSSVTAADTAVYYCARVRYDSSDSYYYSYDYGMDVWGQGTTVTVSS |
| 134 | VH (DNA) | CAGGTGCAGCTACAGCAGTGGGGCGCAGGACTGTTGAAGCCTTCGGAGACCCTGTCCCTCACCTGCGCTGTCTATGGTGGGTCCTTCGAAAAATACTACTGGAGCTGGATCCGCCAGCCCCCAGGGAAGGGGCTGGAGTGGATTGGGGAAATCTACCATAGTGGACTCACCAACTACAACCCGTCCCTCAAGAGTCGAGTCACCATATCAGTAGACACGTCCAAGAACCAGTTCTCCCTGAAGCTGAGCTCTGTGACCGCCGCGGACACGGCGGTGTACTACTGCGCCAGGGTCAGATACGACAGCAGCGACTCCTACTACTATAGCTACGATTATGGAATGGACGTATGGGGCCAGGGAACAACTGTCACCGTCTCCTCA |
| 135 | CDRH1 IMGT (Prot) | GGSFEKYY |
| 136 | CDRH1 Kabat (Prot) | KYYWS |
| 137 | CDRH1 Chothia (Prot) | GGSFEK |
| 138 | CDRH2 IMGT (Prot) | IYHSGLT |
| 139 | CDRH2 Kabat (Prot) | EIYHSGLTNYNPSLKS |
| 140 | CDRH2 Chothia (Prot) | YHSGL |
| 141 | CDRH3 IMGT (Prot) | ARVRYDSSDSYYYSYDYGMDV |
| 142 | CDRH3 Kabat (Prot) | VRYDSSDSYYYSYDYGMDV |

TABLE 10-continued

Exemplary Antibody Sequences 7 (Ab7)

| SEQ ID NO: | Description | Sequence |
|---|---|---|
| 143 | CDRH3 Chothia (Prot) | VRYDSSDSYYYSYDYGMDV |
| 144 | Light Chain Variable Domain | DIVLTQSPDSLAVSLGERATINCKSSQSVLYSSNNKNYLAWYQQKPGQPPKLLIYWASSRESGVPDRFSGSGSGTDFTLTISSLQAEDVAVYYCQQSYSFPWTFGGGTKVEIK |
| 145 | VL (DNA) | GACATCGTGCTGACCCAGTCTCCAGACTCCCTGGCTGTGTCTCTGGGCGAGAGGGCCACCATCAACTGCAAGTCCAGCCAGAGTGTTTTATACAGCTCCAACAATAAGAACTACTTAGCTTGGTACCAGCAGAAACCAGGACAGCCTCCTAAGCTGCTCATTTACTGGGCATCTAGCCGGGAATCCGGGGTCCCTGACCGATTCAGTGGCAGCGGGTCTGGGACAGATTTCACTCTCACCATCAGCAGCCTGCAGGCTGAAGATGTGGCAGTTTATTACTGTCAGCAGTCCTACTCCTTCCCTTGGACTTTTGGCGGAGGGACCAAGGTTGAGATCAAA |
| 146 | CDRL1 IMGT (Prot) | KSSQSVLYSSNNKNYLA |

TABLE 10-continued

Exemplary Antibody Sequences 7 (Ab7)

| SEQ ID NO: | Description | Sequence |
|---|---|---|
| 147 | CDRL1 Kabat (Prot) | KSSQSVLYSSNNKNYLA |
| 148 | CDRL1 Chothia (Prot) | KSSQSVLYSSNNKNYLA |
| 149 | CDRL2 IMGT (Prot) | WASSRES |
| 150 | CDRL2 Kabat (Prot) | WASSRES |
| 151 | CDRL2 Chothia (Prot) | WASSRES |
| 152 | CDRL3 IMGT (Prot) | QQSYSFPWT |
| 153 | CDRL3 Kabat (Prot) | QQSYSFPWT |
| 154 | CDRL3 Chothia (Prot) | QQSYSFPWT |

TABLE 11

Exemplary Antibody Sequences 8 (Ab8)

| SEQ ID NO: | Description | Sequence |
|---|---|---|
| 155 | Heavy Chain Variable Domain | QVQLQQWGAGLLKPSETLSLTCAVYGGSFSRYVWSWIRQPPGKGLEWIGEIDSSGKTNYNPSLKSRVTISVDTSKNQFSLKLSSVTAADTAVYYCARVRYDSSDSYYYSYDYGMDVWGQGTTVTVSS |
| 156 | VH (DNA) | CAGGTGCAGCTACAGCAGTGGGGCGCAGGACTGTTGAAGCCTTCGGAGACCCTGTCCCTCACCTGCGCTGTCTATGGTGGGTCCTTCAGTCGATACGTATGGAGCTGGATCCGCCAGCCCCCAGGGAAGGGGCTGGAGTGGATTGGGGAAATCGACTCCAGTGGAAAAACCAACTACAACCCCGTCCCTCAAGAGTCGAGTCACCATATCAGTAGACACGTCCAAGAACCAGTTCTCCCTGAAGCTGAGCTCTGTGACCGCCGCGGACACGGCGGTGTACTACTGCGCCAGGGTCAGATACGACAGCAGCGACTCCTACTACTATAGCTACGATTATGGAATGGACGTATGGGGCCAGGGAACAACTGTCACCGTCTCCTCA |
| 157 | CDRH1 IMGT (Prot) | GGSFSRYV |
| 158 | CDRH1 Kabat (Prot) | RYVWS |
| 159 | CDRH1 Chothia (Prot) | GGSFSR |
| 160 | CDRH2 IMGT (Prot) | IDSSGKT |
| 161 | CDRH2 Kabat (Prot) | EIDSSGKTNYNPSLKS |
| 162 | CDRH2 Chothia (Prot) | DSSGK |
| 163 | CDRH3 IMGT (Prot) | ARVRYDSSDSYYYSYDYGMDV |
| 164 | CDRH3 Kabat (Prot) | VRYDSSDSYYYSYDYGMDV |
| 165 | CDRH3 Chothia (Prot) | VRYDSSDSYYYSYDYGMDV |

TABLE 11-continued

Exemplary Antibody Sequences 8 (Ab8)

| SEQ ID NO: | Description | Sequence |
|---|---|---|
| 166 | Light Chain Variable Domain | DIVLTQSPDSLAVSLGERATINCKSSQSVLYSSNNKNYL AWYQQKPGQPPKLLIYWASSRESGVPDRFSGSGSGTDF TLTISSLQAEDVAVYYCQQSYSFPWTFGGGTKVEIK |
| 167 | VL (DNA) | GACATCGTGCTGACCCAGTCTCCAGACTCCCTGGCTG TGTCTCTGGGCGAGAGGGCCACCATCAACTGCAAGTC CAGCCAGAGTGTTTTATACAGCTCCAACAATAAGAAC TACTTAGCTTGGTACCAGCAGAAACCAGGACAGCCTC CTAAGCTGCTCATTTACTGGGCATCTAGCCGGGAATC CGGGGTCCCTGACCGATTCAGTGGCAGCGGGTCTGGG ACAGATTTCACTCTCACCATCAGCAGCCTGCAGGCTG AAGATGTGGCAGTTTATTACTGTCAGCAGTCCTACTC CTTCCCTTGGACTTTTGGCGGAGGGACCAAGGTTGAG ATCAAA |
| 168 | CDRL1 IMGT (Prot) | KSSQSVLYSSNNKNYLA |
| 169 | CDRL1 Kabat (Prot) | KSSQSVLYSSNNKNYLA |
| 170 | CDRL1 Chothia (Prot) | KSSQSVLYSSNNKNYLA |
| 171 | CDRL2 IMGT (Prot) | WASSRES |
| 172 | CDRL2 Kabat (Prot) | WASSRES |
| 173 | CDRL2 Chothia (Prot) | WASSRES |
| 174 | CDRL3 IMGT (Prot) | QQSYSFPWT |
| 175 | CDRL3 Kabat (Prot) | QQSYSFPWT |
| 176 | CDRL3 Chothia (Prot) | QQSYSFPWT |

TABLE 12

Exemplary Antibody Sequences 9 (Ab9)

| SEQ ID NO: | Description | Sequence |
|---|---|---|
| 177 | Heavy Chain Variable Domain | QVQLQQWGAGLLKPSETLSLTCAVYGGSFSGYAWSWI RQPPGKGLEWIGEIDHRGFTNYNPSLKSRVTISVDTSKN QFSLKLSSVTAADTAVYYCARVRYDSSDSYYYSYDYG MDVWGQGTTVTVSS |
| 178 | VH (DNA) | CAGGTGCAGCTACAGCAGTGGGGCGCAGGACTGTTG AAGCCTTCGGAGACCCTGTCCCTCACCTGCGCTGTCT ATGGTGGGTCCTTCTCCGGTTACGCATGGAGCTGGAT CCGCCAGCCCCCAGGGAAGGGGCTGGAGTGGATTGG GGAAATCGACCATCGAGGATTCACCAACTACAACCC GTCCCTCAAGAGTCGAGTCACCATATCAGTAGACACG TCCAAGAACCAGTTCTCCCTGAAGCTGAGCTCTGTGA CCGCCGCGGACACGGCGGTGTACTACTGCGCCAGGGT CAGATACGACAGCAGCGACTCCTACTACTATAGCTAC GATTATGGAATGGACGTATGGGGCCAGGGAACAACT GTCACCGTCTCCTCA |
| 179 | CDRH1 IMGT (Prot) | GGSFSGYA |
| 180 | CDRH1 Kabat (Prot) | GYAWS |
| 181 | CDRH1 Chothia (Prot) | GGSFSG |
| 182 | CDRH2 IMGT (Prot) | IDHRGFT |
| 183 | CDRH2 Kabat (Prot) | EIDHRGFTNYNPSLKS |
| 184 | CDRH2 Chothia (Prot) | DHRGF |
| 185 | CDRH3 IMGT (Prot) | ARVRYDSSDSYYYSYDYGMDV |
| 186 | CDRH3 Kabat (Prot) | VRYDSSDSYYYSYDYGMDV |
| 187 | CDRH3 Chothia (Prot) | VRYDSSDSYYYSYDYGMDV |

TABLE 12-continued

Exemplary Antibody Sequences 9 (Ab9)

| SEQ ID NO: | Description | Sequence |
| --- | --- | --- |
| 188 | Light Chain Variable Domain | DIVLTQSPDSLAVSLGERATINCKSSQSVLYSSNNKNYL AWYQQKPGQPPKLLIYWASSRESGVPDRFSGSGSGTDF TLTISSLQAEDVAVYYCQQSYSFPWTFGGGTKVEIK |
| 189 | VL (DNA) | GACATCGTGCTGACCCAGTCTCCAGACTCCCTGGCTG TGTCTCTGGGCGAGAGGGCCACCATCAACTGCAAGTC CAGCCAGAGTGTTTTATACAGCTCCAACAATAAGAAC TACTTAGCTTGGTACCAGCAGAAACCAGGACAGCCTC CTAAGCTGCTCATTTACTGGGCATCTAGCCGGGAATC CGGGGTCCCTGACCGATTCAGTGGCAGCGGGTCTGGG ACAGATTTCACTCTCACCATCAGCAGCCTGCAGGCTG AAGATGTGGCAGTTTATTACTGTCAGCAGTCCTACTC CTTCCCTTGGACTTTTGGCGGAGGGACCAAGGTTGAG ATCAAA |
| 190 | CDRL1 IMGT (Prot) | KSSQSVLYSSNNKNYLA |
| 191 | CDRL1 Kabat (Prot) | KSSQSVLYSSNNKNYLA |
| 192 | CDRL1 Chothia (Prot) | KSSQSVLYSSNNKNYLA |
| 193 | CDRL2 IMGT (Prot) | WASSRES |
| 194 | CDRL2 Kabat (Prot) | WASSRES |
| 195 | CDRL2 Chothia (Prot) | WASSRES |
| 196 | CDRL3 IMGT (Prot) | QQSYSFPWT |
| 197 | CDRL3 Kabat (Prot) | QQSYSFPWT |
| 198 | CDRL3 Chothia (Prot) | QQSYSFPWT |

TABLE 13

Exemplary Antibody Sequences 10 (Ab10)

| SEQ ID NO: | Description | Sequence |
| --- | --- | --- |
| 199 | Heavy Chain Variable Domain | QVQLQQWGAGLLKPSETLSLTCAVYGGSFQKYYWSWI RQPPGKGLEWIGEIDTSGFTNYNPSLKSRVTISVDTSKNQ FSLKLSSVTAADTAVYYCARVGRYSYGYYITAFDIWGQ GTTVTVSS |
| 200 | VH (DNA) | CAGGTGCAGCTACAGCAGTGGGGCGCAGGACTGTTG AAGCCTTCGGAGACCCTGTCCCTCACCTGCGCTGTCT ATGGTGGGTCCTTCCAAAAATACTACTGGAGCTGGAT CCGCCAGCCCCCAGGGAAGGGGCTGGAGTGGATTGG GGAAATCGACACCAGTGGATTCACCAACTACAACCC GTCCCTCAAGAGTCGAGTCACCATATCAGTAGACACG TCCAAGAACCAGTTCTCCCTGAAGCTGAGCTCTGTGA CCGCCGCGGACACGGCGGTGTACTACTGCGCCAGAGT GGGAAGGTACAGCTACGGATACTATATCACCGCATTC GACATATGGGGTCAGGGTACAACTGTCACCGTCTCCT CA |
| 201 | CDRH1 IMGT (Prot) | GGSFQKYY |
| 202 | CDRH1 Kabat (Prot) | KYYWS |
| 203 | CDRH1 Chothia (Prot) | GGSFQK |
| 204 | CDRH2 IMGT (Prot) | IDTSGFT |
| 205 | CDRH2 Kabat (Prot) | EIDTSGFTNYNPSLKS |
| 206 | CDRH2 Chothia (Prot) | DTSGF |
| 207 | CDRH3 IMGT (Prot) | ARVGRYSYGYYITAFDI |
| 208 | CDRH3 Kabat (Prot) | VGRYSYGYYITAFDI |

TABLE 13-continued

Exemplary Antibody Sequences 10 (Ab10)

| SEQ ID NO: | Description | Sequence |
| --- | --- | --- |
| 209 | CDRH3 Chothia (Prot) | VGRYSYGYYITAFDI |
| 210 | Light Chain Variable Domain | DIVMTQSPDSLAVSLGERATINCKSSQSVLYSSNNKNYL AWYQQKPGQPPKLLIYWASTRESGVPDRFSGSGSGTDF TLTISSLQAEDVAVYYCQQHYSFPFTFGGGTKVEIK |
| 211 | VL (DNA) | GACATCGTGATGACCCAGTCTCCAGACTCCCTGGCTG TGTCTCTGGGCGAGAGGGCCACCATCAACTGCAAGTC CAGCCAGAGTGTTTTATACAGCTCCAACAATAAGAAC TACTTAGCTTGGTACCAGCAGAAACCAGGACAGCCTC CTAAGCTGCTCATTTACTGGGCATCTACCCGGGAATC CGGGGTCCCTGACCGATTCAGTGGCAGCGGGTCTGGG ACAGATTTCACTCTCACCATCAGCAGCCTGCAGGCTG AAGATGTGGCAGTTTATTACTGTCAGCAGCACTACTC CTTCCCTTTCACTTTTGGCGGAGGGACCAAGGTTGAG ATCAAA |
| 212 | CDRL1 IMGT (Prot) | KSSQSVLYSSNNKNYLA |
| 213 | CDRL1 Kabat (Prot) | KSSQSVLYSSNNKNYLA |
| 214 | CDRL1 Chothia (Prot) | KSSQSVLYSSNNKNYLA |
| 215 | CDRL2 IMGT (Prot) | WASTRES |
| 216 | CDRL2 Kabat (Prot) | WASTRES |
| 217 | CDRL2 Chothia (Prot) | WASTRES |
| 218 | CDRL3 IMGT (Prot) | QQHYSFPFT |
| 219 | CDRL3 Kabat (Prot) | QQHYSFPFT |
| 220 | CDRL3 Chothia (Prot) | QQHYSFPFT |

The present disclosure comprises antibodies and antigen binding systems that comprise an anti-CD20 binding motif and a second binding motif that binds a second target antigen or epitope, e.g., an antigen that is not CD20 (e.g., CD19). Dual-targeted antigen binding systems comprise bispecific CARs and bicistronic CARs. Many antigen binding motifs are known. In various embodiments, the second target antigen is CD19. The present specification comprises a variety of second target antigens, comprising, without limitation, a second antigen that is 5T4, alphafetoprotein, B cell maturation antigen (BCMA), CA-125, carcinoembryonic antigen, CD19, CD20, CD22, CD23, CD30, CD33, CD56, CD123, CD138, c-Met, CSPG4, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gp120, IL-11Ralpha, kappa chain, lambda chain, melanoma-associated antigen, mesothelin, MUC-1, mutated p53, mutated ras, prostate-specific antigen, ROR1, VEGFR2, or a combination thereof. Accordingly in various embodiments, an antigen binding system or antibody of the present disclosure may comprise a first binding motif that is an anti-CD20 binding motif and a second binding motif that binds a second antigen that is 5T4, alphafetoprotein, B cell maturation antigen (BCMA), CA-125, carcinoembryonic antigen, CD19, CD20, CD22, CD23, CD30, CD33, CD56, CD123, CD138, c-Met, CSPG4, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gp120, IL-11Ralpha, kappa chain, lambda chain, melanoma-associated antigen, mesothelin, MUC-1, mutated p53, mutated ras, prostate-specific antigen, ROR1, VEGFR2, EphA3 (EPH receptor A3), BAFFR (B-cell activating factor receptor), or a combination thereof. In some embodiments, a second antigen is an antigen that is characteristic of B-cells or of a subset thereof, optionally wherein the second antigen is not CD19 or CD20. Examples of binding motifs that target these second antigens are known and/or provided herein.

In some instances, in an antigen binding system such as a bispecific CAR that comprises an anti-CD20 binding motif (e.g., comprising a heavy chain variable domain and/or a light chain variable domain of the present disclosure) and an anti-CD19 binding motif (e.g., comprising a heavy chain variable domain and/or a light chain variable domain of the present disclosure), the anti-CD20 binding motif (or a heavy chain variable domain and/or a light chain variable domain thereof) is closer to the C-terminus of the chimeric antigen receptor than the anti-CD19 binding motif (or than a heavy chain variable domain and/or a light chain variable domain thereof). In some instances, in an antigen binding system such as a bispecific CAR comprising an anti-CD20 binding motif (e.g., comprising a heavy chain variable domain and/or a light chain variable domain of the present disclosure) and an anti-CD19 binding motif (e.g., comprising a heavy chain variable domain and/or a light chain variable domain of the present disclosure), the anti-CD20 binding motif (or a heavy chain variable domain and/or a light chain variable domain thereof) is closer to the N-terminus of the agent than the anti-CD19 binding motif (or than a heavy chain variable domain and/or a light chain variable domain thereof).

CD19 (also known as Cluster of Differentiation 19, B-lymphocyte antigen CD19, B-lymphocyte surface antigen B4, B4, CVID3, Differentiation antigen CD19) is a protein that is encoded by the CD19 gene in humans. Unless otherwise indicated, it is to be appreciated the references to CD19 in the present disclosure relate to human CD19. It is found on the surface of B cells. Since CD19 expression is a hallmark of B cells, it may be useful as an antigen, e.g., in recognizing B cells and cancer cells that arise from B cells, e.g., B-cell lymphomas. Anti-CD19 antibodies may bind CD19 expressed on, e.g., B lymphocytes in peripheral blood and spleen, B cell chronic lymphocytic leukemia (B-CLL) cells, pro lymphocytic leukemia (PLL) cells, hairy cell leukemia (HCL) cells, common acute lymphoblastic leukemia (CALL) cells, pre-B acute lymphoblastic leukemia (pre-B-ALL) cells, and NULL-acute lymphoblastic leukemia (NULL-ALL) cells, to provide a few non limiting examples. An exemplary pharmaceutical product that comprises an antigen binding system that comprises an anti-CD19 binding motif is the pharmaceutical product YESCARTA®. YESCARTA® is a CD19-directed genetically modified autologous T cell immunotherapy indicated for the treatment of adult patients with relapsed or refractory large B-cell lymphoma after two or more lines of systemic therapy, comprising diffuse large B-cell lymphoma (DLBCL) not otherwise specified, primary mediastinal large B-cell lymphoma, high grade B-cell lymphoma, and DLBCL arising from follicular lymphoma (See YESCARTA® FDA-approved package insert, the entirety of which is incorporated herein by reference with respect to methods and compositions relating to immunotherapy). Another exemplary pharmaceutical product that comprises an antigen binding system that comprises an anti-CD19 binding motif is the pharmaceutical product KYMRIAH®. KYMRIAH® is a CD19-directed genetically modified autologous T-cell immunotherapy indicated for the treatment of: (1) Patients up to 25 years of age with B-cell precursor acute lymphoblastic leukemia (ALL) that is refractory or in second or later relapse; and (2) Adult patients with relapsed or refractory (r/r) large B-cell lymphoma after two or more lines of systemic therapy comprising diffuse large B-cell lymphoma (DLBCL) not otherwise specified, high grade B-cell lymphoma and DLBCL arising from follicular lymphoma (See KYMRIAH® FDA-approved package insert, the entirety of which is incorporated herein by reference with respect to methods and compositions relating to immunotherapy).

Both YESCARTA® and KYMRIAH® comprise antibody binding domains derived from an anti-human CD19 antibody. Many anti-CD19 antibodies are thought to bind an epitope of CD19 encoded in exon 4 of the CD19 gene. Other anti-CD19 binding motifs may recognize different epitopes of CD19, or the same epitope with differential affinities. Antigen binding systems may comprise antigen binding domains derived, for example, from SJ25C1. The CD19 antibody, clone SJ25C1 was derived from hybridization of Sp2/0 mouse myeloma cells with spleen cells isolated from BALB/c mice immunized with NALM1 and NALM16 cells. SJ25C1 antigen binding domains were used in other investigational CD19-targeting chimeric antigen receptor (CAR) T-cell therapy.

An anti-CD19 binding motif of the present disclosure may comprise antigen-binding sequences as found in an antibody described herein. In some embodiments, an anti-CD19 binding motif of the present disclosure comprises an antigen binding fragment provided herein.

In various embodiments, an anti-CD19 binding motif of the present disclosure comprises at least one HCDR provided herein, e.g., at least one HCDR disclosed in Table 14. In various embodiments, an anti-CD19 binding motif of the present disclosure comprises two HCDRs provided herein, e.g., at least two HCDRs disclosed in Table 14. In various embodiments, an anti-CD19 binding motif of the present disclosure comprises three HCDRs provided herein, e.g., three HCDRs disclosed in Table 14.

In various embodiments, an anti-CD19 binding motif of the present disclosure comprises at least one LCDR provided herein, e.g., at least one LCDR disclosed in Table 14. In various embodiments, an anti-CD19 binding motif of the present disclosure comprises two LCDRs provided herein, e.g., at least two LCDRs disclosed in Table 14. In various embodiments, an anti-CD19 binding motif of the present disclosure comprises three LCDRs provided herein, e.g., three LCDRs disclosed in Table 14.

In various embodiments, an anti-CD19 binding motif of the present disclosure comprises at least one HCDR provided herein, e.g., at least one HCDR disclosed in Table 14, and at least one LCDR provided herein, e.g., at least one LCDR disclosed in Table 14. In various embodiments, an anti-CD19 binding motif of the present disclosure comprises two HCDRs provided herein, e.g., at least two HCDRs disclosed in Table 14, and two LCDRs provided herein, e.g., at least two LCDRs disclosed in Table 14. In various embodiments, an anti-CD19 binding motif of the present disclosure comprises three HCDRs provided herein, e.g., three HCDRs disclosed in Table 14, and three LCDRs provided herein, e.g., three LCDRs disclosed in Table 14.

In various embodiments, an anti-CD19 binding motif of the present disclosure comprises at least one heavy chain framework region (heavy chain FR) of a heavy chain variable domain disclosed herein, e.g., at least one heavy chain FR of a heavy chain variable domain disclosed in Table 14. In various embodiments, an anti-CD19 binding motif of the present disclosure comprises two heavy chain FRs of a heavy chain variable domain disclosed herein, e.g., at least two heavy chain FRs of a heavy chain variable domain disclosed in Table 14. In various embodiments, an anti-CD19 binding motif of the present disclosure comprises three heavy chain FRs of a heavy chain variable domain disclosed herein, e.g., three heavy chain FRs of a heavy chain variable domain disclosed in Table 14.

In various embodiments, an anti-CD19 binding motif of the present disclosure comprises at least one light chain FR of a light chain variable domain disclosed herein, e.g., at least one light chain FR of a light chain variable domain disclosed in Table 14. In various embodiments, an anti-CD19 binding motif of the present disclosure comprises two light chain FRs of a light chain variable domain disclosed herein, e.g., at least two light chain FRs of a light chain variable domain disclosed in Table 14. In various embodiments, an anti-CD19 binding motif of the present disclosure comprises three light chain FRs of a light chain variable domain disclosed herein, e.g., three light chain FRs of a light chain variable domain disclosed in Table 14.

In various embodiments, an anti-CD19 binding motif of the present disclosure comprises at least one heavy chain FR of a heavy chain variable domain disclosed herein, e.g., at least one heavy chain FR of a heavy chain variable domain disclosed in Table 14, and at least one light chain FR of a light chain variable domain disclosed herein, e.g., at least one light chain FR of a light chain variable domain disclosed in Table 14. In various embodiments, an anti-CD19 binding motif of the present disclosure comprises two heavy chain FRs of a heavy chain variable domain disclosed herein, e.g., at least two heavy chain FRs of a heavy chain variable domain disclosed in Table 14, and two light chain FRs of a light chain variable domain disclosed herein, e.g., at least two light chain FRs of a light chain variable domain disclosed in Table 14. In various embodiments, an anti-CD19 binding motif of the present disclosure comprises three heavy chain FRs of a heavy chain variable domain disclosed herein, e.g., three heavy chain FRs of a heavy chain variable domain disclosed in Table 14, and three light chain FRs of a light chain variable domain disclosed herein, e.g., three light chain FRs of a light chain variable domain disclosed in Table 14.

In various embodiments, an anti-CD19 binding motif of the present disclosure comprises one, two, or three FRs that together or each individually have at least 75% identity (e.g., at least 75%, at least 80%, at least 90%, at least 95%, or 100% identity; e.g., 85-90%, 85-95%, 85-100%, 90-95%, 90-100%, or 95-100%) to corresponding FR(s) of a heavy chain variable domain of a heavy chain variable domain disclosed in in Table 14. In various embodiments, an anti-CD19 binding motif of the present disclosure comprises one, two, or three FRs that together or each individually have at least 75% identity (e.g., at least 75%, at least 80%, at least 90%, at least 95%, or 100% identity; e.g., 85-90%, 85-95%, 85-100%, 90-95%, 90-100%, or 95-100%) to corresponding FR(s) of a light chain variable domain of a light chain variable domain disclosed in Table 14.

In various embodiments, an anti-CD19 binding motif of the present disclosure comprises at least one heavy chain variable domain having at least 75% sequence identity to a heavy chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%). In various embodiments, an anti-CD19 binding motif of the present disclosure comprises two heavy chain variable domains each having at least 75% sequence identity to a heavy chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%), which heavy chain variable domains may be same or different.

In various embodiments, an anti-CD19 binding motif of the present disclosure comprises at least one light chain variable domain having at least 75% sequence identity to a light chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%). In various embodiments, an anti-CD19 binding motif of the present disclosure comprises two light chain variable domains each having at least 75% sequence identity to a light chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%), which light chain variable domains may be same or different.

In various embodiments, an anti-CD19 binding motif of the present disclosure comprises at least one heavy chain variable domain having at least 75% sequence identity to a heavy chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%) and at least one light chain variable domain having at least 75% sequence identity to a light chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%).

In various embodiments, an anti-CD19 binding motif of the present disclosure comprises two heavy chain variable domains each having at least 75% sequence identity to a heavy chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%) and two light chain variable domains each having at least 75% sequence identity to a light chain variable domain disclosed in Table 14 (e.g., at least 75%, at least 80%, at least 90%, at least 95%, or 100% identity; e.g., 85-90%, 85-95%, 85-100%, 90-95%, 90-100%, or 95-100%), where, in various embodiments, (i) each of the heavy chain variable domains may be same or different; or (ii) each of the light chain variable domains may be same or different.

In certain embodiments, an anti-CD19 binding motif of the present disclosure comprises a binding motif that comprises a heavy chain variable domain of the present disclosure, a light chain variable domain of the present disclosure, and a linker having at least 75% sequence identity to SEQ ID NO: 247 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-CD19 binding motif of the present disclosure comprises a binding motif that comprises a linker according to SEQ ID NO: 247 and/or a linker according to any one of SEQ ID NOs: 307-313. In certain embodiments, an anti-CD19 binding motif of the present disclosure comprises a binding motif that comprises a heavy chain variable domain of the present disclosure, a light chain variable domain of the present disclosure, and a leader sequence having at least 75% sequence identity to SEQ ID NO: 245 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-CD19 binding motif of the present disclosure comprises a binding motif that comprises a CSF2RA leader sequence according to SEQ ID NO: 245. In certain embodiments, an anti-CD19 binding motif of the present disclosure comprises a binding motif that comprises a heavy chain variable domain of the present disclosure, a light chain variable domain of the present disclosure, a linker of the present disclosure, and a leader sequence of the present disclosure. In certain embodiments a binding motif has the sequence set forth in SEQ ID NO: 243. Exemplary nucleotide sequences encoding an anti-CD19 binding motif and components thereof are found in SEQ ID NOs: 244, 246, and 248. In various embodiments a binding motif may comprise a linker according to SEQ ID NO: 247 and/or a linker according to any one of SEQ ID NOs: 307-313 adjacent to one or more additional linkers.

TABLE 14

Exemplary anti-CD19 Antibody Sequences (Ab11)

| SEQ ID NO: | Description | Sequence |
|---|---|---|
| 221 | Heavy Chain Variable Domain | EVKLQESGPGLVAPSQSLSVTCTVS<u>GVSLPDYG</u>VSWIRQ PPRKGLEWLG<u>VIWGSET</u>TYYNSALKSRLTIIKDNSKSQV FLKMNSLQTDDTAIYYCAK<u>HYYYGGSYAMDY</u>WGQGT SVTVSS |
| 222 | VH (DNA) | GAGGTGAAACTGCAGGAGTCAGGACCTGGCCTGGTG GCGCCCTCACAGAGCCTGTCCGTCACATGCACTGTCT CAGGGGTCTCATTACCCGACTATGGTGTAAGCTGGAT TCGCCAGCCTCCACGAAAGGGTCTGGAGTGGCTGGG AGTAATATGGGGTAGTGAAACCACATACTATAATTCA GCTCTCAAATCCAGACTGACCATCATCAAGGACAACT CCAAGAGCCAAGTTTTCTTAAAAATGAACAGTCTGCA AACTGATGACACAGCCATTTACTACTGTGCCAAACAT TATTACTACGGTGGTAGCTATGCTATGGACTACTGGG GTCAAGGAACCTCAGTCACCGTCTCCTCA |
| 223 | CDRH1 IMGT (Prot) | GVSLPDYG |
| 224 | CDRH1 Kabat (Prot) | DYGVS |
| 225 | CDRH1 Chothia (Prot) | GVSLPDY |
| 226 | CDRH2 IMGT (Prot) | IWGSETT |
| 227 | CDRH2 Kabat (Prot) | VIWGSETTYYNSALKS |
| 228 | CDRH2 Chothia (Prot) | WGSET |
| 229 | CDRH3 IMGT (Prot) | AKHYYYGGSYAMDY |
| 230 | CDRH3 Kabat (Prot) | HYYYGGSYAMDY |
| 231 | CDRH3 Chothia (Prot) | HYYYGGSYAMDY |
| 232 | Light Chain Variable Domain | DIQMTQTTSSLSASLGDRVTISC<u>RASQDISKYLN</u>WYQQK PDGTVKLLIY<u>HTSRLHS</u>GVPSRFSGSGSGTDYSLTISNLE QEDIATYFC<u>QQGNTLPYT</u>FGGGTKLEIT |
| 233 | VL (DNA) | GACATCCAGATGACACAGACTACATCCTCCCTGTCTG CCTCTCTGGGAGACAGAGTCACCATCAGTTGCAGGGC AAGTCAGGACATTAGTAAATATTTAAATTGGTATCAG CAGAAACCAGATGGAACTGTTAAACTCCTGATCTACC ATACATCAAGATTACACTCAGGAGTCCCATCAAGGTT CAGTGGCAGTGGGTCTGGAACAGATTATTCTCTCACC ATTAGCAACCTGGAGCAAGAAGATATTGCCACTTACT TTTGCCAACAGGGTAATACGCTTCCGTACACGTTCGG AGGGGGGACTAAGTTGGAAATAACA |
| 234 | CDRL1 IMGT (Prot) | RASQDISKYLN |
| 235 | CDRL1 Kabat (Prot) | RASQDISKYLN |
| 236 | CDRL1 Chothia (Prot) | RASQDISKYLN |
| 237 | CDRL2 IMGT (Prot) | HTSRLHS |
| 238 | CDRL2 Kabat (Prot) | HTSRLHS |
| 239 | CDRL2 Chothia (Prot) | HTSRLHS |

TABLE 14-continued

Exemplary anti-CD19 Antibody Sequences (Ab11)

| SEQ ID NO: | Description | Sequence |
|---|---|---|
| 240 | CDRL3 IMGT (Prot) | QQGNTLPYT |
| 241 | CDRL3 Kabat (Prot) | QQGNTLPYT |
| 242 | CDRL3 Chothia (Prot) | QQGNTLPYT |
| 243 | binding motif (Prot) | DIQMTQTTSSLSASLGDRVTISCRASQDISKYLNWYQQK PDGTVKLLIYHTSRLHSGVPSRFSGSGSGTDYSLTISNLE QEDIATYFCQQGNTLPYTFGGGTKLEITGSTSGSGKPGS GEGSTKGEVKLQESGPGLVAPSQSLSVTCTVSGVSLPDY GVSWIRQPPRKGLEWLGVIWGSETTYYNSALKSRLTIIK DNSKSQVFLKMNSLQTDDTAIYYCAKHYYYGGSYAMD YWGQGTSVTVSS |
| 244 | binding motif (DNA) | gacatccagatgacacagactacatcctccctgtctgcctctctggggagacagagtcacc atcagttgcagggcaagtcaggacattagtaaatatttaaattggtatcagcagaaaccag atggaactgttaaactcctgatctaccatacatcaagattacactcaggagtcccatcaag gttcagtggcagtgggtctggaacagattattctctcaccattagcaacctggagcaaga agatattgccacttacttttgccaacagggtaatacgcttccgtacacgttcggaggggg actaagttggaaataacaggctccacctctggatccggcaagcccggatctggcgagg gatccaccaagggcgaggtgaaactgcaggagtcaggacctggcctggtggcgccct cacagagcctgtccgtcacatgcactgtctcagggtctcattacccgactatggtgtaa gctggattcgccagcctccacgaaagggtctggagtggctgggagtaatatgggtagt gaaaccacatactataattcagctctcaaatccagactgaccatcatcaaggacaactcca agagccaagttncttaaaaatgaacagtctgcaaactgatgacacagccatttactactgt gccaaacattattactacggtggtagctatgctatggactactggggtcaaggaacctca gtcaccgtctcctca |
| 245 | Leader (CSF2RA) (Prot) | MLLLVTSLLLCELPHPAFLLIP |
| 246 | Leader (CSF2RA) (DNA) | atgcttctcctggtgacaagccttctgctctgtgagttaccacacccagcattcctcctgat ccca |
| 247 | Linker (Prot) | GSTSGSGKPGSGEGSTKG |
| 248 | Linker (DNA) | ggctccacctctggatccggcaagcccggatctggcgagggatccaccaagggc |

Antigen binding systems comprise, as examples, bispecific and bicistronic chimeric antigen receptors (CARs). The present disclosure provides, among other things, antigen binding systems that target both CD20 and a second target antigen, e.g., CD19. In some embodiments, an antigen binding system of the present disclosure comprises a bispecific antigen binding system. In some embodiments, an antigen binding system of the present disclosure comprises a bicistronic antigen binding system (e.g., a system comprising a first CAR and a second CAR, which first and second CARs are expressed in the same cell). Bicistronic CARs can comprise two CARs that bind different targets and are encoded by a single vector. Bicistronic CARs may comprise a first CAR comprising an anti-CD19 binding motif and a second CAR comprising an anti-CD20 binding motif. The binding motif associated with various CAR frameworks is interchangeable, and combinations of features provided in the present Example are exemplary, not limiting. In some embodiments, a first CAR and a second CAR of a bicistronic CAR (e.g., an anti-CD20 CAR and an anti-CD19 CAR) are encoded by separate genes and/or expressed as separate mRNA molecules. In some embodiments, a first CAR and a second CAR of a bicistronic CAR (e.g., an anti-CD20 CAR and an anti-CD19 CAR) are encoded by a single gene and/or expressed together in a single mRNA molecule, where a protein expressed comprises the first CAR, a cleavable linker domain, and a second CAR. First and second CARs of a bicistronic CAR are generally to be expressed together in immune cells, e.g., in CAR-T cells, so that individual CAR-T cells expressed CARs targeting each of the target antigens (e.g., each of CD20 and CD19).

In various embodiments, a bicistronic CAR vector utilizes a ribosomal skip sequence or internal ribosomal entry sites. A single vector encoding two independent CAR molecules separated by a ribosomal skip sequence may express a bicistronic CAR. In various embodiments, a bicistronic CAR comprises a first CAR and a second CAR where the sequence of the first CAR and the second CAR differ only with respect to the binding motif. In various embodiments, a bicistronic CAR comprises a first CAR and a second CAR where the sequence of the first CAR and the second CAR differ only with respect to a heavy chain variable domain sequence and/or a light chain variable domain sequence. Thus, in some embodiments, a first CAR and a second CAR of a bicistronic CAR may have same or different sequences for any or all of one or more components thereof, e.g., same or different costimulatory domains. For example, one or both of a first CAR and a second CAR of a bicistronic CAR may comprise a costimulatory domain provided herein, such as a CD28, 41BB, OX40, or ICOS costimulatory domain.

A CAR of a bicistronic CAR may comprise a binding motif, a hinge, a transmembrane domain, and an intracellular domain comprising a costimulatory domain and an activation domain. The binding motif may be an anti-CD19 or an anti-CD20 binding motif of the present disclosure. A hinge and transmembrane domain may be a 28T (CD28) domain or a CD8K domain that comprises a hinge domain and a transmembrane domain. A costimulatory domain may be a CD28 or 41BB costimulatory domain. An activation domain may be a CD3z activation domain.

In some embodiments, a first binding motif and a second binding motif (e.g., distinct anti-CD20 and anti-CD19 binding motifs) are both comprised in single bispecific CAR. In such bispecific CARs, a CAR molecule itself may be engineered to recognize more than one antigen. In tandem bispecific CARs, the first and second binding motifs are extracellular and may be characterized as a membrane-proximal binding motif and a membrane-distal binding motif. In some embodiments, an anti-CD20 binding motif is membrane-proximal and an anti-CD19 binding motif is membrane-distal. In other embodiments, an anti-CD19 binding motif is membrane-distal and an anti-CD20 binding motif is membrane proximal.

Chimeric antigen receptors (CARs) are engineered receptors that may direct or redirect T cells (e.g., patient or donor T cells) to target a selected antigen. A CAR may be engineered to recognize an antigen and, when bound to that antigen, activate the immune cell to attack and destroy the cell bearing that antigen. When these antigens exist on tumor cells, an immune cell that expresses the CAR may target and kill the tumor cell. CARs generally comprise an extracellular binding motif that mediates antigen binding (e.g., an anti-CD20 and/or an anti-CD19 binding motif), a transmembrane domain that spans, or is understood to span, the cell membrane when the antigen binding system is present at a cell surface or cell membrane, and an intracellular (or cytoplasmic) signaling domain.

According to at least one non-limiting view, there have been at least three "generations" of CAR compositions. In a first generation of CARs, a binding motif (e.g., a single chain fragment variable, binding motif) is linked or connected to a signaling domain (e.g., CD3) via a transmembrane domain, optionally comprising a hinge domain and one or more spacers. In a second generation of CARs, a costimulatory domain (CM1, such as CD28, 4-1BB, or OX-40) is introduced with the signaling domain (e.g., CD3ζ). In a third generation of CARs, a second costimulatory domain (CM2) is comprised.

TCRs are heterodimers composed of an α-chain and a β-chain. TCR signaling requires recruitment of signaling proteins that generate an immune synapse. In addition, TCR localization at the plasma membrane depends on CD3 complex, which is expressed in T cells. Engineered single chain TCRs may be generated, e.g., using transmembrane and signaling domains of CAR constructs, methods and constructs for which are known (e.g., sTCR and TCR-CAR molecules, e.g., fusion of a TCRβ chain with CD28 TN and CD28 and CD3ζ signaling modules). An anti-CD20 and/or anti-CD19 Antigen binding system of the present disclosure may comprise one or more antigen binding motifs that bind CD20 and/or CD19. In some embodiments, an antigen binding system further comprises a costimulatory domain, and/or an extracellular domain (e.g., a "hinge" or "spacer" region), and/or a transmembrane domain, and/or an intracellular (signaling) domain, and/or a CD3-zeta or CD3-epsilon activation domain. In some embodiments, an -CD20 and/or anti-CD19 Antigen binding system of the present disclosure comprises at least a binding motif that binds human CD20, a costimulatory domain, an extracellular domain, a transmembrane domain, and a CD3-zeta or CD3-epsilon activating domain.

In some embodiments, an antigen binding system of the present disclosure may comprise an antigen binding system that comprises one or more, or all, of a leader peptide (P), a binding motif (B), a costimulatory protein's extracellular domain (E), a transmembrane domain (T), a costimulatory domain (C), a second costimulatory domain (C'), and an activation domain (A). In some instances, an antigen binding system is configured according to the following: B E T A. In some instances, an antigen binding system is configured according to the following: P BET A. In some instances, an antigen binding system is configured according to the following: BE TC A. In some instances, an antigen binding system is configured according to the following: P B E T C A. In some instances, an antigen binding system is configured according to the following: B E T C C' A. In some instances, an antigen binding system is configured according to the following: P B E T C C' A. In some embodiments, the antigen binding system comprises a VH and a VL, optionally wherein the CAR is configured according to the following: P-VH-VL-E-T-C-A or P-VL-VH-E-T-C-A. In some embodiments, the VH and the VL are connected by a linker (L), optionally wherein the CAR is configured according to the following, from N-terminus to C-terminus: P-VH-L-VL-E-T-C-A or P-VH-L-VL-E-T-C-A.

One or more antigen binding motifs determine the target(s) of an antigen binding system. A binding motif of an antigen binding system may comprise any binding motif, e.g., an antibody provided by the present disclosure, e.g., a binding motif of the present disclosure. In some embodiments, a binding motif may comprise an anti-CD20 binding motif and/or anti-CD19 binding motif. In some embodiments, a binding motif may comprise an anti-CD20 binding motif and/or anti-CD19 binding motif.

Binding motifs are used in chimeric antigen receptors at least in part because they may be engineered to be expressed as part of a single chain along with the other CAR components. See, for example, U.S. Pat. Nos. 7,741,465, and 6,319,494 as well as Eshhar et al., Cancer Immunol Immunotherapy (1997) 45: 131-136, Krause et al., J. Exp. Med., Volume 188, No. 4, 1998 (619-626); Finney et al., Journal of Immunology, 1998, 161: 2791-2797, each of which is incorporated herein by reference with respect to binding motif domains in CARs. A binding motif, or scFv, is a single chain antigen binding fragment comprising a heavy chain variable domain and a light chain variable domain, which heavy chain variable domain and light chain variable domain are linked or connected together. See, for example, U.S. Pat. Nos. 7,741,465, and 6,319,494 as well as Eshhar et al., Cancer Immunol Immunotherapy (1997) 45: 131-136, each of which is incorporated herein by reference with respect to binding motif domains. When derived from a parent antibody, a binding motif may retain some of, retain all of, or essentially retain the parent antibody's binding of a target antigen.

A hinge may be an extracellular domain of an antigen binding system positioned between the binding motif and the transmembrane domain. A hinge may also be referred to as an extracellular domain or as a "spacer." A hinge may contribute to receptor expression, activity, and/or stability. In some embodiments, a hinge domain is positioned between a binding motif and a transmembrane domain. A hinge may also provide flexibility to access the targeted antigen. Hinges comprise immunoglobulin-like hinge domains.

In some embodiments, an Antigen binding system of the present disclosure may comprise a hinge that is, is from, or is derived from (e.g., comprises all or a fragment of) an immunoglobulin-like hinge domain. In some embodiments, a hinge domain is from or derived from an immunoglobulin. In some embodiments, a hinge domain is selected from the hinge of IgG1, IgG2, IgG3, IgG4, IgA, IgD, IgE, or IgM, or a fragment thereof.

A hinge may be derived from a natural source or from a synthetic source. In some embodiments, an Antigen binding system of the present disclosure may comprise a hinge that is, is from, or is derived from (e.g., comprises all or a fragment of) CD2, CD3 delta, CD3 epsilon, CD3 gamma, CD4, CD7, CD8.alpha., CD8.beta., CD11a (ITGAL), CD11b (ITGAM), CD11c (ITGAX), CD11 d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, or which is a fragment or combination thereof. In certain embodiments, a CAR does not comprise a CD28 hinge.

In some embodiments, an antigen binding system of the present disclosure may comprise a hinge that is, is from, or is derived from (e.g., comprises all or a fragment of) a hinge of CD8 alpha. In some embodiments a hinge is, is from, or is derived from a hinge of CD28. In some embodiments, a hinge is, is from, or is derived from a fragment of a hinge of CD8 alpha or a fragment of a hinge of CD28, wherein the fragment is anything less than the whole. In some embodiments, a fragment of a CD8 alpha hinge or a fragment of a CD28 hinge comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of a CD8 alpha hinge, or of a CD28 hinge. Exemplary hinge sequences comprise those provided in Table 54 (SEQ ID NOs: 261-269).

Polynucleotide and polypeptide sequences of these hinge domains are known. In some embodiments, the polynucleotide encoding a hinge domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a nucleotide sequence known. In some embodiments, the polypeptide sequence of a hinge domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known polypeptide sequence.

In general, a "transmembrane domain" (e.g., of an antigen binding system) refers to a domain having an attribute of being present in the membrane when present in a molecule at a cell surface or cell membrane (e.g., spanning a portion or all of a cellular membrane). A costimulatory domain for an antigen binding system of the present disclosure may further comprise a transmembrane domain and/or an intracellular signaling domain. It is not required that every amino acid in a transmembrane domain be present in the membrane. For example, in some embodiments, a transmembrane domain is characterized in that a designated stretch or portion of a protein is substantially located in the membrane. Amino acid or nucleic acid sequences may be analyzed using a variety of algorithms to predict protein subcellular localization (e.g., transmembrane localization). The programs psort (PSORT.org) and Prosite (prosite.expasy.org) are exemplary of such programs.

The type of transmembrane domain comprised in an antigen binding system described herein is not limited to any type. In some embodiments, a transmembrane domain is selected that is naturally associated with a binding motif and/or intracellular domain. In some instances, a transmembrane domain comprises a modification of one or more amino acids (e.g., deletion, insertion, and/or substitution), e.g., to avoid binding of such domains to a transmembrane domain of the same or different surface membrane proteins to minimize interactions with other members of the receptor complex.

A transmembrane domain may be derived either from a natural or from a synthetic source. Where the source is natural, a domain may be derived from any membrane-bound or transmembrane protein. Exemplary transmembrane domains may be derived from (e.g., may comprise at least a transmembrane domain of) an alpha, beta or zeta chain of a T-cell receptor, CD28, CD3 epsilon, CD3 delta, CD3 gamma, CD45, CD4, CD5, CD7, CD8, CD8 alpha, CD8beta, CD9, CD11a, CD11b, CD11c, CD11d, CD16, CD22, CD27, CD33, CD37, CD64, CD80, CD86, CD134, CD137, TNFSFR25, CD154, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD276 (B7-H3), CD29, CD30, CD40, CD49a, CD49D, CD49f, CD69, CD84, CD96 (Tactile), CD5, CEACAM1, CRTAM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof. In some embodiments, a transmembrane domain may be synthetic (and can, e.g., comprise predominantly hydrophobic residues such as leucine and valine). In some embodiments, a triplet of phenylalanine, tryptophan and valine are comprised at each end of a synthetic transmembrane domain. In some embodiments, a transmembrane domain is directly linked or connected to a cytoplasmic domain. In some embodiments, a short oligo- or polypeptide linker (e.g., between 2 and 10 amino acids in length) may form a linkage between a transmembrane domain and an intracellular domain. In some embodiments, a linker is a glycine-serine doublet.

Polynucleotide and polypeptide sequences of transmembrane domains provided herein are known. In some embodiments, the polynucleotide encoding a transmembrane domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a nucleotide sequence known. In some embodiments, the polypeptide sequence of a transmembrane domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a polypeptide sequence known. Optionally, short spacers may form linkages between any or some of the extracellular, transmembrane, and intracellular domains of the CAR.

The intracellular domain (or cytoplasmic domain) comprises one or more signaling domains that, upon binding of target antigen to the binding motif, cause and/or mediate an intracellular signal, e.g., that activates one or more immune cell effector functions (e.g., native immune cell effector functions). In some embodiments, signaling domains of an intracellular domain mediate activation at least one of the normal effector functions of the immune cell. Effector function of a T cell, for example, may be cytolytic activity or helper activity comprising the secretion of cytokines. In some embodiments, signaling domains of an intracellular domain mediate T cell activation, proliferation, survival, and/or other T cell function. An intracellular domain may comprise a signaling domain that is an activating domain. An intracellular domain may comprise a signaling domain that is a costimulatory signaling domain.

Intracellular signaling domains that may transduce a signal upon binding of an antigen to an immune cell are known, any of which may be comprised in an antigen binding system of the present disclosure. For example, cytoplasmic sequences of a T cell receptor (TCR) are known to initiate signal transduction following TCR binding to an antigen (see, e.g., Brownlie et al., Nature Rev. Immunol. 13:257-269 (2013)).

In some embodiments, a signaling domain and/or activation domain comprises an immunoreceptor tyrosine-based activation motif (ITAM). Examples of ITAM containing cytoplasmic signaling sequences comprise those derived from TCR zeta, FcR gamma, FcR beta, CD3 zeta, CD3 gamma, CD3 delta, CD3 epsilon, CD5, CD22, CD79a, CD79b, and CD66d (see, e.g., Love et al., Cold Spring Harb. Perspect. Biol. 2:a002485 (2010); Smith-Garvin et al., Annu. Rev. Immunol. 27:591-619 (2009)).

In certain embodiments, suitable signaling domains comprise, without limitation, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CD5, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

A CAR may comprise a costimulatory signaling domain, e.g., to increase signaling potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Annu. Rev. Pharmacol. Toxicol. 56:59-83 (2016). Signals generated through a TCR alone may be insufficient for full activation of a T cell and a secondary or co-stimulatory signal may increase activation. Thus, in some embodiments, a signaling domain further comprises one or more additional signaling domains (e.g., costimulatory signaling domains) that activate one or more immune cell effector functions (e.g., a native immune cell effector function described herein). In some embodiments, a portion of such costimulatory signaling domains may be used, as long as the portion transduces the effector function signal. In some embodiments, a cytoplasmic domain described herein comprises one or more cytoplasmic sequences of a T cell co-receptor (or fragment thereof). Non-limiting examples of such T cell co-receptors comprise CD27, CD28, 4-1BB (CD137), OX40, CD30, CD40, PD-1, ICOS, lymphocyte function-associated antigen-1 (LFA-1), MYD88, CD2, CD7, LIGHT, NKG2C, B7-H3, and a ligand that binds with CD83. An exemplary costimulatory protein has the amino acid sequence of a costimulatory protein found naturally on T cells, the complete native amino acid sequence of which costimulatory protein is described in NCBI Reference Sequence: NP 006130.1. In certain instances, a CAR comprises a 41BB costimulatory domain encoded by the sequence according to SEQ ID NO: 270, as shown below:

SEQ ID NO: 270
AGATTCAGCGTTGTGAAGAGAGGCCGGAAGAAGCTGCTGTACATCTTCA

AGCAGCCCTTCATGAGACCTGTGCAGACCACACAGGAGGAAGACGGCTG

CAGCTGTAGATTCCCCGAGGAAGAGGAGGGCGGCTGTGAGCTGAGAGTT

AAGTTCAGCAGGAGCGCCGACGCCCCTGCCTACCAGCAAGGACAGAATC

AACTGTACAACGAGCTGAACCTGGGCAGACGGGAGGAATACGATGTGCT

GGACAAGAGGAGAGGCAGAGACCCCGAGATGGGCGGCAAACCTAGAAGA

AAGAACCCCCAGGAGGGCCTGTATAACGAGCTCCAGAAGGACAAGATGG

CCGAGGCCTACAGCGAGATCGGCATGAAGGGCGAAAGAAGAAGAGGCAA

GGGCCACGACGGCCTCTACCAGGGCTTAAGCACAGCTACAAAGGACACC

TACGACGCCCTGCACATGCAGGCCCTGCCCCCTAGATGATTAATTAAat cgat

The polynucleotide and polypeptide sequences of signaling domains provided herein are known. In some embodiments, the polynucleotide encoding a signaling domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known nucleotide sequence. In some embodiments, the polypeptide sequence of a signaling domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known polypeptide sequence.

In various embodiments, a mechanism of modulating (e.g., decreasing) antigen binding system activity is desired, e.g., to minimize or curtail adverse events resulting from antigen binding system activity. It may also be desired to comprise an inducible "on" or "accelerator" switch in immune cells. Suitable techniques comprise use of inducible caspase-9 (U.S. Appl. 2011/0286980) or a thymidine kinase, before, after, or at the same time, as the cells are transduced with the CAR construct of the present disclosure. Additional methods for introducing suicide genes and/or "on" switches comprise TALENS, zinc fingers, RNAi, siRNA, shRNA, antisense technology, and other techniques.

In accordance with the present disclosure, on-off or other types of control switch techniques may be incorporated herein. These techniques may comprise use of dimerization domains and optional activators of such domain dimerization, e.g., as disclosed by Wu et al., Science 2014 350 (6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of each of which is also incorporated by reference herein with respect to dimerization technology. Additional dimerization pairs may comprise cyclosporine-A/cyclophilin, receptor, estrogen/estrogen receptor (optionally using tamoxifen, 4-hydroxytamoxifen, or endoxifen), glucocorticoids/glucocorticoid receptor, tetracycline/tetracycline receptor, and/or vitamin D/vitamin D receptor. Further examples of dimerization technology may be found in e.g., WO 2014/127261, WO 2015/090229, US 2014/0286987, US 2015/0266973, US 2016/0046700, U.S. Pat. No. 8,486,693, US 2014/0171649, and US 2012/0130076, the contents of which are further incorporated by reference herein in their entirety.

In some embodiments, an antigen binding system of the present disclosure comprises a leader peptide (also referred to herein as a "signal peptide" or "leader sequence"). In certain embodiments, a leader peptide comprises an amino acid sequence that is at least about 75%, at least about 80%, at least about 85%, at least about 90%, at least about 95%, at least about 96%, at least about 97%, at least about 98%, at least about 99%, or 100% (e.g., 85-90%, 85-95%, 85-100%, 90-95%, 90-100%, or 95-100%) identical to the amino acid sequence MEWTWVFLFLLSVTAGVHS (SEQ ID NO: 249), MALPVTALLLPLALLLHAARP (SEQ ID NO: 250), or MLLLVTSLLLCELPHPAFLLIP (SEQ ID NO: 295).

Components of a CAR may be exchanged or "swapped" using routine techniques of biotechnology for equivalent components. To provide just a few non-limiting and partial examples, a CAR of the present disclosure may comprise a binding motif as provided herein in combination with a hinge provided herein and a costimulatory domain provided herein. In certain examples, a CAR of the present disclosure may comprise a leader sequence as provided herein together with a binding motif as provided herein in combination with a hinge provided herein and s costimulatory domain provided herein. In various embodiments, the present disclosure provides a binding motif according to any one of SEQ ID NOs: 251-260 in combination with (e.g., adjacently fused to) a hinge according to any one of SEQ ID NOs: 261-269, optionally in further combination with (e.g., adjacently fused to) a 41BB costimulatory domain according to SEQ ID NO: 270. A few, non-limiting examples thereof are provided in SEQ ID NOs: 271-290.

A bicistronic CAR may comprise a first CAR sequence and a second CAR sequence expressed as a single polypeptide comprising a cleavable linker between the first and second CARs. An exemplary cleavable linker is Furin-GSG-T2A (see, e.g., Chng et al. MAbs. 2015 March-April; 7(2): 403-412, which is herein incorporated by reference with respect to cleavable linkers; see also Guedan et al. Mol Ther Methods Clin Dev. 2019 Mar. 15; 12: 145-156, which is incorporated herein by reference with respect to bicistronic CAR design). To provide just one non-limiting example of a bicistronic CAR structure, a bicistronic CAR may comprise (a) a first CAR comprising (i) a signal peptide (e.g., a CSF2RA signal peptide); (ii) an anti-CD19 light chain variable domain; (iii) a linker (e.g., a G4S linker or plurality thereof); (iv) an anti-CD19 heavy chain variable domain; (v) a spacer or hinge (e.g., a CD28T spacer); (vi) a transmembrane domain (e.g., a CD28 transmembrane domain); (vii) a costimulatory domain (e.g., a CD28 costimulatory domain); (viii) a stimulatory domain (e.g., a CD3z stimulatory domain); (b) a cleavable linker (e.g., a Furin GSG-T2A linker); and (c) a second CAR comprising (i) a signal peptide (e.g., a CD8a signal peptide); (ii) an anti-CD20 heavy chain variable domain of the present disclosure; (iii) a linker (e.g., a linker according to SEQ ID NO: 247 and/or a linker according to any one of SEQ ID NOs: 307-313); (iv) an anti-CD20 light chain variable domain of the present disclosure; (v) a spacer or hinge (e.g., a CD8a spacer); (vi) a transmembrane domain (e.g., a CD8 transmembrane domain); (vii) a costimulatory domain (e.g., a 41bb costimulatory domain); and (viii) a stimulatory domain (e.g., a CD3z stimulatory domain). Thus, without limitation, an exemplary anti-CD20/anti-CD19 bicistronic CAR may have or comprise the nucleotide and amino acid sequences set forth in SEQ ID NOs: 291 and 292.

A bispecific CAR may be a single polypeptide that comprises a first binding motif of the present disclosure and a second binding motif that is an anti-CD19 binding motif. In a non-limiting exemplary embodiment, a bispecific CAR may comprise (i) a leader (e.g., a CSF2RA signal peptide), (ii) an anti-CD20 light chain variable domain of the present disclosure; (iii) a linker (iv) an anti-CD20 heavy chain variable domain; (v) a linker (e.g., a truncated linker); (vi) an anti-CD19 light chain variable domain; (vii) a linker; (viii) an anti-CD19 heavy chain variable domain; (ix) an extracellular domain (e.g., a CD28T hinge or IgG4 hinge); (x) a transmembrane domain (e.g., a CD28 transmembrane domain); (xi) an intracellular region (e.g., a CD28 intracellular costimulatory domain and/or 41bb costimulatory domain); and a stimulatory domain (e.g., a CD3z stimulatory domain). Thus, without limitation, an exemplary anti-CD20/anti-CD19 bispecific CAR may have or comprise the nucleotide and amino acid sequences set forth in SEQ ID NOs: 293-306.

Various CAR sequences, components, and/or frameworks are known, comprising without limitation sequences of hinges, spacers, transmembrane domains, costimulatory domains, stimulatory domains, binding motifs, and variants of each, and a CAR with desired binding and components or architecture can be readily constructed if, e.g., a heavy chain variable domain sequence or CDR sequences and a light chain variable domain sequence or CDR sequences are provided.

The present disclosure provides, among other things, bispecific antibodies that bind CD20 and a second target antigen, e.g., CD19. Bispecific antibodies comprise antibodies having a first binding motif that binds a first target antigen and a second binding motif that binds a second target antigen. In some embodiments, a bispecific antibody comprises an anti-CD20 binding motif of the present and an anti-CD19 binding motif of the present disclosure. In some embodiments, a bispecific antibody comprises an anti-CD20 binding motif that comprises an anti-CD20 heavy chain variable domain of the present disclosure and an anti-CD20 light chain variable domain of the present disclosure, as well as an anti-CD19 binding motif that comprises an anti-CD19 heavy chain variable domain and an anti-CD19 light chain variable domain.

The present disclosure comprises conjugates in which an antibody of the present disclosure is associated with a therapeutic agent or a detectable moiety. In various embodiments, the therapeutic agent is an anti-cancer agent as provided herein. In certain embodiments, provided conjugate comprises one or more detectable moieties, i.e., is "labeled" with one or more such moieties. In some such embodiments, a conjugate of the present disclosure is useful in diagnostic or imaging applications, e.g., diagnosing or imaging cancer. Any of a wide variety of detectable moieties may be used in labeled antibody conjugates described herein. Suitable detectable moieties comprise, without limitation: various ligands, radionuclides; fluorescent dyes; chemiluminescent agents (such as, for example, acridinum esters, stabilized dioxetanes, and the like); bioluminescent agents; spectrally resolvable inorganic fluorescent semiconductors nanocrystals (i.e., quantum dots); microparticles; metal nanoparticles (e.g., gold, silver, copper, platinum, etc.); nanoclusters; paramagnetic metal ions; enzymes; colorimetric labels (such as, for example, dyes, colloidal gold, and the like); biotin; dioxigenin; haptens; and proteins for which antisera or monoclonal antibodies are available.

The present disclosure comprises nucleic acids encoding anti-CD20 binding motifs and/or anti-CD19 binding motifs provided herein. The present disclosure comprises nucleic acids encoding antibodies of the provided herein, comprising, without limitation, neucleic acids encoding binding motifs (e.g., anti-CD20 binding motifs and anti-CD19 binding motifs). The present disclosure comprises nucleic acids encoding antigen binding systems provided herein, comprising without limitation nucleic acids encoding biscistronic and bispecific chimeric antigen receptors (e.g., bicistronic and bispecific chimeric antigen receptors that bind CD20 and CD19). The nucleic acid sequence of SEQ ID NO: 2 comprises and provides exemplary nucleic acid sequences corresponding to and encoding each of SEQ ID NOs: 1 and 3-11. The nucleic acid sequence of SEQ ID NO: 13 comprises and provides exemplary nucleic acid sequences corresponding to and encoding each of SEQ ID NOs: 12 and 14-22. The nucleic acid sequence of SEQ ID NO: 24 comprises and provides exemplary nucleic acid sequences corresponding to and encoding each of SEQ ID NOs: 23 and 25-33. The nucleic acid sequence of SEQ ID NO: 35 comprises and provides exemplary nucleic acid sequences corresponding to and encoding each of SEQ ID NOs: 34 and 36-44. The nucleic acid sequence of SEQ ID NO: 46 comprises and provides exemplary nucleic acid sequences corresponding to and encoding each of SEQ ID NOs: 45 and 47-55. The nucleic acid sequence of SEQ ID NO: 57 comprises and provides exemplary nucleic acid sequences corresponding to and encoding each of SEQ ID NOs: 56 and 58-66. The nucleic acid sequence of SEQ ID NO: 68 comprises and provides exemplary nucleic acid sequences corresponding to and encoding each of SEQ ID NOs: 67 and 69-77. The nucleic acid sequence of SEQ ID NO: 79 comprises and provides exemplary nucleic acid sequences corresponding to and encoding each of SEQ ID NOs: 78 and 80-88. The nucleic acid sequence of SEQ ID NO: 90 comprises and provides exemplary nucleic acid sequences corresponding to and encoding each of SEQ ID NOs: 89 and 91-99. The nucleic acid sequence of SEQ ID NO: 101 comprises and provides exemplary nucleic acid sequences corresponding to and encoding each of SEQ ID NOs: 100 and 102-110. The nucleic acid sequence of SEQ ID NO: 112 comprises and provides exemplary nucleic acid sequences corresponding to and encoding each of SEQ ID NOs: 111 and 113-121. The nucleic acid sequence of SEQ ID NO: 123 comprises and provides exemplary nucleic acid sequences corresponding to and encoding each of SEQ ID NOs: 122 and 124-132. The nucleic acid sequence of SEQ ID NO: 134 comprises and provides exemplary nucleic acid sequences corresponding to and encoding each of SEQ ID NOs: 133 and 135-143. The nucleic acid sequence of SEQ ID NO: 145 comprises and provides exemplary nucleic acid sequences corresponding to and encoding each of SEQ ID NOs: 144 and 146-154. The nucleic acid sequence of SEQ ID NO: 156 comprises and provides exemplary nucleic acid sequences corresponding to and encoding each of SEQ ID NOs: 155 and 157-165. The nucleic acid sequence of SEQ ID NO: 167 comprises and provides exemplary nucleic acid sequences corresponding to and encoding each of SEQ ID NOs: 166 and 168-176. The nucleic acid sequence of SEQ ID NO: 178 comprises and provides exemplary nucleic acid sequences corresponding to and encoding each of SEQ ID NOs: 177 and 179-187. The nucleic acid sequence of SEQ ID NO: 189 comprises and provides exemplary nucleic acid sequences corresponding to and encoding each of SEQ ID NOs: 188 and 190-198. The nucleic acid sequence of SEQ ID NO: 200 comprises and provides exemplary nucleic acid sequences corresponding to and encoding each of SEQ ID NOs: 199 and 201-209. The nucleic acid sequence of SEQ ID NO: 211 comprises and provides exemplary nucleic acid sequences corresponding to and encoding each of SEQ ID NOs: 210 and 212-220. The present disclosure comprises nucleic acids encoding anti-CD19 binding motifs provided herein. The nucleic acid sequence of SEQ ID NO: 222 comprises and provides exemplary nucleic acid sequences corresponding to and encoding each of SEQ ID NOs: 221 and 223-231. The nucleic acid sequence of SEQ ID NO: 233 comprises and provides exemplary nucleic acid sequences corresponding to and encoding each of SEQ ID NOs: 232 and 234-242.

The present disclosure comprises vectors that comprise nucleic acids of the present disclosure and/or that encode polypeptides of the present disclosure. In various embodiments, the present disclosure comprises a vector that comprises a nucleic acid encoding an anti-CD20 binding motif and/or an anti-CD19 binding motif provided herein. In various embodiments, the present disclosure comprises a vector that comprises a nucleic acid encoding an antibody provided herein, comprising, without limitation, a nucleic acid encoding a binding motif molecule (e.g., an anti-CD20 binding motif or an anti-CD19 binding motif). In various embodiments, the present disclosure comprises a vector that comprises a nucleic acid encoding one or more antigen binding systems provided herein, comprising without limitation nucleic acids encoding a biscistronic or bispecific chimeric antigen receptor (e.g., a bicistronic and bispecific chimeric antigen receptor that bind CD20 and CD19).

Any vector may be suitable for the present disclosure. In some embodiments, the vector is a viral vector. In some embodiments, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof. Suitable exemplary vectors include e.g., pGAR, pBABE-puro, pBABE-neo largeTcDNA, pBABE-hygro-hTERT, pMKO.1 GFP, MSCV-IRES-GFP, pMSCV PIG (Puro IRES GFP empty plasmid), pMSCV-loxp-dsRed-loxp-eGFP-Puro-WPRE, MSCV IRES Luciferase, pMIG, MDH1-PGK-GFP_2.0, TtRMPVIR, pMSCV-IRES-mCherry FP, pRetroX GFP T2A Cre, pRXTN, pLncEXP, and pLXIN-Luc.

A recombinant expression vector may be any suitable recombinant expression vector. Suitable vectors comprise those designed for propagation and expansion or for expression or both, such as plasmids and viruses. For example, a vector may be selected from the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also may be used. Examples of plant expression vectors useful in the context of the disclosure comprise pBI01, pBI101.2, pBI101.3, pBI121 and pBIN19 (Clontech). Examples of animal expression vectors useful in the context of the disclosure comprise pcDNA, pEUK-Cl, pMAM, and pMAMneo (Clontech). In some embodiments, a bicistronic IRES vector (e.g., from Clontech) is used to comprise both a nucleic acid encoding an antigen binding system and an inducible expression construct described herein.

In some embodiments, a recombinant expression vector is a viral vector. Suitable viral vectors comprise, without limitation, retroviral vectors, alphaviral, vaccinial, adenoviral, adeno-associated viral, herpes viral, and fowl pox viral vectors, and preferably have a native or engineered capacity to transform an immune cell (e.g., T cell).

Recombinant expression vectors may be prepared using standard recombinant DNA techniques described in, for example, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994. Constructs of expression vectors, which are circular or linear, may be prepared to contain a replication system functional in a prokaryotic or eukaryotic host cell. Replication systems may be derived, e.g., from ColEl, 2μ plasmid, λ, SV40, bovine papilloma virus, and the like.

A recombinant expression vector may comprise one or more marker genes, which allow for selection of transformed or transfected hosts. Marker genes comprise biocide resistance, e.g., resistance to antibiotics, heavy metals, etc., complementation in an auxotrophic host to provide prototrophy, and the like. Suitable marker genes for the recombinant expression vectors comprise, for instance, neomycin/G418 resistance genes, puromycin resistance genes, hygromycin resistance genes, histidinol resistance genes, tetracycline resistance genes, and ampicillin resistance genes.

Vectors useful in the context of the disclosure may be "naked" nucleic acid vectors (i.e., vectors having little or no proteins, sugars, and/or lipids encapsulating them), or vectors complexed with other molecules. Other molecules that may be suitably combined with the vectors comprise without limitation viral coats, cationic lipids, liposomes, polyamines, gold particles, and targeting moieties such as ligands, receptors, or antibodies that target cellular molecules.

Vector DNA may be introduced into a cell, e.g., an immune cell, via conventional transformation, transfection, or transduction techniques. The terms "transformation" and "transfection" encompass a variety of art-recognized techniques for introducing foreign nucleic acid (e.g., DNA) into a cell, such as calcium phosphate or calcium chloride co-precipitation, DEAE-dextran-mediated transfection, lipofection, gene gun, nanoparticle-mediated delivery, or electroporation. Transduction comprises viral delivery of a vector to a cell, e.g., by a vector disclosed herein, comprising without limitation retrovirus, lentivirus, and AAV.

The present disclosure comprises cells that comprise, express, or are engineered (e.g., transformed or transduced) to comprise or express, at least one vector or nucleic acid of the present disclosure. In some embodiments, a method comprises transducing a cell with a vector that comprises a polynucleotide encoding at least one antigen binding system. The present disclosure comprises cells that comprise, or are transformed to comprise, at least one vector that encodes one or more polypeptides of the present disclosure. The present disclosure comprises cells that comprise, or are transformed to comprise, at least one vector that encodes an anti-CD20 binding motif and/or an anti-CD19 binding motif provided herein. The present disclosure comprises cells that comprise, or are transformed to comprise, at least one vector that encodes an antibody provided herein, comprising, without limitation, a binding motif molecule (e.g., an anti-CD20 binding motif or an anti-CD19 binding motif). The present disclosure comprises cells that comprise, or are transformed to comprise, at least one vector that encodes one or more antigen binding systems provided herein, comprising without limitation a biscistronic or bispecific chimeric antigen receptor (e.g., a bicistronic or bispecific chimeric antigen receptor that bind CD20 and CD19). In some embodiments, cells are co-transfected or co-transduced with two vectors, each vector encoding a different CAR, which two different CARs together are a bicistronic CAR. Transfection or transduction of cells with two different vectors encoding two different CARs that together are a bicistronic CAR may be performed simultaneously on a single population of cells, simultaneously on two different populations of cells with each population transduced with only one of the two vectors, or independently on two different populations of cells each transduced with only one of the two vectors.

The present disclosure comprises cells that comprise one or more polypeptides of the present disclosure. The present disclosure comprises cells that comprise (e.g., express) an anti-CD20 binding motif and/or an anti-CD19 binding motif provided herein. The present disclosure comprises cells that comprise (e.g., express) an antibody provided herein, comprising, without limitation, a binding motif (e.g., an anti-CD20 binding motifor an anti-CD19 binding motif). The present disclosure comprises cells that comprise (e.g., express) one or more antigen binding systems provided herein, comprising without limitation a biscistronic or bispecific chimeric antigen receptor (e.g., a bicistronic and bispecific chimeric antigen receptor that bind CD20 and CD19).

In other aspects, provided herein are cells comprising a polynucleotide or a vector of the present disclosure. In some embodiments, the present disclosure is directed to cells, e.g., in vitro cells, comprising a polynucleotide encoding a CAR or a TCR comprising one or two of the scfv disclosed herein. In other embodiments, the present disclosure is directed to cells, e.g., in vitro cells, comprising a polypeptide encoded by a CAR or a TCR comprising one or two of the scfv disclosed herein. In some embodiments, the polypeptide comprise the amino acid sequence set forth below, or any combination thereof.

```
SEQ ID NO: 232 (anti-CD19 scFv light chain):
DIQMTQTTSSLSASLGDRVTISCRASQDISKYLNWYQQKPDGTVKLLIYH
TSRLHSGVPSRFSGSGSGTDYSLTISNLEQEDIATYFCQQGNTLPYTFGG
GTKLEIT SEQ ID NO: 221 (anti-CD19 scFv heavy chain):
EVKLQESGPGLVAPSQSLSVTCTVSGVSLPDYGVSWIRQPPRKGLEWLGV
IWGSETTYYNSALKSRLTIIKDNSKSQVFLKMNSLQTDDTAIYYCAKHYY
YGGSYAMDYWGQGTSVTVSS SEQ ID NO: 56 (anti-CD20 light chain):
DIQMTQSPSSLSASVGDRVTITCRASQSINSYLNWYQQKPGKAPKLLIYA
ASSLQSGVPSRFSGSGSGTDFTLTISSLQPEDFATYYCQQSLADPFTFGG
GTKVEIK SEQ ID NO: 45 (anti-CD20 heavy chain):
QLQLQESGPGLVKPSETLSLTCTVSGGSISSSSYYWGWIRQPPKGLEWI
GSIYYSGSTYYNPSLKSRVTISVDTSKNQFSLKLSSVTAADTAVYYCARE
TDYSSGMGYGMDVWGQGTTVTVSS SEQ ID NO: 56 (anti-CD20 scFv 2 light chain):
DIQMTQSPSSLSASVGDRVTITCRASQSINSYLNWYQQKPGKAPKLLIYA
ASSLQSGVPSRFSGSGSGTDFTLTISSLQPEDFATYYCQQSLADPFTFGG
GTKVEIK
```

```
-continued
SEQ ID NO: 155 (anti-CD20 scFv 2 heavy chain):
QVQLQQWGAGLLKPSETLSLTCAVYGGSFSRYVWSWIRQPPGKGLEWIGE
IDSSGKTNYNPSLKSRVTISVDTSKNQFSLKLSSVTAADTAVYYCARVRY
DSSDSYYYSYDYGMDVWGQGTTVTVSS SEQ ID NO: 144 (anti-CD20 scFv 3 light chain):
DIVLTQSPDSLAVSLGERATINCKSSQSVLYSSNNKNYLAWYQQKPGQPP
KLLIYWASSRESGVPDRFSGSGSGTDFTLTISSLQAEDVAVYYCQQSYSF
PWTFGGGTKVEIK SEQ ID NO: 177 (anti-CD20 scFv 3 heavy chain):
QVQLQQWGAGLLKPSETLSLTCAVYGGSFSGYAWSWIRQPPGKGLEWIGE
IDHRGFTNYNPSLKSRVTISVDTSKNQFSLKLSSVTAADTAVYYCARVRY
DSSDSYYYSYDYGMDVWGQGTTVTVSS SEQ ID NO: 78 (anti-CD20 scFv 4 light chain):
DIQMTQSPSSLSASVGDRVTITCRASQSISSYLNWYQQKPGKAPKLLIYA
ASSLQSGVPSRFSGSGSGTDFTLTISSLQPEDFATYYCQQSYRFPPTFGQ
GTKVEIK SEQ ID NO: 67 (anti-CD20 scFv 4 heavy chain):
QVQLVQSGAEVKKPGASVKVSCKASGYTFKEYGISWVRQAPGQGLEWMGW
ISAYSGHTYYAQKLQGRVTMTTDTSTSTAYMELRSLRSDDTAVYYCARGP
HYDDWSGFIIWFDPWGQGTLVTVSS
```

Any cell may be used as a host cell for the polynucleotides, the vectors, or the polypeptides of the present disclosure. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Erwinia; Klebsiella; Proteus; Salmonella*, e.g., *Salmonella typhimurium; Serratia*, e.g., *Serratia marcescans*, and *Shigella; Bacilli* such as *B. subtilis* and *B. licheniformis; Pseudomonas* such as *P. aeruginosa*; and *Streptomyces*. In some embodiments, the cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is a T cell. In another embodiment, the immune cell is an NK cell. In certain embodiments, the T cell is a tumor-infiltrating lymphocyte (TIL), autologous T cell, engineered autologous T cell (eACT™), an allogeneic T cell, a heterologous T cell, or any combination thereof.

Chimeric antigen receptors (CARs or CAR-Ts) and engineered T cell receptors (TCRs) may be readily inserted into and expressed by immune cells, e.g., T cells, producing binding agents. In certain embodiments, cells (e.g., immune cells such as T cells) are obtained from a donor subject. In some embodiments, the donor subject is human patient afflicted with a cancer or a tumor. In other embodiments, the donor subject is a human patient not afflicted with a cancer or a tumor. In some embodiments, an engineered cell is autologous to a subject. In some embodiments, an engineered cell is allogeneic to a subject.

The cell of the present disclosure may be obtained through any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. In certain embodiments, the cells collected by apheresis are washed to remove the plasma fraction, and placed in an appropriate buffer or media for subsequent processing. In some embodiments, the cells are washed with PBS. As will be appreciated, a washing step can be used, such as by using a semiautomated flowthrough centrifuge, e.g., the Cobe™ 2991 cell processor, the Baxter CytoMate™, or the like. In some embodiments, the washed cells are resuspended in one or more biocompatible buffers, or other saline solution with or without buffer. In certain embodiments, the undesired components of the apheresis sample are removed. Additional methods of isolating T cells for a T cell therapy are disclosed in U.S. Patent Publication No. 2013/0287748, which is herein incorporated by references in its entirety.

In certain embodiments, T cells are isolated from PBMCs by lysing the red blood cells and depleting the monocytes, e.g., by using centrifugation through a PERCOLL™ gradient. In some embodiments, a specific subpopulation of T cells, such as $CD4^+$, $CD8^+$, $CD28^+$, $CD45RA^+$, and $CD45RO^+$ T cells is further isolated by positive or negative selection techniques known in the art. For example, enrichment of a T cell population by negative selection can be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected can be used. For example, to enrich for $CD4^+$ cells by negative selection, a monoclonal antibody cocktail typically includes antibodies to CD8, CD11b, CD14, CD16, CD20, and HLA-DR. In certain embodiments, flow cytometry and cell sorting are used to isolate cell populations of interest for use in the present disclosure.

In some embodiments, PBMCs are used directly for genetic modification with the immune cells (such as CARs or TCRs) using methods as described herein. In certain embodiments, after isolating the PBMCs, T lymphocytes are further isolated, and both cytotoxic and helper T lymphocytes are sorted into naive, memory, and effector T cell subpopulations either before or after genetic modification and/or expansion.

In some embodiments, $CD8^+$ cells are further sorted into naive, central memory, and effector cells by identifying cell surface antigens that are associated with each of these types of $CD8^+$ cells. In some embodiments, the expression of phenotypic markers of central memory T cells includes CCR7, CD3, CD28, CD45RO, CD62L, and CD127 and are negative for granzyme B. In some embodiments, central memory T cells are $CD8^+$, $CD45RO^+$, and $CD62L^+$ T cells. In some embodiments, effector T cells are negative for CCR7, CD28, CD62L, and CD127 and positive for granzyme B and perforin. In certain embodiments, $CD4^+$ T cells are further sorted into subpopulations. For example, $CD4^+$ T helper cells can be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In various aspects of the present disclosure, a cell that comprises, expresses, encodes, or is transformed to encode a vector or polypeptide of the present disclosure (e.g., an anti-CD20 binding motif of the present disclosure and/or an anti-CD20/anti-CD19 antigen binding system) is a binding agent. A binding agent, or population of binding agents, can be used as a (e.g., as the active agent of) a binding agent (a composition that comprises cells useful as a treatment, e.g., for a cancer).

The present disclosure further comprises methods and process for producing antibody agents as disclosed herein, e.g., by transformation (e.g., transduction) of a cell with a vector or nucleic acid of the present disclosure. In some embodiments, a method or process for producing antibody agents as disclosed herein comprises transforming (e.g., transducing) a cell with a nucleic acid (e.g., a nucleic acid present in a vector) encoding at least one antigen binding system provided herein. In general, antibody agents described herein may be produced from an immune cell, e.g., a cell useful in or capable of use in adoptive cell therapy. In some embodiments, a binding agent is produced from a cell type selected from a group consisting of TILs, T-cells, $CD8^+$ cells, $CD4^+$ cells, NK-cells, gamma-delta T-cells, regulatory T-cells or peripheral blood mononuclear cells. "Tumor-infiltrating lymphocytes" or TILs refer to white blood cells that have left the bloodstream and migrated into a tumor. Lymphocytes may be divided into three groups comprising B cells, T cells and natural killer cells. "T-cells" refers to $CD3^+$ cells, comprising $CD4^+$ helper cells, $CD8^+$ cytotoxic T-cells and gamma-delta T cells.

In certain embodiments a binding agent is produced by genetically modifying (e.g., transforming) a cell, e.g., an immune cell, with a nucleic acid encoding an antigen binding system and/or an expression construct described herein (e.g., (i) a first recombinant expression vector that comprises a nucleic acid encoding an antigen binding system and a second recombinant expression vector that comprises an inducible expression construct, (ii) a single recombinant expression vector that comprises both a nucleic acid encoding an antigen binding system and an inducible expression construct; or (iii) a recombinant expression vector that comprises a constitutive expression construct). The recombinant expression vector may comprise any type of nucleotides, comprising, without limitation, DNA and RNA, which may be single-stranded or double-stranded, synthesized or obtained in part from natural sources, and which may contain natural, non-natural or altered nucleotides. A recombinant expression vector may comprise naturally-occurring or non-naturally-occurring internucleotide linkages, or both types of linkages.

In some embodiments, a method comprises transducing a cell with a polynucleotide encoding an antigen binding system, as disclosed herein. In some embodiments, a method comprises transducing a cell with a vector comprising the polynucleotide encoding an antigen binding system.

In some embodiments, the donor T cells for use in the T cell therapy are obtained from the patient (e.g., for an autologous T cell therapy). In other embodiments, the donor T cells for use in the T cell therapy are obtained from a subject that is not the patient. In an exemplary aspect, subjects may undergo leukapheresis, wherein leukocytes are collected, enriched, or depleted ex vivo to select and/or isolate the cells of interest, e.g., T cells. These T cell isolates may be expanded by methods and treated such that one or more CAR constructs of the disclosure may be introduced, thereby creating a CART cell of the disclosure.

In some embodiments, an immune cell is obtained from a subject and is transformed, e.g., transduced, with inducible expression construct or a constitutive expression construct described herein, e.g., an expression vector comprising an inducible expression construct or a constitutive expression construct described herein, to obtain a binding agent. Thus, in some embodiments, a binding agent comprises an autologous cell that is administered into the same subject from which an immune cell was obtained. In some embodiments, an immune cell is obtained from a subject and is transformed, e.g., transduced, with an inducible expression construct or a constitutive expression construct described herein, e.g., an expression vector comprising an inducible expression construct or a constitutive expression construct described herein, to obtain a binding agent that is allogeneically transferred into another subject.

In certain embodiments, the T cells are obtained from a donor subject. In some embodiments, the donor subject is human patient afflicted with a cancer or a tumor. In other embodiments, the donor subject is a human patient not afflicted with a cancer or a tumor.

Various compositions of the present disclosure comprise populations of engineered cells, which may be produced by any means. In some embodiments, the present disclosure provides populations of human cells engineered to express an antigen binding system as described herein. In some embodiments, such a population comprises binding agents. In some embodiments, such a population comprises a cultured population. In some embodiments, such a population is a cultured population of cells from a single human source who may, in some embodiments, receive administration of the cultured population. As disclosed herein, a binding agent may comprise any single cell or population of cells, e.g. population of engineered cells, as provided herein.

Other aspects of the present disclosure are directed to compositions comprising a polynucleotide described herein, a vector described herein, a polypeptide described herein, or an in vitro cell described herein. In some embodiments, the composition comprises a pharmaceutically acceptable carrier, diluent, solubilizer, emulsifier, preservative and/or adjuvant. In some embodiments, the composition comprises an excipient. In one embodiment, the composition comprises a polynucleotide encoding a CAR or a TCR comprising antigen binding molecules described herein. In another embodiment, the composition comprises a CAR or a TCR comprising a TCD encoded by a polynucleotide of the present disclosure. In another embodiment, the composition comprises a T cell comprising a CAR or a TCR comprising one or two of the scfv disclosed herein.

In other embodiments, the composition is selected for parenteral delivery, for inhalation, or for delivery through the digestive tract, such as orally. The preparation of such pharmaceutically acceptable compositions is within the ability of one skilled in the art. In certain embodiments, buffers are used to maintain the composition at physiological pH or at a slightly lower pH, typically within a pH range of from about 5 to about 8. In certain embodiments, when parenteral administration is contemplated, the composition is in the form of a pyrogen-free, parenterally acceptable aqueous solution comprising a composition described herein, with or without additional therapeutic agents, in a pharmaceutically acceptable vehicle. In certain embodiments, the vehicle for parenteral injection is sterile distilled water in which composition described herein, with or without at least one additional therapeutic agent, is formulated as a sterile, isotonic solution, properly preserved. In certain embodiments, the preparation involves the formulation of the desired molecule with polymeric compounds (such as polylactic acid or polyglycolic acid), beads or liposomes, that provide for the controlled or sustained release of the product, which are then be delivered via a depot injection. In certain embodiments, implantable drug delivery devices are used to introduce the desired molecule.

In some embodiments, the present disclosure provides pharmaceutical compositions that comprise and/or deliver one or more of the present disclosure, e.g., an antigen binding systems of the present disclosure, nucleic acids that encode them, and/or cell(s) or populations thereof that comprise and/or express them.

In some embodiments, the present disclosure provides pharmaceutical compositions that comprise and or deliver one or more cells as provided herein, e.g., a binding agent that encodes or expresses a polypeptide provided herein, e.g., an anti-CD20/anti-CD19 CAR (i.e., a "binding agent pharmaceutical compositions"). A binding agent pharmaceutical composition may comprise one or a plurality of cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Binding agent pharmaceutical composition of the present disclosure may be formulated for administration according to any embodiment set forth herein, at least one non-limiting example of which is intravenous administration. A composition may be formulated for intravenous, intratumoral, intraarterial, intramuscular, intraperitoneal, intrathecal, epidural, and/or subcutaneous administration routes. Preferably, the composition is formulated for a parenteral route of administration. A composition suitable for parenteral administration may be an aqueous or nonaqueous, isotonic sterile injection solution, which may contain antioxidants, buffers, bacteriostats, and solutes, for example, that render the composition isotonic with the blood of the intended recipient. An aqueous or nonaqueous sterile suspension may contain one or more suspending agents, solubilizers, thickening agents, stabilizers, and preservatives. Binding agent pharmaceutical compositions of the present disclosure may be administered in a manner appropriate to the disease to be treated (or prevented).

The sterile composition for injection may be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

Non-limiting examples of oily liquid comprise sesame oil and soybean oil, and it may be combined with benzyl benzoate or benzyl alcohol as a solubilizing agent. Other items that may be comprised are a buffer such as a phosphate buffer, or sodium acetate buffer, a soothing agent such as procaine hydrochloride, a stabilizer such as benzyl alcohol or phenol, and an antioxidant. The formulated injection may be packaged in a suitable ampule.

In one embodiment, a binding agent pharmaceutical composition is substantially free of detectable levels of a contaminant, e.g., of endotoxin, *mycoplasma*, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenzae, Neisseria meningitides, Pseudomonas aeruginosa, Staphylococcus aureus, Streptococcus pneumonia*, and/or *Streptococcus pyogenes* group A.

In various embodiments, cells provided herein (e.g., binding agents, e.g., engineered T cells or engineered NK cells) may be activated and/or expanded from, and/or to produce, a binding agent pharmaceutical composition. In some embodiments, additional steps may be performed prior to administration to a subject. For instance, a binding agent may be expanded in vitro after contacting (e.g., transducing or transfecting) an immune cell with an inducible expression construct or a constitutive expression construct described herein (e.g., an expression vector comprising an inducible expression construct or a constitutive expression construct), prior to the administration to a subject. In vitro expansion may proceed for 1 day or more, e.g., 2 days or more, 3 days or more, 4 days or more, 6 days or more, or 8 days or more, prior to the administration to a subject. In some embodiments, in vitro expansion may proceed for 21 days or less, e.g., 18 days or less, 16 days or less, 14 days or less, 10 days or less, 7 days or less, or 5 days or less, prior to administration to a subject. For example, in vitro expansion may proceed for 1-7 days, 2-10 days, 3-5 days, or 8-14 days prior to the administration to a subject. A binding agent pharmaceutical composition comprising, e.g., binding agents (e.g., engineered T cells or engineered NK cells), may be formulated for administration at a desired dosage, e.g., a dosage of $10^4$ to $10^9$ cells/kg body weight (e.g., $10^5$ to $10^6$ cells/kg body weight). Certain embodiments of the disclosure comprise methods of administering to a subject a pharmaceutical composition as described herein, such as, for example, a binding agent described (e.g., a population of engineered cells of the present disclosure) herein, a protein therapeutic described herein, a composition comprising a binding agent, and/or a composition comprising a protein therapeutic, e.g., in an amount effective to treat a subject, when administered in an appropriate dosing regimen.

In some embodiments, a binding agent is autologous to a subject, and the subject may be immunologically naive, immunized, diseased, or in another condition prior to isolation of an immune cell from the subject. In some embodiments, during in vitro expansion, a binding agent may be stimulated with an antigen (e.g., a TCR antigen). Antigen-stimulated expansion optionally may be supplemented with expansion under conditions that non-specifically stimulate lymphocyte proliferation such as, for example, anti-CD3 antibody, anti-Tac antibody, anti-CD28 antibody, or phytohemagglutinin (PHA). The expanded binding agent may be directly administered into a subject or may be frozen for future use, i.e., for subsequent administrations to a subject.

In some embodiments, a binding agent is treated ex vivo with interleukin-2 (IL-2) prior to infusion into a cancer patient, and the cancer patient is treated with IL-2 after infusion. Furthermore, in some embodiments, a cancer patient may undergo preparative lymphodepletion—the temporary ablation of the immune system—prior to administration of a binding agent. A combination of IL-2 treatment and preparative lymphodepletion may enhance persistence of a binding agent. In some embodiments, a binding agent is transduced or transfected with a nucleic acid encoding a cytokine, which nucleic acid may be engineered to provide for constitutive, regulatable, or temporally-controlled expression of the cytokine. Suitable cytokines comprise, for example, cytokines which act to enhance the survival of T lymphocytes during the contraction phase, which may facilitate the formation and survival of memory T lymphocytes.

In certain embodiments, a binding agent is administered prior to, substantially simultaneously with, or after the administration of another therapeutic agent, such as a cancer therapeutic agent. The cancer therapeutic agent may be, e.g., a chemotherapeutic agent, a biological agent, or radiation treatment. In some embodiments, a subject receiving a binding agent is not administered a treatment which is sufficient to cause a depletion of immune cells, such as lymphodepleting chemotherapy or radiation therapy.

Dosage administered to a subject in some embodiments, may vary with the embodiment, the composition employed, the method of administration, and the site and subject being treated. However, a dose should be sufficient to provide a therapeutic response. A clinician may determine the therapeutically effective amount of a composition to be administered to a human or other subject in order to treat or prevent a medical condition. The precise amount of the composition required to be therapeutically effective may depend upon numerous factors, e.g., such as the activity of the binding agent, and the route of administration.

A suitable number binding agent cells may be administered to a subject. While a single binding agent cell described herein is capable of expanding and providing a therapeutic benefit, in some embodiments, $10^2$ or more, e.g., $10^3$ or more, $10^4$ or more, $10^5$ or more, or $10^8$ or more, binding agent cells are administered. In some embodiments, $10^{12}$ or less, e.g., $10^{11}$ or less, $10^9$ or less, $10^7$ or less, or $10^5$ or less, binding agent cells described herein are administered to a subject. In some embodiments, $10^2$-$10^5$, $10^4$-$10^7$, $10^3$-$10^9$, or $10^5$-$10^{10}$ binding agent cells described herein are administered. A binding agent pharmaceutical composition may be administered, e.g., a dosage of $10^4$ to $10^9$ cells/kg body weight (e.g., $10^5$ to $10^6$ cells/kg body weight). A binding agent pharmaceutical composition may be administered at a dosage of, e.g., about $2 \times 10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

A dose of a binding agent described herein may be administered to a mammal at one time or in a series of subdoses administered over a suitable period of time, e.g., on a daily, semi-weekly, weekly, bi-weekly, semi-monthly, bi-monthly, semi-annual, or annual basis, as needed. A dosage unit comprising an effective amount of a binding agent may be administered in a single daily dose, or the total daily dosage may be administered in two, three, four, or more divided doses administered daily, as needed.

A suitable means of administration may be selected by a medical practitioner. Route of administration may be parenteral, for example, administration by injection, transnasal administration, transpulmonary administration, or transcutaneous administration. Administration may be systemic or local by intravenous injection, intramuscular injection, intraperitoneal injection, subcutaneous injection. In some embodiments, a composition is selected for parenteral delivery, for inhalation, or for delivery through the digestive tract, such as orally. Dose and method of administration may vary depending on the weight, age, condition, and the like of the subject, and may be suitably selected.

In various embodiments, a binding agent described herein may be incorporated into a pharmaceutical composition. Pharmaceutical compositions comprising a binding agent of the present disclosure may be formulated by known methods (such as described in Remington's Pharmaceutical Sciences, 17th edition, ed. Alfonso R. Gennaro, Mack Publishing Company, Easton, Pa. (1985)). In various instances, a pharmaceutical composition comprising a binding agent of the present disclosure may be formulated to comprise a pharmaceutically acceptable carrier or excipient. Examples of pharmaceutically acceptable carriers comprise, without limitation, any and all solvents, dispersion media, coatings, antibacterial and antifungal agents, isotonic and absorption delaying agents, and the like that are physiologically compatible. Compositions comprising a binding agent of the present disclosure may comprise a pharmaceutically acceptable salt, e.g., an acid addition salt or a base addition salt.

In various embodiments, a composition comprising a binding agent as described herein, e.g., a sterile formulation for injection, may be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like. As disclosed herein, a pharmaceutical composition comprising a binding agent may be in any form. Such forms comprise, e.g., liquid, semi-solid and solid dosage forms, such as liquid solutions (e.g., injectable and infusible solutions), dispersions or suspensions, tablets, pills, powders, liposomes and suppositories.

Selection or use of any form may depend, in part, on the intended mode of administration and therapeutic application. For example, a composition comprising a binding agent of the present disclosure intended for systemic or local delivery may be in the form of injectable or infusible solutions. Accordingly, the compositions comprising a binding agent of the present disclosure may be formulated for administration by a parenteral mode (e.g., intravenous, subcutaneous, intraperitoneal, or intramuscular injection). Parenteral administration refers to modes of administration other than enteral and topical administration, usually by injection, and comprise, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

Route of administration may be parenteral, for example, administration by injection, transnasal administration, transpulmonary administration, or transcutaneous administration. Administration may be systemic or local by intravenous injection, intramuscular injection, intraperitoneal injection, subcutaneous injection.

In various embodiments, a pharmaceutical composition comprising a binding agent of the present disclosure may be formulated as a solution, microemulsion, dispersion, liposome, or other ordered structure suitable for stable storage at high concentration. Sterile injectable solutions may be prepared by incorporating a composition comprising a binding agent of the present disclosure in the required amount in an appropriate solvent with one or a combination of ingredients enumerated above, as required, followed by filter sterilization. Generally, dispersions are prepared by incorporating a composition comprising a binding agent of the present disclosure into a sterile vehicle that contains a basic dispersion medium and the required other ingredients from those enumerated above. In the case of sterile powders for the preparation of sterile injectable solutions, methods for preparation comprise vacuum drying and freeze-drying that yield a powder of a composition comprising a binding agent of the present disclosure plus any additional desired ingredient (see below) from a previously sterile-filtered solution thereof. The proper fluidity of a solution may be maintained, for example, by the use of a coating such as lecithin, by the maintenance of the required particle size in the case of dispersion and by the use of surfactants. Prolonged absorption of injectable compositions comprising a binding agent of the present disclosure may be brought about by comprising in the composition comprising a binding agent of the present disclosure a reagent that delays absorption, for example, monostearate salts, and gelatin.

A pharmaceutical composition comprising a binding agent of the present disclosure may be administered parenterally in the form of an injectable formulation comprising a sterile solution or suspension in water or another pharmaceutically acceptable liquid. For example, the pharmaceutical composition comprising a binding agent of the present disclosure may be formulated by suitably combining the therapeutic molecule with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient comprised in the pharmaceutical preparations is such that a suitable dose within the designated range is provided. Nonlimiting examples of oily liquid comprise sesame oil and soybean oil, and it may be combined with benzyl benzoate or benzyl alcohol as a solubilizing agent. Other items that may be comprised are a buffer such as a phosphate buffer, or sodium acetate buffer, a soothing agent such as procaine hydrochloride, a stabilizer such as benzyl alcohol or phenol, and an antioxidant. The formulated injection may be packaged in a suitable ampule.

In some embodiments, a composition comprising a binding agent of the present disclosure may be formulated for storage at a temperature below 0° C. (e.g., −20° C. or −80° C.). In some embodiments, the composition comprising a binding agent of the present disclosure may be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions comprising a binding agent of the present disclosure are stable in storage for at least 1 year at 2-8° C. (e.g., 4° C.).

In some instances, a pharmaceutical composition comprising a binding agent of the present disclosure may be formulated as a solution. In some embodiments, a composition comprising a binding agent of the present disclosure may be formulated, for example, as a buffered solution at a suitable concentration and suitable for storage at 2-8° C. (e.g., 4° C.). Pharmaceutical compositions comprising a binding agent as described herein may be formulated in immunoliposome compositions. Liposomes with enhanced circulation time are disclosed in, e.g., U.S. Pat. No. 5,013, 556.

In certain embodiments, compositions comprising a binding agent of the present disclosure may be formulated with a carrier that will protect the composition against rapid release, such as a controlled release formulation, comprising implants and microencapsulated delivery systems. Biodegradable, biocompatible polymers may be used, such as ethylene vinyl acetate, polyanhydrides, polyglycolic acid, collagen, polyorthoesters, and polylactic acid. Many methods for the preparation of such formulations are known. See, e.g., J. R. Robinson (1978) "Sustained and Controlled Release Drug Delivery Systems," Marcel Dekker, Inc., New York.

In some embodiments, compositions comprising a binding agent of the present disclosure may be formulated in a composition suitable for intrapulmonary administration (e.g., for administration via an inhaler or nebulizer) to a mammal such as a human. Methods for formulating such compositions are known. Dry powder inhaler formulations and suitable systems for administration of the formulations are also known. Pulmonary administration may be oral and/or nasal. Examples of pharmaceutical devices for pulmonary delivery comprise metered dose inhalers, dry powder inhalers (DPIs), and nebulizers. For example, a composition comprising a binding agent of the present disclosure may be administered to the lungs of a subject by way of a dry powder inhaler. These inhalers are propellant-free devices that deliver dispersible and stable dry powder formulations to the lungs. Dry powder inhalers are known and comprise, without limitation: the TURBOHALER® (AstraZeneca; London, England) the AIR® inhaler (ALKERMES®; Cambridge, Mass.); ROTAHALER® (GlaxoSmithKline; London, England); and ECLIPSE™ (Sanofi-Aventis; Paris, France). See also, e.g., PCT Publication Nos. WO 04/026380, WO 04/024156, and WO 01/78693. DPI devices have been used for pulmonary administration of polypeptides such as insulin and growth hormone. In some embodiments, a composition comprising a binding agent of the present disclosure may be intrapulmonarily administered by way of a metered dose inhaler. These inhalers rely on a propellant to deliver a discrete dose of a molecule to the lungs. Additional devices and intrapulmonary administration methods are set forth in, e.g., U.S. Patent Application Publication Nos. 20050271660 and 20090110679, the disclosures of each of which are incorporated herein by reference in their entirety.

In some embodiments, compositions comprising a binding agent of the present disclosure may be formulated for delivery to the eye, e.g., in the form of a pharmaceutically acceptable solution, suspension or ointment. A preparation for use in treating an eye may be in the form of a sterile aqueous solution containing, e.g., additional ingredients such as, without limitation, preservatives, buffers, tonicity agents, antioxidants and stabilizers, nonionic wetting or clarifying agents, and viscosity-increasing agents. A preparation as described herein may be administered topically to the eye of the subject in need of treatment (e.g., a subject afflicted with AMD) by conventional methods, e.g., in the form of drops, or by bathing the eye in a therapeutic solution, containing one or more compositions.

A variety of devices for introducing drugs into the vitreal cavity of the eye may be appropriate, in certain embodiments, for administration of a composition comprising a binding agent of the present disclosure. For example, U.S. Publication No. 2002/0026176 describes a pharmaceutical-containing plug that may be inserted through the sclera such that it projects into the vitreous cavity to deliver the pharmaceutical agent into the vitreous cavity. In another example, U.S. Pat. No. 5,443,505 describes an implantable device for introduction into a suprachoroidal space or an avascular region for sustained release of drug into the interior of the eye. U.S. Pat. Nos. 5,773,019 and 6,001,386 each disclose an implantable drug delivery device attachable to the scleral surface of an eye. Additional methods and devices (e.g., a transscleral patch and delivery via contact lenses) for delivery of a therapeutic agent to the eye are described in, e.g., Ambati and Adamis (2002) Prog Retin Eye Res 21(2):145-151; Ranta and Urtti (2006) Adv Drug Delivery Rev 58(11):1164-1181; Barocas and Balachandran (2008) Expert Opin Drug Delivery 5(1):1-10(10); Gulsen and Chauhan (2004) Invest Opthalmol Vis Sci 45:2342-2347; Kim et al. (2007) Ophthalmic Res 39:244-254; and PCT publication no. WO 04/073551, the disclosures of which are incorporated herein by reference in their entirety.

In various embodiments, subcutaneous administration may be accomplished by means of a device, such as a syringe, a prefilled syringe, an auto-injector (e.g., disposable or reusable), a pen injector, a patch injector, a wearable injector, an ambulatory syringe infusion pump with subcutaneous infusion sets, or other device for combining with binding agent drug for subcutaneous injection.

An injection system of the present disclosure may employ a delivery pen as described in U.S. Pat. No. 5,308,341. Pen devices are commonly used for self-delivery of insulin to patients with diabetes. Such devices may comprise at least one injection needle (e.g., a 31 gauge needle of about 5 to 8 mm in length), are generally pre-filled with one or more therapeutic unit doses of a therapeutic solution, and are useful for rapidly delivering solution to a subject with as little pain as possible. One medication delivery pen comprises a vial holder into which a vial of a therapeutic or other medication may be received. The pen may be an entirely mechanical device or it may be combined with electronic circuitry to accurately set and/or indicate the dosage of medication that is injected into the user. See, e.g., U.S. Pat. No. 6,192,891. In some embodiments, the needle of the pen device is disposable and the kits comprise one or more disposable replacement needles. Pen devices suitable for delivery of any one of the presently featured compositions comprising a binding agent of the present disclosure are also described in, e.g., U.S. Pat. Nos. 6,277,099; 6,200,296; and 6,146,361, the disclosures of each of which are incorporated herein by reference in their entirety. A microneedle-based pen device is described in, e.g., U.S. Pat. No. 7,556,615, the disclosure of which is incorporated herein by reference in its entirety. See also the Precision Pen Injector (PPI) device, MOLLY™, manufactured by Scandinavian Health Ltd.

In some embodiments, a composition comprising a binding agent of the present disclosure may be delivered to a subject by way of local administration that does not rely upon transport of the binding agent to its intended target tissue or site via the vascular system. For example, the composition comprising a binding agent of the present disclosure may be delivered by injection or implantation of the composition comprising a binding agent of the present disclosure or by injection or implantation of a device containing the composition comprising a binding agent of the present disclosure. In certain embodiments, following local administration in the vicinity of a target tissue or site, the composition comprising a binding agent of the present disclosure, or one or more components thereof, may diffuse to an intended target tissue or site that is not the site of administration.

In some embodiments, a composition comprising a binding agent of the present disclosure may be locally administered to a joint, e.g., directly to a joint (e.g., into a joint space) or in the vicinity of a joint. Examples of intraarticular joints to which a composition comprising a binding agent of the present disclosure may be locally administered comprise, e.g., the hip, knee, elbow, wrist, sternoclavicular, temperomandibular, carpal, tarsal, ankle, and any other joint subject to arthritic conditions. A composition comprising a binding agent of the present disclosure may also be administered to bursa such as, e.g., acromial, bicipitoradial, cubitoradial, deltoid, infrapatellar, ischial, and any other bursa.

In some embodiments, the compositions comprising a binding agent of the present disclosure provided herein are present in unit dosage form, which unit dosage form may be suitable for self-administration. Such a unit dosage form may be provided within a container, generally, for example, a vial, cartridge, prefilled syringe or disposable pen. A doser such as the doser device described in U.S. Pat. No. 6,302,855, may also be used, for example, with an injection system as described herein.

A pharmaceutical solution may comprise a therapeutically effective amount of a composition comprising a binding agent of the present disclosure. Such effective amounts may be readily determined based, in part, on the effect of the administered composition comprising a binding agent of the present disclosure, or the combinatorial effect of the composition comprising a binding agent of the present disclosure and one or more additional active agents, if more than one agent is used. A therapeutically effective amount of a composition comprising a binding agent of the present disclosure may also vary according to factors such as the disease state, age, sex, and weight of the individual, and the ability of the composition (and one or more additional active agents) to elicit a desired response in the individual, e.g., amelioration of at least one condition parameter, e.g., amelioration of at least one symptom of the complement-mediated disorder. For example, a therapeutically effective amount of a composition comprising a binding agent of the present disclosure may inhibit (lessen the severity of or eliminate the occurrence of) and/or prevent a disorder, and/or any one of the symptoms of the disorder. A therapeutically effective amount is also one in which any toxic or detrimental effects of the composition comprising a binding agent of the present disclosure are outweighed by the therapeutically beneficial effects.

A composition comprising a binding agent of the present disclosure may be administered as a fixed dose, or in a milligram per kilogram (mg/kg) dose. In some embodiments, the dose may also be chosen to reduce or avoid production of antibodies or other host immune responses against one or more of the antigen-binding molecules in the composition comprising a binding agent of the present disclosure. While in no way intended to be limiting, exemplary dosages of a binding agent, such as a composition comprising a binding agent of the present disclosure comprise, e.g., 1-1000 mg/kg, 1-100 mg/kg, 0.5-50 mg/kg, 0.1-100 mg/kg, 0.5-25 mg/kg, 1-20 mg/kg, and 1-10 mg/kg. Exemplary dosages of a composition comprising a binding agent of the present disclosure comprise, without limitation, 0.1 mg/kg, 0.5 mg/kg, 1.0 mg/kg, 2.0 mg/kg, 4 mg/kg, 8 mg/kg, or 20 mg/kg.

Suitable human doses of any of the compositions comprising a binding agent of the present disclosure may further be evaluated in, e.g., Phase I dose escalation studies. See, e.g., van Gurp et al. (2008) Am J Transplantation 8(8):1711-1718; Hanouska et al. (2007) Clin Cancer Res 13(2, part 1):523-531; and Hetherington et al. (2006) Antimicrobial Agents and Chemotherapy 50(10): 3499-3500.

In various embodiments, a pharmaceutical composition may comprise a nucleic acid of the present disclosure, e.g., a vector. Methods of formulating pharmaceutical compositions comprising a nucleic acid of the present disclosure are known, e.g., in the books in the series Drugs and the Pharmaceutical Sciences: a Series of Textbooks and Monographs (Dekker, N.Y.). For example, solutions or suspensions used for parenteral, intradermal, or subcutaneous application may comprise the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH may be adjusted with acids or bases, such as hydrochloric acid or sodium hydroxide. Parenteral preparations may be enclosed, e.g., in ampoules, disposable syringes, or more than one dose vials made of glass or plastic.

Pharmaceutical compositions comprising a nucleic acid of the present disclosure suitable for injection may comprise sterile aqueous solutions or dispersions and sterile powders for the extemporaneous preparation of sterile injectable solutions or dispersion. For intravenous administration, suitable carriers may comprise physiological saline, bacteriostatic water, Cremophor EL™ (BASF, Parsippany, N.J.) or phosphate buffered saline (PBS). The carrier may be a solvent or dispersion medium containing, for example, water, ethanol, polyol (for example, glycerol, propylene glycol, and liquid polyethylene glycol, and the like), and suitable mixtures thereof.

Sterility, stability, viscosity and other factors relating to effective therapeutic use may be considered. One method of maintaining fluidity, for example, comprises the use of a coating such as lecithin, the maintenance of required particle size, or the use of surfactants. In some instances, it will be preferable to comprise isotonic agents, for example, sugars, polyalcohols such as mannitol, sorbitol, sodium chloride in the composition. In some instances, prolonged absorption of injectable compositions comprising a nucleic acid of the present disclosure may be brought about by comprising in the composition an agent that delays absorption, for example, aluminum monostearate and gelatin.

Sterile injectable solutions may be prepared by incorporating one or a combination of ingredients such as antibacterial and antifungal agents (for example, parabens, chlorobutanol, phenol, ascorbic acid, thimerosal, and the like), and/or by filtered sterilization. In some instances, dispersions are prepared by incorporating the active molecule into a sterile vehicle, which contains a basic dispersion medium and antibacterial or antifungal agents. In the case of sterile powders for the preparation of sterile injectable solutions, methods of preparation comprise vacuum drying and freeze-drying from a previously sterile-filtered solution thereof.

Oral compositions comprising a nucleic acid of the present disclosure may comprise an inert diluent or an edible carrier. For the purpose of oral therapeutic administration, a nucleic acid of the present disclosure may be incorporated with excipients and used, e.g., in the form of tablets, troches, or capsules, e.g., gelatin capsules. Oral compositions comprising a nucleic acid of the present disclosure may also be prepared using a fluid carrier for use as a mouthwash. Pharmaceutically compatible binding agents, and/or adjuvant materials may be comprised as part of the composition. The tablets, pills, capsules, troches and the like may contain any of the following ingredients, or molecules of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate or Sterotes®; a glidant such as colloidal silicon dioxide; a sweetening agent such as sucrose or saccharin; or a flavoring agent such as peppermint, methyl salicylate, or orange flavoring.

In some embodiments, nucleic acids may be administered by any method suitable for administration of nucleic acid agents, such as a DNA vaccine. These methods comprise, e.g., gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, e.g., Hamajima et al., (1998) Clin. Immunol. Immunopathol. 88(2), 205-10. Liposomes (e.g., as described in U.S. Pat. No. 6,472,375). In certain instances, microencapsulation may be used. In addition, biodegradable targetable microparticle delivery systems may be used (e.g., as described in U.S. Pat. No. 6,471,996).

Compositions comprising a nucleic acid of the present disclosure may comprise components such as adjuvants, diluents, binders, stabilizers, buffers, salts, lipophilic solvents, preservatives, mixtures thereof, or any component for inclusion in therapeutic compositions comprising a nucleic acid. A nucleic acid composition may comprise, e.g., saline, solvents, dispersion media, coatings, antibacterial and antifungal agents, isotonic and absorption delaying agents, and the like, a phosphate buffered saline solution, water, and emulsions, such as an oil/water or water/oil emulsion, and various types of wetting agents, compatible with pharmaceutical administration. Supplementary active molecules may also be incorporated into compositions comprising a nucleic acid of the present disclosure of the present disclosure. Compositions comprising a nucleic acid of the present disclosure of the present disclosure may comprise stabilizers and preservatives and any of the carriers described herein with the optional additional proviso that they be acceptable for use in vivo. For examples of additional carriers, stabilizers, and adjuvants, see Martin REMINGTON'S PHARM. SCI., 15th Ed. (Mack Publ. Co., Easton (1975) and Williams & Williams, (1995), and in the "PHYSICIAN'S DESK REFERENCE," 52nd ed., Medical Economics, Montvale, N.J. (1998).

Methods described herein comprise the manufacture and use of pharmaceutical compositions comprising a nucleic acid of the present disclosure. Pharmaceutical compositions comprising a nucleic acid of the present disclosure are generally formulated to be compatible with their intended route of administration. Examples of routes of administration comprise parenteral, e.g., intravenous, intracranial, intradermal, subcutaneous, oral (e.g., inhalation), transdermal (topical), transmucosal, and rectal administration.

A nucleic acid composition may comprise a buffer or a pH adjusting agent. A buffer may be a salt prepared from an organic acid or base. Buffers of the present disclosure comprise organic acid salts such as salts of citric acid, ascorbic acid, gluconic acid, carbonic acid, tartaric acid, succinic acid, acetic acid, or phthalic acid, Tris, tromethamine hydrochloride, and phosphate buffers. Additional carriers comprise polymeric excipients or additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as TWEEN 20® and TWEEN 80®), lipids (e.g., phospholipids, fatty acids), steroids (e.g., cholesterol), and chelating agents (e.g., EDTA).

In certain embodiments in which a nucleic acid of the present disclosure is a vector, the present disclosure comprises a composition for gene transduction and/or gene therapy, e.g., a composition comprising viral particles, e.g., AAV particles and/or retroviral particles such as lentiviral particles. The terms "genome particles (gp)," or "genome equivalents," as used in reference to a viral titer, refer to the number of virions containing the recombinant viral genome, e.g., recombinant AAV DNA genome, regardless of infectivity or functionality. The number of genome particles in a vector preparation may be measured. The terms "infection unit (IU)," "infectious particle," or "replication unit," as used in reference to a viral titer, refer to the number of infectious and replication-competent recombinant virus, e.g., of recombinant AAV vector particles, as may be measured by the infectious center assay, also known as replication center assay. The term "transducing unit (TU)" as used in reference to a viral titer, refers to the number of infectious recombinant vector particles, e.g., recombinant AAV vector particles, that result in the production of a functional transgene product.

In some embodiments, a composition comprises, e.g., $2\times10^6$ to $2\times10^{12}$, $2\times10^7$ to $2\times10^{11}$, or $2\times10^8$ to $2\times10^{11}$ DNA-containing viral particles per dose. In certain embodiments, the concentration or titer of vector in a unit dosage form is, e.g., at least: (a) $1\times10^{12}$ particles per mL, $2\times10^{12}$ particles per mL, $3\times10^{12}$ particles per mL, $4\times10^{12}$ particles per mL, $5\times10^{12}$ particles per mL, $6\times10^{12}$ particles per mL, $7\times10^{12}$ particles per mL, $8\times10^{12}$ particles per mL, $9\times10^{12}$ particles per mL, $10\times10^{12}$ particles per mL, $15\times10^{12}$ particles per mL, $20\times10^{12}$ particles per mL, $25\times10^{12}$ particles per mL, or $50\times10^{12}$ particles per mL; (b) $1\times10^9$ TU/mL, $2\times10^9$ TU/mL, $3\times10^9$ TU/mL, $4\times10^9$ TU/mL, $5\times10^9$ TU/mL, $6\times10^9$ TU/mL, $7\times10^9$ TU/mL, $8\times10^9$ TU/mL, $9\times10^9$ TU/mL, $10\times10^9$ TU/mL, $15\times10^9$ TU/mL, $20\times10^9$ TU/mL, 25, or $50 \times 10^9$ TU/mL; or (c) $1 \times 10^{10}$ IU/mL, $2 \times 10^{10}$ IU/mL, $3 \times 10^{10}$ IU/mL, $4 \times 10^{10}$ IU/mL, $5 \times 10^{10}$ IU/mL, $6 \times 10^{10}$ IU/mL, $7 \times 10^{10}$ IU/mL, $8 \times 10^{10}$ IU/mL, $9 \times 10^{10}$ IU/mL, $10 \times 10^{10}$ IU/mL, $15 \times 10^{10}$ IU/mL, $20 \times 10^{10}$ IU/mL, $25 \times 10^{10}$ IU/mL, or $50 \times 10^{10}$ IU/mL. Such embodiments do not limit the unit dosages encompassed by the present disclosure and do not limit the various measures of dosage that may be used in conjunction with various compositions comprising a nucleic acid of the present disclosure of the present disclosure. For instance, a particle dosage, concentration, or amount may be measured and/or expressed in terms of vector genomes per kilogram subject (Vg/Kg) or Vg/dose. The preferred means of measuring and/or expressing particle dosage, concentration, or amount may vary depending upon various factors, e.g., route of administration.

The present disclosure provides technologies for simultaneously targeting CD20 and another antigen, e.g., CD19. In some embodiments, the present disclosure provides technologies for initiating and/or modulating immune responses. In some embodiments, the present disclosure provides technologies for treating cancer (e.g., cancer characterized by cell(s) with surface-expressed CD20).

The present specification comprises use of a binding agent pharmaceutical composition provided herein to treat or prevent cancer. Another aspect of the present disclosure is directed to a method for treating or preventing a malignancy, said method comprising administering to a subject in need thereof an effective amount of a binding agent pharmaceutical composition, e.g., where the cells comprises at least one Antigen binding system provided herein. Methods of the present disclosure comprising administration of an pharmaceutically effective amount of a binding agent pharmaceutical composition of the present disclosure may be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain embodiments, a method provided herein induces a complete response. In some embodiments, a method provided herein induces a partial response. In certain embodiments the binding agent pharmaceutical composition is, comprises, comprises as the active agent, or comprises as the sole active agent, cells provided herein, e.g., cells that comprise or express at least one CAR of the present disclosure. In some embodiments, the binding agent pharmaceutical composition comprises a bicistronic CAR system comprising an anti-CD20 car and an anti-CD19 CAR, or the binding agent pharmaceutical composition comprises a bispecific anti-C20/anti-CD19 CAR of the present disclosure.

In various embodiments, the present disclosure comprises use of a binding agent pharmaceutical composition provided herein to induce in a subject, or provide a subject with, immunity against a cancer. The present disclosure further comprises a method of preventing cancer in a subject by administering to the subject a binding agent pharmaceutical composition provided herein. The present disclosure further comprises a method of inducing an immune response in a subject by administering to the subject a binding agent pharmaceutical composition provided herein. In certain embodiments the binding agent pharmaceutical composition is, comprises, comprises as the active agent, or comprises as the sole active agent, cells provided herein, e.g., cells that comprise or express at least one CAR of the present disclosure. In some embodiments, the binding agent pharmaceutical composition comprises a bicistronic CAR system comprising an anti-CD20 car and an anti-CD19 CAR, or the binding agent pharmaceutical composition comprises a bispecific anti-C20/anti-CD19 CAR of the present disclosure.

In certain embodiments, a method of treating a cancer in a subject in need thereof comprises administering to the subject a polynucleotide, vector, antibody, or antigen binding system disclosed herein. In one embodiment, the method comprises administering a polynucleotide encoding an antigen binding system or antibody (e.g., an antigen binding system). In another embodiment, the method comprises administering a vector comprising a polynucleotide encoding an antigen binding system or antibody. In another embodiment, the method comprises administering an antigen binding system or antibody to the subject.

Another aspect of the disclosure is directed to a method of making a cell expressing a CAR or a TCR comprising transducing a cell with a polynucleotide disclosed herein under suitable conditions. In some embodiments, the method comprises transducing a cell with a polynucleotide encoding a CAR or a TCR, as disclosed herein. In some embodiments, the method comprises transducing a cell with a vector comprising the polynucleotide encoding a CAR or a TCR. In certain embodiments, the present disclosure provides a T cell therapy in which a binding agent pharmaceutical composition comprises T cells transfected or transduced with a vector comprising a polynucleotide sequence encoding an antigen-binding agent of the present disclosure (e.g., an antigen binding system). In some embodiments, the donor T cells for use in the T cell therapy are obtained from the patient (e.g., for an autologous T cell therapy). In other embodiments, the donor T cells for use in the T cell therapy are obtained from a subject that is not the patient. In one embodiment, the T cell therapy of the present disclosure is an Autologous Cell Therapy (eACT™). According to this embodiment, the method may comprise collecting blood cells from the patient. The isolated blood cells (e.g., T cells) may then be engineered to express an antigen binding system of the present disclosure. In certain embodiments, the binding agents are administered to the patient. In some embodiments, the binding agents treat or are intended to treat or a cancer in the patient. For instance, in one embodiment the binding agents reduce the size of a tumor. In various embodiments, cells of the present disclosure may be cells freshly isolated from a human subject, cells freshly isolated from a cell culture, or cells having been stored, e.g., frozen.

Another aspect of the present disclosure is directed to a method of inducing an immunity against a tumor comprising administering to a subject an effective amount of a cell comprising a polynucleotide described herein, a vector described herein, or a CAR or a TCR described herein. In one embodiment, the method comprises administering to a subject an effective amount of a cell comprising a polynucleotide encoding a CAR or a TCR disclosed herein. In another embodiment, the method comprises administering to a subject an effective amount of a cell comprising a vector comprising a polynucleotide encoding a CAR or a TCR disclosed herein. In another embodiment, the method comprises administering to a subject an effective amount of a cell comprising a CAR or a TCR encoded by a polynucleotide disclosed herein.

Another aspect of the present disclosure is directed to a method of inducing an immune response in a subject comprising administering an effective amount of the engineered immune cells of the present application. In some embodiments, the immune response is a T cell-mediated immune response. In some embodiments, the T cell-mediated immune response is directed against one or more target cells.

In some embodiments, the engineered immune cell comprises a CAR or a TCR, wherein the CAR or the TCR comprises a THD described in the present disclosure. In some embodiments, the target cell is a tumor cell.

Another aspect of the present disclosure is directed to a method for treating or preventing a malignancy, said method comprising administering to a subject in need thereof an effective amount of at least one immune cell, wherein the immune cell comprises at least one CAR or TCR, and wherein the CAR or the TCR comprises one or two of the scfv disclosed herein.

Another aspect of the present disclosure is directed to a method of treating a cancer in a subject in need thereof comprising administering to the subject a polynucleotide, a vector, a CAR or a TCR, a cell, or a composition disclosed herein. In one embodiment, the method comprises administering a polynucleotide encoding a CAR or a TCR. In another embodiment, the method comprises administering a vector comprising a polynucleotide encoding a CAR or a TCR. In another embodiment, the method comprises administering a CAR or a TCR encoded by a polynucleotide disclosed herein. In another embodiment, the method comprises administering a cell comprising the polynucleotide, or a vector comprising the polynucleotide, encoding a CAR or a TCR.

In some embodiments, the methods of treating a cancer in a subject in need thereof comprise a T cell therapy. In one embodiment, the T cell therapy of the present disclosure is engineered Autologous Cell Therapy (eACT™). According to this embodiment, the method can include collecting blood cells from the patient. The isolated blood cells (e.g., T cells) can then be engineered to express a CAR or a TCR of the present disclosure. In a particular embodiment, the CAR T cells or the TCR T cells are administered to the patient. In some embodiments, the CAR T cells or the TCR T cells treat a tumor or a cancer in the patient. In one embodiment the CAR T cells or the TCR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient.

The T cells can be administered at a therapeutically effective amount. For example, a therapeutically effective amount of the T cells can be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In one particular embodiment, the therapeutically effective amount of the CAR T cells or the TCR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

The methods of the disclosure can be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain embodiments, the methods induce a complete response. In other embodiments, the methods induce a partial response.

In certain embodiments, the cancer comprises cells that express CD19, e.g., on the surface of the cell. In certain embodiments the cancer comprises cells that express CD20, e.g., on the surface of the cell. In certain embodiments the cancer comprises cells that each individually express both CD19 and CD20, e.g., on the surface of the cell.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In certain embodiments, the cancer is acute lymphoblastic leukemia (ALL) (including non T cell ALL), acute lymphoid leukemia (ALL), and hemophagocytic lymphohistocytosis (HLH)), B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia (CML), chronic or acute granulomatous disease, chronic or acute leukemia, diffuse large B cell lymphoma, diffuse large B cell lymphoma (DLBCL), follicular lymphoma, follicular lymphoma (FL), hairy cell leukemia, hemophagocytic syndrome (Macrophage Activating Syndrome (MAS), Hodgkin's Disease, large cell granuloma, leukocyte adhesion deficiency, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome (MDS), myeloid diseases including but not limited to acute myeloid leukemia (AML), non-Hodgkin's lymphoma (NHL), plasma cell proliferative disorders (e.g., asymptomatic myeloma (smoldering multiple myeloma or indolent myeloma), plasmablastic lymphoma, plasmacytoid dendritic cell neoplasm, plasmacytomas (e.g., plasma cell dyscrasia; solitary myeloma; solitary plasmacytoma; extramedullary plasmacytoma; and multiple plasmacytoma), POEMS syndrome (Crow-Fukase syndrome; Takatsuki disease; PEP syndrome), primary mediastinal large B cell lymphoma (PMBC), small cell- or a large cell-follicular lymphoma, splenic marginal zone lymphoma (SMZL), systemic amyloid light chain amyloidosis, T-cell acute lymphoid leukemia ("TALL"), T-cell lymphoma, transformed follicular lymphoma, Waldenstrom macroglobulinemia, or a combination thereof. In one embodiment, the cancer is a myeloma. In one particular embodiment, the cancer is multiple myeloma. In another embodiment, the cancer is a leukemia. In one embodiment, the cancer is acute myeloid leukemia.

In various instances, a method of using a binding agent pharmaceutical composition provided herein to treat cancer is an autologous cell therapy. In various instances, a method of using a binding agent pharmaceutical composition provided herein to treat cancer is an allogeneic cell therapy.

Certain method using a binding agent pharmaceutical composition provided herein comprise collecting blood cells from the subject. Isolated subject blood cells (e.g., T cells) may then be engineered to express, e.g., an antigen binding system of the present disclosure. In some embodiments, the binding agents are administered to the subject. In some embodiments, the binding agents treat cancer in the subject. In one embodiment the binding agents reduce the size of a tumor.

In various embodiments, a cell therapy provided herein for use in the present disclosure may be administered to a subject in a course of treatment that further comprises administration of one or more additional therapeutic agents or therapies that are not a cell therapy provided herein. In certain embodiments, the present disclosure provides combination therapy for the treatment of cancer, the treatment comprising administering an anti-cancer agent to a subject receiving and/or in need of a binding agent provided herein.

In certain embodiments, administration of a binding agent provided herein may be to a subject having previously received, scheduled to receive, or in the course of a treatment regimen comprising an additional anti-cancer therapy. In various embodiments, an additional agent or therapy administered in combination with a binding agent provided herein as described herein may be administered at the same time as binding agent provided herein, on the same day as binding agent provided herein, or in the same week as binding agent provided herein. In various embodiments, an additional agent or therapy administered in combination with a binding agent provided herein as described herein may be administered such that administration of the binding agent provided herein and the additional agent or therapy are separated by one or more hours before or after, one or more days before or after, one or more weeks before or after, or one or more months before or after administration of binding agent provided herein. In various embodiments, the administration frequency of one or more additional agents may be the same as, similar to, or different from the administration frequency of a binding agent provided herein.

An agent or therapy used in combination with binding agent provided herein may be administered in a single therapeutic composition or dose together with binding agent provided herein, at the same time as binding agent provided herein in the form of a separate composition, or in a manner temporally distinct from the administration of binding agent provided herein. When a binding agent provided herein is to be used in combination with an additional agent, the binding agent provided herein may be co-formulated with the additional agent or the binding agent provided herein may be formulated separately from the additional agent formulation.

In some embodiments, the methods further comprise administering a chemotherapeutic. In certain embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750 which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). One such dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient. In other embodiments, the antigen binding molecule, transduced (or otherwise engineered) cells (such as CARs or TCRs), and the chemotherapeutic agent are administered each in an amount effective to treat the disease or condition in the subject.

In certain embodiments, compositions comprising CAR- and/or TCR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (OPDIVO®), pembrolizumab (KEYTRUDA®), pembrolizumab, pidilizumab (CureTech), and atezolizumab (Roche). Additional therapeutic agents suitable for use in combination with the disclosure include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In additional embodiments, the composition comprising CAR- and/or TCR-containing immune are administered with an anti-inflammatory agent. Anti-inflammatory agents or drugs can include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In certain embodiments, the compositions described herein are administered in conjunction with a cytokine. "Cytokine" is meant to refer to proteins released by one cell population that act on another cell as intercellular mediators. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-C SF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines. In various embodiments, a binding agent provided herein for use in the present disclosure may be administered to a subject in a course of treatment that further comprises administration of an anti-inflammatory agent. Anti-inflammatory agents may comprise, without limitation, steroids and glucocorticoids (comprising betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) comprising aspirin, ibuprofen, naproxen, methotrexate, sulfasalazine, leflunomide, anti-TNF medications, cyclophosphamide and mycophenolate. Exemplary NSAIDs comprise ibuprofen, naproxen, naproxen sodium, Cox-2 inhibitors, and sialylates. Exemplary analgesics comprise acetaminophen, oxycodone, tramadol of proporxyphene hydrochloride. Exemplary glucocorticoids comprise cortisone, dexamethasone, hydrocortisone, methylprednisolone, prednisolone, or prednisone. Exemplary biological response modifiers comprise molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers comprise monoclonal antibodies as well as recombinant forms of molecules. Exemplary DMARDs comprise azathioprine, cyclophosphamide, cyclosporine, methotrexate, penicillamine, leflunomide, sulfasalazine, hydroxychloroquine, Gold (oral (auranofin) and intramuscular), and minocycline.

In various embodiments, a binding agent provided herein for use in the present disclosure may be administered to a subject in a course of treatment that further comprises administration of a CHOP. CHOP consists of (C)yclophosphamide, an alkylating agent which damages DNA by binding to it and causing the formation of cross-links; (H)ydroxydaunorubicin (also called doxorubicin or adriamycin), an intercalating agent which damages DNA by inserting itself between DNA bases; (O)ncovin (vincristine), which prevents cells from duplicating by binding to the protein tubulin; and (P)rednisone or (P)rednisolone, which are corticosteroids.

Additional Exemplary Embodiments. The present disclosure comprises, without limitation, the following exemplary embodiments:

Embodiment 1

An isolated polynucleotide encoding a chimeric antigen receptor (CAR) or a T cell receptor (TCR), which comprises (i) an antigen binding molecule, (ii) a costimulatory domain, and (iii) an activating domain, wherein the costimulatory domain comprises an extracellular domain, a transmembrane domain, and an intracellular domain, wherein the extracellular domain comprises an antigen binding molecule consisting essentially of or consisting of (i) an amino acid sequence at least about 80%, at least about 85%, at least about 90%, at least about 95%, at least about 96%, at least about 97%, at least about 98%, at least about 99%, or about 100% identical to the amino acid sequence of any of the constructs described in SEQ ID NO. 232, 221, 56, 45, 155, 144, 177, 78, and 67.

Embodiment 2

The polynucleotide of embodiment 1, wherein the transmembrane domain is a transmembrane domain of 4-1BB/CD137, an alpha chain of a T cell receptor, a beta chain of a T cell receptor, CD3 epsilon, CD4, CD5, CD8 alpha, CD9, CD16, CD19, CD22, CD33, CD37, CD45, CD64, CD80, CD86, CD134, CD137, CD154, or a zeta chain of a T cell receptor, or any combination thereof.

Embodiment 3

The polynucleotide of embodiment 1 or 2, wherein the intracellular domain comprises a signaling region of 4-1BB/CD137, activating NK cell receptors, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CD5, CEACAM1, CRT AM, cytokine receptors, DAP-10, DNAM1 (CD226), Fc gamma receptor, GADS, GITR, HVEM (LIGHTR), IA4, ICAM-1, ICAM-1, Ig alpha (CD79a), IL2R beta, IL2R gamma, IL7R alpha, Immunoglobulin-like proteins, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that specifically binds with CD83, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX-40, PAG/Cbp, programmed death-1 (PD-1), PSGL1, SELPLG (CD162), signaling lymphocytic activation molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, a Toll ligand receptor, TRANCE/RANKL, VLA1, or VLA-6, or a combination thereof.

Embodiment 4

The polynucleotide of embodiments 1 to 3, wherein at least one of the antigen binding molecule specifically binds an antigen selected from the group consisting of 5T4, alphafetoprotein, B cell maturation antigen (BCMA), CA-125, carcinoembryonic antigen, CD19, CD20, CD22, CD23, CD30, CD33, CD56, CD123, CD138, c-Met, CSPG4, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gp120, IL-11Ralpha, kappa chain, lambda chain, melanoma-associated antigen, mesothelin, MUC-1, mutated p53, mutated ras, prostate-specific antigen, ROR1, or VEGFR2, or a combination thereof.

Embodiment 5

The polynucleotide of any of embodiments 1 to 4, wherein the polynucleotide encodes a polypeptide comprising the amino acid sequence set forth in SEQ ID NOs 232, 221, 56, 45, 155, 144, 177, 78, and 67.

Embodiment 6

A polypeptide encoded by the polynucleotide of any one of embodiments 1 to 5.

Embodiment 7

A polypeptide comprising the amino acid sequence as set forth in SEQ ID NOs. 232, 221, 56, 45, 155, 144, 177, 78, and 67.

Embodiment 8

A vector comprising the polynucleotide of any one of embodiments 1 to 5.

Embodiment 9

The vector of embodiment 7, wherein the vector is an adenoviral vector, an adenovirus-associated vector, a DNA vector, a lentiviral vector, a plasmid, a retroviral vector, or an RNA vector, or any combination thereof.

Embodiment 10

A cell comprising the polynucleotide of any one of embodiments 1 to 5, the polypeptide of claim 6 or 7, the vector of claim 8 or 9, or any combination thereof.

Embodiment 11

A composition comprising the polynucleotide of any one of embodiments 1 to 5, the polypeptide of claim 6 or 7, the vector of claim 8 or 9, the cell of claim 10, or any combination thereof.

Embodiment 12

A method of making a cell comprising the polynucleotide of any one of claims 1 to 5, the polypeptide of embodiment 6 or 7, the vector of claim 8 or 9, or any combination thereof.

Embodiment 13

A method of inducing an immunity against a tumor comprising administering to a subject an effective amount the polynucleotide of any one of claims 1 to 5, the polypeptide of embodiment 6 or 7, the vector of embodiment 8 or 9, the cell of embodiment 10, the composition of embodiment 11 or any combination thereof.

Embodiment 14

Use of the polynucleotide of any one of embodiments 1 to 5, the polypeptide of embodiment 6 or 7, the vector of embodiment 8 or 9, the cell of embodiment 11, or the composition of embodiment 12 for the manufacture of a medicament for treating a cancer in a subject in need thereof.

Embodiment 15

The use of embodiment 15, wherein the cancer is acute lymphoblastic leukemia (ALL) (including non T cell ALL), acute myeloid leukemia, B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia, chronic or acute leukemia, diffuse large B cell lymphoma (DLBCL), follicular lymphoma (FL), hairy cell leukemia, Hodgkin's Disease, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome, non-Hodgkin's lymphoma (NHL), plasma cell proliferative disorder (including asymptomatic myeloma (smoldering multiple myeloma or indolent myeloma), plasmablastic lymphoma, plasmacytoid dendritic cell neoplasm, plasmacytomas (including plasma cell dyscrasia; solitary myeloma; solitary plasmacytoma; extramedullary plasmacytoma; and multiple plasmacytoma), POEMS syndrome (also known as Crow-Fukase syndrome; Takatsuki disease; and PEP syndrome), primary mediastinal large B cell lymphoma (PMBC), small cell- or a large cell-follicular lymphoma, splenic marginal zone lymphoma (SMZL), systemic amyloid light chain amyloidosis, T-cell acute lymphoid leukemia ("TALL"), T-cell lymphoma, transformed follicular lymphoma, or Waldenstrom macroglobulinemia, or a combination thereof.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present disclosure. To the extent that any of the definitions or terms provided in the references incorporated by reference differ from the terms and discussion provided herein, the present terms and definitions control. The contents of all references cited throughout this application are expressly incorporated herein by reference.

EXAMPLES

Example 1

The present Example provides exemplary produced anti-CD20 heavy chain variable domains and light chain variable domains, and combinations thereof. CDR sequences of exemplary anti-CD20 heavy chain variable domains and anti-CD20 light chain variable domains, and thereby exemplary combinations of HCDRs and LCDRs, are also provided in below Tables 4-13. Tables 4-13 comprise exemplary nucleic acid sequences encoding exemplary variable domains (and thus also provides exemplary nucleic acid sequences encoding the identified CDRs of the exemplary variable domains).

To determine cell binding by exemplary heavy chain variable domains and light chain variable domains of the present disclosure, purified IgGs were characterized for cell binding at a concentration of 10 nM by flow cytometry. Antibodies were incubated with CHO-S cells overexpressing CD20, Raji, and Namalwa CD20+ cell lines; and with EoL-1 and CHO-S CD20− cell lines. FITC-LC was used to detect IgGs. The ratio of binding over negative controls was calculated for each antibody. Exemplary cell binding by selected anti-CD20 antibodies is provided in Table 15.

TABLE 15

| Ab | CHO-CD20 Cell Binding FOB (Fold Over Background) | Raji Cell Binding FON (Fold Over Negative) | Namalwa Cell Binding FON (Fold Over Negative) | EOL-1 Cell Binding FON (Fold Over Negative) |
|---|---|---|---|---|
| Ab1 | 813 | 266 | 12 | 1 |
| Ab2 | 2790 | 101 | 3 | 1 |
| Ab3 | 2002 | 316 | 16 | 1 |
| Ab4 | 3617 | 479 | 19 | 1 |
| Ab5 | 2480 | 185 | 17 | 1 |
| Ab6 | 2525 | 13 | 2 | 1 |
| Ab7 | 4083 | 549 | 11 | 1 |
| Ab8 | 3831 | 562 | 10 | 1 |
| Ab9 | 3618 | 562 | 11 | 1 |
| Ab10 | 3159 | 186 | 4 | 1 |

Example 2

The present Example provides bicistronic and bispecific CARs. Bicistronic and bispecific CARs comprise two binding motifs (in two CAR molecules or on a single CAR molecule, respectively). A first binding motif binds CD20 and a second binding motif binds CD19. Antibody sequences that bind CD19, and/or are useful in constructing binding motifs, antibodies, and antigen binding systems that bind CD19 are known. The present Example uses antibody sequences of an anti-CD19 binding agent referred to here as antibody Ab11, which are set forth in Table 14.

Bispecific CARs of the present Example were generated to comprise the following domains: a first binding motif, a second binding motif, a hinge, a transmembrane domain, and an intracellular domain comprising a costimulatory domain and an activation domain. In the present Example, each bispecific CAR comprised a first binding motif comprising a heavy chain variable domain and a light chain variable domain, which heavy chain and light chain variable domains are the heavy chain variable domain and the light chain variable domain from a single set of exemplary antibody sequences of Example 1 (i.e., both are from the same table of Tables 4-13, corresponding to Ab1-Ab10).

Thus, binding motifs can be identified by reference to a source antibody or source table, and refer to a binding motif having the heavy chain variable domain and light chain variable domain of the source antibody as set out in the corresponding table. In the present Example, each bispecific CAR comprised a second binding motif comprising a heavy chain variable domain and a light chain variable domain, which heavy chain and light chain variable domains are the heavy chain variable domain and the light chain variable domain of antibody Ab11 (i.e., SEQ ID NOs: 221 and 232). Bispecific CARs of the present Example comprised a 28T (CD28) domain that comprises a hinge domain and a transmembrane domain. Bispecific CARs of the present Example comprised a CD28 costimulatory domain. Bispecific CARs of the present Example comprised a CD3z activation domain.

The present Example comprises four bicistronic CARs, identified as Bic-2, Bic-8, Bic-9, and Bic-14. Each of the four bicistronic CARs comprised a first CAR construct comprising an anti-CD20 binding motif that comprises a heavy chain variable domain and light chain variable domain pair of Example 1, as set forth in Table 16 below, and a second CAR construct comprising an anti-CD19 binding motif

TABLE 16 anti-CD20 binding motif sequences of bicistronic CARs

| CAR | Binding motif | VH SEQ ID | VL SEQ ID |
|---|---|---|---|
| Bic-2 | Ab3 | 45 | 56 |
| Bic-8 | Ab8 | 155 | 166 |
| Bic-9 | Ab9 | 177 | 188 |
| Bic-14 | Ab4 | 67 | 78 |

Example 3

$CD4^+$ and $CD8^+$ T cells were isolated by positive selection from apheresis material from healthy donors and used to generate anti-CD20 monovalent or anti-CD20/anti-CD19 bicistronic CAR T-cell products. T cells were activated with bound-anti-CD3 and soluble CD28 antibodies and transduced with a lentiviral vector encoding for a CAR construct. As a control, non-transduced (NTD) T cells were generated from the same donor T cells in parallel. On the harvest day (Days 8-10 of manufacture), CAR T-cell products were stained and analyzed by flow cytometry to assess transduction efficiency and used in co-culture assays. Transduction efficiency of T cells with vector encoding monovalent CAR and vector encoding bicistronic CAR were monitored.

To determine the T cell transduction efficiency of vector encoding a monovalent CAR, CAR-T products were stained with a panel of antibodies (anti-CD3, anti-CD4, anti-CD8, and anti-linker antibodies) in the presence of a fixable viability dye and analyzed by flow cytometry to assess the percentage of viable CAR-positive cells (see WO/US2017/041534, which is incorporated herein by reference with respect to the anti-linker antibody). The anti-linker antibody is an antibody that binds the linker between the heavy and light chains of the binding motif of the anti-CD20 CAR and is used to measure transduction efficiency. Controls comprised non-transduced cells (NTD), cells transduced with a retrovirus comprising a control anti-CD19 binding agent, and cells transduced with a control anti-CD20 binding agent (Ab12 binding motif).

To determine the T cell transduction efficiency of vector encoding a bicistronic CAR, CAR-T products were stained with a panel of antibodies (comprising anti-CD3, anti-CD4, anti-CD8, anti-idiotypic, and anti-linker antibodies) in the presence of a fixable viability dye and analyzed by flow cytometry to assess the percentage of viable CAR-positive cells. The anti-idiotypic antibody binds the binding motif of the Ab11 anti-CD19 binding motif Thus, the anti-idiotypic antibody binds the anti-CD19 CAR. It is used to measure the transduction efficiency of the anti-CD19 CAR. The anti-linker antibody is used to measure transduction efficiency of the anti-CD20 CAR. Controls comprised non-transduced cells (NTD), cells transduced with a retrovirus comprising a control anti-CD19 binding agent, and cells transduced with control anti-CD20/anti-CD19 bispecific CARs (Ab13/Ab14 bispecific; Ab11/Ab12 bispecific).

TABLE 17A

Transduction efficiency of anti-CD20 monovalent CARs

| binding motif # | Transduction Efficiency (% CD20 CAR+) |
|---|---|
| Ab3 | 65.6 |
| Ab5 | 60.9 |
| Ab6 | 70.7 |
| Ab10 | 51.1 |
| Ab7 | 52.8 |
| Ab8 | 40.6 |
| Ab9 | 33 |
| Ab1 | 44.4 |
| Ab4 | 62.6 |
| Ab2 | 35.8 |
| NTD | 0.25 |
| Ab11 | 47.8 |
| Ab12 | 60.7 |

TABLE 17B

Transduction Efficiency of anti-CD20/anti-CD19 Bicistronic CARs

| | | Transduction Efficiency (%) | |
|---|---|---|---|
| Bic-binding motif # | Anti-CD20 binding motif | % CD19 CAR+ | % CD20 CAR+ |
| Bic-2 | Ab3 | 52.72 | 46.42 |
| Bic-8 | Ab8 | 50.2 | 45.57 |
| Bic-9 | Ab9 | 44.72 | 41.36 |
| Bic-14 | Ab4 | 40.28 | 37.04 |
| NTD | N/A | 0.56 | 0.09 |
| Ab11 | N/A | 59.52 | 69.3 |
| Ab13/Ab14 bispecific | N/A | 56.77 | 60.99 |
| Ab11/Ab12 bispecific | N/A | 47.54 | 49.33 |

Example 4

The present Example provides, among other things, an exemplary method of co-culturing CAR-T cells with cells expressing CAR-T target antigens. To facilitate tracking of T cells in culture, CAR-T cells were labeled with CellTrace™ Violet (CTV) reagent according to the manufacturer's instructions and subsequently washed with R-10% media. To facilitate tracking of cells expressing CAR-T target antigens ("target cells"), target cells were engineered to express luciferase. Luciferase-expressing target cells comprised Nalm6 and Raji, both of which expresses both the CD19 and CD20 antigens. In addition, Nalm6 and Raji cells not expressing CD19 or CD20 (knockout cells, or KO) were prepared. These CD19KO and CD20KO cells were clonally selected from Nalm6 and Raji parental cells and express CD20 but not CD19, or CD19 but not CD20, respectively. The CD19KO and CD20KO strains were generated and used as controls to functionally assess antigen binding of each CAR of cells expressing bicistronic anti-CD20/anti-CD19 CAR.

Luciferase-expressing target cells were plated together with CTV labeled CAR-T cells at various ratios in R-10% media (Day 0 of co-culture). The ratio may be referred to as the ratio of effector (CAR-T) cells to target cells (effector:target or E:T). To plate cells at desired ratios, CAR-T cells were serially diluted 2 to 3-fold while the number of target cells per well was held constant at 25,000 cells. Co-cultures were incubated at 37° C. for either 16 hours (h) or 4 days and functional assessments were performed as described below.

Example 5

In this example, T cells were co-cultured with target cells as described in Example 4. T-cell mediated cytotoxicity was measured as a function of the reduction in target luciferase signal in co-culture wells compared to the signal emitted by target cells plated alone. On Day 4 after co-culture initiation, D-luciferin substrate was added to the co-culture wells at a final concentration of 0.14 mg/mL and plates were incubated at 37° C. in the dark for 10 minutes. Luminescent signal was read immediately after in a VarioSkan™ LUX or VarioSkan® Flash multimode microplate reader. T cell-mediated cytotoxicity was calculated as follows: % Cytotoxicity=[1−luciferase signal of (sample of interest/target alone control)]*100.

Controls comprised non-transduced (NTD) T cells (i.e., T cells not expressing a CAR) as a negative control, cells transduced with a retrovirus comprising a control anti-CD19 binding agent, cells transduced with a control anti-CD20 binding agent, cells transduced with control anti-CD20/anti-CD19 bispecific CARs (Ab13/Ab14 bispecific; Ab15/Ab16 bispecific).

TABLE 18

Percent cytotoxicity of anti-CD20 CAR-T in co-culture after 4 days (Nalm6 wild type cells)

| binding motif # | Ab # | Nalm6 WT Cells at Various E:T Ratios | | | | | | | | |
|---|---|---|---|---|---|---|---|---|---|---|
| | | 3 to 1 | | | 1 to 1 | | | 1 to 3 | | |
| 2 | Ab3 | 92 | 91 | 92 | 72 | 73 | 77 | 64 | 62 | 53 |
| 3 | Ab5 | 97 | 96 | 97 | 65 | 74 | 77 | 68 | 67 | 60 |
| 5 | Ab6 | 12 | 21 | 23 | −11 | −10 | −13 | −12 | −20 | −22 |
| 6 | Ab10 | 37 | 46 | 55 | 11 | 4 | 6 | −4 | −8 | −8 |
| 7 | Ab7 | 98 | 98 | 98 | 89 | 91 | 90 | 79 | 76 | 75 |
| 8 | Ab8 | 99 | 99 | 99 | 86 | 91 | 93 | 89 | 86 | 90 |
| 9 | Ab9 | 70 | 68 | 66 | 71 | 72 | 72 | 91 | 90 | 92 |
| 10 | Ab1 | 23 | 23 | 27 | 7 | 4 | 5 | −8 | −6 | −17 |
| 14 | Ab4 | 100 | 100 | 100 | 52 | 70 | 68 | 65 | 70 | 70 |
| 16 | Ab2 | 22 | 20 | 27 | −13 | −7 | −13 | −20 | −23 | −30 |
| NTD | N/A | 17 | 20 | 24 | −7 | 0 | 4 | −4 | −2 | −18 |
| Ab11 | N/A | 100 | 100 | 100 | 93 | 95 | 96 | 96 | 94 | 96 |
| Ab12 | N/A | 100 | 100 | 100 | 82 | 90 | 88 | 83 | 86 | 83 |

| binding motif # | Ab # | 1 to 9 | | | 1 to 27 | | |
|---|---|---|---|---|---|---|---|
| 2 | Ab3 | 19 | 21 | 20 | 13 | 4 | 2 |
| 3 | Ab5 | 21 | 18 | 22 | 21 | 12 | 7 |
| 5 | Ab6 | −8 | −12 | −3 | −9 | −21 | −21 |
| 6 | Ab10 | −7 | −8 | −1 | −2 | −15 | −18 |
| 7 | Ab7 | 32 | 34 | 40 | 28 | 24 | 21 |
| 8 | Ab8 | 66 | 63 | 59 | 63 | 58 | 59 |
| 9 | Ab9 | 88 | 84 | 78 | 99 | 100 | 99 |
| 10 | Ab1 | −16 | −9 | 3 | −8 | 3 | −9 |
| 14 | Ab4 | 36 | 37 | 40 | 65 | 64 | 59 |
| 16 | Ab2 | −9 | −8 | 0 | −18 | −4 | −9 |
| NTD | N/A | 0 | −2 | 1 | −4 | 1 | −3 |
| Ab11 | N/A | 73 | 65 | 68 | 84 | 79 | 76 |
| Ab12 | N/A | 45 | 43 | 41 | 58 | 62 | 56 |

TABLE 19

Percent cytotoxicity of anti-CD20 CAR-T in co-culture after 4 days (Raji wild type cells)

| binding motif # | Ab # | Raji WT Cells at Various E:T Ratios | | | | | | | | |
|---|---|---|---|---|---|---|---|---|---|---|
| | | 3 to 1 | | | 1 to 1 | | | 1 to 3 | | |
| 2 | Ab3 | 100 | 100 | 100 | 61 | 75 | 82 | 58 | 53 | 50 |
| 3 | Ab5 | 100 | 100 | 100 | 61 | 55 | 59 | 55 | 60 | 57 |
| 5 | Ab6 | 33 | 40 | 46 | 5 | 2 | 5 | −7 | −9 | −8 |
| 6 | Ab10 | 99 | 99 | 99 | 57 | 62 | 71 | 36 | 34 | 30 |
| 7 | Ab7 | 100 | 100 | 100 | 65 | 70 | 78 | 55 | 44 | 43 |

TABLE 19-continued

Percent cytotoxicity of anti-CD20 CAR-T in co-culture after 4 days (Raji wild type cells)

| | | | | | | | | | |
|---|---|---|---|---|---|---|---|---|---|
| 8 | Ab8 | 100 | 100 | 100 | 70 | 68 | 57 | 67 | 62 | 65 |
| 9 | Ab9 | 100 | 100 | 100 | 63 | 60 | 63 | 73 | 72 | 61 |
| 10 | Ab1 | 18 | 17 | 23 | −15 | −28 | −25 | −24 | −12 | −10 |
| 14 | Ab4 | 100 | 100 | 100 | 17 | −1 | 5 | 31 | 36 | 31 |
| 16 | Ab2 | 60 | 63 | 69 | 2 | −6 | −6 | −6 | −2 | −8 |
| NTD | N/A | 29 | 24 | 27 | −8 | 4 | 5 | 11 | 18 | 3 |
| Ab11 | N/A | 100 | 100 | 100 | 47 | 42 | 43 | 61 | 64 | 58 |
| Ab12 | N/A | 100 | 100 | 100 | 40 | 30 | 27 | 47 | 52 | 40 |

| binding motif # | Ab # | 1 to 9 | | | 1 to 27 | | |
|---|---|---|---|---|---|---|---|
| 2 | Ab3 | 15 | 16 | 29 | 10 | 6 | 0 |
| 3 | Ab5 | 12 | 14 | 28 | 10 | 4 | −6 |
| 5 | Ab6 | 2 | 2 | 8 | −16 | −15 | −29 |
| 6 | Ab10 | 9 | 7 | 21 | 2 | −3 | −16 |
| 7 | Ab7 | 9 | 21 | 32 | 6 | 7 | 0 |
| 8 | Ab8 | 40 | 30 | 40 | 39 | 30 | 24 |
| 9 | Ab9 | 33 | 37 | 55 | 37 | 33 | 21 |
| 10 | Ab1 | 0 | −1 | 7 | −13 | −10 | 1 |
| 14 | Ab4 | 6 | 19 | 28 | 24 | 35 | 26 |
| 16 | Ab2 | 15 | 13 | 12 | 11 | 7 | 2 |
| NTD | N/A | 9 | 16 | 13 | 0 | 12 | 7 |
| Ab11 | N/A | 10 | 18 | 29 | 40 | 40 | 31 |
| Ab12 | N/A | 12 | 22 | 29 | 25 | 26 | 15 |

TABLE 20

Percent cytotoxicity of anti-CD20/anti-CD19 bicistronic CAR-T in co-culture after 4 days (Nalm6 wild type cells)

| | | Nalm6 WT Cells at Various E:T Ratios | | | | | |
|---|---|---|---|---|---|---|---|
| Bic-binding motif # | Ab # | 3 to 1 | | 1 to 1 | | 1 to 3 | |
| Bic-2 | Ab3 | 100.11 | 100.05 | 100.08 | 100.02 | 99.54 | 98.84 |
| Bic-8 | Ab8 | 100.2 | 100.18 | 100.19 | 100.13 | 100.06 | 99.54 |
| Bic-9 | Ab9 | 100.21 | 100.19 | 100.19 | 100.17 | 99.45 | 96.37 |
| Bic-14 | Ab4 | 100.21 | 100.18 | 100.17 | 100.13 | 99.86 | 99.69 |
| NTD | N/A | 8.92 | −12.24 | −17.23 | −29.28 | −17.13 | −30.68 |
| Ab11 | N/A | 100.21 | 100.17 | 100.19 | 100.16 | 99.79 | 99.01 |
| Ab13/Ab14 bispecific | N/A | 100.17 | 100.06 | 99.91 | 99.48 | 93.02 | 83.24 |
| Ab15/Ab16 bispecific | N/A | 100.05 | 100.06 | 99.89 | 99.89 | 98.89 | 96.03 |

| Bic-binding motif # | Ab # | 1 to 9 | | 1 to 27 | | 1 to 81 | |
|---|---|---|---|---|---|---|---|
| Bic-2 | Ab3 | 77.98 | 72.64 | 46.65 | 33.58 | 20.07 | 9.87 |
| Bic-8 | Ab8 | 97.6 | 87.64 | 67.03 | 51.79 | 28.36 | 12.92 |
| Bic-9 | Ab9 | 91.03 | 77.15 | 53.63 | 32.1 | 21.94 | 2.87 |
| Bic-14 | Ab4 | 99.5 | 99.49 | 84.68 | 76.42 | 48.83 | 38.37 |
| NTD | N/A | −10.7 | −19.68 | −3.76 | −11.49 | 0.02 | −8.9 |
| Ab11 | N/A | 89.83 | 87.75 | 55.83 | 43.85 | 22.23 | 0.48 |
| Ab13/Ab14 bispecific | N/A | 77.28 | 50.19 | 22.73 | 11.85 | 11.58 | −2.9 |
| Ab15/Ab16 bispecific | N/A | 66.63 | 40.98 | 25.75 | 10.27 | 5.66 | −9.98 |

TABLE 21

Percent cytotoxicity of anti-CD20/anti-CD19 bicistronic CAR-T in co-culture after 4 days (Raji wild type cells)

| | | Raji WT Cells at Various E:T Ratios | | | | | |
|---|---|---|---|---|---|---|---|
| Bic-binding motif # | Ab # | 3 to 1 | | 1 to 1 | | 1 to 3 | |
| Bic-2 | Ab3 | 99.96 | 100.01 | 88.29 | 85.71 | 53.5 | 42.14 |
| Bic-8 | Ab8 | 100.02 | 100.05 | 70.5 | 74.72 | 53.41 | 56.52 |
| Bic-9 | Ab9 | 100.06 | 100.06 | 77.3 | 64.45 | 27.42 | 43.62 |
| Bic-14 | Ab4 | 100.09 | 100.11 | 99.58 | 99.47 | 78.71 | 90.26 |
| NTD | N/A | | 14.29 | | 7.61 | | −20.48 |

TABLE 21-continued

Percent cytotoxicity of anti-CD20/anti-CD19 bicistronic CAR-T in co-culture after 4 days (Raji wild type cells)

| | | | | | | | |
|---|---|---|---|---|---|---|---|
| Ab11 | N/A | 100.1 | 100.11 | 96.49 | 98.25 | 71.1 | 70.95 |
| Ab13/Ab14 bispecific | N/A | 99.96 | 100.07 | 96.49 | 97.86 | 33.42 | 34.31 |
| Ab15/Ab16 bispecific | N/A | 99.6 | 99.08 | 85.33 | 89.26 | 29.88 | 32.49 |

| Bic-binding motif # | Ab # | 1 to 9 | | 1 to 27 | | 1 to 81 | |
|---|---|---|---|---|---|---|---|
| Bic-2 | Ab3 | 24.84 | 34.73 | −14.98 | −2.59 | −25.65 | 3.89 |
| Bic-8 | Ab8 | 20.34 | 8.78 | −1.02 | 4.33 | −0.83 | 7.66 |
| Bic-9 | Ab9 | 18.64 | 18.79 | −6.64 | 1.03 | −11.66 | −5.01 |
| Bic-14 | Ab4 | 40.22 | 30.49 | 14.88 | 15.82 | −0.97 | 4.59 |
| NTD | N/A | | −6.05 | | −4.56 | | −8.23 |
| Ab11 | N/A | 23.88 | 14.55 | 11.65 | 5.89 | −8.43 | −0.33 |
| Ab13/Ab14 bispecific | N/A | 10.08 | 30.72 | 12.69 | 10.41 | −7.6 | −7.03 |
| Ab15/Ab16 bispecific | N/A | 5.83 | 9.17 | −8.37 | 8.85 | −18.35 | −7.06 |

TABLE 22

Percent cytotoxicity of anti-CD20/anti-CD19 bicistronic CAR-T in co-culture after 4 days (Nalm6 CD19KO cells)

| | | Nalm6 CD19KO Cells at Various E:T Ratios | | | | | |
|---|---|---|---|---|---|---|---|
| Bic-binding motif # | Ab # | 3 to 1 | | 1 to 1 | | 1 to 3 | |
| Bic-2 | Ab3 | 41.94 | 47.16 | 22.68 | 21.26 | −16.73 | −4.21 |
| Bic-8 | Ab8 | 43.75 | 40.8 | 16.79 | 1.89 | −22.77 | −11.37 |
| Bic-9 | Ab9 | 43.71 | 39.92 | 0.98 | −4.54 | −17.33 | −20.52 |
| Bic-14 | Ab4 | 75.1 | 74.88 | 39.07 | 26.69 | 10.6 | 31.47 |
| NTD | N/A | −16.73 | −5.35 | −31.94 | −30.48 | −23.75 | −36.72 |
| Ab11 | N/A | 31.93 | 36.32 | −8.57 | −7.77 | −26.58 | −23.61 |
| Ab13/Ab14 bispecific | N/A | 81.71 | 85.04 | 72.06 | 51.9 | 39.52 | 38.16 |
| Ab15/Ab16 bispecific | N/A | 67.95 | 73.67 | 47.26 | 54.21 | 20 | 32.61 |

| Bic-binding motif # | Ab # | 1 to 9 | | 1 to 27 | | 1 to 81 | |
|---|---|---|---|---|---|---|---|
| Bic-2 | Ab3 | −22.58 | −8.65 | −26.2 | −22.17 | −11.82 | −18.02 |
| Bic-8 | Ab8 | −28.81 | −21.81 | −34.06 | −28.68 | −29.45 | −20.23 |
| Bic-9 | Ab9 | −26.39 | −22.98 | −41.15 | −32.2 | −34.02 | −29.96 |
| Bic-14 | Ab4 | 2.6 | 4.87 | −12.92 | −12.22 | −26.69 | −10.49 |
| NTD | N/A | −27.18 | −14.79 | −15.71 | −22.76 | −15.37 | −17.73 |
| Ab11 | N/A | −30.02 | −24.23 | −37.34 | −25.77 | −28.09 | −15.96 |
| Ab13/Ab14 bispecific | N/A | 7.05 | 7.22 | −16.35 | −23.2 | −25.86 | −25.63 |
| Ab15/Ab16 bispecific | N/A | 9.13 | −6.85 | −22.84 | −15.85 | −33.56 | −18.83 |

TABLE 23

Percent cytotoxicity of anti-CD20/anti-CD19 bicistronic CAR-T in co-culture after 4 days (Nalm6 CD20KO cells)

| | | Nalm6 CD20KO Cells at Various E:T Ratios | | | | | |
|---|---|---|---|---|---|---|---|
| Bic-binding motif # | Ab # | 3 to 1 | | 1 to 1 | | 1 to 3 | |
| Bic-2 | Ab3 | 100.01 | 100.06 | 100.02 | 100.05 | 97.34 | 97.11 |
| Bic-8 | Ab8 | 100.14 | 100.17 | 100 | 100.12 | 95.96 | 94.9 |
| Bic-9 | Ab9 | 100.15 | 100.19 | 100.13 | 100.13 | 84.99 | 81.09 |
| Bic-14 | Ab4 | 100.15 | 100.2 | 100.11 | 100.13 | 99.31 | 99.01 |
| NTD | N/A | 13.47 | 20.49 | −5.54 | 4.54 | −11.02 | −3.62 |
| Ab11 | N/A | 100.14 | 100.15 | 100.11 | 100.16 | 89.94 | 90.48 |
| Ab13/Ab14 bispecific | N/A | 100.13 | 100.12 | 99.25 | 99.19 | 72.92 | 79.13 |
| Ab15/Ab16 bispecific | N/A | 100.01 | 100.06 | 99.54 | 99.63 | 90.53 | 87.4 |

| Bic-binding motif # | Ab # | 1 to 9 | | 1 to 27 | | 1 to 81 | |
|---|---|---|---|---|---|---|---|
| Bic-2 | Ab3 | 75.37 | 74.98 | 30.97 | 14.79 | 3.49 | 19.71 |
| Bic-8 | Ab8 | 59.25 | 71.18 | 16.46 | 24.12 | 3.67 | 9.64 |
| Bic-9 | Ab9 | 43.28 | 48.23 | 11.87 | 13.08 | −0.46 | 5.06 |
| Bic-14 | Ab4 | 96.4 | 96.13 | 58.68 | 58.6 | 17.97 | 20.79 |

TABLE 23-continued

Percent cytotoxicity of anti-CD20/anti-CD19 bicistronic CAR-T in co-culture after 4 days (Nalm6 CD20KO cells)

| | | | | | | | |
|---|---|---|---|---|---|---|---|
| NTD | N/A | −6.55 | 2.96 | −3.3 | 2.3 | 8.61 | 11 |
| Ab11 | N/A | 82.02 | 74.55 | 12.37 | 7.52 | −8.48 | −1.93 |
| Ab13/Ab14 bispecific | N/A | 38.53 | 30.15 | −5.74 | 1.34 | −18.63 | −18.22 |
| Ab15/Ab16 bispecific | N/A | 34.92 | 32.63 | 0.2 | 9.2 | −5.64 | 1.78 |

TABLE 24

Percent cytotoxicity of anti-CD20/anti-CD19 bicistronic CAR-T in co-culture after 4 days (Raji CD19KO cells)

| | | Raji CD19KO Cells at Various E:T Ratios | | | | | |
|---|---|---|---|---|---|---|---|
| Bic-binding motif # | Ab # | 3 to 1 | | 1 to 1 | | 1 to 3 | |
| Bic-2 | Ab3 | 100.02 | 100.1 | 91.85 | 89.69 | 55.92 | 52.39 |
| Bic-8 | Ab8 | 100.14 | 100.16 | 68.63 | 67.49 | 57.76 | 55.82 |
| Bic-9 | Ab9 | 100.09 | 100.16 | 91.11 | 83.72 | 33.32 | 45.71 |
| Bic-14 | Ab4 | 100.03 | 100.05 | 97.97 | 97.47 | 64.86 | 69.55 |
| NTD | N/A | | 40.71 | | 15.06 | | 3.97 |
| Ab11 | N/A | 33.35 | 27.24 | 12.88 | 16.32 | −8.36 | 3.73 |
| Ab13/Ab14 bispecific | N/A | 100.03 | 100.01 | 76.44 | 82.17 | 56.77 | 55.08 |
| Ab15/Ab16 bispecific | N/A | 99.84 | 99.92 | 92.45 | 90.15 | 42.9 | 52.01 |

| Bic-binding motif # | Ab # | 1 to 9 | | 1 to 27 | | 1 to 81 | |
|---|---|---|---|---|---|---|---|
| Bic-2 | Ab3 | 24.24 | 44.1 | −3.13 | 21.88 | −7.78 | 15.73 |
| Bic-8 | Ab8 | 30.49 | 32.83 | 23.56 | 33.43 | 6.7 | 19.54 |
| Bic-9 | Ab9 | 20.8 | 32.03 | 12.07 | 17.72 | −4.15 | 14.19 |
| Bic-14 | Ab4 | 47.46 | 54.56 | 33.42 | 36.33 | 9.45 | 22.34 |
| NTD | N/A | | 6.28 | | −1.56 | | −2.01 |
| Ab11 | N/A | −15.98 | 0.93 | −6.53 | −6.94 | −3.47 | −2.64 |
| Ab13/Ab14 bispecific | N/A | 26.72 | 35.95 | 11.49 | 25.38 | 20.53 | 19.5 |
| Ab15/Ab16 bispecific | N/A | 33.11 | 35.35 | 12.34 | 22.23 | −0.75 | 5.69 |

TABLE 25

Percent cytotoxicity of anti-CD20/anti-CD19 bicistronic CAR-T in co-culture after 4 days (Raji CD20KO cells)

| Bic-binding motif # | Ab # | Raji CD20KO Cells at Various E:T Ratios | | | | | |
|---|---|---|---|---|---|---|---|
| | | 3 to 1 | | 1 to 1 | | 1 to 3 | |
| Bic-2 | Ab3 | 100.04 | 100.1 | 95 | 90.48 | 67.63 | 74.09 |
| Bic-8 | Ab8 | 100.15 | 100.18 | 84.19 | 84.25 | 81.09 | 80.16 |
| Bic-9 | Ab9 | 100.19 | 100.18 | 97.38 | 93.04 | 63.87 | 58.26 |
| Bic-14 | Ab4 | 100.18 | 100.19 | 98.61 | 97.05 | 85.53 | 82.29 |
| NTD | N/A | | 56.92 | | 28.9 | | 16.55 |
| Ab11 | N/A | 100.19 | 100.16 | 99.93 | 99.39 | 81.15 | 76.78 |
| Ab13/Ab14 bispecific | N/A | 99.24 | 99.36 | 86.31 | 86.76 | 77.15 | 75.46 |
| Ab15/Ab16 bispecific | N/A | 99.16 | 99.74 | 87.16 | 79.93 | 67.07 | 67.48 |

| Bic-binding motif # | Ab # | 1 to 9 | | 1 to 27 | | 1 to 81 | |
|---|---|---|---|---|---|---|---|
| Bic-2 | Ab3 | 60.58 | 60.16 | 31.83 | 46.37 | 0.15 | 39.97 |
| Bic-8 | Ab8 | 65.44 | 64.02 | 48.52 | 51.56 | 23.53 | 35.21 |
| Bic-9 | Ab9 | 49.76 | 54.83 | 25.93 | 30.53 | 20.54 | 23.32 |
| Bic-14 | Ab4 | 73.45 | 74 | 55.92 | 57.01 | 31.8 | 36.38 |
| NTD | N/A | | 8.06 | | −2.8 | | −5.43 |
| Ab11 | N/A | 60.19 | 62.53 | 47.63 | 39.67 | 10.91 | 15.16 |
| Ab13/Ab14 bispecific | N/A | 58.77 | 52.6 | 32.16 | 39.92 | 15.56 | 20.28 |
| Ab15/Ab16 bispecific | N/A | 49.49 | 54.48 | 18.17 | 19.02 | −3.47 | −3.58 |

Example 6

In this example, T cells were co-cultured with target cells as described in Example 4. After 16 h in co-culture, supernatants were collected and analyzed for cytokine levels using the Meso Scale Discovery V-PLEX Proinflammatory Panel 1 human kit according to the manufacturer's instructions. Supernatants from the co-cultures of T-cell products plated at the 1:1 E:T ratio with antigen-expressing target cells were analyzed for levels of interferon gamma (IFN-γ), IL-2, tumor necrosis factor alpha (TNF-α), and IL-10 secretion mediated by antigen engagement. All samples were diluted to be within the range of detection. The level of each cytokine is reported as pg/mL and the lower limit of quantitation and upper limit of quantitation of each assay is reported.

Controls comprised non-transduced (NTD) T cells (i.e., T cells not expressing a CAR) as a negative control, cells transduced with a retrovirus comprising a control anti-CD19 binding agent, cells transduced with a control anti-CD20 binding agent, cells transduced with a control bispecific antigen binding system (Ab13/Ab14 bispecific), and cells transduced with a bispecific antigen binding system (Ab15/Ab16 bispecific).

TABLE 26

Cytokine production (pg/mL) in 16 h co-culture of anti-CD20 CAR-T with Nalm6 wild type cells

| binding motif # | Ab # | IL-10 | | | IL-2 | | |
|---|---|---|---|---|---|---|---|
| 2 | Ab3 | 2.886 | 2.251 | 3.438 | 110.474 | 86.758 | 70.6158 |
| 3 | Ab5 | 4.305 | 4.194 | 3.125 | 163.198 | 174.192 | 167.524 |
| 5 | Ab6 | 0.277 | 0.147 | 0.327 | 1.39082 | 1.08314 | 2.446 |
| 6 | Ab10 | 0.769 | 0.772 | 0.832 | 2.70375 | 6.86764 | 4.13888 |
| 7 | Ab7 | 3.170 | 4.423 | 6.179 | 209.604 | 272.439 | 233.01 |
| 8 | Ab8 | 5.736 | 4.562 | 5.283 | 314.496 | 273.505 | 259.131 |
| 9 | Ab9 | 7.970 | 8.754 | 6.446 | 455.254 | 445.985 | 408.829 |
| 10 | Ab1 | 0.321 | 0.573 | 0.296 | 1.25038 | 2.8819 | 0.3113 |
| 14 | Ab4 | 5.948 | 5.325 | 3.942 | 383.166 | 351.627 | 364.473 |
| 16 | Ab2 | 0.276 | 0.312 | 0.191 | 1.52526 | 1.84837 | 0.5235 |
| NTD | N/A | 0.157 | 0.348 | 0.451 | 4.83766 | 2.43654 | 5.10316 |
| Ab11 | N/A | 19.959 | 13.241 | 16.798 | 860.093 | 843.101 | 690.879 |
| Ab12 | N/A | 7.613 | 6.145 | 5.710 | 750.441 | 802.013 | 704.947 |
| | LLOQ | | 1.360 | | | 1.78 | |
| | ULOQ | | 466.000 | | | 1876 | |

| binding motif # | Ab # | TNF-a | | | IFN-g | | |
|---|---|---|---|---|---|---|---|
| 2 | Ab3 | 87.1829 | 70.8648 | 71.7046 | 5669.7 | 4265.89 | 4974.73 |
| 3 | Ab5 | 154.755 | 143.572 | 142.014 | 9479.79 | 8824.55 | 9192.87 |
| 5 | Ab6 | 1.1906 | 1.2789 | 1.53004 | 67.7508 | 61.6543 | 75.6417 |
| 6 | Ab10 | 5.08074 | 6.14829 | 5.80572 | 172.603 | 188.02 | 229.674 |
| 7 | Ab7 | 112.546 | 143.963 | 137.234 | 5556.7 | 7514.95 | 6939.41 |
| 8 | Ab8 | 249.849 | 201.326 | 194.1 | 12452.8 | 12117.7 | 10956.6 |
| 9 | Ab9 | 263.572 | 286.889 | 267.453 | 12689.3 | 12716.4 | 10847.6 |
| 10 | Ab1 | 2.51653 | 2.46732 | 1.80637 | 134.553 | 103.288 | 90.2425 |
| 14 | Ab4 | 314.402 | 240.486 | 251.363 | 17113.1 | 14123.9 | 13754.6 |
| 16 | Ab2 | 2.05431 | 2.63529 | 2.19805 | 107.334 | 136.239 | 100.073 |
| NTD | N/A | 1.72614 | 1.68826 | 1.3141 | 83.4983 | 106.559 | 77.1905 |
| Ab11 | N/A | 392.426 | 395.229 | 347.665 | 38674.9 | 37969.3 | 32962.3 |
| Ab12 | N/A | 381.969 | 387.54 | 307.418 | 20023.6 | 18118.9 | 15659.7 |
| | LLOQ | | 1.38 | | | 149.4 | |
| | ULOQ | | 496 | | | 18760 | |

TABLE 27

Cytokine production (pg/mL) in 16 h co-culture of anti-CD20 CAR-T with Raji wild type cells

| binding motif # | Ab # | IL-10 | | | IL-2 | | |
|---|---|---|---|---|---|---|---|
| 2 | Ab3 | 4.22791 | 4.06553 | 4.09989 | 1470.48 | 1168.14 | 1572.25 |
| 3 | Ab5 | 4.71127 | 4.54175 | 5.42819 | 1098.24 | 959.202 | 1242.67 |
| 5 | Ab6 | 2.94802 | 3.02925 | 3.27569 | 48.5778 | 46.0853 | 36.4492 |
| 6 | Ab10 | 4.12995 | 6.20356 | 4.34137 | 532.235 | 638.548 | 477.869 |
| 7 | Ab7 | 6.22517 | 4.41875 | 5.68705 | 1632.41 | 1256.81 | 1629.67 |
| 8 | Ab8 | 6.82197 | 5.50928 | 5.61023 | 1406.26 | 1167.16 | 1552.86 |
| 9 | Ab9 | 8.0439 | 6.16812 | 8.28169 | 1493.89 | 1541.38 | 1341.7 |
| 10 | Ab1 | 2.57139 | 2.58163 | 2.76773 | 1.61246 | 1.07776 | 2.95043 |
| 14 | Ab4 | 3.83274 | 4.91531 | 4.91929 | 559.513 | 846.005 | 1004.86 |
| 16 | Ab2 | 4.33862 | 4.97592 | 5.1657 | 44.1423 | 63.8978 | 75.554 |

TABLE 27-continued

Cytokine production (pg/mL) in 16 h co-culture of anti-CD20 CAR-T with Raji wild type cells

| | | | | | | | |
|---|---|---|---|---|---|---|---|
| NTD | N/A | 3.54859 | 3.26674 | 3.67311 | 4.17588 | 5.40813 | 2.67597 |
| Ab11 | N/A | 8.76434 | 7.89571 | 10.5552 | 562.35 | 531.706 | 574.047 |
| Ab12 | N/A | 5.66881 | 4.89856 | 4.90972 | 1309.6 | 1156.2 | 1335.23 |
| | LLOQ | | 0.600 | | | 17.8 | |
| | ULOQ | | 466.000 | | | 18760 | |

| binding motif # | Ab # | TNF-a | | | IFN-g | | |
|---|---|---|---|---|---|---|---|
| 2 | Ab3 | 355.825 | 330.247 | 415.31 | 34934.1 | 27937.3 | 40433.3 |
| 3 | Ab5 | 299.426 | 287.003 | 372.212 | 35868.4 | 29774.6 | 42922.3 |
| 5 | Ab6 | 49.2653 | 47.2393 | 44.2108 | 1325.8 | 2259.4 | 1672.66 |
| 6 | Ab10 | 230.666 | 295.155 | 213.26 | 17114.2 | 24139.8 | 18852.1 |
| 7 | Ab7 | 385.919 | 272.502 | 371.498 | 30569.3 | 21404.7 | 30464.6 |
| 8 | Ab8 | 400.397 | 322.357 | 409.831 | 30576.4 | 23842.2 | 38718.6 |
| 9 | Ab9 | 379.925 | 424.475 | 338.892 | 34630.1 | 39572.9 | 35143.5 |
| 10 | Ab1 | 10.2538 | 11.2538 | 10.461 | 64.3593 | 84.505 | 87.5275 |
| 14 | Ab4 | 189.652 | 276.922 | 313.618 | 15464.9 | 22870.4 | 26823.3 |
| 16 | Ab2 | 76.1237 | 81.5253 | 92.838 | 1755.37 | 2782.59 | 3461.08 |
| NTD | N/A | 8.11105 | 6.99595 | 7.40474 | 52.2049 | 42.1524 | 51.0898 |
| Ab11 | N/A | 216.851 | 209.783 | 211.514 | 35496.6 | 33980.6 | 32858.6 |
| Ab12 | N/A | 354.528 | 350.431 | 328.904 | 30852.3 | 26033 | 28850.7 |
| | LLOQ | | 13.8 | | | 352 | |
| | ULOQ | | 4960 | | | 187600 | |

TABLE 28

Cytokine production (pg/mL) in 16 h co-culture of anti-CD20/anti-CD19 bicistronic CAR-T with Nalm6 wild type cells

| | | Nalm6 WT | | | |
|---|---|---|---|---|---|
| Bic-binding motif # | Ab # | IL-10 | | IL-2 | |
| Bic-2 | Ab3 | 319.96 | 148.07 | 3841.67 | 997.02 |
| Bic-8 | Ab8 | 340.60 | 198.04 | 4787.34 | 2351.16 |
| Bic-9 | Ab9 | 339.47 | 228.56 | 4472.49 | 3070.04 |
| Bic-14 | Ab4 | 310.71 | 306.43 | 3456.34 | 2075.77 |
| NTD | N/A | 22.11 | 26.07 | 47.13 | 57.14 |
| Ab11 | N/A | 156.72 | 129.75 | 5898.60 | 5164.57 |
| Ab13/Ab14 bispecific | N/A | 175.34 | 137.17 | 466.18 | 462.89 |
| Ab15/Ab16 bispecific | N/A | 220.27 | 184.11 | 914.97 | 609.44 |
| | LLOQ | 13.60 | | 17.80 | |
| | ULOQ | 4660.00 | | 18760.00 | |

| Bic-binding motif # | Ab # | TNF-a | | IFN-g | |
|---|---|---|---|---|---|
| Bic-2 | Ab3 | 1162.13 | 547.11 | 31344.55 | 17704.04 |
| Bic-8 | Ab8 | 1326.76 | 943.35 | 41201.40 | 26645.47 |
| Bic-9 | Ab9 | 1297.88 | 1123.15 | 44205.89 | 30919.65 |
| Bic-14 | Ab4 | 1314.55 | 1092.37 | 41473.90 | 32712.72 |
| NTD | N/A | 15.38 | 17.73 | 127.03 | 310.15 |
| Ab11 | N/A | 1765.65 | 1481.87 | 50877.54 | 46996.98 |
| Ab13/Ab14 bispecific | N/A | 716.26 | 700.12 | 33318.42 | 26294.09 |
| Ab15/Ab16 bispecific | N/A | 845.64 | 801.45 | 44585.96 | 36507.97 |
| | LLOQ | 13.80 | | 1494.00 | |
| | ULOQ | 4960.00 | | 187600.00 | |

TABLE 29

Cytokine production (pg/mL) in 16 h co-culture of anti-CD20/anti-CD19 bicistronic CAR-T with Raji wild type cells

| | | Raji WT | | | |
|---|---|---|---|---|---|
| Bic-binding motif # | Ab # | IL-10 | | IL-2 | |
| Bic-2 | Ab3 | 249.61 | 302.79 | 5716.65 | 6324.53 |
| Bic-8 | Ab8 | 286.93 | 375.44 | 5657.78 | 6398.44 |
| Bic-9 | Ab9 | 199.97 | 364.30 | 5311.75 | 6221.35 |
| Bic-14 | Ab4 | 289.02 | 441.49 | 4524.40 | 5178.06 |
| NTD | N/A | 20.08 | 31.64 | 52.78 | 68.18 |
| Ab11 | N/A | 158.93 | 168.48 | 6913.98 | 6266.77 |
| Ab13/Ab14 bispecific | N/A | 104.07 | 120.62 | 7388.26 | 7908.03 |
| Ab15/Ab16 bispecific | N/A | 152.99 | 196.19 | 6620.35 | 7598.18 |
| | LLOQ | 13.60 | | 17.80 | |
| | ULOQ | 4660.00 | | 18760.00 | |

| Bic-binding motif # | Ab # | TNF-a | | IFN-g | |
|---|---|---|---|---|---|
| Bic-2 | Ab3 | 1276.98 | 1348.49 | 46275.13 | 39485.80 |
| Bic-8 | Ab8 | 1248.22 | 1538.31 | 44611.85 | 52535.86 |
| Bic-9 | Ab9 | 1329.21 | 1649.67 | 37559.20 | 49128.37 |
| Bic-14 | Ab4 | 1500.30 | 1815.74 | 50827.49 | 65974.91 |
| NTD | N/A | 24.85 | 31.77 | 132.97 | 290.37 |
| Ab11 | N/A | 1833.09 | 1748.65 | 43391.37 | 47478.31 |
| Ab13/Ab14 bispecific | N/A | 2599.76 | 2726.70 | 84185.42 | 118333.60 |
| Ab15/Ab16 bispecific | N/A | 2270.58 | 2434.51 | 62974.89 | 85048.84 |
| | LLOQ | 13.80 | | 1494.00 | |
| | ULOQ | 4960.00 | | 187600.00 | |

TABLE 30

Cytokine production (pg/mL) in 16 h co-culture of anti-CD20/anti-CD19 bicistonic CAR-T with Nalm6 CD19KO cells

| Bic-binding motif # | Ab # | Nalm6 CD19KO | | | |
|---|---|---|---|---|---|
| | | IL-10 | | IL-2 | |
| Bic-2 | Ab3 | 20.85 | 21.32 | 415.03 | 397.66 |
| Bic-8 | Ab8 | 25.07 | 23.96 | 371.09 | 419.08 |
| Bic-9 | Ab9 | 17.46 | 16.68 | 315.63 | 308.79 |
| Bic-14 | Ab4 | 27.34 | 37.57 | 239.42 | 263.16 |
| NTD | N/A | 12.07 | 12.33 | 13.90 | 5.93 |
| Ab11 | N/A | 11.94 | 10.61 | 7.24 | 8.06 |
| Ab13/Ab14 bispecific | N/A | 22.57 | 25.85 | 1373.50 | 1344.97 |
| Ab11/Ab12 bispecific | N/A | 19.22 | 27.92 | 758.03 | 769.46 |
| LLOQ | | 3.4 | | 4.45 | |
| ULOQ | | 1165 | | 4690 | |

| Bic-binding motif # | Ab # | TNF-a | | IFN-g | |
|---|---|---|---|---|---|
| Bic-2 | Ab3 | 317.89 | 371.73 | 33687.05 | 41534.70 |
| Bic-8 | Ab8 | 414.53 | 293.49 | 33669.96 | 46572.37 |
| Bic-9 | Ab9 | 386.27 | 293.61 | 41476.85 | 32400.90 |
| Bic-14 | Ab4 | 418.64 | 307.18 | 44847.72 | 41189.26 |
| NTD | N/A | 21.43 | 30.02 | 2183.86 | 1360.11 |
| Ab11 | N/A | 33.88 | 28.23 | 1707.39 | 2083.68 |
| Ab13/Ab14 bispecific | N/A | 836.78 | 842.73 | 113383.20 | 130673.40 |
| Ab11/Ab12 bispecific | N/A | 720.37 | 614.86 | 98809.63 | 79846.05 |
| LLOQ | | 17.25 | | 933.75 | |
| ULOQ | | 13700 | | 117250 | |

TABLE 31

Cytokine production (pg/mL) in 16 h co-culture of anti-CD20/anti-CD19 bicistronic CAR-T with Nalm6 CD20KO cells

| Bic-binding motif # | Ab # | Nalm6 CD20KO | | | |
|---|---|---|---|---|---|
| | | IL-10 | | IL-2 | |
| Bic-2 | Ab3 | 12.82183 | 8.967694 | 300.3656 | 255.746 |
| Bic-8 | Ab8 | 3.530049 | 4.734808 | 158.655 | 112.5326 |
| Bic-9 | Ab9 | 13.69715 | 12.26638 | 464.8549 | 435.2715 |
| Bic-14 | Ab4 | 27.21842 | 23.67642 | 238.8009 | 202.8983 |
| NTD | N/A | 3.795072 | 3.924667 | 5.336147 | 10.97881 |
| Ab11 | N/A | 13.97866 | 10.62249 | 170.2153 | 136.2659 |
| Ab13/Ab14 bispecific | N/A | 5.964617 | 6.354307 | 192.2036 | 214.7087 |
| Ab15/Ab16 bispecific | N/A | | 25.07804 | | 389.0046 |
| LLOQ | | 1.36 | | 1.78 | |
| ULOQ | | 466 | | 1876 | |

| Bic-binding motif # | Ab # | TNF-a | | IFN-g | |
|---|---|---|---|---|---|
| Bic-2 | Ab3 | 208.4781 | 184.026 | 25169.65 | 20518.19 |
| Bic-8 | Ab8 | 173.3662 | 143.7201 | 17698.8 | 14222.19 |
| Bic-9 | Ab9 | 302.2407 | 268.2183 | 174.1232 | 143.1469 |
| Bic-14 | Ab4 | 295.3972 | 261.3406 | 46810.13 | 41911.35 |
| NTD | N/A | 7.415782 | 7.415782 | 108.3741 | 3143.67 |
| Ab11 | N/A | 448.6204 | 337.0853 | 81984.54 | 65671.96 |
| Ab13/Ab14 bispecific | N/A | 182.4278 | 144.6086 | 23278.19 | 20362.21 |
| Ab15/Ab16 bispecific | N/A | | 419.7012 | | 81159.51 |
| LLOQ | | 13.8 | | 1494 | |
| ULOQ | | 4960 | | 87600 | |

Example 7

T cells were co-cultured with target cells as described in Example 4. After 16 h co-culture, T-cell products plated at the specified E:T ratio with antigen-positive target cells were harvested, stained with a panel of antibody-fluorophores to identify T cells (CD3, CD4, CD8) and 4-1BB, an activation marker, and analyzed by flow cytometry. A fixable viability dye allowed analysis of viable cells. Events were systematically gated on live cells (viability dye-negative), lymphocytes (using forward scatter [FSC]-area by side scatter [SSC]-area plot), single cells (using FSC-area by FSC-height plot), and then T cells (CD3$^+$). T cells were then analyzed for level of activation (ie, percentage of 4-1BB$^+$ cells); the 4-1BB gating threshold was set based on the level expressed by the NTD control T cells.

Controls comprised non-transduced (NTD) T cells (i.e., T cells not expressing a CAR) as a negative control, cells transduced with a retrovirus comprising a control anti-CD19 binding agent, cells transduced with a control anti-CD20 binding agent, cells transduced with a control bispecific antigen binding system (Ab13/Ab14 bispecific), and cells transduced with a bispecific antigen binding system.

TABLE 32

Activation of anti-CD20 CAR-T cells in 16 h co-culture with Nalm6 wild type and Raji wild type cells

| binding motif # | Ab # | %4-1BB Upon 16 h Co-culture with Target Cells | |
|---|---|---|---|
| | | Nalm6 | Raji |
| 2 | Ab3 | 32.54 | 36.85 |
| 3 | Ab5 | 35.72 | 38.89 |

TABLE 32-continued

Activation of anti-CD20 CAR-T cells in 16 h co-culture with Nalm6 wild type and Raji wild type cells

| binding motif # | Ab # | %4-1BB Upon 16 h Co-culture with Target Cells | |
|---|---|---|---|
| | | Nalm6 | Raji |
| 5 | Ab6 | 8.99 | 16.81 |
| 6 | Ab10 | 14.62 | 33.19 |
| 7 | Ab7 | 36.28 | 35.65 |
| 8 | Ab8 | 46.66 | 58.46 |
| 9 | Ab9 | 56.88 | 61.44 |
| 10 | Ab1 | 6.48 | 8.66 |
| 14 | Ab4 | 39.49 | 36.66 |
| 16 | Ab2 | 8.29 | 32.31 |
| NTD | N/A | 5.6 | 6.08 |
| Ab11 | N/A | 57.68 | 45.09 |
| Ab12 | N/A | 50.26 | 40.1 |

TABLE 33

Activation of anti-CD20/anti-CD19 bicistronic CAR-T cells in 16 h co-culture with Nalm6 wild type, Nalm6 CD20KO, and Nalm6 CD19KO cells

| Bic-binding motif # | Ab # | % 4-1BB Upon 16 h Co-culture with Target Cells | | | | | |
|---|---|---|---|---|---|---|---|
| | | Nalm6 WT | | Nalm6 CD19KO | | Nalm6 CD20KO | |
| Bic-2 | Ab3 | 31.93 | 33.75 | 42.84 | 31.46 | 28.57 | 22.82 |
| Bic-8 | Ab8 | 25.23 | 27.71 | 39.2 | 40.04 | 25.57 | 27.1 |
| Bic-9 | Ab9 | 24.35 | 32.54 | 25.95 | 26.99 | 18.87 | 21.66 |
| Bic-14 | Ab4 | 28.33 | 27.05 | 27.81 | 28.21 | 18.65 | 22.4 |
| NTD | N/A | 1.31 | 1.51 | 5.01 | 6.1 | 2.66 | 2.23 |
| Ab11 | N/A | 23.63 | 20.6 | 5.39 | 5.58 | 24.33 | 19.05 |
| Ab13/Ab14 bispecific | N/A | 17.56 | 19.25 | 18.85 | 19.06 | 15.22 | 13.31 |
| Ab11/Ab12 bispecific | N/A | 25.89 | 22.71 | 22.24 | 22.93 | 19.82 | 15.46 |

Example 8

T cells were co-cultured with target cells as described in Example 4. The proliferative capacity of the T-cell products was determined by flow cytometric analysis of the cell division-driven dilution of CTV dye compared with NTD control T cells in response to antigen-expressing target cells. On Day 4 after co-culture initiation, T-cell products plated at the 3:1 E:T ratio with antigen-expressing target cells were harvested, stained with a panel of antibody-fluorophores (CD3, CD4, CD8) in the presence of a fixable viability dye to identify viable T cells and analyzed by flow cytometry. The percentage of proliferating cells as well as the mean fluorescence intensity (MFI) of CTV signal is reported. The decrease in MFI of CTV is proportional to the number of rounds of cell division the product has undergone (i.e., the lower the CTV MFI, the more proliferation the cell has undergone).

Controls comprised non-transduced (NTD) T cells (i.e., T cells not expressing a CAR) as a negative control, cells transduced with a retrovirus comprising a control anti-CD19 binding agent, cells transduced with a control anti-CD20 binding agent, cells transduced with a control bispecific antigen binding system (Ab13/Ab14 bispecific), and cells transduced with a Ab11/Ab12 bispecific antigen binding system.

TABLE 34

Fluorescence of anti-CD20 CAR-T cells in four day co-culture with Nalm6 wild type and Raji wild type cells

| binding motif # | Ab # | Nalm6 WT CTV MFI | Raji WT CTV MFI |
|---|---|---|---|
| 2 | Ab3 | 4902.56 | 3100.8 |
| 3 | Ab5 | 3426.83 | 2640.14 |
| 5 | Ab6 | 6396.87 | 3041.46 |
| 6 | Ab10 | 5645.62 | 2177.05 |
| 7 | Ab7 | 4698.94 | 2483.31 |
| 8 | Ab8 | 4905.7 | 2068.97 |
| 9 | Ab9 | 5039.64 | 2033.59 |
| 10 | Ab1 | 10316.89 | 5653.56 |
| 14 | Ab4 | 4640.49 | 2200.1 |
| 16 | Ab2 | 9129.9 | 3097.49 |
| NTD | N/A | 7739.37 | 4816.32 |

TABLE 34-continued

Fluorescence of anti-CD20 CAR-T cells in four day co-culture with Nalm6 wild type and Raji wild type cells

| binding motif # | Ab # | Nalm6 WT CTV MFI | Raji WT CTV MFI |
|---|---|---|---|
| Ab11 | N/A | 3548.72 | 2113.72 |
| Ab12 | N/A | 2909.96 | 2498.54 |

TABLE 34

Percent proliferation of anti-CD20 CAR-T cells in four day co-culture with Nalm6 wild type and Raji wild type cells

| binding motif # | Ab # | Nalm6 WT % Proliferation | Raji WT % Proliferation |
|---|---|---|---|
| 2 | Ab3 | 68.77 | 74.95 |
| 3 | Ab5 | 81.21 | 78.35 |
| 5 | Ab6 | 40.43 | 78.68 |
| 6 | Ab10 | 52.31 | 87.53 |
| 7 | Ab7 | 76.23 | 78.48 |
| 8 | Ab8 | 76.6 | 84.79 |
| 9 | Ab9 | 75.91 | 87.42 |
| 10 | Ab1 | 33.94 | 53.61 |
| 14 | Ab4 | 76.1 | 80.6 |
| 16 | Ab2 | 38.16 | 85.05 |
| NTD | N/A | 37.38 | 48.15 |
| Ab11 | N/A | 74.96 | 86.98 |
| Ab12 | N/A | 86.32 | 72.9 |

TABLE 35

Fluorescence of anti-CD20/anti-CD19 bicistronic CAR-T cells in four day co-culture with Nalm6 wild type, Nalm6 CD19KO, Raji wild type, and Raji CD19KO cells

| | | CellTrace Violet (MFI) | | | |
|---|---|---|---|---|---|
| Bic-binding motif # | Ab # | Nalm6 WT | | Nalm6 CD19KO | |
| Bic-2 | Ab3 | 1196.99 | 1191.69 | 1433.19 | 1433.24 |
| Bic-8 | Ab8 | 1266.27 | 1297.78 | 1503.07 | 1486.28 |
| Bic-9 | Ab9 | 1533.09 | 1503.48 | 1747.27 | 1815.87 |
| Bic-14 | Ab4 | 1242.68 | 1241.04 | 1421.57 | 1405.64 |
| NTD | N/A | 2823.57 | 2775.76 | 2269.11 | 2500.3 |
| Ab11 | N/A | 1307.52 | 1273.51 | 2392.63 | 2350.37 |
| Ab13/Ab14 bispecific | N/A | 1434.19 | 1406.81 | 1409.42 | 1614.71 |
| Ab11/Ab12 bispecific | N/A | 1207.67 | 1358.15 | 1319.45 | 1448.75 |

| Bic-binding motif # | Ab # | Raji WT | | Raji CD19KO | |
|---|---|---|---|---|---|
| Bic-2 | Ab3 | 1166.68 | 1277.03 | 1227.25 | 1249.14 |
| Bic-8 | Ab8 | 1286.29 | 1426.14 | 1285.56 | 1271.65 |
| Bic-9 | Ab9 | 1613.51 | 1474.92 | 1453.13 | 1456.33 |
| Bic-14 | Ab4 | 1767.75 | 1820.79 | 1115.55 | 1113.95 |
| NTD | N/A | 2150.62 | 2065.69 | 2050.38 | 2016.25 |
| Ab11 | N/A | 1575.17 | 1438.12 | 2011.85 | 1793.87 |
| Ab13/Ab14 bispecific | N/A | 1330.39 | 1708.95 | 1407.7 | 1628.62 |
| Ab11/Ab12 bispecific | N/A | 1636.56 | 1773.56 | 1347.75 | 1426.61 |

TABLE 36

Percent proliferation of anti-CD20/anti-CD19 bicistronic CAR-T cells in four day co-culture with Nalm6 wild type, Nalm6 CD19KO, Raji wild type, and Raji CD19KO cells

| | | % Proliferation | | | |
|---|---|---|---|---|---|
| Bic-binding motif # | Ab # | Nalm6 WT | | Nalm6 CD19KO | |
| Bic-2 | Ab3 | 91.59 | 92.65 | 87.03 | 87.51 |
| Bic-8 | Ab8 | 90.61 | 90.43 | 81.44 | 81.91 |
| Bic-9 | Ab9 | 86.97 | 86.6 | 78.09 | 79.86 |
| Bic-14 | Ab4 | 90.56 | 88.55 | 84.14 | 83.74 |
| NTD | N/A | 32.78 | 35.81 | 55.57 | 50.62 |
| Ab11 | N/A | 90.4 | 90.37 | 43.6 | 46.56 |
| Ab13/Ab14 bispecific | N/A | 87.37 | 86.42 | 89.06 | 80.19 |
| Ab11/Ab12 bispecific | N/A | 91.92 | 89.53 | 89.29 | 86.6 |

| Bic-binding motif # | Ab # | Raji WT | | Raji CD19KO | |
|---|---|---|---|---|---|
| Bic-2 | Ab3 | 92.78 | 89.58 | 92.52 | 92.77 |
| Bic-8 | Ab8 | 84.65 | 87.63 | 88.89 | 90.11 |
| Bic-9 | Ab9 | 85.06 | 77.69 | 87.2 | 87.81 |
| Bic-14 | Ab4 | 83.43 | 88.9 | 91.96 | 91.38 |
| NTD | N/A | 64.5 | 65.09 | 61.81 | 60.57 |
| Ab11 | N/A | 92.01 | 88.46 | 57.51 | 56.55 |
| Ab13/Ab14 bispecific | N/A | 92.56 | 77.42 | 90.38 | 81.8 |
| Ab11/Ab12 bispecific | N/A | 89.16 | 87.23 | 91.48 | 88.6 |

Example 9

The present Example provides data relating to hinges for use in anti-CD20 antigen binding systems. CAR T cells of the present Example comprise a monovalent anti-CD20 CAR. The present Example tests CAR-T constructs against a disseminated luciferase-expressing Raji human B-Cell lymphoma model in NSG mice. Weekly blood samples were monitored for CAR-T persistence. Response was evaluated based on bioluminescence imaging (BLI) and survival endpoints. Whole blood was drawn for analysis at days 7, 13, 20, 27, 34, and 41. BLI was performed on days 5, 12, 19, 26, 33, and 47. Study was terminated on day 55.

CAR-T cells of this study are shown in Table 37 below, each of which CAR-T cell types of Table 37 was administered to six mice. Table 37 provides the experimental conditions or groups referred to in subsequent tables of this Example. All CAR-T cells were administered intravenously (QDx1) at a dose of 2E+07 cells/mL. All mice also received a human IL-2 dosage of 36 µg ((Q12Hx2)QDx3). Human IL-2 promotes CAR-T persistence and survival. Constructs of CART cells identified as groups 4, 5, and 7-10 of Table 37 comprised a 41BB costimulatory domain. CAR T cells identified as group 6 of Table 37 comprised a CD28 costimulatory domain.

TABLE 37

| | |
|---|---|
| 1 | PBS control |
| 2 | Mock CAR-T cells control (non-transduced T cells) |
| 3 | CAR-T cells comprising anti-CD19 control CAR |
| 4 | CAR-T cells comprising anti-CD20 CAR with CD8 hinge (8k) and an anti-CD19 CAR (bicistronic CAR) |
| 5 | CAR-T cells comprising anti-CD20 CAR with IgG4 hinge and an anti-CD19 CAR (bicistronic CAR) |
| 6 | CAR-T cells comprising anti-CD20 CAR with 28T (CD28) hinge and an anti-CD19 CAR (bicistronic CAR) |
| 7 | CAR-T cells comprising anti-CD20 CAR with 28T (CD28) hinge and an anti-CD19 CAR (bicistronic CAR) |
| 8 | CAR-T cells comprising anti-CD20 CAR with G4sx1 linker and an anti-CD19 CAR (bicistronic CAR) |
| 9 | CAR-T cells comprising anti-CD20 CAR with G4sx2 linker and an anti-CD19 CAR (bicistronic CAR) |
| 10 | CAR-T cells comprising anti-CD20 CAR with G4sx3 linker and an anti-CD19 CAR (bicistronic CAR) |

All CAR-T cell treatments were well tolerated by study mice. Within each group, a number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan. Results are shown in Table 38 below, noting that data reflect monitoring through termination of the experiment at day 55.

TABLE 38

| Group # | Treatment Related Weight Change (%) | Treatment Related Deaths (%) | Median Tumor Growth Delay (Days) | Median % T/C (Day 12) | % PR | % CR | % TFS | Increased Life Span % |
|---|---|---|---|---|---|---|---|---|
| 1 | −6.5 | 0 | 0 | 100 | 0 | 0 | 0 | 0.0 |
| 2 | −15.9 | 0 | 0.4 | 73.8 | 0 | 0 | 0 | 0.1 |
| 3 | 5.6 | 0 | >37.3 | 2.5 | 0 | 83 | 83 | >345.5 |
| 4 | −6 | 0 | >37.3 | 2.1 | 0 | 100 | 100 | >345.5 |
| 5 | 5.5 | 0 | >37.3 | 2.4 | 0 | 100 | 83 | >345.5 |
| 6 | −2.7 | 0 | 15.5 | 4.6 | 0 | 0 | 0 | 131.8 |
| 7 | 4 | 0 | >37.3 | 2.4 | 0 | 100 | 33 | >345.5 |
| 8 | 1.3 | 0 | 35.6 | 3.8 | 0 | 33 | 0 | 331.8 |
| 9 | 3 | 0 | 23.3 | 2.3 | 0 | 100 | 0 | 186.4 |
| 10 | −3.1 | 0 | 18.3 | 2.8 | 0 | 67 | 17 | 200.0 |

Example 10

The present Example provides data relating to the anti-tumor efficacy of CAR-T cells comprising bicistronic CARs comprising an anti-CD19 CAR and an anti-CD20 CAR, the anti-CD20 CARS comprising various anti-CD20 binding motifs and/or hinges.

Bicistronic anti-CD20/anti-CD19 CAR-T cells were tested against disseminated luciferase-expressing Raji CD19KO B cell lymphoma tumors in NSG mice. Weekly blood samples were monitored for CAR-T persistence. Response was evaluated based on bioluminescence imaging (BLI) and survival endpoints. Whole blood was drawn for analysis at days 7, 13, 20, 27, 34, and 41. BLI was performed on days 5, 12, 19, 26, 33, 40, and 48. Study was terminated on day 55. CAR-T cells of this study as shown in rows 5-14 of Table 39 below are bicistronic CAR-T cells comprising an anti-CD20 CAR as indicated in Table 39 and an anti-CD19 CAR (Ab11 CAR comprising a 28T (CD28) hinge and a CD28 costimulatory domain). Table 39 provides the experimental conditions or groups referred to in subsequent tables of this Example. CAR-T cells were administered to six mice (except that four mice received non-transduced T cells (row 2 of Table 39)). All CAR-T cells were administered intravenously (QDx1) at a dose of 1E+07 cells/mL (rows 2-7, 9, 11, and 13) or 4E+06 (rows 8, 10, 12, and 14). All mice also received a human IL-2 dosage of 36 ng ((Q12Hx2)QDx3).

TABLE 39

| 1 | PBS control |
| 2 | Mock CAR-T cells control (non-transduced T cells) |
| 3 | CAR-T cells comprising anti-CD20 control CAR (CD8 hinge (8k), 41BB costimulatory domain) |
| 4 | CAR-T cells comprising anti-CD20 control CAR |
| 5 | CAR-T cells comprising anti-CD20 control CAR (CD8 hinge (8k), 41BB costimulatory domain) and an anti-CD19 CAR |
| 6 | CAR-T cells comprising anti-CD20 CAR comprising binding motif #9 (CD28 hinge, 41BB costimulatory domain) and an anti-CD19 CAR (bicistronic CAR) |
| 7 | CAR-T cells comprising anti-CD20 CAR comprising binding motif #2 (CD8 hinge (8k), 41BB costimulatory domain) and an anti-CD19 CAR (bicistronic CAR) |
| 8 | CAR-T cells comprising anti-CD20 CAR comprising binding motif #2 (CD8 hinge (8k), 41BB costimulatory domain) and an anti-CD19 CAR (bicistronic CAR) |
| 9 | CAR-T cells comprising anti-CD20 CAR comprising binding motif #8 (CD8 hinge (8k), 41BB costimulatory domain) and an anti-CD19 CAR (bicistronic CAR) |

TABLE 39-continued

| 10 | CAR-T cells comprising anti-CD20 CAR comprising binding motif #8 (CD8 hinge (8k), 41BB costimulatory domain) and an anti-CD19 CAR (bicistronic CAR) |
| 11 | CAR-T cells comprising anti-CD20 CAR comprising binding motif #9 (CD8 hinge (8k), 41BB costimulatory domain) and an anti-CD19 CAR (bicistronic CAR) |
| 12 | CAR-T cells comprising anti-CD20 CAR comprising binding motif #9 (CD8 hinge (8k), 41BB costimulatory domain) and an anti-CD19 CAR (bicistronic CAR) |
| 13 | CAR-T cells comprising anti-CD20 CAR comprising binding motif #14 (CD8 hinge (8k), 41BB costimulatory domain) and an anti-CD19 CAR (bicistronic CAR) |
| 14 | CAR-T cells comprising anti-CD20 CAR comprising binding motif #14 (CD8 hinge (8k), 41BB costimulatory domain) and an anti-CD19 CAR (bicistronic CAR) |

A number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan (ILS %). Results are shown in Table 40 below, noting that data reflect monitoring through termination of the experiment at day 55.

All CAR-T cell treatments were well tolerated by study mice. All CAR-T cell treatments tested elicited an anti-tumor response. All treatment regimens resulted in median tumor growth delays of >30.2 days and increase in life spans (ILS) of >226.7%. All treatment regimens resulted in median % T/C on Day 19 of 0%, except treatment with non-transduced (NTD) cells (24%).

TABLE 40

| Group # | Treatment Related Weight Change (%) | Treatment Related Deaths (%) | Median Tumor Growth Delay (Days) | Median % T/C (Day 19) | % PR | % CR | % TFS | Increased Life Span (ILS) % |
|---|---|---|---|---|---|---|---|---|
| 1 | −18.0 | 0.0 | 0.0 | 100.0 | 0.0 | 0.0 | 0.0 | 0.0 |
| 2 | −2.1 | 0.0 | >30.2 | 23.8 | 0.0 | 0.0 | 0.0 | >226.7 |
| 3 | −5.2 | 0.0 | >30.2 | 0.0 | 0.0 | 100.0 | 100.0 | >226.7 |
| 4 | 1.1 | 16.7 | >30.2 | 0.0 | 0.0 | 100.0 | 100.0 | >226.7 |
| 5 | −1.0 | 0.0 | >30.2 | 0.0 | 16.7 | 66.7 | 66.7 | >226.7 |
| 6 | 2.0 | 0.0 | >30.2 | 0.0 | 50.0 | 50.0 | 16.7 | >226.7 |
| 7 | −4.4 | 0.0 | >30.2 | 0.0 | 0.0 | 66.7 | 66.7 | >226.7 |
| 8 | −2.4 | 0.0 | >30.2 | 0.0 | 0.0 | 100.0 | 33.3 | >226.7 |
| 9 | −3.0 | 0.0 | >30.2 | 0.0 | 33.3 | 66.7 | 50.0 | >226.7 |
| 10 | 2.5 | 0.0 | >30.2 | 0.0 | 0.0 | 83.3 | 33.0 | >226.7 |
| 11 | −2.7 | 0.0 | >30.2 | 0.0 | 0.0 | 100.0 | 50.0 | >226.7 |
| 12 | 4.6 | 0.0 | >30.2 | 0.0 | 0.0 | 66.7 | 33.3 | >226.7 |
| 13 | 4.0 | 0.0 | >30.2 | 0.0 | 16.7 | 83.3 | 66.7 | >226.7 |
| 14 | 5.4 | 0.0 | >30.2 | 0.0 | 0.0 | 100.0 | 66.7 | >226.7 |

Example 11

The present Example provides data relating to the anti-tumor efficacy of CAR-T cells comprising bispecific CARs comprising an anti-CD19 binding motif and an anti-CD20 binding motif. Bispecific anti-CD20/anti-CD19 CAR-T cells were tested against disseminated luciferase-expressing Raji B cell lymphoma tumors in NSG mice. Weekly blood samples were monitored for CAR-T persistence. Response was evaluated based on bioluminescence imaging (BLI) and survival endpoints. Whole blood was drawn for analysis at days 7, 13, 20, 27, 32, and 41. BLI was performed on days 5, 12, 19, 26, 33, 40, and 47. The study was terminated on day 54.

CAR-T cells of this study as shown in rows 4-8 of Table 41 below are bispecific CAR-T cells comprising an anti-CD19 binding motif and an anti-CD20 binding motif, where the anti-CD19 binding motif is Ab11. Table 41 provides the experimental conditions or groups referred to in subsequent tables of this Example. CAR-T cells were administered at a dose, and to a number of mice, shown in Table 41. All CAR-T cells were administered intravenously (QDx1). All mice also received a human IL-2 dosage of 36 µg ((Q12Hx2) QDx3).

TABLE 41

| 1 | PBS control (6 mice) |
|---|---|
| 2 | Mock CAR-T cells control (non-transduced T cells) (1.5E+07 cells; 6 mice) |

TABLE 41-continued

| 3 | CAR-T cells comprising anti-CD19 control CAR (1.2E+07 cells; 6 mice) |
|---|---|
| 4 | Monospecific ant-CD19 CAR (1.5E+07 cells; 6 mice) |
| 5 | CAR-T cells comprising anti-CD20/anti-CD19 bispecific CAR comprising an anti-CD20 binding motif #2 (1.5E+07 cells; 5 mice) |
| 6 | CAR-T cells comprising anti-CD20/anti-CD19 bispecific CAR comprising an anti-CD20 binding motif #2 (1.0E+07 cells; 4 mice) |
| 7 | CAR-T cells comprising anti-CD20/anti-CD19 bispecific CAR comprising an anti-CD20 binding motif #8 (7.0E+06 cells; 6 mice) |
| 8 | CAR-T cells comprising anti-CD20/anti-CD19 bispecific CAR comprising an anti-CD20 binding motif #8 (1.5E+07 cells; 6 mice) |

A number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan (ILS %). Results are shown in Table 42 below. Anti-tumor efficacy was observed.

TABLE 42

| Group # | Treatment Related Weight Change (%) | Treatment Related Deaths (%) | Median Tumor Growth Delay (Days) | Median % T/C (Day 12) | % PR | % CR | % TFS | Increased Life Span (ILS) % |
|---|---|---|---|---|---|---|---|---|
| 1 | −10.2 | 0.0 | 0.0 | 100.0 | 0.0 | 0.0 | 0.0 | 0.0 |
| 2 | −15.7 | 0.0 | 1.3 | 58.7 | 0.0 | 0.0 | 0.0 | 21.7 |
| 3 | −4.1 | 0.0 | 25.5 | 6.0 | 0.0 | 83.3 | 0.0 | 295.7 |
| 4 | −8.8 | 0.0 | 7.2 | 13.2 | 0.0 | 0.0 | 0.0 | 73.9 |
| 5 | −3.5 | 0.0 | 11.7 | 12.2 | 0.0 | 0.0 | 0.0 | 113.0 |
| 6 | 0.2 | 0.0 | 10.4 | 9.6 | 0.0 | 0.0 | 0.0 | 160.9 |
| 7 | 1.9 | 50.0 | >25.5 | 5.4 | 0.0 | 100.0 | 0.0 | 195.7 |
| 8 | 1.9 | 17.0 | 15.0 | 7.1 | 0.0 | 0.0 | 0.0 | 126.1 |

Example 12

The present Example provides data relating to anti-tumor efficacy of (i) CAR-T cells comprising bicistronic CARs comprising an anti-CD19 CAR and an anti-CD20 CAR; and (ii) bispecific CARs comprising an anti-CD19 binding motif and an anti-CD20 binding motif. Bicistronic and bispecific anti-CD20/anti-CD19 CAR-T cells were tested against disseminated luciferase-expressing Raji B cell lymphoma tumors in NSG mice. Weekly blood samples were monitored for CAR-T persistence. Response was evaluated based on bioluminescence imaging (BLI) and survival endpoints. Whole blood was drawn for analysis at days 7, 13, 20, 27, 34, and 40. BLI was performed on days 5, 12, 19, 26, 33, and 40. Study was terminated on day 48.

CAR-T cells of this study as shown in Table 43 below are bicistronic or bispecific CAR-T cells comprising an anti-CD20 binding motif an anti-CD19 binding motif (Ab11). Table 43 provides the experimental conditions or groups referred to in subsequent tables of this Example. CAR-T cells were administered at a dose of 6.0E+06, each of which CAR-T cell types was administered to six mice. All CAR-T cells were administered intravenously (QDx1). All mice also received a human IL-2 dosage of 36 μg ((Q12Hx2)QDx3) intraperitoneally.

TABLE 43

| | |
|---|---|
| 1 | PBS control |
| 2 | Mock CAR-T cells control (non-transduced T cells) (60.0E+06 cells) |
| 3 | CAR-T cells comprising anti-CD19 control CAR (2.6E+06 cells) |
| 4 | CAR-T cells comprising an anti-CD19 CAR with a linker according to SEQ ID NO: 247 |
| 5 | CAR-T cells comprising an anti-CD19 CAR with a G4S linker |
| 6 | CAR-T cells comprising a bicistronic CAR comprising binding motif #2 |
| 7 | CAR-T cells comprising a bicistronic CAR comprising binding motif #9 |
| 8 | CAR-T cells comprising a bicistronic CAR comprising binding motif #14 |
| 9 | CAR-T cells comprising a bispecific CAR comprising binding motif #2 |
| 10 | CAR-T cells comprising a bispecific CAR comprising binding motif #9 |
| 11 | CAR-T cells comprising a bispecific CAR comprising binding motif #14 |
| 12 | CAR-T cells comprising a control bispecific anti-CD20/anti-CD19 CAR |
| 13 | CAR-T cells comprising a control bispecific anti-CD20/anti-CD19 CAR |

A number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan (ILS %). Results are shown in Table 44 below, noting that data reflect monitoring through termination of the experiment at day 48.

All treatments were tolerated. All treatment regimens, excluding non-transduced cells and LG cells, resulted in median tumor growth delays of at least 21 days, increase in life span (ILS) of >223%, median % T/C on Day 12 of approximately 0%, and many resulted partial and/or complete tumor regressions.

TABLE 44

| Group # | Treatment Related Weight Change (%) | Treatment Related Deaths (%) | Median Tumor Growth Delay (Days) | Median % T/C (Day 12) | % PR | % CR | % TFS | Increased Life Span (ILS) % |
|---|---|---|---|---|---|---|---|---|
| 1 | −21.8 | 0.0 | 0.0 | 100.0 | 0.0 | 0.0 | 0.0 | 0.0 |
| 2 | −22.2 | 0.0 | 0.1 | 108.3 | 0.0 | 0.0 | 0.0 | 0.0 |
| 3 | −7 | 0.0 | >28.5 | 0.1 | 50.0 | 33.3 | 0.0 | >223.1 |
| 4 | −6.8 | 0.0 | >28.5 | 0.2 | 33.3 | 66.6 | 50.0 | >223.1 |
| 5 | −4.8 | 0.0 | >28.5 | 0.3 | 67.0 | 33.3 | 0.0 | >223.1 |
| 6 | −5.8 | 0.0 | >28.5 | 0.4 | 16.6 | 66.6 | 0.0 | >223.1 |
| 7 | −5.4 | 0.0 | >28.5 | 0.8 | 50.0 | 16.6 | 0.0 | >223.1 |
| 8 | −3.3 | 0.0 | >28.5 | 0.1 | 33.3 | 66.6 | 0.0 | >223.1 |
| 9 | −5.1 | 0.0 | >28.5 | 0.7 | 16.6 | 0.0 | 0.0 | >223.1 |
| 10 | −4.6 | 0.0 | 25.2 | 0.5 | 0.0 | 0.0 | 0.0 | >223.1 |
| 11 | −4.4 | 0.0 | >28.5 | 0.2 | 16.6 | 33.3 | 0.0 | >223.1 |
| 12 | −6.6 | 0.0 | 3.8 | 26.7 | 0.0 | 0.0 | 0.0 | 81.5 |
| 13 | −3.3 | 0.0 | 20.8 | 3.2 | 16.6 | 0.0 | 0.0 | >223.1 |

Example 13

The present Example provides data relating to the anti-tumor efficacy of CAR-T cells comprising monovalent anti-CD20 CARs. Anti-CD20 CAR-T cells were tested against disseminated luciferase-expressing Raji B cell lymphoma tumors (CD19 WT) in NSG mice. Weekly blood samples were monitored for CAR-T persistence. Response was evaluated based on bioluminescence imaging (BLI) and survival endpoints. BLI was performed on days 5, 12, 21, 28, 33, 40, and 47. Study was terminated on day 55. CAR-T cells of this study as shown in Table 45 below, administered at the dosage and number of mice shown in Table 45. Table 45 provides the experimental conditions or groups referred to in subsequent tables of this Example. All CAR-T cells were administered intravenously (QDx1). All mice received a human IL-2 dosage of 36 ng ((Q12Hx2)QDx3).

TABLE 45

| | |
|---|---|
| 1 | PBS control (6 mice) |
| 2 | Mock CAR-T cells control (non-transduced T cells) (1.5E+07 cells) (6 mice) |
| 3 | CAR-T cells comprising anti-CD19 CAR (6.58E+06 cells) + non-transduced T cells (8.39E+06 cells) (5 mice) |
| 4 | CAR-T cells comprising anti-CD19 CAR (1.32E+06 cells) + non-transduced T cells (1.37E+07 cells) (6 mice) |

TABLE 45-continued

5. CAR-T cells comprising anti-CD20 CAR (1.1E+07 cells) + non-transduced T cells (4.1E+06 cells) (5 mice)
6. CAR-T cells comprising anti-CD20 CAR (2.2E+06 cells) + non-transduced T cells (1.3E+07 cells) (5 mice)
7. CAR-T cells comprising anti-CD20 CAR comprising binding motif #8 (1.5E+07 cells) (5 mice)
8. CAR-T cells comprising anti-CD20 CAR comprising binding motif #8 (3.0E+06 cells) (5 mice)
9. CAR-T cells comprising anti-CD20 CAR comprising binding motif #9 (1.1E+07 cells) (5 mice)
10. CAR-T cells comprising anti-CD20 CAR comprising binding motif #9 (1.3E+06 cells) (4 mice)
11. CAR-T cells comprising anti-CD20 CAR comprising binding motif #14 (1.1E+07 cells) + non-transduced T cells (4.0E+06 cells) (6 mice)
12. CAR-T cells comprising anti-CD20 CAR comprising binding motif #14 (2.2E+06 cells) + non-transduced T cells (1.3E+07 cells) (5 mice)

A number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan (ILS %). Results are shown in Table 46 below.

TABLE 46

| Group # | Treatment Related Weight Change (%) | Increased Life Span (%) | Median % T/C Day 12 | Tumor Growth Delay (days) | % CR | % PR | % TFS |
|---|---|---|---|---|---|---|---|
| 1 | −17.1 | 0.0 | 100.0 | 0.0 | 0.0 | 0.0 | 0.0 |
| 2 | −23.6 | 27.3 | 61.7 | 0.9 | 0.0 | 0.0 | 0.0 |
| 3 | −4.9 | 218.2 | 3.7 | 20.5 | 0.0 | 0.0 | 0.0 |
| 4 | −9.4 | 118.2 | 26.6 | 4.1 | 0.0 | 0.0 | 0.0 |
| 5 | −8.4 | >290.9 | 36.3 | >35.9 | 60.0 | 0.0 | 0.0 |
| 6 | −10.3 | >290.9 | 59.2 | 29.5 | 0.0 | 0.0 | 0.0 |
| 7 | −8.7 | >290.9 | 4.6 | >35.9 | 0.0 | 0.0 | 0.0 |
| 8 | −6.1 | >290.9 | 42.7 | 5.7 | 0.0 | 0.0 | 0.0 |
| 9 | −10.2 | >290.9 | 3.3 | >35.9 | 40.0 | 0.0 | 40.0 |
| 10 | −11.2 | 263.6 | 58.0 | 4.4 | 0.0 | 0.0 | 0.0 |
| 11 | −5.9 | 227.3 | 24.0 | 18.7 | 0.0 | 0.0 | 0.0 |
| 12 | −10.0 | 254.5 | 50.7 | 2.9 | 0.0 | 0.0 | 0.0 |

Example 14

The present Example provides data relating to the anti-tumor efficacy of CAR-T cells comprising bicistronic CARs comprising an anti-CD19 CAR and an anti-CD20 CAR, and to the anti-tumor efficacy of CAR-T cells comprising monovalent anti-CD20 CARs. CAR-T cells were tested against disseminated luciferase-expressing Raji B cell lymphoma tumors in NSG mice. Weekly blood samples were monitored for CAR-T persistence. Response was evaluated based on bioluminescence imaging (BLI) and survival endpoints. BLI was performed on days 5, 12, 19, 26, 33, and 40.

CAR-T cells of this this study are shown in Table 47 below. Table 47 provides the experimental conditions or groups referred to in subsequent tables of this Example. Groups 1-10 comprise only controls and monospecific CAR-T cells, while groups 11-16 comprise bicistronic CAR-T cells. Bicistronic CAR-T cells comprise an anti-CD20 CAR as indicated in Table 39 and an anti-CD19 CAR (Ab11 CAR). Each condition shown in Table 47 comprised 6 mice. All CAR-T cells were administered intravenously (QDx1) at the indicated dose. All mice also received intraperitoneal human IL-2 at a dosage of 36 ng ((Q12Hx2) QDx3).

TABLE 47

1. PBS control
2. Mock CAR-T cells control (non-transduced T cells) (9.0E+06 cells)
3. Mock CAR-T cells control (non-transduced T cells) (1.4E+07 cells)
4. CAR-T cells comprising anti-CD19 control CAR comprising an Ab11 binding motif (1.40E+07 cells)
5. CAR-T cells comprising anti-CD19 control CAR comprising an Ab11 binding motif (7.0E+06 cells) + Non-transduced T cells (2.00E+06 cells)
6. CAR-T cells comprising anti-CD19 control CAR comprising an Ab11 binding motif (1.40E+06 cells) + Non-transduced T cells (7.60E+06 cells)
7. CAR-T cells comprising anti-CD20 CAR comprising binding motif #14 (6.80E+06 cells) + Non-transduced T cells (2.20E+06 cells)
8. CAR-T cells comprising anti-CD20 CAR comprising binding motif #14 (1.40E+06 cells) + Non-transduced T cells (7.60E+06 cells)
9. CAR-T cells comprising control anti-CD20 CAR (7.0E+06 cells) + Non-transduced T cells (2.00E+06 cells)
10. CAR-T cells comprising control anti-CD20 CAR (1.40E+06 cells) + Non-transduced T cells (7.60E+06 cells)
11. CAR-T cells comprising anti-CD20 CAR comprising binding motif #14 and an anti-CD19 CAR (bicistronic CAR) (7.50E+06 cells) + Non-transduced T cells (1.40E+06 cells)
12. CAR-T cells comprising anti-CD20 CAR comprising binding motif #14 and an anti-CD19 CAR (bicistronic CAR) (1.50E+06 cells) + Non-transduced T cells (7.50E+06 cells)
13. CAR-T cells comprising anti-CD20 CAR control and an anti-CD19 CAR (bicistronic CAR) (8.0E+06 cells) + Non-transduced T cells (9.50E+06 cells)
14. CAR-T cells comprising anti-CD20 CAR control and an anti-CD19 CAR (bicistronic CAR) (1.60E+06 cells) + Non-transduced T cells (7.40E+06 cells)
15. CAR-T cells comprising anti-CD20 CAR comprising binding motif #14 and an anti-CD19 CAR (bicistronic CAR) (9.0E+06 cells)
16. CAR-T cells comprising anti-CD20 CAR comprising binding motif #14 and an anti-CD19 CAR (bicistronic CAR) (1.80E+06 cells) + Non-transduced T cells (7.20E+06 cells)

A number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan (ILS %). Results are shown in Table 48 below. All CAR-T cell treatments were well tolerated by study mice.

TABLE 48

| Group # | Treatment Related Weight Change (%) | Treatment Related Death (%) | Increased Life Span (%) | Median ΔT/ΔC Day 12 (%) | Tumor Growth Delay (days) | % CR | % PR | % TFS |
|---|---|---|---|---|---|---|---|---|
| 1 | −16.5 | 0.0 | 0.0 | 100.0 | 0.0 | 0.0 | 0.0 | 0.0 |
| 2 | −23.9 | 0.0 | 28.0 | 67.3 | 0.9 | 0.0 | 0.0 | 0.0 |
| 3 | −23.0 | 0.0 | 28.0 | 84.8 | 0.3 | 0.0 | 0.0 | 0.0 |
| 4 | −10.8 | 0.0 | >188.0 | 4.6 | >28.3 | 33.3 | 0.0 | 0.0 |
| 5 | −2.6 | 0.0 | >188.0 | 5.6 | >28.3 | 0.0 | 0.0 | 0.0 |
| 6 | −4.2 | 0.0 | 164.0 | 6.9 | 20.4 | 0.0 | 0.0 | 0.0 |
| 7 | −9.0 | 0.0 | >188.0 | 4.9 | >28.3 | 16.6 | 0.0 | 16.6 |
| 8 | −4.4 | 0.0 | >188.0 | 9.0 | >28.3 | 0.0 | 0.0 | 0.0 |
| 9 | −9.1 | 0.0 | >188.0 | 4.5 | >28.3 | 0.0 | 0.0 | 0.0 |
| 10 | −0.5 | 0.0 | 188.0 | 9.0 | 24.5 | 0.0 | 0.0 | 0.0 |
| 11 | −7.3 | 0.0 | >188.0 | 4.8 | >28.3 | 0.0 | 0.0 | 0.0 |
| 12 | −2.9 | 0.0 | >188.0 | 7.6 | 24.5 | 0.0 | 0.0 | 0.0 |
| 13 | −4.6 | 0.0 | >188.0 | 4.4 | >28.3 | 0.0 | 0.0 | 0.0 |
| 14 | −0.8 | 0.0 | >188.0 | 7.2 | >28.3 | 0.0 | 0.0 | 0.0 |
| 15 | −6.2 | 0.0 | >188.0 | 5.0 | >28.3 | 0.0 | 0.0 | 0.0 |
| 16 | −4.9 | 0.0 | >188.0 | 5.0 | >28.3 | 0.0 | 0.0 | 0.0 |

Example 15

The present Example provides data relating to the anti-tumor efficacy of CAR-T cells comprising bicistronic CARs comprising an anti-CD19 CAR and an anti-CD20 CAR, and to the anti-tumor efficacy of CAR-T cells comprising monovalent anti-CD20 CARs. CAR-T cells were tested against a luciferase-expressing NALM6 human acute lymphoblastic leukemia model in NSG mice. Blood samples were monitored for CAR-T persistence. Response was evaluated based on bioluminescence imaging (BLI) and survival endpoints. Whole blood was drawn for analysis at days 4, 11, 20, 25, 32, and 39. BLI was performed on days 3, 10, 18, 24, 31, 38, and 45. The study was terminated on day 48.

CAR-T cells of this this study are shown in Table 49 below. Table 49 provides the experimental conditions or groups referred to in subsequent tables of this Example. Groups 1-8 comprise only controls and monospecific CAR-T cells, while groups 9-12 comprise bicistronic CAR-T cells. Bicistronic CAR-T cells comprise an anti-CD20 CAR as indicated in Table 49 and an anti-CD19 CAR (Ab11 CAR). Each condition shown in Table 49 comprised 6 mice. All CAR-T cells were administered intravenously (QDx1) at the indicated dose.

TABLE 49

1 PBS control
2 Mock CAR-T cells control (non-transduced T cells) (1.1E+07 cells)
3 CAR-T cells comprising anti-CD19 control CAR comprising an Ab11 binding motif (9.70E+06 cells) + Non-transduced T cells (8.90E+05 cells)
4 CAR-T cells comprising anti-CD19 control CAR comprising an Ab11 binding motif (1.90E+06 cells) + Non-transduced T cells (8.70E+06 cells)

TABLE 49-continued

5 CAR-T cells comprising anti-CD20 CAR comprising binding motif #14 (6.50E+06 cells) + Non-transduced T cells (4.10E+06 cells)
6 CAR-T cells comprising anti-CD20 CAR comprising binding motif #14 (1.30E+06 cells) + Non-transduced T cells (9.30E+06 cells)
7 CAR-T cells comprising control anti-CD20 CAR (7.00E+06 cells) + Non-transduced T cells (3.60E+06 cells)
8 CAR-T cells comprising control anti-CD20 CAR (1.40E+06 cells) + Non-transduced T cells (9.20E+06 cells)
9 CAR-T cells comprising anti-CD20 CAR comprising binding motif #14 and an anti-CD19 CAR (bicistronic CAR) (1.10E+07 cells)
10 CAR-T cells comprising anti-CD20 CAR comprising binding motif #14 and an anti-CD19 CAR (bicistronic CAR) (2.10E+06 cells) + Non-transduced T cells (8.50E+06 cells)
11 CAR-T cells comprising anti-CD20 CAR control and an anti-CD19 CAR (bicistronic CAR) (8.4E+06 cells) + Non-transduced T cells (2.30E+06 cells)
12 CAR-T cells comprising anti-CD20 CAR control and an anti-CD19 CAR (bicistronic CAR) (1.70E+06 cells) + Non-transduced T cells (9.00E+06 cells)

A number of metrics were monitored, comprising treatment related weight change, treatment related deaths, median tumor growth delay, median tumor burden as compared to control (% T/C), percent of animals showing partial tumor regression (% PR), percent of animals showing complete tumor regression (% CR), percent of tumor free survivors (% TFS), and percent increased lifespan (ILS %). Results are shown in Table 50 below. All CAR-T cell treatments were tolerated by study mice.

TABLE 50

| Group # | Treatment Related Weight Change (%) | Treatment Related Deaths (%) | Increased Life Span (ILS) (%) | Median Tumor Growth Delay (Days) | Median % T/C (Day 18) | % PR | % CR | % TFS |
| --- | --- | --- | --- | --- | --- | --- | --- | --- |
| 1 | 2.8 | 0.0 | 0.0 | 0.0 | 100.0 | 0.0 | 0.0 | 0.0 |
| 2 | 3.8 | 0.0 | 0.0 | 0.0 | 121.6 | 0.0 | 0.0 | 0.0 |
| 3 | −2.2 | 0.0 | >150.0 | 27.0 | 0.0 | 50.0 | 50.0 | 16.6 |
| 4 | 3.9 | 0.0 | 72.2 | 13.0 | 0.2 | 33.3 | 0.0 | 0.0 |
| 5 | −8.7 | 0.0 | >150.0 | 27.0 | 0.0 | 66.6 | 0.0 | 0.0 |
| 6 | −2.2 | 0.0 | 86.1 | 15.5 | 13.5 | 0.0 | 0.0 | 0.0 |
| 7 | −5.4 | 0.0 | 106.6 | 19.0 | 1.25 | 0 | 0.0 | 0.0 |
| 8 | −2.4 | 0.0 | 97.2 | 17.5 | 39.4 | 0.0 | 0.0 | 0.0 |
| 9 | −2.2 | 0.0 | >150.0 | 27.0 | 0.0 | 83.3 | 16.6 | 16.6 |
| 10 | −2.2 | 0.0 | >150.0 | 27.0 | 0.1 | 100.0 | 0.0 | 0.0 |
| 11 | 6.5 | 0.0 | >150.0 | 27.0 | 0.0 | 100.0 | 0.0 | 0.0 |
| 12 | 10.3 | 0.0 | 111.1 | 20.0 | 0.2 | 16.6 | 0.0 | 0.0 |

Example 16

The present Example provides data relating to sequences for use as components of CARs. Four anti-CD20 binding motifs are tested in combination with 4 hinges (CD8 hinge (8k), truncated CD28 hinge (28T), truncated CD28 hinge with a G4S linker; and IgG4 hinge (I4)). All bispecific and bicistronic CARs comprise an Ab11 anti-CD19 binding motif. $CD4^+$ and $CD8^+$ T cells were isolated by positive selection from apheresis material from healthy donors and used to generate anti-CD20 monovalent or anti-CD20/anti-CD19 bicistronic CAR T-cell products. T cells were activated with bound-anti-CD3 and soluble CD28 antibodies and transduced with a lentiviral vector encoding for a CAR construct. As a control, non-transduced (NTD) T cells were generated from the same donor T cells in parallel. On the harvest day (Days 8-10 of manufacture), CAR T-cell products were stained and analyzed by flow cytometry to assess transduction efficiency and used in co-culture assays. Transduction efficiency of T cells with vector encoding monovalent CAR and vector encoding bicistronic CAR were monitored.

To determine the T cell transduction efficiency of vector encoding a monovalent CAR, CAR-T products were stained with a panel of antibodies (anti-CD3, anti-CD4, anti-CD8, and anti-linker) in the presence of a fixable viability dye and analyzed by flow cytometry to assess the percentage of viable CAR-positive cells. The anti-linker antibody is an antibody that binds the linker between the heavy and light chains of the binding motif of the anti-CD20 CAR and is used to measure transduction efficiency. Controls comprised non-transduced cells (NTD), cells transduced with a retrovirus comprising a control anti-CD19 binding agent, and cells transduced with a control anti-CD20 binding agent (Ab12 binding motif).

To determine the T cell transduction efficiency of vector encoding a bicistronic CAR, CAR-T products were stained with a panel of antibodies (comprising anti-CD3, anti-CD4, anti-CD8, anti-idiotypic, and anti-linker) in the presence of a fixable viability dye and analyzed by flow cytometry to assess the percentage of viable CAR-positive cells. The anti-idiotypic antibody binds the binding motif of the Ab11 anti-CD19 binding motif Thus, the anti-idiotypic antibody binds the anti-CD19 CAR. It is used to measure the transduction efficiency of the anti-CD19 CAR. The anti-linker antibody is used to measure transduction efficiency of the anti-CD20 CAR. Controls comprised non-transduced cells (NTD), cells transduced with a retrovirus comprising a control anti-CD19 binding agent, and cells transduced with control anti-CD20/anti-CD19 bispecific CARs (Ab13/Ab14 bispecific; Ab11/Ab12 bispecific).

To facilitate tracking of T cells in culture, CAR-T cells were labeled with CellTrace™ Violet (CTV) reagent according to the manufacturer's instructions and subsequently washed with R-10% media. To facilitate tracking of cells expressing CAR-T target antigens ("target cells"), target cells were engineered to express luciferase. Luciferase-expressing target cells comprised Nalm6 and Raji, both of which expresses both the CD19 and CD20 antigens. In addition, Nalm6 and Raji cells not expressing CD19 or CD20 (knockout cells, or KO) were prepared. These CD19KO and CD20KO cells were clonally selected from Nalm6 and Raji parental cells and express CD20 but not CD19, or CD19 but not CD20, respectively. The CD19KO and CD20KO strains were generated and used as controls to functionally assess antigen binding of each CAR of cells expressing bicistronic anti-CD20/anti-CD19 CAR.

Luciferase-expressing target cells were plated together with CTV labeled CAR-T cells at various ratios in R-10% media (Day 0 of co-culture). The ratio may be referred to as the ratio of effector (CAR-T) cells to target cells (effector:target or E:T). To plate cells at desired ratios, CAR-T cells were serially diluted 2 to 3-fold while the number of target cells per well was held constant at 25,000 cells. Co-cultures were incubated at 37° C. for either 16 hours (h) or 4 days and functional assessments were performed as described below.

T-cell mediated cytotoxicity was measured as a function of the reduction in target luciferase signal in co-culture wells compared to the signal emitted by target cells plated alone. On Day 4 after co-culture initiation, D-luciferin substrate was added to the co-culture wells at a final concentration of 0.14 mg/mL and plates were incubated at 37° C. in the dark for 10 minutes. Luminescent signal was read immediately after in a VarioSkan™ LUX or VarioSkan® Flash multimode microplate reader. T cell-mediated cytotoxicity was calculated as follows: % Cytotoxicity=[1−luciferase signal of (sample of interest/target alone control)]*100.

Cytokine production was measured after 16 h in co-culture, at which time supernatants were collected and analyzed for cytokine levels using the Meso Scale Discovery V-PLEX Proinflammatory Panel 1 human kit according to the manufacturer's instructions. Supernatants from the co-cultures of T-cell products plated at the 1:1 E:T ratio with antigen-expressing target cells were analyzed for levels of interferon gamma (IFN-γ), IL-2, tumor necrosis factor alpha (TNF-α), and IL-10 secretion mediated by antigen engagement. All samples were diluted to be within the range of detection. The level of each cytokine is reported as pg/mL and the lower limit of quantitation and upper limit of quantitation of each assay is reported.

To determine T cell activation after 16 h co-culture, T-cell products were plated at the specified E:T ratio with antigen-positive target cells were harvested, stained with a panel of antibody-fluorophores to identify T cells (CD3, CD4, CD8) and 4-1BB, an activation marker, and analyzed by flow cytometry. A fixable viability dye allowed analysis of viable cells. Events were systematically gated on live cells (viability dye-negative), lymphocytes (using forward scatter [FSC]-area by side scatter [SSC]-area plot), single cells (using FSC-area by FSC-height plot), and then T cells (CD3$^+$). T cells were then analyzed for level of activation (ie, percentage of 4-1BB$^+$ cells); the 4-1BB gating threshold was set based on the level expressed by the NTD control T cells.

The proliferative capacity of the T-cell products was determined by flow cytometric analysis of the cell division-driven dilution of CTV dye compared with NTD control T cells in response to antigen-expressing target cells. On Day 4 after co-culture initiation, T-cell products plated at the 3:1 E:T ratio with antigen-expressing target cells were harvested, stained with a panel of antibody-fluorophores (CD3, CD4, CD8) in the presence of a fixable viability dye to identify viable T cells and analyzed by flow cytometry. The percentage of proliferating cells as well as the mean fluorescence intensity (MFI) of CTV signal is reported. The decrease in MFI of CTV is proportional to the number of rounds of cell division the product has undergone.

CAR-T cells used in this Example comprised the CARs identified in Table 51 below. Table 51 provides the experimental conditions or groups referred to in subsequent tables of this Example. Transduction efficiency is shown in Table 52. Day 4 cytotoxicity in Nalm6 (CD19+; CD20low), Nalm6CD19KO (CD19−; CD20+), Raji (CD19+, CD20+) and Raji CD19KO (CD19−, CD20+) is shown in Tables 53A-53D. Cytokine production at 14 h post-co-culture at a 1:3 E:T ratio in Nalm6 CD19KO target cells is shown in Tables 54A-54D, as measured in pg/mL (2 replicates per condition). T cell activation as measured by upregulation of 41BB (percent 41BB+ live T cells) at 16 h post co-culture is shown in Tables 55A-D (2 replicates per condition). Proliferation of T cells at 4d post co-culture is shown in Table 56 (percent proliferating CD3+, two replicates per condition).

TABLE 51

| | Type (e.g., Bicistronic v. Bispecific) |
|---|---|
| 1 | Non-transduced control |
| 2 | Monospecific anti-CD19 CAR comprising G4S linker |
| 3 | Monospecific anti-CD19 CAR comprising G4S linker |
| 4 | Monospecific anti-CD19 CAR comprising G4S linker |
| 5 | Monospecific anti-CD20 CAR comprising CD8 hinge (8k) |
| 6 | Bicistronic anti-CD20/anti-CD19 CAR, the anti-CD20 CAR comprising CD8 hinge (8k) |
| 7 | Bicistronic anti-CD20/anti-CD19 CAR, the anti-CD20 CAR comprising IgG4 hinge |
| 8 | Bicistronic anti-CD20/anti-CD19 CAR |
| 9 | Bicistronic anti-CD20/anti-CD19 CAR, the anti-CD20 CAR comprising binding motif #2 and a CD8 hinge (8k) |
| 10 | Bicistronic anti-CD20/anti-CD19 CAR, the anti-CD20 CAR comprising binding motif #8 and a CD8 hinge (8k) |
| 11 | Bicistronic anti-CD20/anti-CD19 CAR, the anti-CD20 CAR comprising binding motif #9 and a CD8 hinge (8k) |
| 12 | Bicistronic anti-CD20/anti-CD19 CAR, the anti-CD20 CAR comprising binding motif #14 and a CD8 hinge (8k) |
| 13 | Bicistronic anti-CD20/anti-CD19 CAR, the anti-CD20 CAR comprising binding motif #2 and an CD28 hinge |
| 14 | Bicistronic anti-CD20/anti-CD19 CAR, the anti-CD20 CAR comprising binding motif #8 and an CD28 hinge |
| 15 | Bicistronic anti-CD20/anti-CD19 CAR, the anti-CD20 CAR comprising binding motif #9 and an CD28 hinge |
| 16 | Bicistronic anti-CD20/anti-CD19 CAR, the anti-CD20 CAR comprising binding motif #14 and an CD28 hinge |
| 17 | Bicistronic anti-CD20/anti-CD19 CAR, the anti-CD20 CAR comprising binding motif #2 and an CD28 hinge with a G4S linker |
| 18 | Bicistronic anti-CD20/anti-CD19 CAR, the anti-CD20 CAR comprising binding motif #8 and an CD28 hinge |
| 19 | Bicistronic anti-CD20/anti-CD19 CAR, the anti-CD20 CAR comprising binding motif #9 and an CD28 hinge with a G4S linker |
| 20 | Bicistronic anti-CD20/anti-CD19 CAR, the anti-CD20 CAR comprising binding motif #14 and an CD28 hinge with a G4S linker |
| 21 | Bicistronic anti-CD20/anti-CD19 CAR, the anti-CD20 CAR comprising binding motif #2 and an IgG4 hinge |
| 22 | Bicistronic anti-CD20/anti-CD19 CAR, the anti-CD20 CAR comprising binding motif #8 and an IgG4 hinge |
| 23 | Bicistronic anti-CD20/anti-CD19 CAR, the anti-CD20 CAR comprising binding motif #9 and an IgG4 hinge |
| 24 | Bicistronic anti-CD20/anti-CD19 CAR, the anti-CD20 CAR comprising binding motif #14 and an IgG4 hinge |

TABLE 52

| | Group | | | | | |
|---|---|---|---|---|---|---|
| | 1 | 2 | 5 | 6 | 7 | 8 |
| % CD19 CAR + Live T Cells | 0.56 | 59.52 | 2.35 | 47.54 | 29.05 | 56.77 |
| % CD20 CAR + Live T Cells | 0.09 | 69.3 | 75.76 | 49.33 | 40.13 | 60.99 |

| | Group | | | | | |
|---|---|---|---|---|---|---|
| | 9 | 10 | 11 | 12 | 13 | 14 |
| % CD19 CAR + Live T Cells | 52.72 | 50.2 | 44.72 | 40.28 | 38.99 | 34.12 |
| % CD20 CAR + Live T Cells | 46.42 | 45.57 | 41.36 | 37.04 | 37.15 | 34.7 |

TABLE 52-continued

|  | Group | | | | | |
|---|---|---|---|---|---|---|
|  | 15 | 16 | 17 | 18 | 19 | 20 |
| % CD19 CAR + Live T Cells | 34.87 | 51.32 | 28.89 | 41.69 | 41.34 | 36.22 |
| % CD20 CAR + Live T Cells | 33.78 | 47.97 | 28.87 | 41.82 | 41.95 | 35.14 |

|  | Group | | | |
|---|---|---|---|---|
|  | 21 | 22 | 23 | 24 |
| % CD19 CAR + Live T Cells | 37.07 | 30.62 | 32.18 | 39.93 |
| % CD20 CAR + Live T Cells | 38.69 | 41 | 41.23 | 46.43 |

TABLE 53A

Nalm6 WT

| E:T Ratio | Group | | | | | | | |
|---|---|---|---|---|---|---|---|---|
|  | 1 | | 2 | | 3 | | 4 | |
| 1 to 243 | 30.2 | 21.9 | −22.9 | −11.5 | −0.5 | −12.1 | −13.8 | −11.7 |
| 1 to 81 | −0.8 | −7.5 | −20.9 | −16.4 | −8.1 | −10.2 | −27.6 | −11.9 |
| 1 to 27 | −19.5 | −37.2 | −5.7 | −17.2 | −13.3 | −15.9 | −2.1 | −13.2 |
| 1 to 9 | −13.6 | −20.2 | 14.9 | −1.5 | 8.7 | −5.9 | 13.4 | 1.2 |
| 1 to 3 | −7.1 | −28.9 | 100 | 100 | 100.1 | 100.1 | 100.1 | 100.1 |
| 3 to 1 | 16 | 4.6 | 100.4 | 100.1 | 100.5 | 100.1 | 100.5 | 100.1 |

| E:T Ratio | Group | | | | | | | |
|---|---|---|---|---|---|---|---|---|
|  | 5 | | 6 | | 7 | | 8 | |
| 1 to 243 | −14.6 | −12.6 | −4 | −10.2 | −7.3 | −11.6 | −9.8 | −9.9 |
| 1 to 81 | 5.2 | −20.1 | −6.2 | −20.5 | −5.7 | −15 | −2.2 | −7 |
| 1 to 27 | −8 | −21.2 | 3.2 | −10.9 | 6 | −5.5 | −8.1 | −8.9 |
| 1 to 9 | −1.8 | 0.6 | 19.4 | 16.1 | 19 | 1.7 | 18.7 | 11 |
| 1 to 3 | 100.1 | 99.9 | 100.1 | 100.1 | 100.1 | 100.1 | 100 | 99.9 |
| 3 to 1 | 100.5 | 100.1 | 100.5 | 100.1 | 100.5 | 100.1 | 100.4 | 100 |

| E:T Ratio | Group | | | | | | | |
|---|---|---|---|---|---|---|---|---|
|  | 9 | | 10 | | 11 | | 12 | |
| 1 to 243 | 43.6 | 48.1 | −16 | 0.7 | −8.3 | −14.3 | −3.1 | −19.9 |
| 1 to 81 | 9.5 | 20.1 | −7.5 | −2.4 | −10.7 | −22.4 | −10.2 | −14.2 |
| 1 to 27 | −8.2 | 0.9 | −8.9 | −1.6 | −12.8 | −9.7 | 3 | −13 |
| 1 to 9 | 6.5 | 10.3 | 0.3 | 5 | −2.3 | −10.9 | −0.4 | −16.9 |
| 1 to 3 | 100 | 100.1 | 100.1 | 100.1 | 100.1 | 100.1 | 100.1 | 100.1 |
| 3 to 1 | 100.1 | 100.1 | 100.1 | 100.1 | 100.1 | 100.1 | 100.1 | 100.1 |

| E:T Ratio | Group | | | | | | | |
|---|---|---|---|---|---|---|---|---|
|  | 13 | | 14 | | 15 | | 16 | |
| 1 to 243 | −11.6 | −21.9 | −13.8 | −21.2 | −9 | −16.6 | −2.9 | −12.6 |
| 1 to 81 | −11 | −31.6 | −20.8 | −25 | −15.7 | −20.6 | −6.3 | −8 |
| 1 to 27 | −13.6 | −10.1 | −22.3 | −4.6 | −15.4 | −11.1 | 0.9 | 3.2 |
| 1 to 9 | −6.5 | −20.4 | −7.1 | −7.5 | −13.3 | −17.6 | 14.1 | 17.3 |
| 1 to 3 | 100.1 | 100.1 | 100.1 | 100.1 | 100.1 | 100.1 | 100 | 99.9 |
| 3 to 1 | 100.1 | 100.1 | 100.1 | 100.1 | 100.1 | 100.1 | 100 | 100 |

| E:T Ratio | Group | | | | | | | |
|---|---|---|---|---|---|---|---|---|
|  | 17 | | 18 | | 19 | | 20 | |
| 1 to 243 | 30.4 | 32.6 | −1.9 | −6.4 | −2.2 | −16 | −18.5 | −13 |
| 1 to 81 | 8.7 | 9.1 | −8.1 | −5.6 | −20.8 | −19.4 | −31.6 | −26.7 |
| 1 to 27 | 1.5 | −3.7 | −0.9 | −6 | 41 | −7 | −15.6 | −10.9 |
| 1 to 9 | 6.5 | 0 | −4.7 | −1.4 | −0.6 | 11.7 | −22 | −4.2 |
| 1 to 3 | 100.1 | 100 | 100.1 | 100.1 | 100.1 | 100.1 | 100.1 | 100 |
| 3 to 1 | 100.1 | 100.5 | 100.1 | 100.5 | 100.1 | 100.5 | 100.1 | 100.5 |

TABLE 53A-continued

Nalm6 WT

| E:T Ratio | Group | | | | | | | |
|---|---|---|---|---|---|---|---|---|
|  | 21 | | 22 | | 23 | | 24 | |
| 1 to 243 | −11.2 | −12.1 | −9.4 | −32.5 | −10.9 | −29.1 | −17.9 | −19.8 |
| 1 to 81 | −22.6 | −17.9 | −20.9 | −26.9 | −17.6 | −24.6 | −17.4 | −19.2 |
| 1 to 27 | −5.1 | −8.3 | 6.1 | −7.6 | −2.2 | −9.4 | 3.6 | −2.6 |
| 1 to 9 | −8.6 | −2.4 | 0.4 | 14.4 | 22.5 | −3.5 | 19.5 | 5.3 |
| 1 to 3 | 100.1 | 100.1 | 100.1 | 100.1 | 100.1 | 100.1 | 100 | 99.9 |
| 3 to 1 | 100.1 | 100.5 | 100.1 | 100.5 | 100.1 | 100.5 | 100 | 100.4 |

TABLE 53B

Nalm6 CD19KO

| E:T Ratio | Group | | | | | | | |
|---|---|---|---|---|---|---|---|---|
|  | 1 | | 2 | | 3 | | 4 | |
| 1 to 243 | −10.2 | −10.7 | −14.4 | −14.8 | −7.3 | −11.3 | −15.8 | −14.1 |
| 1 to 81 | −8.7 | −21.5 | −5 | −14.6 | −5.8 | −16.6 | −7.8 | −12.2 |
| 1 to 27 | 3.8 | −18.2 | −2.3 | −13.6 | −4.7 | −21.8 | −1 | −18.8 |
| 1 to 9 | −0.2 | −11.2 | −3.5 | −10.3 | −3.8 | −13.7 | −4.8 | −3.6 |
| 1 to 3 | 39.2 | 30.5 | 33.6 | 19.8 | 33.2 | 24.5 | 33.9 | 26.7 |
| 3 to 1 | 56.2 | 41.9 | 39.4 | 32.6 | 43.8 | 40.7 | 38 | 32.9 |

| E:T Ratio | Group | | | | | | | |
|---|---|---|---|---|---|---|---|---|
|  | 5 | | 6 | | 7 | | 8 | |
| 1 to 243 | −9 | −15.4 | −8.2 | −13.9 | −12.9 | −11.9 | −11.1 | −9.2 |
| 1 to 81 | 6.3 | −4.5 | −1.9 | −9.9 | −3.6 | −13.4 | 5.3 | 5.3 |
| 1 to 27 | 13.6 | 16.5 | 18.8 | 5.5 | 10 | −0.6 | 23.1 | 19.3 |
| 1 to 9 | 40.5 | 33.2 | 45.3 | 44.7 | 35.7 | 20.2 | 59.2 | 46.4 |
| 1 to 3 | 100.1 | 99.9 | 100.3 | 100.1 | 99.8 | 99.7 | 100.1 | 99.8 |
| 3 to 1 | 100.9 | 101.1 | 101.1 | 101.2 | 101.1 | 101.2 | 101 | 101 |

| E:T Ratio | Group | | | | | | | |
|---|---|---|---|---|---|---|---|---|
|  | 9 | | 10 | | 11 | | 12 | |
| 1 to 243 | −6 | −8 | −6 | −11.4 | −8.2 | −7.6 | −7.8 | −4.3 |
| 1 to 81 | 4.4 | 10.8 | −1.5 | −0.1 | 2.3 | 0.3 | 8.5 | 10.4 |
| 1 to 27 | −2.7 | 6.1 | 12 | −5.9 | 4.5 | 21.5 | 38.2 | 21.7 |
| 1 to 9 | 32.2 | 34.6 | 17.6 | 14.1 | 17.3 | 11.4 | 30.8 | 22.7 |
| 1 to 3 | 100.2 | 100.8 | 100.1 | 100.9 | 100.2 | 100.8 | 100.1 | 100.8 |
| 3 to 1 | 101 | 101.4 | 101 | 101.4 | 101 | 101.5 | 101 | 101.4 |

| E:T Ratio | Group | | | | | | | |
|---|---|---|---|---|---|---|---|---|
|  | 13 | | 14 | | 15 | | 16 | |
| 1 to 243 | −5.3 | −7.2 | −8.6 | 5.8 | −5.3 | 18.7 | −7.4 | 8.1 |
| 1 to 81 | 5 | 0.5 | −2.5 | 9.6 | −1.7 | 5.8 | 7.1 | 13 |
| 1 to 27 | 13.6 | 18.6 | 10.4 | 40.6 | 11.9 | 27.8 | 27.8 | 28.2 |
| 1 to 9 | 8.4 | 3.1 | 31.3 | 20.3 | 2.2 | 7.9 | 32.3 | 42.4 |
| 1 to 3 | 98.2 | 99.8 | 100.2 | 100.8 | 100.1 | 100.8 | 100 | 100.6 |
| 3 to 1 | 99.6 | 100.1 | 101.1 | 101.4 | 101.1 | 101.3 | 101 | 101.3 |

| E:T Ratio | Group | | | | | | | |
|---|---|---|---|---|---|---|---|---|
|  | 17 | | 18 | | 19 | | 20 | |
| 1 to 243 | −1.9 | −5 | −8.5 | −12.4 | −9 | −7.7 | −12.7 | −14.3 |
| 1 to 81 | −5.9 | −10.3 | −10.6 | −10.5 | −4.8 | −11 | −11.2 | −15.9 |
| 1 to 27 | −5.6 | −2.8 | 1.4 | −0.4 | 16.1 | 14.8 | −0.7 | 2.4 |
| 1 to 9 | 21.5 | 4.9 | 8.9 | 3.7 | 20.6 | 35.4 | 1.3 | 7 |
| 1 to 3 | 97 | 94.4 | 100.2 | 100 | 100.3 | 100.1 | 100.2 | 99.3 |
| 3 to 1 | 99.6 | 101.3 | 100.2 | 101.9 | 100.2 | 101.9 | 100.2 | 101.9 |

TABLE 53B-continued

Nalm6 CD19KO

| | Group | | | | | | | |
|---|---|---|---|---|---|---|---|---|
| E:T Ratio | 21 | | 22 | | 23 | | 24 | |
| 1 to 243 | −5.8 | 0.2 | −4.2 | −9.4 | 7 | −12.5 | −2 | −10.2 |
| 1 to 81 | −0.5 | −5.4 | 8.3 | −4.3 | 4.1 | −10.1 | 6.2 | 2.1 |
| 1 to 27 | 32.9 | 13.9 | 41.7 | 27.8 | 34.2 | 14.4 | 35.6 | 26.8 |
| 1 to 9 | 22.9 | 32.9 | 38.3 | 46 | 44.5 | 19.7 | 43.5 | 25.5 |
| 1 to 3 | 100.3 | 100.1 | 100.3 | 100.1 | 100.2 | 100 | 100.2 | 100 |
| 3 to 1 | 100.2 | 101.9 | 100.2 | 101.8 | 100.1 | 101.7 | 100 | 101.7 |

TABLE 53C

Raji WT

| | Group | | | | | | | |
|---|---|---|---|---|---|---|---|---|
| E:T Ratio | 1 | | 2 | | 3 | | 4 | |
| 1 to 243 | 2.2 | −33.8 | −12.6 | −23 | −19.4 | −30.3 | −8.1 | −22.8 |
| 1 to 81 | 16.3 | −29.2 | −2.5 | −15 | −2.8 | −16.3 | −6.4 | −17.7 |
| 1 to 27 | −9.2 | −48.8 | 1.6 | −33.1 | −2 | −29.4 | 2.7 | −25.3 |
| 1 to 9 | −6.5 | −35.9 | 13.5 | −9.7 | 14 | −10.5 | 11.6 | −5.5 |
| 1 to 3 | 8.9 | −17.9 | 99.8 | 99.9 | 99.9 | 99.9 | 100.1 | 100 |
| 3 to 1 | 19.5 | 5.9 | 103.8 | 100.1 | 103.9 | 100.2 | 103.9 | 100.2 |

| | Group | | | | | | | |
|---|---|---|---|---|---|---|---|---|
| E:T Ratio | 5 | | 6 | | 7 | | 8 | |
| 1 to 243 | −11 | −21.7 | −7.9 | −25.1 | −6.5 | −18.8 | −5.1 | −14.7 |
| 1 to 81 | −4.6 | −14.9 | −0.5 | −19.2 | 0.4 | −2 | −0.1 | −0.1 |
| 1 to 27 | −0.1 | −14.1 | 8.6 | −20.6 | 7.9 | −6.6 | 10.4 | −8.8 |
| 1 to 9 | 13.6 | −2.6 | 16.5 | 5.1 | 22.2 | −3.3 | 23.8 | −0.5 |
| 1 to 3 | 100.2 | 99.9 | 100.1 | 100.1 | 100.1 | 100 | 99.9 | 99.8 |
| 3 to 1 | 104 | 100.2 | 103.9 | 100.2 | 103.9 | 100.1 | 103.8 | 100 |

| | Group | | | | | | | |
|---|---|---|---|---|---|---|---|---|
| E:T Ratio | 9 | | 10 | | 11 | | 12 | |
| 1 to 243 | −30.8 | −24.1 | −30.9 | −12.5 | −17.6 | −14.4 | −23.9 | −6.8 |
| 1 to 81 | −26.7 | −15.7 | −9.8 | −14.6 | −6.9 | −6 | −6.5 | −13.2 |
| 1 to 27 | −20.6 | −22.8 | −6.5 | −3.3 | −4.1 | −4 | 0.3 | 2.3 |
| 1 to 9 | −7.4 | −15.1 | −1.5 | −14.6 | −2.5 | −12.8 | 9.3 | −3.7 |
| 1 to 3 | 104.4 | 104.6 | 104.4 | 104.6 | 104.4 | 104.5 | 104.5 | 104.5 |
| 3 to 1 | 108 | 105.9 | 108.1 | 105.9 | 108.1 | 105.8 | 108.1 | 105.9 |

| | Group | | | | | | | |
|---|---|---|---|---|---|---|---|---|
| E:T Ratio | 13 | | 14 | | 15 | | 16 | |
| 1 to 243 | −28.5 | −8.4 | −17.4 | −11.5 | −11.1 | −11 | −9.9 | −5.6 |
| 1 to 81 | −11.4 | −7.2 | −16.4 | −13.8 | −9.9 | −10.4 | 4.7 | 1.7 |
| 1 to 27 | 1 | 0.7 | −1.6 | 5.2 | 6.9 | −3.3 | 10.2 | 13.5 |
| 1 to 9 | 3.3 | −12 | 7.7 | −11 | 4 | −2.3 | 14.4 | 9.9 |
| 1 to 3 | 104.4 | 104.6 | 104.4 | 104.5 | 104.4 | 104.5 | 104.3 | 104.4 |
| 3 to 1 | 108.1 | 105.9 | 108 | 105.9 | 108 | 105.8 | 107.8 | 105.7 |

| | Group | | | | | | | |
|---|---|---|---|---|---|---|---|---|
| E:T Ratio | 17 | | 18 | | 19 | | 20 | |
| 1 to 243 | −28.3 | −21 | −22.1 | −16.4 | −11.4 | −11.8 | −10.6 | −11.1 |
| 1 to 81 | −18.5 | −22.7 | −14.6 | −26.2 | −11.4 | −34.7 | −12.6 | −28.9 |
| 1 to 27 | −23 | −21.7 | −14.5 | −26.5 | 8.2 | −5.9 | −5.3 | −14.9 |
| 1 to 9 | −9.5 | −34.2 | −11.2 | −39.6 | −6.9 | −15.5 | −17.8 | −27.7 |
| 1 to 3 | 100 | 100.2 | 100 | 100.2 | 100.1 | 100.2 | 100.1 | 100.2 |
| 3 to 1 | 101.2 | 120.1 | 101.2 | 120.1 | 101.2 | 120.1 | 101.2 | 120.1 |

TABLE 53C-continued

Raji WT

| | Group | | | | | | | |
|---|---|---|---|---|---|---|---|---|
| E:T Ratio | 21 | | 22 | | 23 | | 24 | |
| 1 to 243 | −7 | −4.1 | −9.6 | −6.3 | −8.1 | −11.1 | −7.5 | −1.1 |
| 1 to 81 | −5.8 | −14.4 | −2.6 | −19.2 | 9 | −19.9 | 19.2 | −4.6 |
| 1 to 27 | 5.3 | −6.3 | −5.1 | 2.4 | 4.9 | 0.7 | 13.3 | 5.4 |
| 1 to 9 | −6.7 | −14.2 | −7.4 | −6.1 | 9.6 | −16.6 | 15.3 | −9 |
| 1 to 3 | 100.1 | 100.2 | 100.1 | 100.2 | 100.1 | 100.2 | 99.9 | 100.1 |
| 3 to 1 | 101.2 | 120.1 | 101.2 | 120.1 | 101.2 | 120.1 | 101 | 119.9 |

TABLE 53D

Raji CD19KO

| | Group | | | | | | | |
|---|---|---|---|---|---|---|---|---|
| E:T Ratio | 1 | | 2 | | 3 | | 4 | |
| 1 to 243 | 51 | 55 | 36.7 | 26.2 | −18.2 | 12.5 | −44.9 | 0 |
| 1 to 81 | −0.4 | 33.7 | −85.1 | 3.4 | −143.7 | 3 | −190.3 | 9.3 |
| 1 to 27 | 15.3 | −0.9 | 4.5 | 6.3 | −0.5 | 2.7 | 4 | 1.1 |
| 1 to 9 | −1.9 | 3.3 | 2.9 | 2 | 8.4 | 6.5 | 1.5 | 15.2 |
| 1 to 3 | 34.5 | 20.9 | 37.3 | 20.8 | 16.3 | 16 | 5.5 | 11.7 |
| 3 to 1 | 41.3 | 14.2 | 14.6 | 2.1 | 11.2 | 19.7 | 4.6 | 3.8 |

| | Group | | | | | | | |
|---|---|---|---|---|---|---|---|---|
| E:T Ratio | 5 | | 6 | | 7 | | 8 | |
| 1 to 243 | −15.1 | −3.2 | 22.8 | −1.4 | −5.5 | 0.2 | −85.7 | −2.4 |
| 1 to 81 | −217.9 | 3.3 | −201.5 | −2.2 | −227.3 | −0.9 | −210.3 | 2.5 |
| 1 to 27 | −0.6 | 7 | 11.8 | 3.4 | 1.9 | −1.6 | 1.4 | 9.5 |
| 1 to 9 | 8.5 | 17 | 22.1 | 21.5 | 13.5 | 12.6 | 30.9 | 21 |
| 1 to 3 | 98.8 | 99.8 | 99.4 | 100.6 | 91.9 | 93.5 | 98.8 | 99.6 |
| 3 to 1 | 99.6 | 99.7 | 99.8 | 100.1 | 99.1 | 99.6 | 99.7 | 99.9 |

| | Group | | | | | | | |
|---|---|---|---|---|---|---|---|---|
| E:T Ratio | 9 | | 10 | | 11 | | 12 | |
| 1 to 243 | 9 | 11.5 | −2.9 | 10.2 | −0.6 | 2.2 | −2.4 | 17.6 |
| 1 to 81 | 10.3 | 17.5 | 6.6 | 9.6 | 8.1 | 8.5 | −2.6 | 3.2 |
| 1 to 27 | 15.7 | 21.5 | 16 | 21.2 | 20.2 | 32 | 16.2 | 22 |
| 1 to 9 | 25.6 | 35 | 38.1 | 32.2 | 32.9 | 27.9 | 23.7 | 28.8 |
| 1 to 3 | 99.7 | 100.2 | 99.7 | 100 | 99.9 | 100 | 99.8 | 100.1 |
| 3 to 1 | 99.9 | 100.9 | 99.8 | 100.9 | 100 | 101 | 99.9 | 101 |

| | Group | | | | | | | |
|---|---|---|---|---|---|---|---|---|
| E:T Ratio | 13 | | 14 | | 15 | | 16 | |
| 1 to 243 | −1.8 | 9.8 | −3 | 2.6 | 5.6 | 1.9 | −7.7 | 14.5 |
| 1 to 81 | −2.8 | 0.5 | −0.4 | −2.7 | −6.3 | −11.5 | −3.3 | −2.5 |
| 1 to 27 | 10.5 | 19.6 | −0.8 | 11.7 | −4.4 | 8.6 | 8.7 | 16.7 |
| 1 to 9 | 14.7 | 15.7 | 24.3 | 22.5 | 7.3 | 10.8 | 15 | 12.3 |
| 1 to 3 | 96.1 | 98.5 | 97.2 | 99.7 | 95.3 | 97 | 92.3 | 97.7 |
| 3 to 1 | 96.2 | 96.2 | 98.4 | 98.7 | 97.5 | 97.5 | 96.1 | 95.7 |

| | Group | | | | | | | |
|---|---|---|---|---|---|---|---|---|
| E:T Ratio | 17 | | 18 | | 19 | | 20 | |
| 1 to 243 | 7.6 | 20.4 | 5.1 | 6.1 | −0.1 | 8.8 | 4.6 | 11.8 |
| 1 to 81 | 9.7 | 13.2 | 11.1 | 11.8 | 8.9 | 13.2 | 3 | 6.8 |
| 1 to 27 | 18.1 | 10.1 | 29.9 | 18.7 | 24.4 | 21.3 | 13.8 | 15.8 |
| 1 to 9 | 44.9 | 19.3 | 37 | 26.8 | 33.6 | 32.3 | 24.1 | 16 |
| 1 to 3 | 87.9 | 84.7 | 99.7 | 99.1 | 98.7 | 97.5 | 93.8 | 92.5 |
| 3 to 1 | 95 | 96.5 | 99.7 | 100 | 99.7 | 99.9 | 96.1 | 95 |

TABLE 53D-continued

Raji CD19KO

| E:T Ratio | Group 21 | | Group 22 | | Group 23 | | Group 24 | |
|---|---|---|---|---|---|---|---|---|
| 1 to 243 | -5.9 | 6.6 | 2.9 | -9.9 | 2.7 | -2.6 | -4.3 | -3.4 |
| 1 to 81 | 11.5 | -5.2 | 10.7 | -0.3 | 8 | -3.2 | 7.3 | 0.4 |

TABLE 53D-continued

Raji CD19KO

| | | | | | | | | |
|---|---|---|---|---|---|---|---|---|
| 1 to 27 | 26 | 20.7 | 21.9 | 16.7 | 22.1 | 14.1 | 31.7 | 20.6 |
| 1 to 9 | 18.6 | 28.9 | 21.2 | 25.8 | 32.1 | 9.2 | 28.7 | 19.7 |
| 1 to 3 | 100.4 | 100.2 | 100.4 | 100.1 | 100.4 | 100.2 | 100.2 | 100 |
| 3 to 1 | 100 | 100.1 | 100 | 100.1 | 100 | 100.1 | 99.8 | 100 |

TABLE 54A

TNFa

| Group | | | | | | | |
|---|---|---|---|---|---|---|---|
| 1 | | 2 | | 3 | | 4 | |
| 21.43362 | 30.0185 | 33.8795 | 28.22578 | 23.07486 | 21.60766 | 28.62412 | 32.4843 |

| Group | | | | | | | |
|---|---|---|---|---|---|---|---|
| 5 | | 6 | | 7 | | 8 | |
| 769.5068 | 750.8404 | 720.3671 | 614.8629 | 229.2041 | 233.5543 | 836.7802 | 842.7271 |

| Group | | | | | | | |
|---|---|---|---|---|---|---|---|
| 9 | | 10 | | 11 | | 12 | |
| 317.8869 | 371.7266 | 414.5337 | 293.488 | 386.2704 | 293.6139 | 418.6442 | 307.1845 |

| Group | | | | | | | |
|---|---|---|---|---|---|---|---|
| 13 | | 14 | | 15 | | 16 | |
| 252.4179 | 152.0566 | 185.1981 | 253.8267 | 180.7021 | 249.8017 | 208.5401 | 327.4072 |

| Group | | | | | | | |
|---|---|---|---|---|---|---|---|
| 17 | | 18 | | 19 | | 20 | |
| 203.6143 | 217.2118 | 405.7839 | 345.8976 | 467.5809 | 425.1003 | 269.5771 | 258.1286 |

| Group | | | | | | | |
|---|---|---|---|---|---|---|---|
| 21 | | 22 | | 23 | | 24 | |
| 472.2237 | 421.9478 | 446.7417 | 402.7078 | 430.8759 | 441.7219 | 432.4396 | 494.9866 |

TABLE 54B

IL10

| Group | | | | | | | |
|---|---|---|---|---|---|---|---|
| 1 | | 2 | | 3 | | 4 | |
| 12.06837 | 12.32633 | 11.93813 | 10.60854 | 11.04015 | 12.18301 | 9.930545 | 14.15293 |

| Group | | | | | | | |
|---|---|---|---|---|---|---|---|
| 5 | | 6 | | 7 | | 8 | |
| 17.26261 | 17.49864 | 19.22346 | 27.91504 | 28.00769 | 25.40533 | 22.57109 | 25.85191 |

| Group | | | | | | | |
|---|---|---|---|---|---|---|---|
| 9 | | 10 | | 11 | | 12 | |
| 20.85123 | 21.31715 | 25.06719 | 23.96362 | 17.45668 | 16.68065 | 27.34339 | 37.56894 |

TABLE 54B-continued

IL10

| Group | | | | | | | |
|---|---|---|---|---|---|---|---|
| 13 | | 14 | | 15 | | 16 | |
| 15.01034 | 17.85805 | 21.4962 | 15.99171 | 17.25999 | 16.67803 | 29.79311 | 30.33925 |

| Group | | | | | | | |
|---|---|---|---|---|---|---|---|
| 17 | | 18 | | 19 | | 20 | |
| 20.35921 | 24.0903 | 22.76352 | 23.08782 | 15.64091 | 19.16565 | 25.07248 | 18.56677 |

| Group | | | | | | | |
|---|---|---|---|---|---|---|---|
| 21 | | 22 | | 23 | | 24 | |
| 16.28242 | 12.91556 | 15.43415 | 18.99226 | 16.57846 | 14.00925 | 22.48675 | 23.85015 |

TABLE 54C

IL-2

| Group | | | | | | | |
|---|---|---|---|---|---|---|---|
| 1 | | 2 | | 3 | | 4 | |
| 13.90412 | 5.925647 | 7.239758 | 8.057854 | 3.416301 | 10.05507 | 5.481665 | 4.24322 |

| Group | | | | | | | |
|---|---|---|---|---|---|---|---|
| 5 | | 6 | | 7 | | 8 | |
| 1979.747 | 1880.755 | 758.0331 | 769.4632 | 136.3706 | 143.4531 | 1373.496 | 1344.97 |

| Group | | | | | | | |
|---|---|---|---|---|---|---|---|
| 9 | | 10 | | 11 | | 12 | |
| 415.0335 | 397.6617 | 371.0906 | 419.0813 | 315.6276 | 308.785 | 239.4187 | 263.1596 |

| Group | | | | | | | |
|---|---|---|---|---|---|---|---|
| 13 | | 14 | | 15 | | 16 | |
| 81.99199 | 101.7831 | 191.2544 | 191.099 | 258.0696 | 200.4818 | 149.9144 | 150.8354 |

| Group | | | | | | | |
|---|---|---|---|---|---|---|---|
| 17 | | 18 | | 19 | | 20 | |
| 83.13918 | 96.59951 | 234.2623 | 273.2762 | 400.7794 | 439.0895 | 132.4347 | 146.6177 |

| Group | | | | | | | |
|---|---|---|---|---|---|---|---|
| 21 | | 22 | | 23 | | 24 | |
| 324.6525 | 284.3169 | 312.9986 | 304.5192 | 284.8684 | 245.4556 | 171.9664 | 220.1387 |

TABLE 54D

IFNg

| Group | | | | | | | |
|---|---|---|---|---|---|---|---|
| 1 | | 2 | | 3 | | 4 | |
| 2183.862 | 1360.111 | 1707.394 | 2083.675 | 1077.22 | 1338.666 | 1977.427 | 1416.691 |

TABLE 54D-continued

IFNg

| Group | | | | | | | |
|---|---|---|---|---|---|---|---|
| 5 | | 6 | | 7 | | 8 | |
| 82883.42 | 90801.34 | 98809.63 | 79846.05 | 25763.3 | 22756.31 | 113383.2 | 130673.4 |

| Group | | | | | | | |
|---|---|---|---|---|---|---|---|
| 9 | | 10 | | 11 | | 12 | |
| 33687.05 | 41534.7 | 33669.96 | 46572.37 | 41476.85 | 32400.9 | 44847.72 | 41189.26 |

| Group | | | | | | | |
|---|---|---|---|---|---|---|---|
| 13 | | 14 | | 15 | | 16 | |
| 18695.39 | 13259.19 | 22300.69 | 18887.22 | 19159.02 | 26725.05 | 27437.53 | 38194.28 |

| Group | | | | | | | |
|---|---|---|---|---|---|---|---|
| 17 | | 18 | | 19 | | 20 | |
| 19441.39 | 19547.47 | 36846.64 | 34373.3 | 30178.64 | 49566.75 | 27345.52 | 24419.34 |

| Group | | | | | | | |
|---|---|---|---|---|---|---|---|
| 21 | | 22 | | 23 | | 24 | |
| 42811.57 | 31839.23 | 44792.28 | 37959.75 | 40016.19 | 41814.98 | 56819.12 | 56847.75 |

TABLE 55A

Raji CD19KO

| Group | | | | | | | |
|---|---|---|---|---|---|---|---|
| 1 | | 2 | | 3 | | 4 | |
| 5.09 | 4.2 | 3.34 | 4.04 | 3.54 | 3.98 | 4.31 | 3.94 |
| 5 | | 6 | | 7 | | 8 | |
| 21.8 | 17.92 | 18.12 | 18.53 | 15.05 | 12.81 | 18.42 | 15.43 |
| 9 | | 10 | | 11 | | 12 | |
| 17.44 | 21.84 | 18.46 | 14.89 | 17.75 | 16.01 | 20.06 | 16.96 |
| 13 | | 14 | | 15 | | 16 | |
| 9.52 | 9.53 | 10.54 | 11.11 | 12 | 11.99 | 16.69 | 16.19 |
| 17 | | 18 | | 19 | | 20 | |
| 8.38 | 7.48 | 16.6 | 14.92 | 15.64 | 11.99 | 13.78 | 14.05 |
| 21 | | 22 | | 23 | | 24 | |
| 18.7 | 18.72 | 13.26 | 14.9 | 16.55 | 18.4 | 17.12 | 17.54 |

TABLE 55B

Raji parental

| Group | | | | | | | |
|---|---|---|---|---|---|---|---|
| 1 | | 2 | | 3 | | 4 | |
| 24.53 | 4.51 | 22.54 | 23.61 | 17.08 | 18.23 | 23.65 | 24.2 |
| 5 | | 6 | | 7 | | 8 | |
| 21.84 | 23.46 | 25.65 | 19.57 | 20.96 | 20.04 | 17.69 | 17.27 |
| 9 | | 10 | | 11 | | 12 | |
| 25.04 | 24.38 | 22.53 | 25.75 | 25.69 | 21.61 | 23.93 | 27.4 |
| 13 | | 14 | | 15 | | 16 | |
| 21.25 | 23.01 | 19.43 | 21.15 | 18.99 | 21.92 | 27.95 | 30.26 |
| 17 | | 18 | | 19 | | 20 | |
| 15.13 | 15.72 | 26.86 | 28 | 27.46 | 25.72 | 24.49 | 23.03 |
| 21 | | 22 | | 23 | | 24 | |
| 25.59 | 25.04 | 20.98 | 19.29 | 23.01 | 20.78 | 22.14 | 21.49 |

TABLE 55C

Nalm6 CD19KO

| Group | | | | | | | |
|---|---|---|---|---|---|---|---|
| 1 | | 2 | | 3 | | 4 | |
| 5.12 | 5.19 | 3.6 | 3.55 | 5.1 | 4.64 | 5.12 | 5.07 |
| 5 | | 6 | | 7 | | 8 | |
| 14.47 | 20.84 | 18.69 | 19.81 | 13.33 | 17.17 | 18.12 | 17.87 |
| 9 | | 10 | | 11 | | 12 | |
| 22.37 | 23.08 | 19.86 | 19.82 | 19.28 | 18.98 | 19.01 | 23.35 |
| 13 | | 14 | | 15 | | 16 | |
| 8.87 | 10.25 | 10.83 | 12.05 | 13.18 | 14.8 | 17.6 | 17.86 |

TABLE 55C-continued

Nalm6 CD19KO Group

| 17 | | 18 | | 19 | | 20 | |
|---|---|---|---|---|---|---|---|
| 9.04 | 8.8 | 19.73 | 18.54 | 18.22 | 16.83 | 16.11 | 14.89 |

| 21 | | 22 | | 23 | | 24 | |
|---|---|---|---|---|---|---|---|
| 19.29 | 18.03 | 18.25 | 15.5 | 18.01 | 15.89 | 15.89 | 16.97 |

TABLE 55D

Nalm6 parental Group

| 1 | | 2 | | 3 | | 4 | |
|---|---|---|---|---|---|---|---|
| 1.95 | 1.53 | 23.14 | 25.28 | 19.79 | 19.69 | 23.06 | 23.75 |

| 5 | | 6 | | 7 | | 8 | |
|---|---|---|---|---|---|---|---|
| 19.06 | 23.01 | 21.27 | 20.07 | 18.62 | 20.4 | 15.82 | 14.64 |

| 9 | | 10 | | 11 | | 12 | |
|---|---|---|---|---|---|---|---|
| 25.8 | 28.75 | 26.91 | 26.98 | 32.3 | 27.59 | 23.53 | 25.26 |

| 13 | | 14 | | 15 | | 16 | |
|---|---|---|---|---|---|---|---|
| 24.38 | 28.81 | 21.38 | 21.64 | 21.2 | 23.73 | 23.59 | 28.61 |

| 17 | | 18 | | 19 | | 20 | |
|---|---|---|---|---|---|---|---|
| 20.24 | 19.63 | 28.58 | 30.28 | 28.35 | 26.96 | 26.32 | 23.5 |

| 21 | | 22 | | 23 | | 24 | |
|---|---|---|---|---|---|---|---|
| 26.96 | 24.02 | 24.71 | 20.78 | 23.5 | 24.06 | 23.58 | 20.73 |

TABLE 56

| | Raji parental | | Raji CD19KO | | Nalm6 CD19KO | | Nalm6 parental | |
|---|---|---|---|---|---|---|---|---|
| Group | replicate 1 | replicate 2 | replicate 1 | replicate 2 | replicate 1 | replicate 2 | replicate 1 | replicate 2 |
| 1 | 64.5 | 65.1 | 61.8 | 60.6 | 55.6 | 50.6 | 32.8 | 35.8 |
| 2 | 92 | 88.5 | 57.5 | 56.6 | 43.6 | 46.6 | 90.4 | 72.1 |
| 3 | 84.1 | 84.6 | 58.3 | 59.8 | 43.4 | 50.3 | 87.1 | 83.9 |
| 4 | 91.8 | 90.4 | 63.5 | 59.9 | 44.3 | 47.6 | 91 | 89.7 |
| 5 | 77 | 69.1 | 78.6 | 78.4 | 64.7 | 70.7 | 90 | 88.7 |
| 6 | 89.2 | 87.2 | 91.5 | 88.6 | 89.3 | 86.6 | 91.9 | 89.5 |
| 7 | 87.2 | 83 | 88.8 | 86.4 | 84 | 82 | 91.7 | 90.2 |
| 8 | 92.6 | 77.4 | 90.4 | 81.8 | 89.1 | 80.2 | 87.4 | 86.4 |
| 9 | 92.8 | 89.6 | 92.5 | 92.8 | 87 | 87.5 | 91.6 | 92.6 |
| 10 | 84.6 | 87.6 | 88.9 | 90.1 | 81.4 | 81.9 | 90.6 | 90.4 |
| 11 | 85.1 | 77.7 | 87.2 | 87.8 | 78.1 | 79.9 | 87 | 86.6 |
| 12 | 83.4 | 88.9 | 92 | 91.4 | 84.1 | 83.7 | 90.6 | 88.5 |
| 13 | 88 | 81.8 | 80.4 | 78.2 | 65.2 | 66.6 | 89.1 | 88.5 |
| 14 | 81 | 74.4 | 81.4 | 80.6 | 77.3 | 76.8 | 88.5 | 89.2 |
| 15 | 74.8 | 72.5 | 81 | 81 | 75.9 | 77.5 | 85.5 | 84.2 |
| 16 | 91.8 | 91.6 | 87.9 | 88.1 | 81.7 | 81.4 | 92.4 | 92.1 |
| 17 | 83.3 | 84.3 | 77.6 | 80.7 | 62.2 | 62.9 | 88.1 | 86.8 |
| 18 | 70.2 | 76.4 | 82 | 83.4 | 74.5 | 78.1 | 85.6 | 108 |
| 19 | 81.8 | 85.6 | 88.9 | 89.6 | 82.4 | 82.7 | 88 | 90.4 |
| 20 | 77.5 | 81.2 | 83.6 | 84.4 | 78.1 | 79.6 | 88.1 | 88.5 |
| 21 | 80.1 | 86.8 | 90.5 | 90.2 | 85.3 | 84.6 | 90.9 | 91.9 |
| 22 | 82.6 | 77.9 | 88.5 | 88.4 | 83.7 | 83.7 | 90.3 | 89.7 |
| 23 | 75.8 | 71.2 | 86.8 | 85.7 | 79.2 | 80.1 | 84.6 | 89.4 |
| 24 | 84.6 | 84.9 | 89.7 | 89.7 | 82.6 | 84.2 | 89.7 | 89.5 |

Example 17

Comparison of hinges was undertaken in anti-CD20 monovalent CARs. Data presented in this Example was obtained using the methods set forth in the Example above. CAR-T cells used in this Example comprised the CARs identified in Table 57 below. Table 57 provides the experimental conditions or groups referred to in subsequent tables of this Example. The Example utilized four anti-CD20 binding motifs, identified in this Example as binding motif A, binding motif B, binding motif C, and binding motif D. Hinges tested comprise a truncated CD28 hinge (28T), a CD8 hinge (8k), and an IgG4 hinge (14).

Transduction efficiency is shown in Table 58. Day 4 cytotoxicity in Raji (CD19+, CD20high), Raji CD20KO (CD19+, CD20−), Namalwa (CD19+, CD20low) and Nalm6 (CD19+, CD20low) is shown in Tables 59 and 60. Cytokine production at 14 h post-co-culture at a 1:1 E:T ratio is shown in Tables 61A-D. T cell activation as measured by upregulation of 41BB at 16 h post co-culture is shown at E:T 1:1 or 1:4 in Tables 62 and 63 respectively. Proliferation of T cells at 4d post co-culture is shown at E:T 1:1 or 1:4 in Tables 64 and 65, respectively.

TABLE 57

| | Type (e.g., Bicistronic v. Bispecific) |
|---|---|
| 1 | Non-transduced control |
| 2 | Monovalent anti-CD20 CAR comprising scFv#A and a CD28 hinge |
| 3 | Monovalent anti-CD20 CAR comprising binding motif #A and a CD8 hinge |
| 4 | Monovalent anti-CD20 CAR comprising binding motif #A and a IgG4 hinge |
| 5 | Monovalent anti-CD20 CAR comprising binding motif #B and a CD28 hinge |
| 6 | Monovalent anti-CD20 CAR comprising binding motif #B and a CD8 hinge |
| 7 | Monovalent anti-CD20 CAR comprising binding motif #B and a IgG4 hinge |
| 8 | Monovalent anti-CD20 CAR comprising binding motif #C and a CD28 hinge |
| 9 | Monovalent anti-CD20 CAR comprising binding motif #C and a CD8 hinge |
| 10 | Monovalent anti-CD20 CAR comprising binding motif #C and a IgG4 hinge |
| 11 | Monovalent anti-CD20 CAR comprising binding motif #D and a CD28 hinge |
| 12 | Monovalent anti-CD20 CAR comprising binding motif #D and a CD8 hinge |
| 13 | Monovalent anti-CD20 CAR comprising binding motif #D and a IgG4 hinge |

TABLE 58

| Group | Transduction efficiency (% CAR+) |
|---|---|
| 1 | 0.15 |
| 2 | 62.3 |
| 3 | 56.3 |
| 4 | 89.2 |
| 5 | 51.6 |
| 6 | 66.5 |
| 7 | 71.6 |
| 8 | 73.9 |
| 9 | 77.0 |
| 10 | 85.4 |
| 11 | 66.8 |
| 12 | 80.8 |
| 13 | 84.8 |

TABLE 59

| Cell Type | Targets Alone | 1 | 2 | 3 |
|---|---|---|---|---|
| Raji | 79202.8 / 70452 | 71294.3 / 59370.9 | 60525.3 / 62135.5 | 16844.6 / 18439.3 |
| Raji CD20KO | 94864.6 / 93729.3 | 107518 / 80627 | 79824.4 / 59886.5 | 52181.7 / 57347.3 |
| Namalwa | 38530.1 / 44751.2 | 33016.5 / 37313.6 | 30919.3 / 4394.22 | 2694.15 / 3891.21 |
| Nalm6 | 90735.3 / 91482.2 | 59924.4 / 59786.6 | 64853.3 / 2658.44 | 3592.39 / 5366.27 |
| T Cells Alone | 76.2154 / 31.0058 | 19.5781 / 31.3053 | 784287 / 81.2964 | 25.6924 / 18.7526 |

| Cell Type | 4 | 5 | 6 | 7 |
|---|---|---|---|---|
| Raji | 11014.1 / 12652.8 | 22070.7 / 28253 | 17675.7 / 14077.7 | 14314.2 / 10548.3 |
| Raji CD20KO | 5957.66 / 3498.72 | 10671 / 12115.3 | 7939.32 / 5497.05 | 4740.32 / 3396.25 |
| Namalwa | 3115.59 / 3057.82 | 2134.36 / 1335.68 | 1012.9 / 209.453 | 3599.39 / 112.932 |
| Nalm6 | 2897.74 / 3346.3 | 379.48 / 231.061 | 1459.7 / 386.438 | 393.678 / 259.554 |
| T Cells Alone | 20.1956 / -1.40636 | 76.2154 / 50.5227 | 19.5781 / 61.926 | 24.5794 / 4.43293 |

| Cell Type | 8 | 9 | 10 | 11 |
|---|---|---|---|---|
| Raji | 18323.8 / 13738 | 11526.1 / 13121.6 | 20733.1 / 21458.2 | 17483 / 23005.8 |
| Raji CD20KO | 16686.9 / 10419.2 | 15896.4 / 12334.8 | 52536.7 / 49496 | 44758.5 / 9961.2 |
| Namalwa | 294.986 / 262.702 | 290.627 / 84.3594 | 847.869 / 815.512 | 533.335 / 532.712 |
| Nalm6 | 274.516 / 183.039 | 319.083 / 188.334 | 427.827 / 272.767 | 816.448 / 248.126 |
| T Cells Alone | 48.7191 / 15.8604 | 32.1614 / 59.7065 | 31.0058 / 17.5848 | 1.5163 / 34.0876 |

| Cell Type | 12 | 13 |
|---|---|---|
| Raji | 20136 / 21075.7 | 15456.7 / 13376.7 |
| Raji CD20KO | 10555.9 / 5704.38 | 1032.2 / 867.172 |
| Namalwa | 306.157 / 265.491 | 173.011 / 170.523 |
| Nalm6 | 248.976 / 188.004 | 309.551 / 236.001 |
| T Cells Alone | 48.9268 / 4.17612 | 48.6274 / 28.5599 |

| Cell Type | Group (cont.) | | | |
|---|---|---|---|---|
| Raji | 9450.65 / 6450.55 | 13738 / 13121.6 | 14053.5 / 17263.2 | 11094.7 / 15470.9 |
| Raji CD20KO | 23411.8 / 46859.6 | 10419.2 / 15896.4 | 15535.6 / 17771.9 | 13844.9 / 14099.5 |
| Namalwa | 180.832 / 376.613 | 156.625 / 188.334 | 326.695 / 492.742 | 221.914 / 487.203 |
| Nalm6 | 1231.56 / 1128.79 | 185.179 / 188.334 | 718.3 / 704.494 | 680.758 / 925.057 |
| T Cells Alone | 55.8118 / 16.6736 | 35.2493 / 59.7065 | 25.8577 / 13.3904 | 24.335 / 47.1967 |

| Cell Type | 13 (cont.) |
|---|---|
| Raji | 13763.4 / 10694 |
| Raji CD20KO | 14913.9 / 8969.65 |
| Namalwa | 504.029 / 297.42 |
| Nalm6 | 960.085 / 641.792 |
| T Cells Alone | 22.3783 / -3.57676 |

TABLE 60

| Cell Type | Targets Alone | | | Group 1 | | | 2 | | | 3 | | |
|---|---|---|---|---|---|---|---|---|---|---|---|---|
| Raji | 79202.8 | 70452 | 71294.3 | 70496.5 | 65321.5 | 58423.9 | 42813 | 44348.5 | 37624.9 | 39257.9 | 38721.7 | 30611 |
| Namalwa | 38530.1 | 44751.2 | 48600.5 | 33819.1 | 32454.5 | 41126 | 22632.1 | 19889.3 | 18162 | 22050.6 | 12958.9 | 7359.29 |
| Nalm6 | 90735.3 | 91482.2 | 98863.8 | 73391.3 | 65922.4 | 72170.8 | 46819.9 | 38689.7 | 34293.5 | 21699.7 | 33426.3 | 9867.04 |

| | 4 | | | 5 | | | 6 | | | 7 | | |
|---|---|---|---|---|---|---|---|---|---|---|---|---|
| Raji | 44017.5 | 43902.4 | 33164 | 38984.7 | 36843.5 | 36870.2 | 40930.5 | 39351.8 | 36485.6 | 39262.2 | 41832.7 | 34967.1 |
| Namalwa | 22821.8 | 19476.6 | 18126.5 | 13029.1 | 11967.4 | 9916 | 11781.4 | 9822.72 | 9658.94 | 7294.71 | 7892.54 | 12538.3 |
| Nalm6 | 44203.2 | 41959.1 | 35773 | 21237.1 | 33388 | 20677.9 | 28267.6 | 23091.1 | 34779.9 | 20386.4 | 18653.5 | 27414.2 |

| | 8 | | | 9 | | | 10 | | | 11 | | |
|---|---|---|---|---|---|---|---|---|---|---|---|---|
| Raji | 41713 | 45451.7 | 32434 | 39503.7 | 46552.6 | 32453.8 | 39272 | 45873.5 | 27479.8 | 41628.7 | 48931.1 | 30158.6 |
| Namalwa | 17375.7 | 15523.3 | 16927.4 | 15573.5 | 13148.5 | 10366.2 | 13962.5 | 14478.1 | 7466.35 | 17478.4 | 11443.5 | 2857.6 |
| Nalm6 | 40265.3 | 34385.2 | 44712.1 | 29146.2 | 33328.6 | 45078.6 | 27153.9 | 24678.3 | 23030.7 | 35739.8 | 25712.2 | 19693.8 |

| | 12 | | | 13 | | |
|---|---|---|---|---|---|---|
| Raji | 35491 | 40527.2 | 26702.8 | 40345.8 | 43589.9 | 32952.6 |
| Namalwa | 12422.4 | 9309.45 | 5395.27 | 20039.8 | 18096.3 | 8713.27 |
| Nalm6 | 32197.1 | 22364.4 | 6859.16 | 21170.7 | 23463 | 18225.7 |

TABLE 61A

| TNFa Cell type | Group | Replicates | | | Group | Replicates | | |
|---|---|---|---|---|---|---|---|---|
| Raji | 1 | 742.7049 | 719.9322 | 860.8748 | 2 | 13789.44 | 1000.926 | 13787.09 |
| | | | | | 3 | 40482.31 | 10509.95 | 22032.99 |
| | | | | | 4 | 29963.57 | 10729.04 | 30770.2 |
| Raji CD20KO | 1 | 141.045 | 123.2006 | 193.527 | 2 | 2335.533 | 136.1735 | 1378.167 |
| | | | | | 3 | 12412.38 | 1591.951 | 6519.058 |
| | | | | | 4 | 19806.9 | 5900.966 | 28857.1 |
| Namalwa | 1 | 51.37436 | 54.13314 | 67.40804 | 2 | 5755.176 | 760.4728 | 4287.225 |
| | | | | | 3 | 13230.78 | 5171.471 | 4564.486 |
| | | | | | 4 | 16464.95 | 1756.426 | 29002.14 |
| Nalm6 | 1 | 85.77411 | 41.52716 | 65.44027 | 2 | 2071.754 | 243.4781 | 1436.396 |
| | | | | | 3 | 5188.394 | 354.1513 | 3276.759 |
| | | | | | 4 | 8136.712 | 3462.309 | 9516.77 |
| T cells alone | 1 | 32.09018 | 27.34532 | 41.75542 | 2 | 60.93963 | | 73.35283 |
| | | | | | 3 | 53.7447 | 132.6905 | 40.34432 |
| | | | | | 4 | 202.1004 | 49.30805 | 404.2379 |
| Raji | 5 | 5234.629 | 29643.24 | 25173.66 | 8 | 11804.04 | 5948.771 | 17987.23 |
| | 6 | 5881.73 | 11238.04 | 12382.32 | 9 | 23295.94 | 32399.1 | 41903.58 |
| | 7 | 14913.76 | 7566.033 | 20158.56 | 10 | 25189.57 | 6263.5 | 30133.63 |
| Raji CD20KO | 5 | 5938.115 | 6402.741 | 5130.22 | 8 | 215.2762 | 905.5388 | 2441.275 |
| | 6 | 13127.4 | 3087.198 | 2251.109 | 9 | 1131.756 | 11010.04 | 17227.01 |
| | 7 | 5314.634 | 3215.46 | 968.1883 | 10 | 1335.315 | 4004.466 | 19501.31 |
| Namalwa | 5 | 10163.08 | 41246.69 | 4330.718 | 8 | 769.9154 | 1797.08 | 12106.37 |
| | 6 | 16230.87 | 15604.86 | 3141.588 | 9 | 1521.87 | 8562.425 | 28414.64 |
| | 7 | 12714.45 | 16044.57 | 5474.505 | 10 | 2997.275 | 2239.813 | 23060.28 |
| Nalm 6 | 5 | 2356.156 | 601.0444 | 4148.512 | 8 | 2480.164 | 547.2608 | 1625.393 |
| | 6 | 4695.265 | 555.9875 | 735.1625 | 9 | 5150.879 | 998.5473 | 7296.929 |
| | 7 | 3560.739 | 2614.049 | 485.996 | 10 | 5296.607 | 666.9747 | 3631.616 |
| T cells alone | 5 | 35.14156 | 55.05909 | 86.07184 | 8 | 60.31223 | 26.13958 | 107.2801 |
| | 6 | 79.07053 | 56.76139 | 11.75329 | 9 | 48.80656 | 33.28641 | 122.8503 |
| | 7 | 94.67347 | 121.4341 | 87.89045 | 10 | 54.93238 | 77.29811 | 41.86264 |
| Raji | 11 | 2228.672 | 3952.296 | 5817.774 | | | | |
| | 12 | 3639.337 | 7400.496 | 9585.174 | | | | |
| | 13 | 4699.947 | 13583.39 | 10646.23 | | | | |
| Raji CD20KO | 11 | 343.0228 | 138.8956 | 455.7918 | | | | |
| | 12 | 666.3561 | 1570.956 | 2033.204 | | | | |
| | 13 | 904.006 | 2134.385 | 1311.669 | | | | |
| Namalwa | 11 | 712.1625 | 1751.303 | 1156.45 | | | | |
| | 12 | 1605.915 | 5712.698 | 1989.63 | | | | |
| | 13 | 1850.41 | 7176.859 | 1563.88 | | | | |
| Nalm6 | 11 | 1952.569 | 90.90757 | 194.5827 | | | | |
| | 12 | 1909.742 | 237.1462 | 229.7622 | | | | |
| | 13 | 623.5514 | 305.8666 | 204.3989 | | | | |

TABLE 61A-continued

| TNFa Cell type | Group | Replicates | | | Group | Replicates | | |
|---|---|---|---|---|---|---|---|---|
| T cells alone | 11 | 53.96276 | 48.59063 | 37.73721 | | | | |
| | 12 | 73.1479 | 38.83681 | 45.07434 | | | | |
| | 13 | 59.63715 | 65.16515 | 32.03268 | | | | |

TABLE 61B

| IL-2 Cell type | Group | Replicates | | | Group | Replicates | | |
|---|---|---|---|---|---|---|---|---|
| Raji | 1 | 322.5795 | 320.5048 | 350.4306 | 2 | 2073.658 | 100.1265 | 1416.118 |
| | | | | | 3 | 20921.12 | 8886.709 | 26954.08 |
| | | | | | 4 | 10616.69 | 2267.245 | 8153.757 |
| Raji CD20KO | 1 | 144.0881 | 141.6475 | 157.9271 | 2 | 114.382 | 35.60637 | 55.48347 |
| | | | | | 3 | 6247.868 | 1515.275 | 6207.359 |
| | | | | | 4 | 3882.511 | 839.9909 | 3086.204 |
| Namalwa | 1 | 143.7966 | 154.0605 | 106.577 | 2 | 85.0148 | 24.75363 | 71.28991 |
| | | | | | 3 | 2232.844 | 952.9922 | 4293.162 |
| | | | | | 4 | 668.272 | 175.3299 | 638.2828 |
| Nalm6 | 1 | 83.28817 | 95.77933 | 86.58723 | 2 | 39.02308 | 28.937 | 30.45196 |
| | | | | | 3 | 345.5094 | 81.29567 | 483.7254 |
| | | | | | 4 | 55.70095 | 10.65965 | 45.28578 |
| T cells alone | 1 | 2.475707 | 2.907949 | 3.047796 | 2 | 7.311224 | 14.58527 | 15.62037 |
| | | | | | 3 | 2.694135 | 186.4649 | 6.853129 |
| | | | | | 4 | 2.898734 | 7.362667 | 5.307659 |
| Raji | 5 | 3510.081 | 9491.165 | 16208.74 | 8 | 9435.531 | 3440.359 | 7830.216 |
| | 6 | 3804.56 | 15811.23 | 31095.21 | 9 | 36918.38 | 16658.88 | 38763.1 |
| | 7 | 1753.378 | 7711.317 | 11902.51 | 10 | 14906.08 | 5990.056 | 18862.47 |
| Raji CD20KO | 5 | 2277.17 | 1268.5 | 1623.264 | 8 | 70.68176 | 108.5994 | 239.3027 |
| | 6 | 5142.875 | 3411.332 | 4541.088 | 9 | 1584.179 | 2889.009 | 8581.598 |
| | 7 | 2575.962 | 1500.105 | 1613.56 | 10 | 666.248 | 3000.571 | 9240.457 |
| Namalwa | 5 | 2547.378 | 3062.228 | 1450.611 | 8 | 303.5536 | 593.7966 | 1560.495 |
| | 6 | 6034.566 | 10971.02 | 6869.738 | 9 | 2305.998 | 3875.078 | 11899.19 |
| | 7 | 2975.146 | 4558.808 | 1835.84 | 10 | 595.2925 | 1550.197 | 4864.39 |
| Nalm6 | 5 | 132.1701 | 71.77628 | 102.7936 | 8 | 72.12333 | 50.96007 | 80.62564 |
| | 6 | 183.3285 | 176.8246 | 267.3849 | 9 | 823.2917 | 299.8667 | 901.03 |
| | 7 | 51.11399 | 50.24134 | 57.06661 | 10 | 221.3179 | 102.692 | 234.6751 |
| T cells alone | 5 | 12.70908 | 18.65894 | 16.35375 | 8 | 17.00011 | 13.59572 | 15.75731 |
| | 6 | 8.719928 | 7.591335 | 11.91575 | 9 | 8.642956 | 4.919328 | 11.89729 |
| | 7 | 5.717691 | 4.289614 | 6.980622 | 10 | 5.387739 | 3.932472 | 9.043607 |
| Raji | 11 | 823.133 | 3402.324 | 896.7429 | | | | |
| | 12 | 2799.535 | 6101.386 | 1873.887 | | | | |
| | 13 | 2180.811 | 6525.733 | 2506.268 | | | | |
| Raji CD20KO | 11 | 43.58357 | 76.1947 | 47.89087 | | | | |
| | 12 | 84.85969 | 225.7324 | 65.41539 | | | | |
| | 13 | 101.4673 | 179.8601 | 106.4787 | | | | |
| Namalwa | 11 | 96.9067 | 180.8989 | 87.23379 | | | | |
| | 12 | 228.7018 | 503.392 | 198.3201 | | | | |
| | 13 | 201.064 | 208.7059 | 125.427 | | | | |
| Nalm6 | 11 | 36.04238 | 35.06366 | 29.59289 | | | | |
| | 12 | 6.91882 | 11.08133 | 4.670726 | | | | |
| | 13 | 12.17589 | 7.01667 | 5.499756 | | | | |
| T cells alone | 11 | 14.98063 | 15.91492 | 13.15346 | | | | |
| | 12 | 5.901473 | 6.110295 | 5.688816 | | | | |
| | 13 | 4.758223 | 3.894212 | 3.511602 | | | | |

TABLE 61C

| 1L-10 Cell type | Group | Replicates | | | Group | Replicates | | |
|---|---|---|---|---|---|---|---|---|
| Raji | 1 | 178.0432 | 142.8539 | 120.4695 | 2 | 895.8653 | 69.6716 | 892.6929 |
| | | | | | 3 | 1097.383 | 275.2268 | 630.683 |
| | | | | | 4 | 1609.907 | 633.7046 | 1807.731 |
| Raji CD20KO | 1 | 97.01133 | 85.2923 | 53.7706 | 2 | 309.4966 | 28.25922 | 239.7828 |
| | | | | | 3 | 606.8257 | 91.35382 | 309.2822 |
| | | | | | 4 | 1253.292 | 391.0293 | 1863.251 |

TABLE 61C-continued

| IL-10 Cell type | Group | Replicates | | | Group | Replicates | | |
|---|---|---|---|---|---|---|---|---|
| Namalwa | 1 | 33.10979 | 35.6513 | 34.88744 | 2 | 573.4806 | 68.91302 | 432.3923 |
| | | | | | 3 | 646.463 | 239.0274 | 221.7614 |
| | | | | | 4 | 1527.354 | 192.0951 | 2717.487 |
| Nalm 6 | 1 | 50.10573 | 56.39945 | 79.07014 | 2 | 185.7021 | 24.16594 | 125.913 |
| | | | | | 3 | 443.9515 | 46.61747 | 273.2845 |
| | | | | | 4 | 1161.58 | 507.9296 | 1320.574 |
| T cells alone | 1 | 30.33024 | 36.6716 | 31.08655 | 2 | 30.82579 | 5.067228 | 35.02344 |
| | | | | | 3 | 32.25264 | 2.559772 | 29.35922 |
| | | | | | 4 | 64.27 | 10.88138 | 106.1506 |
| Raji | 5 | 251.3409 | 1515.368 | 1375.689 | 8 | 510.7076 | 293.819 | 798.0907 |
| | 6 | 161.179 | 290.4449 | 338.9459 | 9 | 273.8515 | 394.2801 | 513.9037 |
| | 7 | 773.2684 | 422.0451 | 1022.366 | 10 | 463.0497 | 110.0162 | 621.5802 |
| Raji CD20KO | 5 | 872.8176 | 934.0822 | 703.4425 | 8 | 47.28079 | 112.9426 | 333.4111 |
| | 6 | 1060.602 | 244.7751 | 222.7141 | 9 | 48.86976 | 422.8751 | 674.2297 |
| | 7 | 807.5648 | 530.7835 | 124.8675 | 10 | 79.00288 | 134.7437 | 641.66 |
| Namalwa | 5 | 1079.3 | 3961.233 | 446.361 | 8 | 92.83561 | 137.2657 | 913.6063 |
| | 6 | 953.3019 | 746.7817 | 191.549 | 9 | 67.28244 | 274.0883 | 832.4924 |
| | 7 | 1364.544 | 1637.356 | 531.6147 | 10 | 150.1814 | 100.8329 | 968.0775 |
| Nalm 6 | 5 | 412.9091 | 114.515 | 600.812 | 8 | 317.099 | 52.03268 | 148.2565 |
| | 6 | 908.1756 | 76.49075 | 123.8227 | 9 | 394.3369 | 82.53729 | 417.2169 |
| | 7 | 853.5691 | 573.8378 | 106.7992 | 10 | 553.2771 | 50.80476 | 227.2295 |
| T cells alone | 5 | 22.4375 | 26.96257 | 45.5054 | 8 | 22.21889 | 10.15072 | 41.45767 |
| | 6 | 28.556 | 26.16897 | 37.44123 | 9 | 20.68183 | 22.8389 | 39.23846 |
| | 7 | 33.4457 | 30.93852 | 32.09581 | 10 | 17.24112 | 20.44047 | 27.8371 |
| Raji | 11 | 95.38296 | 176.1182 | 207.3491 | | | | |
| | 12 | 73.72115 | 147.9041 | 157.5053 | | | | |
| | 13 | 183.7121 | 443.0117 | 331.2405 | | | | |
| Raji CD20KO | 11 | 66.01768 | 35.65559 | 60.18955 | | | | |
| | 12 | 83.15986 | 186.4922 | 223.6873 | | | | |
| | 13 | 168.1965 | 401.8826 | 210.6137 | | | | |
| Namalwa | 11 | 69.36119 | 159.804 | 92.54174 | | | | |
| | 12 | 108.0373 | 334.7655 | 119.5407 | | | | |
| | 13 | 192.2065 | 1887.085 | 163.9822 | | | | |
| Nalm 6 | 11 | 249.6969 | 34.90282 | 21.92475 | | | | |
| | 12 | 219.2402 | 53.1071 | 41.7788 | | | | |
| | 13 | 124.2308 | 84.31646 | 49.04896 | | | | |
| T cells alone | 11 | 27.12001 | 36.7858 | 18.54694 | | | | |
| | 12 | 20.80955 | 28.15541 | 15.18784 | | | | |
| | 13 | 26.48491 | 31.52268 | 22.26345 | | | | |

TABLE 61D

| IFNg Cell type | Group | Replicates | | | Group | Replicates | | |
|---|---|---|---|---|---|---|---|---|
| Raji | 1 | 41464.96 | 30963.75 | 25447.23 | 2 | 1432613 | 84135.23 | 1386317 |
| | | | | | 3 | 2397286 | 821594.6 | 1846574 |
| | | | | | 4 | 2274190 | 942782.2 | 1937710 |
| Raji CD20K | 1 | 11561.27 | 8586.159 | 5026.661 | 2 | 213743.2 | 12565.5 | 131488.3 |
| | | | | | 3 | 664001.4 | 69248.71 | 373145.3 |
| | | | | | 4 | 1163951 | 304488.7 | 1465425 |
| Namalwa | 1 | 3530.81 | 1842.586 | 2716.459 | 2 | 510701.3 | 52054.34 | 360549.4 |
| | | | | | 3 | 904990.4 | 300162.3 | 336275.7 |
| | | | | | 4 | 1253120 | 116275.2 | 1855904 |
| Nalm 6 | 1 | 3899.43 | 3281.217 | 6749.83 | 2 | 163300.5 | 13171.62 | 96551.14 |
| | | | | | 3 | 294888.9 | 14905.42 | 202445.1 |
| | | | | | 4 | 503047.8 | 189820.4 | 597772.9 |
| T cells alon | 1 | 1753.5 | 1876.623 | 1557.067 | 2 | 5403.774 | 1746.713 | 7399.695 |
| | | | | | 3 | 5454.525 | 6663.711 | 5861.042 |
| | | | | | 4 | 23112.12 | 5606.156 | 49759.7 |
| Raji | 5 | 575698 | 1687352 | 1965687 | 8 | 1078730 | 402925.4 | 1348360 |
| | 6 | 519005.7 | 614491.4 | 1018404 | 9 | 1803657 | 1518159 | 2003596 |
| | 7 | 1578042 | 517803 | 1788915 | 10 | 2490064 | 419647.4 | 1932058 |
| Raji CD20K | 5 | 513259.5 | 347633.9 | 357939.6 | 8 | 24994.79 | 67790.24 | 231769.2 |
| | 6 | 784775.3 | 111826.9 | 115041.6 | 9 | 59348.85 | 419743.6 | 852087.2 |
| | 7 | 487082.8 | 204193.3 | 69028.4 | 10 | 108512.4 | 237310.2 | 1327924 |
| Namalwa | 5 | 1095254 | 1828112 | 422922.4 | 8 | 70351.05 | 121957.9 | 1029824 |
| | 6 | 1460396 | 852559.7 | 222410.3 | 9 | 100939.4 | 489723.7 | 1834780 |
| | 7 | 1421146 | 1201823 | 475557.9 | 10 | 309207.5 | 160166.7 | 1874998 |
| Nalm 6 | 5 | 219984.2 | 32995.87 | 314350.1 | 8 | 220363.4 | 32273.67 | 135918 |
| | 6 | 418594.9 | 25470.36 | 50276.03 | 9 | 361549.7 | 49278.98 | 433392.1 |
| | 7 | 364977.2 | 182266.8 | 39687.06 | 10 | 554730 | 52797.1 | 337819.6 |
| T cells alon | 5 | 1805.136 | 1126.776 | 6229.361 | 8 | 5965.458 | 948.2716 | 8793.781 |

TABLE 61D-continued

| IFNg Cell type | Group | Replicates | | | Group | Replicates | | |
|---|---|---|---|---|---|---|---|---|
| | 6 | 10846.88 | 2035.132 | 8678.811 | 9 | 10854 | 1365.383 | 13795.46 |
| | 7 | 10220.63 | 7642.1 | 8708.371 | 10 | 7452.874 | 5353.539 | 6430.798 |
| Raji | 11 | 205423.6 | 305476.1 | 512645.3 | | | | |
| | 12 | 392821.5 | 750606.6 | 903119.7 | | | | |
| | 13 | 554100.1 | 1314131 | 1028525 | | | | |
| Raji CD20K | 11 | 34116.67 | 12335.53 | 45684.74 | | | | |
| | 12 | 69699.52 | 134538 | 208660.6 | | | | |
| | 13 | 100355.9 | 206666.2 | 149680.4 | | | | |
| Namalwa | 11 | 80511.69 | 155485.4 | 106748 | | | | |
| | 12 | 175944.5 | 544014 | 210348.9 | | | | |
| | 13 | 264515.8 | 565138.4 | 187873.3 | | | | |
| Nalm6 | 11 | 176019.5 | 5267.248 | 15715.26 | | | | |
| | 12 | 229324.8 | 24222.55 | 26877.11 | | | | |
| | 13 | 76258.82 | 31998.6 | 26876.26 | | | | |
| T cells alon | 11 | 2279.092 | 180.2089 | 392.9496 | | | | |
| | 12 | 9621.94 | 1391.83 | 1901.967 | | | | |
| | 13 | 1775.067 | 2816.077 | 947.6876 | | | | |

TABLE 62

| | Group | | | | | | | | | | | |
|---|---|---|---|---|---|---|---|---|---|---|---|---|
| Cell Type | 1 | | | 2 | | | 3 | | | 4 | | |
| Raji | 11.9 | 11.8 | 12.9 | 45 | 31 | 48.7 | 54.1 | 39.9 | 59.7 | 44.2 | 34.3 | 51.2 |
| Raji CD20KO | 12.1 | 12 | 13.2 | 24.7 | 22.4 | 30.2 | 54.7 | 36.9 | 56.4 | 45 | 37.7 | 52.2 |
| Namalwa | 6.78 | 6.78 | 6.72 | 17.9 | 18 | 32.3 | 37.5 | 26.7 | 43.1 | 36.9 | 28.7 | 41.8 |
| Nalm6 | 6.75 | 7.04 | 6.92 | 19.3 | 13.3 | 20.5 | 26.5 | 19.7 | 30.1 | 25.7 | 20.7 | 31.3 |
| T Cells Alone | 3.23 | 2.78 | 3.12 | 7.4 | 6.33 | 9.02 | 679 | 6.13 | 8.11 | 13.3 | 11.6 | 16.4 |
| Cell Type | 5 | | | 6 | | | 7 | | | 8 | | |
| Raji | 56.6 | 43.3 | 59.9 | 55.1 | 40.8 | 61.6 | 53.7 | 42.2 | 59.1 | 44.2 | 32.2 | 53.4 |
| Raji CD20KO | 45 | 33.7 | 47.8 | 44.7 | 34.5 | 48.2 | 46.5 | 35.1 | 48.5 | 26.2 | 24.8 | 29.5 |
| Namalwa | 41.4 | 26 | 42.7 | 45.1 | 31 | 50.8 | 44.1 | 28.8 | 48.5 | 33.4 | 20.7 | 35.3 |
| Nalm6 | 23.3 | 17.7 | 25.5 | 23.9 | 18.7 | 28.2 | 24.6 | 18.6 | 28.7 | 19.1 | 15.4 | 20.8 |
| T Cells Alone | 3.78 | 3.97 | 5.09 | 5.62 | 5.91 | 7.36 | 8.13 | 8.18 | 9.92 | 4.53 | 4.68 | 4.6 |
| Cell Type | 9 | | | 10 | | | 11 | | | 12 | | |
| Raji | 53.1 | 40.8 | 57.6 | 55.2 | 42.2 | 60.1 | 49.2 | 35.8 | 55.7 | 51.9 | 37.3 | 58 |
| Raji CD20KO | 48.2 | 38.8 | 53 | 56.4 | 41.8 | 56.3 | 28.2 | 25.3 | 32.6 | 42.3 | 33.8 | 48.6 |
| Namalwa | 44.2 | 30.9 | 41.2 | 42.2 | 30.6 | | 31.9 | 24.8 | | 38.9 | 33.2 | 46.5 |
| Nalm6 | 28.6 | 22.3 | 33 | 28.1 | 23.5 | 32.5 | 17.2 | 17.4 | 22.1 | 21.2 | 19.1 | 28.2 |
| T Cells Alone | 5.01 | 5.5 | 7.29 | 5.37 | 6.24 | 7.4 | 2.9 | 4.18 | 3.67 | 6.67 | 7.27 | 9.39 |
| Cell Type | 13 | | | | | | | | | | | |
| Raji | 57 | 42 | 61.1 | | | | | | | | | |
| Raji CD20KO | 41.8 | 32.7 | 49.4 | | | | | | | | | |
| Namalwa | 38 | 28.1 | 43.6 | | | | | | | | | |
| Nalm6 | 19.9 | 17.9 | 25.1 | | | | | | | | | |
| T Cells Alone | 3.8 | 4.76 | 5.87 | | | | | | | | | |

TABLE 63

| | Group | | | | | | | | | | | |
|---|---|---|---|---|---|---|---|---|---|---|---|---|
| Cell Type | 1 | | | 2 | | | 3 | | | 4 | | |
| Raji 1:4 | 14.8 | 13.4 | 14.7 | 31.6 | 18.5 | 31.1 | 38.8 | 23.7 | 35.8 | 39.2 | 24.5 | 33.8 |
| Nannlwa 1:4 | 6.6 | 6.61 | 6.55 | 25.5 | 15.4 | 23 | 38.1 | 20.9 | 34.5 | 34.1 | 20.8 | 29.8 |
| Nalm6 1:4 | 9.92 | 9.96 | 10.7 | 21.7 | 16.2 | 19.5 | 31.2 | 22 | 27.8 | 27.5 | 20.7 | 28.5 |
| T Cells Alone | 3.23 | 2.78 | 3.12 | 7.4 | 6.33 | 9.02 | 6.79 | 6.13 | 8.11 | 13.3 | 11.6 | 16.4 |

TABLE 63-continued

| Cell Type | Group 5 | | | 6 | | | 7 | | | 8 | | |
|---|---|---|---|---|---|---|---|---|---|---|---|---|
| Raji 1:4 | 35.9 | 26.4 | 32.5 | 39.9 | 28 | 36.3 | 37.4 | 27.3 | 37.6 | 26.3 | 21.6 | 30.3 |
| Nannlwa 1:4 | 32 | 20 | 32.7 | 37.7 | 23.9 | 42.4 | 36.3 | 20.8 | 36.6 | 25.2 | 17.8 | 25.7 |
| Nalm6 1:4 | 26 | 18.7 | 26.8 | 30.3 | 20.9 | 32.8 | 27.5 | 21.1 | 28.9 | 20.3 | 16.1 | 21.3 |
| T Cells Alone | 3.78 | 3.97 | 5.09 | 5.62 | 5.91 | 7.36 | 8.13 | 8.18 | 9.92 | 453 | 4.68 | 4.6 |

| Cell Type | 9 | | | 10 | | | 11 | | | 12 | | |
|---|---|---|---|---|---|---|---|---|---|---|---|---|
| Raji 1:4 | 35.3 | 28.6 | 39.5 | 33.1 | 28.8 | 40 | 28.2 | 27.9 | 35.6 | 39.3 | 33.7 | 42 |
| Nannlwa 1:4 | 33.8 | 22 | 33.8 | 29.9 | 20.4 | 31.2 | 25 | 19.3 | 27 | 32.2 | 24.6 | 36.4 |
| Nalm6 1:4 | 27.5 | 19.9 | 29 | 26.5 | 20.8 | 26 | 20.4 | 18.6 | 21.8 | 27.4 | 19.5 | 27.9 |
| T Cells Alone | 5.01 | 5.5 | 7.29 | 537 | 6.24 | 7.4 | 2.9 | 4.18 | 3.67 | 6.67 | 7.27 | 9.39 |

| Cell Type | 13 | | |
|---|---|---|---|
| Raji 1:4 | 40 | 36.3 | 44.4 |
| Nannlwa 1:4 | 31 | 22.9 | 36.9 |
| Nalm6 1:4 | 27.8 | 22.4 | 29 |
| T Cells Alone | 3.8 | 4.76 | 5.87 |

TABLE 64

| Cell Type | Group 1 | | | 2 | | | 3 | | | 4 | | |
|---|---|---|---|---|---|---|---|---|---|---|---|---|
| Raji | 1.49 | 1.1 | 1.28 | 9.95 | 8.23 | 8.26 | 8.36 | 6.88 | 4.62 | 29.5 | 28.5 | 27.8 |
| Raji CD20KO | 6.95 | 6.65 | 6.57 | 15.9 | 14.1 | 31.3 | 19.8 | 12 | 25.4 | 39.4 | 38 | 48.7 |
| Namalwa | 1.11 | 1.26 | 1.6 | 28.7 | 28.5 | 29.1 | 23.2 | 19.4 | 19 | 41.7 | 38.6 | 39.8 |
| Nalm6 | 5.44 | 5.04 | 4.13 | 52.2 | 50.4 | 55.8 | 58.5 | 63.8 | 63 | 69.3 | 70.7 | 72.6 |
| T Cells Alone | 4.65 | 2.28 | 3.88 | 15.9 | 14.9 | 16.8 | 22.2 | 23.1 | 22.7 | 67.2 | 68.1 | 70.3 |

| Cell Type | 5 | | | 6 | | | 7 | | | 8 | | |
|---|---|---|---|---|---|---|---|---|---|---|---|---|
| Raji | 23 | 17.5 | 11.2 | 14.3 | 10.9 | 10.4 | 15.1 | 11.9 | 10.7 | 15 | 12.8 | 9.6 |
| Raji CD20KO | 34.9 | 34.3 | 51 | 21.7 | 16.3 | 30.5 | 13.8 | 11.5 | 23 | 16.3 | 19.6 | 29.8 |
| Namalwa | 39.8 | 31.7 | 38.3 | 30.3 | 22.5 | 28.1 | 30 | 25.3 | 26.2 | 28.4 | 23.7 | 24.8 |
| Nalm6 | 68.5 | 72.6 | 74.6 | 60 | 62.2 | 64.6 | 60.5 | 65.3 | 69.4 | 58.6 | 63.5 | 67.1 |
| T Cells Alone | 11.7 | 14 | 14.7 | 26.2 | 27 | 28.7 | 23.9 | 28.9 | 30.2 | 11.2 | 13.4 | 15.1 |

| Cell Type | 9 | | | 10 | | | 11 | | | 12 | | |
|---|---|---|---|---|---|---|---|---|---|---|---|---|
| Raji | 9.59 | 9.11 | 7.33 | 18.4 | 17.3 | 15.6 | 17.4 | 17.4 | 12.6 | 13.1 | 13.4 | 10.1 |
| Raji CD20KO | 21 | 14.7 | 21.4 | 33.3 | 31.1 | 37.5 | 18.6 | 19.2 | 32.1 | 28.7 | 23.7 | 35.7 |
| Namalwa | 19.5 | 14.7 | 14.6 | 32.4 | 30 | 30.8 | 38.7 | 44.1 | 40.8 | 34.2 | 33.1 | 31.7 |
| Nalm6 | 43.5 | 44.1 | 49.2 | 61.7 | 69.8 | 68.8 | 48.6 | 47.8 | 56.2 | 65.8 | 68.3 | 67.8 |
| T Cells Alone | 23.3 | 28.1 | 30 | 22.6 | 28.1 | 29 | 5.18 | 5.6 | 7.22 | 36.9 | 43.5 | 45.2 |

| Cell Type | 13 | | |
|---|---|---|---|
| Raji | 9.02 | 8.5 | 5.41 |
| Raji CD20KO | 14.4 | 10.4 | 21.3 |
| Namalwa | 16 | 17.2 | 18.3 |
| Nalm6 | 53.1 | 58 | 58.2 |
| T Cells Alone | 8.53 | 10.8 | 13.7 |

TABLE 65

| Cell Type | Group 1 | | | 2 | | | 3 | | | 4 | | |
|---|---|---|---|---|---|---|---|---|---|---|---|---|
| Raji | 1.66 | 1.42 | 1.4 | 11.3 | 9.83 | 18.6 | 12.8 | 11.2 | 18.3 | 36 | 31.4 | 44.3 |
| Namalwa | 1.2 | 1.41 | 1.05 | 18.8 | 17.4 | 25.2 | 20.8 | 19.2 | 32.8 | 33.3 | 37.8 | 44.2 |
| Nalm6 | 2.34 | 2.23 | 2.22 | 31 | 28.9 | 38.3 | 28.7 | 30.4 | 39.1 | 40.2 | 46.1 | 51.9 |
| T Cells Alone | 4.65 | 2.28 | 3.88 | 15.9 | 14.9 | 16.8 | 22.2 | 23.1 | 22.7 | 67.2 | 68.1 | 70.3 |

TABLE 65-continued

| Cell Type | Group 5 | | | 6 | | | 7 | | | 8 | | |
|---|---|---|---|---|---|---|---|---|---|---|---|---|
| Raji | 18.6 | 20.5 | 25.8 | 14.8 | 13 | 21.3 | 15.6 | 13.2 | 21.2 | 11.3 | 12.7 | 20.4 |
| Namalwa | 22.5 | 25.8 | 31.3 | 23.6 | 25.6 | 34.4 | 22.2 | 22.9 | 31 | 17.1 | 16.9 | 24.8 |
| Nalm6 | 45.9 | 43.3 | 48.4 | 39.9 | 43.2 | 44.6 | 37.6 | 45.6 | 49.7 | 27.3 | 31.2 | 39.4 |
| T Cells Alone | 11.7 | 14 | 14.7 | 26.2 | 27 | 28.7 | 23.9 | 28.9 | 30.2 | 11.2 | 13.4 | 15.1 |

| Cell Type | 9 | | | 10 | | | 11 | | | 12 | | |
|---|---|---|---|---|---|---|---|---|---|---|---|---|
| Raji | 9.42 | 9.78 | 15.3 | 17.6 | 15.3 | 22.6 | 12.2 | 16.5 | 18.3 | 10.2 | 11.4 | 18.1 |
| Namalwa | 13.3 | 14.5 | 22.6 | 23.6 | 23.5 | 29.5 | 20.3 | 17.1 | 26.9 | 20.7 | 20.2 | 31 |
| Nalm6 | 30.3 | 27.4 | 34.9 | 35.6 | 36.8 | 50.7 | 32.9 | 48.3 | 65.4 | 41 | 50 | 60.7 |
| T Cells Alone | 23.3 | 28.1 | 30 | 22.6 | 28.1 | 29 | 518 | 5.6 | 7.22 | 36.9 | 43.5 | 45.2 |

| Cell Type | 13 | | |
|---|---|---|---|
| Raji | 6.57 | 8.41 | 8.1 |
| Namalwa | 9.64 | 7.92 | 14.8 |
| Nalm6 | 22.1 | 22.9 | 38.9 |
| T Cells Alone | 8.53 | 10.8 | 13.7 |

Example 18

TABLE 66

Exemplary Binding motif sequences

| SEQ ID NO | VH/VL Of Table: | Sequence |
|---|---|---|
| 251 | Table 4 | ggtaccCCCGGgCCCATGGCTCTTCCTGTGACAGCTCTTCTGCTGCCCCTGGCCCTGCTTCTGCATGCTGCTAGACCTCAGGTTCAGTTGCAGCAATGGGGAGCTGGCCTGTTAAAGCCCAGCGAAACCCTGTCCCTCACCTGCGCTGTGTATGGCGGAAGCTTCAGCGGCTATTACTGGAGCTGGATCCGGCAGCCTCCTGGAAAAGGATTAGAATGGATCGGCGAGATAGACCACAGCGGGAGCACAAACTACAACCCCAGCCTGAAATCGCGGGTTACAATCTCTGTGGACACAAGCAAGAATCAGTTCTCCCTGAAGCTGAGCAGCGTTACTGCCGCCGACACAGCTGTGTACTATTGCGCCAGAGGCGGAGGCTCCTGGTACAGCAACTGGTTCGATCCTTGGGGCCAAGGCACCATGGTGACCGTTTCCAGCGGCTCTACAAGCGGCAGCGGGAAACCTGGTTCTGGAGAGGGCAGCACAAAGGGCGACATCCAGATGACACAGAGCCCCAGCACCCTTAGCGCCTCTGTGGGAGATAGGGTTACCATTACCTGCAGGGCTTCCCAGAGCATCAGCAGCTGGCTGGCATGGTATCAACAGAAGCCTGGCAAGGCTCCCAAGCTGCTCATCTATGACGCCTCCAGCCTGGAAAGCGGGGTTCCCTCCAGATTTAGCGGCTCAGGCTCCGGAACAGAGTTCACCCTTACCATCTCTAGCCTGCAACCCGACGACTTCGCTACTTATTACTGTCAACAAGACAGAAGCTTGCCCCCCACATTCGGCGGAGGGACCAAGGTTGAGATCAAG |
| 252 | Table 5 | ggtaccCCCGGgCCCATGGCTCTTCCTGTGACAGCTCTTCTGCTGCCCCTGGCCCTGCTTCTGCATGCTGCTAGACCTCAGGTTCAGTTGCAGCAATGGGGAGCTGGCCTGTTAAAGCCCAGCGAAACCCTGTCCCTCACCTGCGCTGTGTATGGCGGAAGCTTCAGCGGCATCCACTGGAACTGGATCCGGCAGCCTCCTGGCAAAGGCCTTGAATGGATCGGCGATATCGACACCAGCGGCTCCACCAACTACAACCCCAGCCTGAAATCGAGGGTTACAATCTCTGTGGACACAAGCAAGAATCAGTTCTCCCTGAAGCTGAGCAGCGTTACTGCCGCCGACACAGCTGTGTACTATTGCGCCAGACTGGGCCAGGAAAGCGCTACCTACCTTGGCATGGATGTGTGGGGCAGGGCACCACCGTTACTGTTAGCTCTGGCTCAACAAGCGGCAGCGGCAAGCCTGGCTCAGGAGAAGGAAGCACAAAGGGCGACATTGTAATGACTCAGAGCCCCGACAGCCTGGCCGTTAGCTTAGGCGAAAGGGCTACAATCAATTGCAAGAGCAGCCAGAGCGTTCTGTACAGCAGCAACAACAAGAACTACCTCGCATGGTATCAACAGAAGCCAGGCCAGCCTCCCAAGCTGCTCATCTACTGGGCTTCACCAGAGAGAGCGGGGTTCCCGATAGATTCTCCGGCTCCGGTTCTGGAACAGATTTCACGCTCACAATCAGCAGCTTACAGGCCGAGGATGTGGCTGTCTACTATTGTCAGCAGTTGTACACCTACCCCTTCACATTCGGCGGAGGCACCAAGGTTGAGATCAAG |

TABLE 66-continued

Exemplary Binding motif sequences

| SEQ ID NO | VH/VL Of Table: | Sequence |
|---|---|---|
| 253 | Table 6 | ggtaccCCCGGgCCCATGGCTCTTCCTGTGACAGCTCTTCTGCTGC CCCTGGCCCTGCTTCTGCATGCTGCTAGACCTCAGCTTCAGCTC CAAGAGAGCGGACCTGGCTTAGTGAAGCCCAGCGAAACCCTGT CCCTCACCTGCACCGTTTCTGGCGGAAGCATCAGCAGCTCCAG CTATTACTGGGGATGGATCAGGCAGCCCCTGGCAAGGGTTTA GAATGGATCGGCTCGATATATTACTCCGGCAGCACCTACTATA ACCCCAGCTTGAAGAGCCGGGTTACCATTTCTGTGGACACATC AAAGAACCAGTTCAGCCTGAAGCTGAGCTCTGTGACTGCCGCC GACACAGCTGTGTACTACTGTGCCAGAGAGACAGACTACTCCA GCGGCATGGGCTACGGCATGGATGTGTGGGGACAAGGAACCA CCGTTACTGTGAGCAGCGGTTCCACCAGCGGCTCAGGCAAGCC TGGCTCAGGAGAAGGAAGCACCAAGGGGGATATACAGATGAC ACAGAGCCCCTCCAGCCTGTCCGCCAGCGTTGGCGATCGTGTA ACGATCACCTGCCGGGCCTCTCAGAGCATCAACTCCTACCTCA ATTGGTATCAACAGAAGCCAGGCAAGGCCCCCAAATTACTCAT CTACGCCGCCAGCAGCTTACAGAGCGGGGTTCCCTCTAGATTC TCCGGCTCCGGTTCTGGAACAGATTTCACCCTCACTATCTCCAG CTTGCAGCCCGAGGATTTCGCCACTTATTACTGTCAGCAGAGC CTGGCCGACCCCTTCACATTCGGCGGAGGCACAAAGGTTGAGA TCAAG |
| 254 | Table 7 | ggtaccCCCGGgCCCATGGCTCTTCCTGTGACAGCTCTTCTGCTGC CCCTGGCCCTGCTTCTGCATGCTGCTAGACCTCAGGTTCAGCTT GTGCAGAGCGGAGCTGAAGTTAAGAAGCCTGGCGCCTCTGTGA AGGTTAGCTGCAAGGCCAGCGGCTACACATTCAAGGAATATGG CATCTCCTGGGTTAGGCAGGCTCCCGGCCAAGGCTTAGAATGG ATGGGCTGGATCTCCGCCTACTCCGGCCACACCTACTACGCCC AGAAGCTTCAGGGCAGGGTTACCATGACCACCGACACCAGCAC CTCTACCGCCTATATGGAGCTGAGGAGCCTGAGATCGGACGAC ACAGCTGTGTATTACTGCGCCAGAGGCCCCCACTACGACGACT GGTCTGGATTTATCATCTGGTTCGACCCCTGGGGGCAGGGCAC CCTGGTCACAGTTTCTTCTGGCTCCACCAGCGGAAGCGGCAAG CCAGGCTCAGGCGAAGGATCTACAAAAGGCGACATCCAAATG ACACAGAGCCCCAGCAGCTTGAGCGCCTCCGTTGGCGACAGAG TTACAATCACCTGCAGGGCCTCTCAGAGCATCAGCAGCTATTT GAATTGGTATCAACAGAAGCCAGGAAAGGCCCCTAAGCTGCTC ATCTACGCTGCCAGCTCGCTCCAATCTGGCGTTCCTAGCAGATT TAGCGGCTCCGGCAGCGGCACAGACTTTACTCTTACCATTAGC TCCCTGCAGCCCGAGGACTTCGCTACCTACTATTGCCAGCAAA GCTACAGATTCCCTCCCACCTTTGGCCAGGGCACAAAGGTTGA GATCAAG |
| 255 | Table 8 | ggtaccCCCGGgCCCATGGCTCTTCCTGTGACAGCTCTTCTGCTGC CCCTGGCCCTGCTTCTGCATGCTGCTAGACCTCAGGTTCAGTTA CAAGAGAGCGGACCTGGCTTAGTGAAGCCCAGCGAAACCCTGT CCCTCACCTGCACCGTTTCTGGCGGAAGCATCAGCTCTCCCGAC CATTACTGGGGATGGATCAGGCAGCCCCTGGCAAGGGTTTGG AATGGATCGGCAGCATCTACGCCAGCGGCAGCACATTCTACAA CCCCTCGCTCAAAAGCAGGGTTACTATTTCTGTGGACACAAGC AAAAATCAGTTCAGCCTGAAGCTGAGCTCTGTGACTGCCGCCG ACACAGCTGTGTACTACTGTGCCAGAGAGACAGACTACTCCAG CGGGATGGGCTACGGCATGGATGTGTGGGGACAAGGAACCAC CGTTACTGTGAGCAGCGGCTCCACAAGCGGCTCAGGCAAGCCT GGCTCAGGAGAAGGAAGCACCAAGGGGGACATTCAAATGACC CAAAGCCCCTCCAGCCTGTCCGCCAGCGTTGGCGATAGGGTTA CCATTACCTGCAGGGCCAGCCAAAGCATCAACTCCTACCTAAA TTGGTATCAACAGAAGCCAGGCAAGGCCCCCAAACTACTCATT TACGCCGCCAGCAGCTTACAGAGCGGGGTTCCCTCTAGATTCT CCGGCAGCGGTTCTGGAACAGATTTCACTCTCACAATATCTTCG CTGCAGCCCGAGGATTTCGCTACCTACTATTGCCAGCAATCCCT GGCCGACCCCTTCACATTCGGCGGAGGCACAAAGGTTGAGATC AAG |
| 256 | Table 9 | ggtaccCCCGGgCCCATGGCTCTTCCTGTGACAGCTCTTCTGCTGC CCCTGGCCCTGCTTCTGCATGCTGCTAGACCTCAGATCACATTA AAAGAGAGCGGACCTACACTGGTGAAGCCCACCCAAACGCTT ACCCTCACCTGCACCTTTAGCGGGTTCAGCCTGGACACAGAGG GCGTTGGCGTTGGATGGATCAGGCAGCCTCCTGGCAAAGCCCT CGAATGGCTTGCCCTCATCTACTTCAACGACCAGAAGAGATAC AGCCCCTCCTTAAAATCTCGGCTCACAATCACCAAAGACACAA GCAAAAATCAGGTTGTGCTCACCATGACCAACATGGACCCTGT GGACACCGCTGTGTACTACTGTGCCAGAGACACCGGCTACAGC AGATGGTACTACGGGATGGACGTTTGGGGCCAAGGCACCACTG TGACCGTTTCCAGCGGCTCTACAAGCGGCAGCGGGAAACCTGG |

TABLE 66-continued

Exemplary Binding motif sequences

| SEQ ID NO | VH/VL Of Table: | Sequence |
|---|---|---|
| | | TTCTGGAGAGGGCAGCACAAAGGGCGACATCCAGATGACGCA<br>ATCCCCCAGCTCTGTGAGCGCCTCTGTGGGAGACAGAGTTACA<br>ATCACATGCCGGGCCTCCCAGGGCATCAGCTCTTGGCTGGCAT<br>GGTATCAACAGAAGCCTGGCAAGGCTCCCAAGCTGCTCATCTA<br>TGCCGCCTCCTCCTTACAATCTGGAGTTCCCTCCAGGTTCAGCG<br>GGAGCGGCTCAGGAACAGACTTCACCCTTACCATCTCTAGCCT<br>GCAACCCGAGGACTTCGCTACTTATTACTGTCAGCAGGCCTAC<br>GCCTACCCCATCACATTCGGCGGAGGAACAAAGGTTGAGATCA<br>AG |
| 257 | Table 10 | ggtaccCCCGGgCCCATGGCTCTTCCTGTGACAGCTCTTCTGCTGC<br>CCCTGGCCCTGCTTCTGCATGCTGCTAGACCTCAGGTTCAGTTG<br>CAGCAATGGGGAGCTGGCCTGTTAAAGCCCAGCGAAACCCTGT<br>CCCTCACCTGCGCTGTGTATGGCGGAAGCTTCGAGAAATACTA<br>CTGGAGCTGGATCCGGCAGCCTCCCGGCAAAGGCTTAGAATGG<br>ATCGGCGAGATTTATCACAGCGGGCTCACCAACTACAACCCCA<br>GCCTGAAATCTCGAGTTACAATCTCTGTGGACACAAGCAAGAA<br>TCAGTTCTCCCTGAAGCTGAGCAGCGTTACTGCCGCCGACACA<br>GCTGTGTACTATTGCGCCAGAGTTAGATACGACAGCAGCGACA<br>GCTATTACTACAGCTATGACTACGGCATGGATGTGTGGGGGCA<br>GGGCACCACCGTTACTGTCTCCTCTGGATCTACCAGCGGCAGC<br>GGCAAGCCTGGATCTGGCGAAGGAAGCACAAAGGGCGACATT<br>GTGCTCACCCAGAGCCCCGACAGCCTGGCTGTGTCTTTAGGCG<br>AAAGGGCTACCATCAACTGCAAGAGCAGCCAGAGCGTTCTGTA<br>CAGCAGCAACAACAAGAACTACCTTGCTTGGTATCAACAGAAG<br>CCTGGCCAGCCCCCTAAGCTGCTCATCTACTGGGCCTCTAGCA<br>GAGAGAGCGGGGTTCCCGATCGGTTTAGCGGCTCCGGCTCAGG<br>AACCGATTTCACCCTCACTATCTCCAGCCTCCAGGCCGAGGAT<br>GTGGCTGTCTACTATTGTCAGCAGAGCTATAGCTTCCCCTGGAC<br>ATTCGGCGGAGGCACCAAGGTTGAGATCAAG |
| 258 | Table 11 | ggtaccCCCGGgCCCATGGCTCTTCCTGTGACAGCTCTTCTGCTGC<br>CCCTGGCCCTGCTTCTGCATGCTGCTAGACCTCAGGTTCAGTTA<br>CAACAATGGGGAGCTGGCCTGTTAAAGCCCAGCGAAACCCTGT<br>CCCTCACCTGCGCTGTGTATGGCGGAAGCTTCAGCCGCTATGT<br>GTGGAGCTGGATCCGGCAGCCTCCTGGCAAAGGCCTTGAATGG<br>ATCGGAGAGATAGACAGCAGCGGCAAGACCAACTACAACCCC<br>AGCCTGAAATCACGCGTTACAATCTCTGTGGACACAAGCAAGA<br>ATCAGTTCTCCCTGAAGCTGAGCAGCGTTACTGCCGCCGACAC<br>AGCTGTGTACTATTGCGCCAGAGTTAGATACGACAGCTCCGAC<br>AGCTATTACTACAGCTATGACTACGGCATGGATGTGTGGGGGC<br>AGGGCACCACCGTTACAGTTAGCTCTGGAAGCACCAGCGGCTC<br>CGGCAAGCCTGGATCTGGTGAAGGAAGCACAAAGGGCGACAT<br>TGTGCTCACCCAGAGCCCCGACAGCCTGGCTGTGTCTTTAGGC<br>GAAAGGGCTACCATCAACTGCAAGAGCAGCCAGAGCGTTCTGT<br>ACAGCAGCAACAACAAGAACTACCTTGCATGGTATCAACAGA<br>AGCCTGGCCAGCCTCCCAAGCTGCTCATCTACTGGGCCTCTAG<br>CAGAGAGAGCGGGGTTCCCGATCGCTTTAGCGGCAGCGGTTCT<br>GGCACCGATTTCACTCTTACAATCAGCAGCTTACAGGCCGAGG<br>ATGTGGCTGTCTACTATTGTCAGCAGAGCTATAGCTTCCCCTGG<br>ACATTCGGCGGAGGCACCAAGGTTGAGATCAAG |
| 259 | Table 12 | ggtaccCCCGGgCCCATGGCTCTTCCTGTGACAGCTCTTCTGCTGC<br>CCCTGGCCCTGCTTCTGCATGCTGCTAGACCTCAGGTTCAGTTA<br>CAACAATGGGGAGCTGGCCTGTTAAAGCCCAGCGAAACCCTGT<br>CCCTCACCTGCGCTGTGTATGGCGGAAGCTTCAGCGGCTACGC<br>TTGGAGCTGGATTAGACAGCCTCCTGGCAAAGGACTAGAATGG<br>ATCGGAGAGATCGACCACAGAGGCTTCACCAACTACAACCCCA<br>GCCTGAAATCCAGAGTTACAATCTCTGTGGACACAAGCAAGAA<br>TCAGTTCTCCCTGAAGCTGAGCAGCGTTACTGCCGCCGACACA<br>GCTGTGTACTATTGCGCCAGGGTTAGATACGACAGCAGCGACA<br>GCTATTACTACAGCTATGACTACGGCATGGATGTGTGGGGGCA<br>GGGCACCACCGTTACGGTTAGCTCTGGATCTACCAGCGGCAGC<br>GGCAAGCCTGGCTCAGGAGAAGGAAGCACAAAGGGCGACATT<br>GTGCTCACCCAGAGCCCCGACAGCCTGGCCGTTTCTTTAGGCG<br>AAAGGGCTACCATCAACTGCAAGAGCAGCCAGAGCGTTCTGTA<br>CAGCAGCAACAACAAGAACTACCTTGCATGGTATCAACAGAA<br>GCCAGGCCAGCCTCCCAAGCTGCTCATCTACTGGGCCTCTAGC<br>AGAGAGAGCGGGGTTCCCGATAGATTTTCGGGATCAGGCTCCG<br>GCACCGATTTCACTCTTACGATCAGCAGCTTACAGGCCGAGGA<br>TGTGGCTGTCTACTATTGTCAGCAGAGCTATAGCTTCCCCTGGA<br>CATTCGGCGGAGGCACCAAGGTTGAGATCAAG |

TABLE 66-continued

Exemplary Binding motif sequences

| SEQ ID NO | VH/VL Of Table: | Sequence |
|---|---|---|
| 260 | Table 13 | ggtaccCCCGGgCCCATGGCTCTTCCTGTGACAGCTCTTCTGCTGC<br>CCCTGGCCCTGCTTCTGCATGCTGCTAGACCTCAGGTTCAGTTA<br>CAACAATGGGGAGCTGGCCTGTTAAAGCCCAGCGAAACCCTGT<br>CCCTCACCTGCGCTGTGTATGGCGGAAGCTTCCAGAAATACTA<br>CTGGAGCTGGATCCGGCAGCCTCCCGGCAAAGGCTTAGAATGG<br>ATCGGAGAGATAGACACCAGCGGCTTCACCAACTACAACCCCA<br>GCCTGAAATCTAGGGTTACAATCTCTGTGGACACAAGCAAGAA<br>TCAGTTCTCCCTGAAGCTGAGCAGCGTTACTGCCGCCGACACA<br>GCTGTGTACTATTGCGCCAGAGTTGGCAGATACAGCTACGGCT<br>ACTACATCACCGCCTTCGACATTTGGGGCCAAGGCACCACTGT<br>GACCGTTTCCAGCGGAAGCACTAGCGGCAGCGGGAAACCTGGT<br>TCTGGAGAGGGCTCAACCAAGGGCGACATCGTGATGACACAG<br>AGCCCCGACTCTCTGGCTGTGTCCCTGGGAGAGAGAGCCACCA<br>TCAACTGCAAGAGCAGCCAGAGCGTTCTGTACAGCAGCAACAA<br>CAAGAACTACCTGGCATGGTATCAACAGAAGCCTGGCCAGCCC<br>CCTAAGCTGCTCATCTACTGGGCTTCCACCAGAGAATCAGGCG<br>TTCCAGACAGGTTCTCCGGCTCGGGTTCAGGCACAGACTTCAC<br>CCTTACCATCTCTTCCCTGCAGGCCGAAGATGTGGCCGTTTACT<br>ACTGTCAGCAGCACTACAGCTTCCCTTTCACATTCGGCGGAGG<br>CACCAAGGTTGAGATCAAG |

Example 19

TABLE 67

Exemplary hinge sequences

| SEQ ID NO | Hinge | Sequence |
|---|---|---|
| 261 | C8K | GCAGCTGCTTTCGTGCCTGTGTTCCTGCCTGCTAAGCCCACCAC<br>CACTCCTGCTCCAAGACCTCCTACCCCCGCTCCTACAATCGCCA<br>GCCAACCTCTGAGCCTGAGACCGGAGGCATGCAGACCTGCGGC<br>AGGGGGAGCAGTTCACACAAGAGGCTTGGACTTCGCTTGCGAC<br>ATCTACATCTGGGCCCCTCTGGCCGGCATGCGGAGTTCTTCT<br>TCTTAGCCTGGTGATCACCCTGTACTGCAACCACAGAAAC |
| 262 | C28T | GCTGCTGCATTGGATAATGAAAAATCGAACGGCACAATCATTC<br>ATGTGAAGGGCAAACACCTGTGTCCCAGCCCCTTGTTCCCAGG<br>ACCTAGCAAGCCTTTTTGGGTTCTCGTGGTGGTGGGCGGCGTTC<br>TGGCTTGCTACTCTCTACTTGTAACTGTCGCATTTATTATATTCT<br>GGGTT |
| 263 | C28T1x | GGAGGAGGAGGATCTCTGGATAACGAGAAAAGCAACGGGACC<br>ATCATTCATGTGAAGGGAAAACATCTGTGTCCCAGCCCCTTGTT<br>CCCCGGACCTAGCAAGCCGTTTTGGGTTCTCGTGGTGGTGGGC<br>GGCGTTCTGGCTTGCTACTCTCTGCTTGTGACCGTTGCCTTCAT<br>TATCTTCTGGGTT |
| 264 | C28T2x | GGAGGAGGAGGATCTGGTGGAGGAGGTTCTCTGGACAATGAG<br>AAATCAAATGGAACGATCATCCATGTGAAGGGGAAGCACCTCT<br>GCCCCTCTCCCCTGTTTCCTGGTCCTAGCAAGCCCTTCTGGGTT<br>TTGGTGGTCGTGGGCGGCGTTCTGGCTTGCTACAGCCTGTTAGT<br>GACCGTTGCATTTATCATATTTTGGGTT |
| 265 | C28T2x_NC | GGAGGAGGAGGATCTGGTGGAGGAGGTTCTCTGGACAATGAG<br>AAATCGAATGGGACAATCATCCATGTGAAGGGGAAGCACCTG<br>AGCCCCTCTCCCCTGTTTCCTGGTCCTAGCAAGCCCTTCTGGGT<br>TTTGGTGGTCGTGGGCGGCGTTCTGGCCGTTTACAGCCTGTTAG<br>TGACCGTTGCTTTTATCATATTTTGGGTT |
| 266 | C28T2x_NG | GGAGGAGGAGGATCTGGTGGAGGAGGTTCTCTGGACAATGAA<br>AAGAGCAATGGCACAATCATCCATGTGAAGGGGAAGCACCTG<br>AACGGCTCCGCCCCTGTTTCCTGGTCCTAGCAAGCCATTTTGGGT<br>TCTCGTGGTGGTGGGCGGCGTTCTGGCCGTTTACAGCCTGTTAG<br>TGACCGTTGCGTTCATAATCTTCTGGGTT |
| 267 | C28T3x | GGAGGAGGAGGATCTGGTGGAGGAGGTTCTGGAGGAGGCGGC<br>TCTCTCGACAACGAAAAGAGCAATGGCACCATTATTCACGTTA<br>AAGGCAAGCATCTGTGCCCCTCCCCCCTGTTCCCCGGACCTTCA |

TABLE 67-continued

Exemplary hinge sequences

| SEQ ID NO | Hinge | Sequence |
|---|---|---|
| | | AAACCTTTTTGGGTTCTCGTGGTGGTGGGCGGCGTTCTGGCCTG<br>CTATTCTTTGCTGGTAACTGTAGCCTTCATTATCTTCTGGGTT |
| 268 | I4 | GAGAGCAAGTACGGACCTCCTTGTCCTCCATGTCCTGCTCCCG<br>AGTTCGAGGGCGGACCTTCAGTGTTCCTGTTCCCCCCTAAACCC<br>AAGGATACTCTTATGATCAGCCGGACCCCCGAGGTCACCTGTG<br>TGGTGGTAGATGTTAGCCAGGAGGATCCCGAGGTGCAGTTCAA<br>CTGGTACGTCGACGGCGTCGAGGTACACAACGCCAAGACCAA<br>GCCTAGGGAGGAGCAGTTCCAGTCCACCTATAGGGTCGTGAGC<br>GTGCTTACCGTGCTGCACCAGGACTGGTTGAACGGCAAGGAGT<br>ACAAGTGCAAGGTGTCCAACAAGGGCCTCCCCAGCAGCATCGA<br>GAAGACCATTAGCAAGGCAAAGGGACAGCCCAGGGAGCCCCA<br>GGTGTACACATTACCTCCTTCCCAGGAAGAGATGACCAAGAAC<br>CAGGTGTCGCTTACCTGCCTGGTCAAGGGCTTCTACCCCTCCGA<br>CATTGCAGTTGAATGGGAGTCAAACGGCCAGCCGGAGAACAA<br>TTACAAGACCACCCCCCCAGTCTTGGACAGCGACGGCTCTTTCT<br>TCCTCTACTCGCGGCTTACTGTAGATAAAAGTCGTTGGCAGGA<br>GGGAAACGTGTTCAGCTGCTCTGTGATGCACGAGGCCCTCCAT<br>AACCACTACACCCAGAAGAGCCTCTCCCTGTCTCTGGGCAAGA<br>TGTTCTGGGTGCTGGTCGTGGTGGGCGGAGTTCTTGCTTGCTAC<br>TCCCTGCTCGTGACCGTCGCTTTCATTATATTCTGGGTC |
| 269 | I1-2 | GAGAGAAAGTGTTGTGTTGAGTGTCCTCCTTGTCCTCCCTGCCC<br>TGCTCCCGAGTTACTTGGCGGACCTTCAGTGTTCCTGTTCCCCC<br>CAAGCCCAAGGATACTCTCATGATCAGCCGGACCCCCGAGGT<br>CACCTGTGTGGTGGTAGATGTTAGCCACGAGGACCCTGAGGTC<br>AAGTTCAACTGGTACGTCGACGGCGTCGAGGTGCACAACGCCA<br>AGACCAAGCCTCGTGAAGAACAGTACCAGTCCACCTACAGAGT<br>TGTGAGCGTGCTTACCGTGCTGCACCAGGACTGGCTGAACGGC<br>AAGGAGTACAAGTGCAAGGTGTCCAACAAGGCCCTCCCCGCTC<br>CCATCGAGAAGACAATCAGCAAGGCCAAGCCCTGTCCAGCCCC<br>TGAGCTCTTAGGAGGACCTAGCGTTTTCCTTTTCCCTCCCAAGC<br>CTAAGGACACTCTTATGATCTCCAGAACACCAGAGGTTACCTG<br>CGTCGTGGTGGACGTGTCCCATGAGGACCCAGAAGTCAAATTC<br>AATTGGTATGTAGATGGGGTCGAGGTCCACAACGCTAAGACAA<br>AGCCCCGCGAGGAGCAGTACAACTCTACCTACAGGGTCGTGTC<br>CGTGCTCACAGTGCTGCATCAGGATTGGCTCAACGGGAAGGAG<br>TATAAGTGCAAAGTGTCCAATAAGGCCCTTCCCGCCCCTATCG<br>AGAAAACCATCTCTAAGGCCAAATTCTGGGTGCTGGTGGTTGT<br>GGGCGGCGTGCTTGCTTGTTACTCCCTGCTGGTCACTGTAGCTT<br>TCATCATATTTTGGGTG |

Example 20

TABLE 68

Exemplary nucleotide sequences encoding a binding motif, hinge, and 41BB costimulatory domain

| SEQ ID NO | Sequence |
|---|---|
| 271 | ggtaccCCCGggCCCATGGCTCTTCCTGTGACAGCTCTTCTGCTGCCCCTGGCCC<br>TGCTTCTGCATGCTGCTAGACCTCAGCTTCAGCTCCAAGAGAGCGGACCTGG<br>CTTAGTGAAGCCCAGCGAAACCCTGTCCCTCACCTGCACCGTTTCTGGCGGA<br>AGCATCAGCAGCTCCAGCTATTACTGGGGATGGATCAGGCAGCCCCCTGGCA<br>AGGGTTTAGAATGGATCGGCTCGATATATTACTCCGGCAGCACCTACTATAA<br>CCCCAGCTTGAAGAGCCGGGTTACCATTTCTGTGGACACATCAAAGAACCAG<br>TTCAGCCTGAAGCTGAGCTCTGTGACTGCCGCCGACACAGCTGTGTACTACT<br>GTGCCAGAGAGACAGACTACTCCAGCGGCATGGGCTACGGCATGGATGTGT<br>GGGGACAAGGAACCACCGTTACTGTGAGCAGCGGTTCCACCAGCGGCTCAG<br>GCAAGCCTGGCTCAGGAGAAGGAAGCACCAAGGGGGATATACAGATGACAC<br>AGAGCCCCTCCAGCCTGTCCGCCAGCGTTGGCGATCGTGTAACGATCACCTG<br>CCGGGCCTCTCAGAGCATCAACTCCTACCTCAATTGGTATCAACAGAAGCCA<br>GGCAAGGCCCCAAATTACTCATCTACGCCGCCAGCAGCTTACAGAGCGGG<br>GTTCCCTCTAGATTCTCCGGCTCCGGTTCTGGAACAGATTTCACCCTCACTAT<br>CTCCAGCTTGCAGCCCGAGGATTTCGCCACTTATTACTGTCAGCAGAGCCTG<br>GCCGACCCCTTCACATTCGGCGGAGGCACAAAGGTTGAGATCAAGGCAGCT<br>GCTTTCGTGCCTGTGTTCCTGCCTGCTAAGCCCACCACCACTCCTGCTCCAAG<br>ACCTCCTACCCCCGCTCCTACAATCGCCAGCCAACCTCTGAGCCTGAGACCG<br>GAGGCATGCAGACCTGCGGCAGGGGAGCAGTTCACACAAGAGGCTTGGAC |

TABLE 68-continued

Exemplary nucleotide sequences encoding a binding motif, hinge, and 41BB costimulatory domain

| SEQ ID NO | Sequence |
|---|---|
|  | TTCGCTTGCGACATCTACATCTGGGCCCCTCTGGCCGGCACATGCGGAGTTCT<br>TCTTCTTAGCCTGGTGATCACCCTGTACTGCAACCACAGAAACAGATTCAGC<br>GTTGTGAAGAGAGGCCGGAAGAAGCTGCTGTACATCTTCAAGCAGCCCTTCA<br>TGAGACCTGTGCAGACCACACAGGAGGAAGACGGCTGCAGCTGTAGATTCC<br>CCGAGGAAGAGGAGGGCGGCTGTGAGCTGAGAGTTAAGTTCAGCAGGAGCG<br>CCGACGCCCCTGCCTACCAGCAAGGACAGAATCAACTGTACAACGAGCTGA<br>ACCTGGGCAGACGGGAGGAATACGATGTGCTGGACAAGAGGAGAGGCAGA<br>GACCCCGAGATGGGCGGCAAACCTAGAAGAAAGAACCCCCAGGAGGGCCTG<br>TATAACGAGCTCCAGAAGGACAAGATGGCCGAGGCCTACAGCGAGATCGGC<br>ATGAAGGGCGAAAGAAGAAGAGGCAAGGGCCACGACGGCCTCTACCAGGG<br>CTTAAGCACAGCTACAAAGGACACCTACGACGCCCTGCACATGCAGGCCCT<br>GCCCCCTAGATGATTAATTAAatcgat |
| 272 | ggtaccCCCGGgCCCATGGCTCTTCCTGTGACAGCTCTTCTGCTGCCCCTGGCCC<br>TGCTTCTGCATGCTGCTAGACCTCAGGTTCAGTTACAAGAGAGCGGACCTGG<br>CTTAGTGAAGCCCAGCGAAACCCTGTCCCTCACCTGCACCGTTTCTGGCGGA<br>AGCATCAGCTCTCCCGACCATTACTGGGGATGGATCAGGCAGCCCCTGGCA<br>AGGGTTTGGAATGGATCGGCAGCATCTACGCCAGCGGCAGCACATTCTACAA<br>CCCCTCGCTCAAAAGCAGGGTTACTATTTCTGTGGACACAAGCAAAAATCAG<br>TTCAGCCTGAAGCTGAGCTCTGTGACTGCCGCCGACACAGCTGTGTACTACT<br>GTGCCAGAGAGACAGACTACTCCAGCGGGATGGGCTACGGCATGGATGTGT<br>GGGGACAAGGAACCACCGTTACTGTGAGCAGCGGCTCCACAAGCGGCTCAG<br>GCAAGCCTGGCTCAGGAGAAGGAAGCACCAAGGGGGACATTCAAATGACCC<br>AAAGCCCCTCCAGCCTGTCCGCCAGCGTTGGCGATAGGGTTACCATTACCTG<br>CAGGGCCAGCCAAAGCATCAACTCCTACCTAAATTGGTATCAACAGAAGCC<br>AGGCAAGGCCCCCAAACTACTCATTTACGCCGCCAGCAGCTTACAGAGCGG<br>GGTTCCCTCTAGATTCTCCGGCAGCGGTTCTGGAACAGATTTCACTCTCACAA<br>TATCTTCGCTGCAGCCCGAGGATTTCGCTACCTACTATTGCCAGCAATCCCTG<br>GCCGACCCCTTCACATTCGGCGGAGGCACAAAGGTTGAGATCAAGGCAGCT<br>GCTTTCGTGCCTGTGTTCCTGCCTGCTAAGCCCACCACCACTCCTGCTCCAAG<br>ACCTCCTACCCCCGCTCCTACAATCGCCAGCCAACCTCTGAGCCTGAGACCG<br>GAGGCATGCAGACCTGCGGCAGGGGGAGCAGTTCACACAAGAGGCTTGGAC<br>TTCGCTTGCGACATCTACATCTGGGCCCCTCTGGCCGGCACATGCGGAGTTCT<br>TCTTCTTAGCCTGGTGATCACCCTGTACTGCAACCACAGAAACAGATTCAGC<br>GTTGTGAAGAGAGGCCGGAAGAAGCTGCTGTACATCTTCAAGCAGCCCTTCA<br>TGAGACCTGTGCAGACCACACAGGAGGAAGACGGCTGCAGCTGTAGATTCC<br>CCGAGGAAGAGGAGGGCGGCTGTGAGCTGAGAGTTAAGTTCAGCAGGAGCG<br>CCGACGCCCCTGCCTACCAGCAAGGACAGAATCAACTGTACAACGAGCTGA<br>ACCTGGGCAGACGGGAGGAATACGATGTGCTGGACAAGAGGAGAGGCAGA<br>GACCCCGAGATGGGCGGCAAACCTAGAAGAAAGAACCCCCAGGAGGGCCTG<br>TATAACGAGCTCCAGAAGGACAAGATGGCCGAGGCCTACAGCGAGATCGGC<br>ATGAAGGGCGAAAGAAGAAGAGGCAAGGGCCACGACGGCCTCTACCAGGG<br>CTTAAGCACAGCTACAAAGGACACCTACGACGCCCTGCACATGCAGGCCCT<br>GCCCCCTAGATGATTAATTAAatcgat |
| 273 | ggtaccCCCGGgCCCATGGCTCTTCCTGTGACAGCTCTTCTGCTGCCCCTGGCCC<br>TGCTTCTGCATGCTGCTAGACCTCAGATCACATTAAAAGAGAGCGGACCTAC<br>ACTGGTGAAGCCCACCCAAACGCTTACCCTCACCTGCACCTTTAGCGGGTTC<br>AGCCTGGACACAGAGGGCGTTGGCGTTGGATGGATCAGGCAGCCTCCTGGC<br>AAAGCCCTCGAATGGCTTGCCCTCATCTACTTCAACGACCAGAAGAGATACA<br>GCCCCTCCTTAAAATCTCGGCTCACAATCACCAAAGACACAAGCAAAAATCA<br>GGTTGTGCTCACCATGACCAACATGGACCCTGTGGACACCGCTGTGTACTAC<br>TGTGCCAGAGACACCGGCTACAGCAGATGGTACTACGGGATGGACGTTTGG<br>GGCCAAGGCACCACTGTGACCGTTTCCAGCGGCTCTACAAGCGGCAGCGGG<br>AAACCTGGTTCTGGAGAGGGCAGCACAAAGGGCGACATCCAGATGACGCAA<br>TCCCCCAGCTCTGTGAGCGCCTCTGTGGGAGACAGAGTTACAATCACATGCC<br>GGGCCTCCCAGGGCATCAGCTCTTGGCTGGCATGGTATCAACAGAAGCCTGG<br>CAAGGCTCCCAAGCTGCTCATCTATGCCGCCTCCTCCTTACAATCTGGAGTTC<br>CCTCCAGGTTCAGCGGGAGCGGCTCAGGAACAGACTTCACCCTTACCATCTC<br>TAGCCTGCAACCCGAGGACTTCGCTACTTATTACTGTCAGCAGGCCTACGCC<br>TACCCCATCACATTCGGCGGAGGAACAAAGGTTGAGATCAAGGCAGCTGCTT<br>TCGTGCCTGTGTTCCTGCCTGCTAAGCCCACCACCACTCCTGCTCCAAGACCT<br>CCTACCCCCGCTCCTACAATCGCCAGCCAACCTCTGAGCCTGAGACCGGAGG<br>CATGCAGACCTGCGGCAGGGGGAGCAGTTCACACAAGAGGCTTGGACTTCG<br>CTTGCGACATCTACATCTGGGCCCCTCTGGCCGGCACATGCGGAGTTCTTCTT<br>CTTAGCCTGGTGATCACCCTGTACTGCAACCACAGAAACAGATTCAGCGTTG<br>TGAAGAGAGGCCGGAAGAAGCTGCTGTACATCTTCAAGCAGCCCTTCATGA<br>GACCTGTGCAGACCACACAGGAGGAAGACGGCTGCAGCTGTAGATTCCCCG<br>AGGAAGAGGAGGGCGGCTGTGAGCTGAGAGTTAAGTTCAGCAGGAGCGCCG<br>ACGCCCCTGCCTACCAGCAAGGACAGAATCAACTGTACAACGAGCTGAACC<br>TGGGCAGACGGGAGGAATACGATGTGCTGGACAAGAGGAGAGGCAGAGAC<br>CCCGAGATGGGCGGCAAACCTAGAAGAAAGAACCCCCAGGAGGGCCTGTAT<br>AACGAGCTCCAGAAGGACAAGATGGCCGAGGCCTACAGCGAGATCGGCATG<br>AAGGGCGAAAGAAGAAGAGGCAAGGGCCACGACGGCCTCTACCAGGGCTTA |

TABLE 68-continued

Exemplary nucleotide sequences encoding a binding motif, hinge, and 41BB costimulatory domain

| SEQ ID NO | Sequence |
|---|---|
|  | AGCACAGCTACAAAGGACACCTACGACGCCCTGCACATGCAGGCCCTGCCC<br>CCTAGATGATTAATTAAatcgat |
| 274 | ggtaccCCCGGgCCCATGGCTCTTCCTGTGACAGCTCTTCTGCTGCCCCTGGCCC<br>TGCTTCTGCATGCTGCTAGACCTCAGGTTCAGTTACAACAATGGGGAGCTGG<br>CCTGTTAAAGCCCAGCGAAACCCTGTCCCTCACCTGCGCTGTGTATGGCGGA<br>AGCTTCCAGAAATACTACTGGAGCTGGATCCGGCAGCCTCCCGGCAAAGGCT<br>TAGAATGGATCGGAGAGATAGACACCAGCGGCTTCACCAACTACAACCCCA<br>GCCTGAAATCTAGGGTTACAATCTCTGTGGACAAGCAAGAATCAGTTCTC<br>CCTGAAGCTGAGCAGCGTTACTGCCGCCGACACAGCTGTGTACTATTGCGCC<br>AGAGTTGGCAGATACAGCTACGGCTACTACATCACCGCCTTCGACATTTGGG<br>GCCAAGGCACCACTGTGACCGTTTCCAGCGGAAGCACTAGCGGCAGCGGGA<br>AACCTGGTTCTGGAGAGGGCTCAACCAAGGGCGACATCGTGATGACACAGA<br>GCCCCGACTCTCTGGCTGTGTCCCTGGGAGAGAGAGCCACCATCAACTGCAA<br>GAGCAGCCAGAGCGTTCTGTACAGCAGCAACAACAAGAACTACCTGGCATG<br>GTATCAACAGAAGCCTGGCCAGCCCCCTAAGCTGCTCATCTACTGGGCTTCC<br>ACCAGAGAATCAGGCGTTCCAGACAGGTTCTCCGGCTCGGGTTCAGGCACAG<br>ACTTCACCCCTTACCATCTCTTCCCTGCAGGCCGAAGATGTGGCCGTTTACTAC<br>TGTCAGCAGCACTACAGCTTCCCTTTCACATTCGGCGGAGGCACCAAGGTTG<br>AGATCAAGGCAGCTGCTTTCGTGCCTGTGTTCCTGCCTGCTAAGCCCACCAC<br>CACTCCTGCTCCAAGACCTCCTACCCCCGCTCCTACAATCGCCAGCCAACCT<br>CTGAGCCTGAGACCGGAGGCATGCAGACCTGCGGCAGGGGGAGCAGTTCAC<br>ACAAGAGGCTTGGACTTCGCTTGCGACATCTACATCTGGGCCCCTCTGGCCG<br>GCACATGCGGAGTTCTTCTTCTTAGCCTGGTGATCACCCTGTACTGCAACCAC<br>AGAAACAGATTCAGCGTTGTGAAGAGAGGCCGGAAGAAGCTGCTGTACATC<br>TTCAAGCAGCCCTTCATGAGACCTGTGCAGACCACACAGGAGGAAGACGGC<br>TGCAGCTGTAGATTCCCCGAGGAAGAGGAGGGCGGCTGTGAGCTGAGAGTT<br>AAGTTCAGCAGGAGCGCCGACGCCCCTGCCTACCAGCAAGGACAGAATCAA<br>CTGTACAACGAGCTGAACCTGGGCAGACGGGAGGAATACGATGTGCTGGAC<br>AAGAGGAGAGGCAGAGACCCCGAGATGGGCGGCAAACCTAGAAGAAAGAA<br>CCCCCAGGAGGGCCTGTATAACGAGCTCCAGAAGGACAAGATGGCCGAGGC<br>CTACAGCGAGATCGGCATGAAGGGCGAAAGAAGAAGAGGCAAGGGCCACG<br>ACGGCCTCTACCAGGGCTTAAGCACAGCTACAAAGGACACCTACGACGCCC<br>TGCACATGCAGGCCCTGCCCCCTAGATGATTAATTAAatcgat |
| 275 | ggtaccCCCGGgCCCATGGCTCTTCCTGTGACAGCTCTTCTGCTGCCCCTGGCCC<br>TGCTTCTGCATGCTGCTAGACCTCAGGTTCAGTTGCAGCAATGGGGAGCTGG<br>CCTGTTAAAGCCCAGCGAAACCCTGTCCCTCACCTGCGCTGTGTATGGCGGA<br>AGCTTCGAGAAATACTACTGGAGCTGGATCCGGCAGCCTCCCGGCAAAGGCT<br>TAGAATGGATCGGCGAGATTTATCACAGCGGGCTCACCAACTACAACCCCAG<br>CCTGAAATCTCGAGTTACAATCTCTGTGGACACAAGCAAGAATCAGTTCTCC<br>CTGAAGCTGAGCAGCGTTACTGCCGCCGACACAGCTGTGTACTATTGCGCCA<br>GAGTTAGATACGACAGCAGCGACAGCTATTACTACAGCTATGACTACGGCAT<br>GGATGTGTGGGGCAGGGCACCACCGTTACTGTCTCCTCTGGATCTACCAGC<br>GGCAGCGGCAAGCCTGGATCTGGCGAAGGAAGCACAAAGGGCGACATTGTG<br>CTCACCCAGAGCCCCGACAGCCTGGCTGTGTCTTTAGGCGAAAGGGCTACCA<br>TCAACTGCAAGAGCAGCCAGAGCGTTCTGTACAGCAGCAACAACAAGAACT<br>ACCTTGCTTGGTATCAACAGAAGCCTGGCCAGCCCCCTAAGCTGCTCATCTA<br>CTGGGCCTCTAGCAGAGAGAGCGGGGTTCCCGATCGGTTTAGCGGCTCCGGC<br>TCAGGAACCGATTTCACCCTCACTATCTCCAGCCTCCAGGCCGAGGATGTGG<br>CTGTCTACTATTGTCAGCAGAGCTATAGCTTCCCCTGGACATTCGGCGGAGG<br>CACCAAGGTTGAGATCAAGGCAGCTGCTTTCGTGCCTGTGTTCCTGCCTGCT<br>AAGCCCACCACCACTCCTGCTCCAAGACCTCCTACCCCCGCTCCTACAATCG<br>CCAGCCAACCTCTGAGCCTGAGACCGGAGGCATGCAGACCTGCGGCAGGGG<br>GAGCAGTTCACACAAGAGGCTTGGACTTCGCTTGCGACATCTACATCTGGGC<br>CCCTCTGGCCGGCACATGCGGAGTTCTTCTTCTTAGCCTGGTGATCACCCTGT<br>ACTGCAACCACAGAAACAGATTCAGCGTTGTGAAGAGAGGCCGGAAGAAGC<br>TGCTGTACATCTTCAAGCAGCCCTTCATGAGACCTGTGCAGACCACACAGGA<br>GGAAGACGGCTGCAGCTGTAGATTCCCCGAGGAAGAGGAGGGCGGCTGTGA<br>GCTGAGAGTTAAGTTCAGCAGGAGCGCCGACGCCCCTGCCTACCAGCAAGG<br>ACAGAATCAACTGTACAACGAGCTGAACCTGGGCAGACGGGAGGAATACGA<br>TGTGCTGGACAAGAGGAGAGGCAGAGACCCCGAGATGGGCGGCAAACCTAG<br>AAGAAAGAACCCCCAGGAGGGCCTGTATAACGAGCTCCAGAAGGACAAGAT<br>GGCCGAGGCCTACAGCGAGATCGGCATGAAGGGCGAAAGAAGAAGAGGCA<br>AGGGCCACGACGGCCTCTACCAGGGCTTAAGCACAGCTACAAAGGACACCT<br>ACGACGCCCTGCACATGCAGGCCCTGCCCCCTAGATGATTAATTAAatcgat |
| 276 | ggtaccCCCGGgCCCATGGCTCTTCCTGTGACAGCTCTTCTGCTGCCCCTGGCCC<br>TGCTTCTGCATGCTGCTAGACCTCAGGTTCAGTTACAACAATGGGGAGCTGG<br>CCTGTTAAAGCCCAGCGAAACCCTGTCCCTCACCTGCGCTGTGTATGGCGGA<br>AGCTTCAGCCGCTATGTGTGGAGCTGGATCCGGCAGCCTCCTGGCAAAGGCC<br>TTGAATGGATCGGAGAGATAGACAGCAGCGGCAAGACCAACTACAACCCCA<br>GCCTGAAATCACGCGTTACAATCTCTGTGGACAAGCAAGAATCAGTTCTC<br>CCTGAAGCTGAGCAGCGTTACTGCCGCCGACACAGCTGTGTACTATTGCGCC |

TABLE 68-continued

Exemplary nucleotide sequences encoding a binding motif, hinge, and 41BB costimulatory domain

| SEQ ID NO | Sequence |
|---|---|
| | AGAGTTAGATACGACAGCTCCGACAGCTATTACTACAGCTATGACTACGGCA TGGATGTGTGGGGGCAGGGCACCACCGTTACAGTTAGCTCTGGAAGCACCA GCGGCTCCGGCAAGCCTGGATCTGGTGAAGGAAGCACAAAGGGCGACATTG TGCTCACCCAGAGCCCCGACAGCCTGGCTGTGTCTTTAGGCGAAAGGGCTAC CATCAACTGCAAGAGCAGCCAGAGCGTTCTGTACAGCAGCAACAACAAGAA CTACCTTGCATGGTATCAACAGAAGCCTGGCCAGCCTCCCAAGCTGCTCATC TACTGGGCCTCTAGCAGAGAGAGCGGGGTTCCCGATCGCTTTAGCGGCAGCG GTTCTGGCACCGATTTCACTCTTACAATCAGCAGCTTACAGGCCGAGGATGT GGCTGTCTACTATTGTCAGCAGAGCTATAGCTTCCCCTGGACATTCGGCGGA GGCACCAAGGTTGAGATCAAGGCAGCTGCTTTCGTGCCTGTGTTCCTGCCTG CTAAGCCCACCACCACTCCTGCTCCAAGACCTCCTACCCCCGCTCCTACAAT CGCCAGCCAACCTCTGAGCCTGAGACCGGAGGCATGCAGACCTGCGGCAGG GGGAGCAGTTCACACAAGAGGCTTGGACTTCGCTTGCGACATCTACATCTGG GCCCCTCTGGCCGGCACATGCGGAGTTCTTCTTCTTAGCCTGGTGATCACCCT GTACTGCAACCACAGAAACAGATTCAGCGTTGTGAAGAGAGGCCGGAAGAA GCTGCTGTACATCTTCAAGCAGCCCTTCATGAGACCTGTGCAGACCACACAG GAGGAAGACGGCTGCAGCTGTAGATTCCCCGAGGAAGAGGAGGGCGGCTGT GAGCTGAGAGTTAAGTTCAGCAGGAGCGCCGACGCCCCTGCCTACCAGCAA GGACAGAATCAACTGTACAACGAGCTGAACTGGGCAGACGGGAGGAATAC GATGTGCTGGACAAGAGGAGAGGCAGAGACCCCGAGATGGGCGGCAAACCT AGAAGAAAGAACCCCAGGAGGGCCTGTATAACGAGCTCCAGAAGGACAAG ATGGCCGAGGCCTACAGCGAGATCGGCATGAAGGGCGAAAGAAGAAGAGG CAAGGGCCACGACGGCCTCTACCAGGGCTTAAGCACAGCTACAAAGGACAC CTACGACGCCCTGCACATGCAGGCCCTGCCCCCTAGATGATTAATTAAatcgat |
| 277 | ggtaccCCCGGgCCCATGGCTCTTCCTGTGACAGCTCTTCTGCTGCCCCTGGCCC TGCTTCTGCATGCTGCTAGACCTCAGGTTCAGTTACAACAATGGGGAGCTGG CCTGTTAAAGCCCAGCGAAACCCTGTCCCTCACCTGCGCTGTGTATGGCGGA AGCTTCAGCGGCTACGCTTGGAGCTGGATTAGACAGCCTCCTGGCAAAGGAC TAGAATGGATCGGAGAGATCGACCACAGAGGCTTCACCAACTACAACCCCA GCCTGAAATCCAGAGTTACAATCTCTGTGGACACAAGCAAGAATCAGTTCTC CCTGAAGCTGAGCAGCGTTACTGCCGCCGACACAGCTGTGTACTATTGCGCC AGGGTTAGATACGACAGCAGCGACAGCTATTACTACAGCTATGACTACGGC ATGGATGTGTGGGGGCAGGGCACCACCGTTACGGTTAGCTCTGGATCTACCA GCGGCAGCGGCAAGCCTGGCTCAGGAGAAGGAAGCACAAAGGGCGACATTG TGCTCACCCAGAGCCCCGACAGCCTGGCCGTTTCTTTAGGCGAAAGGGCTAC CATCAACTGCAAGAGCAGCCAGAGCGTTCTGTACAGCAGCAACAACAAGAA CTACCTTGCATGGTATCAACAGAAGCCAGGCCAGCCTCCCAAGCTGCTCATC TACTGGGCCTCTAGCAGAGAGAGCGGGGTTCCCGATAGATTTTCGGGATCAG GCTCCGGCACCGATTTCACTCTTACGATCAGCAGCTTACAGGCCGAGGATGT GGCTGTCTACTATTGTCAGCAGAGCTATAGCTTCCCCTGGACATTCGGCGGA GGCACCAAGGTTGAGATCAAGGCAGCTGCTTTCGTGCCTGTGTTCCTGCCTG CTAAGCCCACCACCACTCCTGCTCCAAGACCTCCTACCCCCGCTCCTACAAT CGCCAGCCAACCTCTGAGCCTGAGACCGGAGGCATGCAGACCTGCGGCAGG GGGAGCAGTTCACACAAGAGGCTTGGACTTCGCTTGCGACATCTACATCTGG GCCCCTCTGGCCGGCACATGCGGAGTTCTTCTTCTTAGCCTGGTGATCACCCT GTACTGCAACCACAGAAACAGATTCAGCGTTGTGAAGAGAGGCCGGAAGAA GCTGCTGTACATCTTCAAGCAGCCCTTCATGAGACCTGTGCAGACCACACAG GAGGAAGACGGCTGCAGCTGTAGATTCCCCGAGGAAGAGGAGGGCGGCTGT GAGCTGAGAGTTAAGTTCAGCAGGAGCGCCGACGCCCCTGCCTACCAGCAA GGACAGAATCAACTGTACAACGAGCTGAACTGGGCAGACGGGAGGAATAC GATGTGCTGGACAAGAGGAGAGGCAGAGACCCCGAGATGGGCGGCAAACCT AGAAGAAAGAACCCCAGGAGGGCCTGTATAACGAGCTCCAGAAGGACAAG ATGGCCGAGGCCTACAGCGAGATCGGCATGAAGGGCGAAAGAAGAAGAGG CAAGGGCCACGACGGCCTCTACCAGGGCTTAAGCACAGCTACAAAGGACAC CTACGACGCCCTGCACATGCAGGCCCTGCCCCCTAGATGATTAATTAAatcgat |
| 278 | ggtaccCCCGGgCCCATGGCTCTTCCTGTGACAGCTCTTCTGCTGCCCCTGGCCC TGCTTCTGCATGCTGCTAGACCTCAGGTTCAGTTGCAGCAATGGGGAGCTGG CCTGTTAAAGCCCAGCGAAACCCTGTCCCTCACCTGCGCTGTGTATGGCGGA AGCTTCAGCGGCTATTACTGGAGCTGGATCCGGCAGCCTCCTGGAAAAGGAT TAGAATGGATCGGCGAGATAGACCACAGCGGGAGCACAAACTACAACCCCA GCCTGAAATCGCGGGTTACAATCTCTGTGGACACAAGCAAGAATCAGTTCTC CCTGAAGCTGAGCAGCGTTACTGCCGCCGACACAGCTGTGTACTATTGCGCC AGAGGCGGAGGCTCCTGGTACAGCAACTGGTTCGATCCTTGGGGCCAAGGC ACCATGGTGACCGTTTCCAGCGGCTCTACAAGCGGCAGCGGGAAACCTGGTT CTGGAGAGGGCAGCACAAAGGGCGACATCCAGATGACACAGAGCCCCAGCA CCCTTAGCGCCTCTGTGGGAGATAGGGTTACCATTACCTGCAGGGCTTCCCA GAGCATCAGCAGCTGGCTGGCATGGTATCAACAGAAGCCTGGCAAGGCTCC CAAGCTGCTCATCTATGACGCCTCCAGCCTGGAAAGCGGGGTTCCCTCCAGA TTTAGCGGCTCAGGCTCCGGAACAGAGTTCACCCTTACCATCTCTAGCCTGC AACCCGACGACTTCGCTACTTATTACTGTCAACAAGACAGAAGCTTGCCCCC CACATTCGGCGGAGGGACCAAGGTTGAGATCAAGGCAGCTGCTTTCGTGCCT GTGTTCCTGCCTGCTAAGCCCACCACCACTCCTGCTCCAAGACCTCCTACCCC |

TABLE 68-continued

Exemplary nucleotide sequences encoding a binding motif, hinge, and 41BB costimulatory domain

| SEQ ID NO | Sequence |
|---|---|
|  | CGCTCCTACAATCGCCAGCCAACCTCTGAGCCTGAGACCGGAGGCATGCAG<br>ACCTGCGGCAGGGGGAGCAGTTCACACAAGAGGCTTGGACTTCGCTTGCGA<br>CATCTACATCTGGGCCCCTCTGGCCGGCACATGCGGAGTTCTTCTTCTTAGCC<br>TGGTGATCACCCTGTACTGCAACCACAGAAACAGATTCAGCGTTGTGAAGAG<br>AGGCCGGAAGAAGCTGCTGTACATCTTCAAGCAGCCCTTCATGAGACCTGTG<br>CAGACCACACAGGAGGAAGACGGCTGCAGCTGTAGATTCCCCGAGGAAGAG<br>GAGGGCGGCTGTGAGCTGAGAGTTAAGTTCAGCAGGAGCGCCGACGCCCCT<br>GCCTACCAGCAAGGACAGAATCAACTGTACAACGAGCTGAACCTGGGCAGA<br>CGGGAGGAATACGATGTGCTGGACAAGAGGAGAGGCAGAGACCCCGAGAT<br>GGGCGGCAAACCTAGAAGAAAGAACCCCCAGGAGGGCCTGTATAACGAGCT<br>CCAGAAGGACAAGATGGCCGAGGCCTACAGCGAGATCGGCATGAAGGGCGA<br>AAGAAGAAGAGGCAAGGGCCACGACGGCCTCTACCAGGGCTTAAGCACAGC<br>TACAAAGGACACCTACGACGCCCTGCACATGCAGGCCCTGCCCCCTAGATGA<br>TTAATTAAatcgat |
| 279 | ggtaccCCCGGgCCCATGGCTCTTCCTGTGACAGCTCTTCTGCTGCCCCTGGCCC<br>TGCTTCTGCATGCTGCTAGACCTCAGGTTCAGCTTGTGCAGAGCGGAGCTGA<br>AGTTAAGAAGCCTGGCGCCTCTGTGAAGGTTAGCTGCAAGGCCAGCGGCTAC<br>ACATTCAAGGAATATGGCATCTCCTGGGTTAGGCAGGCTCCCGGCCAAGGCT<br>TAGAATGGATGGGCTGGATCTCCGCCTACTCCGGCCACACCTACTACGCCCA<br>GAAGCTTCAGGGCAGGGTTACCATGACCACCGACACCAGCACCTCTACCGCC<br>TATATGGAGCTGAGGAGCCTGAGATCGGACGACACAGCTGTGTATTACTGCG<br>CCAGAGGCCCCCACTACGACGACTGGTCTGGATTTATCATCTGGTTCGACCC<br>CTGGGGGCAGGGCACCCTGGTCACAGTTTCTTCTGGCTCCACCAGCGGAAGC<br>GGCAAGCCAGGCTCAGGCGAAGGATCTACAAAAGGCGACATCCAAATGACA<br>CAGAGCCCCAGCAGCTTGAGCGCCTCCGTTGGCGACAGAGTTACAATCACCT<br>GCAGGGCCTCTCAGAGCATCAGCAGCTATTTGAATTGGTATCAACAGAAGCC<br>AGGAAAGGCCCCTAAGCTGCTCATCTACGCTGCCAGCTCGCTCCAATCTGGC<br>GTTCCTAGCAGATTTAGCGGCTCCGGCAGCGGCACAGACTTTACTCTTACCA<br>TTAGCTCCCTGCAGCCCGAGGACTTCGCTACCTACTATTGCCAGCAAAGCTA<br>CAGATTCCCTCCCACCTTTGGCCAGGGCACAAAGGTTGAGATCAAGGCAGCT<br>GCTTTCGTGCCTGTGTTCCTGCCTGCTAAGCCCACCACCACTCCTGCTCCAAG<br>ACCTCCTACCCCCGCTCCTACAATCGCCAGCCAACCTCTGAGCCTGAGACCG<br>GAGGCATGCAGACCTGCGGCAGGGGGAGCAGTTCACACAAGAGGCTTGGAC<br>TTCGCTTGCGACATCTACATCTGGGCCCCTCTGGCCGGCACATGCGGAGTTCT<br>TCTTCTTAGCCTGGTGATCACCCTGTACTGCAACCACAGAAACAGATTCAGC<br>GTTGTGAAGAGAGGCCGGAAGAAGCTGCTGTACATCTTCAAGCAGCCCTTCA<br>TGAGACCTGTGCAGACCACACAGGAGGAAGACGGCTGCAGCTGTAGATTCC<br>CCGAGGAAGAGGAGGGCGGCTGTGAGCTGAGAGTTAAGTTCAGCAGGAGCG<br>CCGACGCCCCTGCCTACCAGCAAGGACAGAATCAACTGTACAACGAGCTGA<br>ACCTGGGCAGACGGGAGGAATACGATGTGCTGGACAAGAGGAGAGGCAGA<br>GACCCCGAGATGGGCGGCAAACCTAGAAGAAAGAACCCCCAGGAGGGCCTG<br>TATAACGAGCTCCAGAAGGACAAGATGGCCGAGGCCTACAGCGAGATCGGC<br>ATGAAGGGCGAAAGAAGAAGAGGCAAGGGCCACGACGGCCTCTACCAGGG<br>CTTAAGCACAGCTACAAAGGACACCTACGACGCCCTGCACATGCAGGCCCT<br>GCCCCCTAGATGATTAATTAAatcgat |
| 280 | ggtaccCCCGGgCCCATGGCTCTTCCTGTGACAGCTCTTCTGCTGCCCCTGGCCC<br>TGCTTCTGCATGCTGCTAGACCTCAGGTTCAGTTGCAGCAATGGGGAGCTGG<br>CCTGTTAAAGCCCAGCGAAACCCTGTCCCTCACCTGCGCTGTGTATGGCGGA<br>AGCTTCAGCGGCATCCACTGGAACTGGATCCGGCAGCCTCCTGGCAAAGGCC<br>TTGAATGGATCGGCGATATCGACACCAGCGGCTCCACCAACTACAACCCCAG<br>CCTGAAATCGAGGGTTACAATCTCTGTGGACACAAGCAAGAATCAGTTCTCC<br>CTGAAGCTGAGCAGCGTTACTGCCGCCGACACAGCTGTGTACTATTGCGCCA<br>GACTGGGCAGGAAAGCGCTACCTACCTTGGCATGGATGTGTGGGGGCAGG<br>GCACCACCGTTACTGTTAGCTCTGGCTCAACAAGCGGCAGCGGCAAGCCTGG<br>CTCAGGAGAAGGAAGCACAAAGGGCGACATTGTAATGACTCAGAGCCCCGA<br>CAGCCTGGCCGTTAGCTTAGGCGAAAGGGCTACAATCAATTGCAAGAGCAG<br>CCAGAGCGTTCTGTACAGCAGCAACAACAAGAACTACCTCGCATGGTATCAA<br>CAGAAGCCAGGCCAGCCTCCCAAGCTGCTCATCTACTGGGCTTCCACCAGAG<br>AGAGCGGGGTTCCCGATAGATTCTCCGGCTCCGGTTCTGGAACAGATTTCAC<br>GCTCACAATCAGCAGCTTACAGGCCGAGGATGTGGCTGTCTACTATTGTCAG<br>CAGTTGTACACCTACCCCTTCACATTCGGCGGAGGCACCAAGGTTGAGATCA<br>AGGCAGCTGCTTTCGTGCCTGTGTTCCTGCCTGCTAAGCCCACCACCACTCCT<br>GCTCCAAGACCTCCTACCCCCGCTCCTACAATCGCCAGCCAACCTCTGAGCC<br>TGAGACCGGAGGCATGCAGACCTGCGGCAGGGGGAGCAGTTCACACAAGAG<br>GCTTGGACTTCGCTTGCGACATCTACATCTGGGCCCCTCTGGCCGGCACATG<br>CGGAGTTCTTCTTCTTAGCCTGGTGATCACCCTGTACTGCAACCACAGAAAC<br>AGATTCAGCGTTGTGAAGAGAGGCCGGAAGAAGCTGCTGTACATCTTCAAG<br>CAGCCCTTCATGAGACCTGTGCAGACCACACAGGAGGAAGACGGCTGCAGC<br>TGTAGATTCCCCGAGGAAGAGGAGGGCGGCTGTGAGCTGAGAGTTAAGTTC<br>AGCAGGAGCGCCGACGCCCCTGCCTACCAGCAAGGACAGAATCAACTGTAC<br>AACGAGCTGAACCTGGGCAGACGGGAGGAATACGATGTGCTGGACAAGAGG<br>AGAGGCAGAGACCCCGAGATGGGCGGCAAACCTAGAAGAAAGAACCCCCA |

TABLE 68-continued

Exemplary nucleotide sequences encoding a binding motif, hinge, and 41BB costimulatory domain

| SEQ ID NO | Sequence |
|---|---|
| | GGAGGGCCTGTATAACGAGCTCCAGAAGGACAAGATGGCCGAGGCCTACAG<br>CGAGATCGGCATGAAGGGCGAAAGAAGAAGAGGCAAGGGCCACGACGGCC<br>TCTACCAGGGCTTAAGCACAGCTACAAAGGACACCTACGACGCCCTGCACAT<br>GCAGGCCCTGCCCCCTAGATGATTAATTAAatcgat |
| 281 | ggtaccCCCGGgCCCATGGCTCTTCCTGTGACAGCTCTTCTGCTGCCCCTGGCCC<br>TGCTTCTGCATGCTGCTAGACCTCAGCTTCAGCTCCAAGAGAGCGGACCTGG<br>CTTAGTGAAGCCCAGCGAAACCCTGTCCCTCACCTGCACCGTTTCTGGCGGA<br>AGCATCAGCAGCTCCAGCTATTACTGGGGATGGATCAGGCAGCCCCCTGGCA<br>AGGGTTTAGAATGGATCGGCTCGATATATTACTCCGGCAGCACCTACTATAA<br>CCCCAGCTTGAAGAGCCGGGTTACCATTTCTGTGGACACATCAAAGAACCAG<br>TTCAGCCTGAAGCTGAGCTCTGTGACTGCCGCCGACACAGCTGTGTACTACT<br>GTGCCAGAGAGACAGACTACTCCAGCGGCATGGGCTACGGCATGGATGTGT<br>GGGGACAAGGAACCACCGTTACTGTGAGCAGCGGTTCCACCAGCGGCTCAG<br>GCAAGCCTGGCTCAGGAGAAGGAAGCACCAAGGGGGATATACAGATGACAC<br>AGAGCCCCTCCAGCCTGTCCGCCAGCGTTGGCGATCGTGTAACGATCACCTG<br>CCGGGCCTCTCAGAGCATCAACTCCTACCTCAATTGGTATCAACAGAAGCCA<br>GGCAAGGCCCCCAAATTACTCATCTACGCCGCCAGCAGCTTACAGAGCGGG<br>GTTCCCTCTAGATTCTCCGGCTCCGGTTCTGGAACAGATTTCACCCTCACTAT<br>CTCCAGCTTGCAGCCCGAGGATTTCGCCACTTATTACTGTCAGCAGAGCCTG<br>GCCGACCCCTTCACATTCGGCGGAGGCACAAAGGTTGAGATCAAGGCTGCTG<br>CATTGGATAATGAAAAATCGAACGGCACAATCATTCATGTGAAGGGCAAAC<br>ACCTGTGTCCCAGCCCCTTGTTCCCAGGACCTAGCAAGCCTTTTTGGGTTCTC<br>GTGGTGGTGGGCGGCGTTCTGGCTTGCTACTCTCTACTTGTAACTGTCGCATT<br>TATTATATTCTGGGTTAGATTCAGCGTTGTGAAGAGAGGCCGGAAGAAGCTG<br>CTGTACATCTTCAAGCAGCCCTTCATGAGACCTGTGCAGACCACACAGGAGG<br>AAGACGGCTGCAGCTGTAGATTCCCCGAGGAAGAGGAGGGCGGCTGTGAGC<br>TGAGAGTTAAGTTCAGCAGGAGCGCCGACGCCCCTGCCTACCAGCAAGGAC<br>AGAATCAACTGTACAACGAGCTGAACCTGGGCAGACGGGAGGAATACGATG<br>TGCTGGACAAGAGGAGAGGCAGAGACCCCGAGATGGGCGGCAAACCTAGA<br>AGAAAGAACCCCCAGGAGGGCCTGTATAACGAGCTCCAGAAGGACAAGATG<br>GCCGAGGCCTACAGCGAGATCGGCATGAAGGGCGAAAGAAGAAGAGGCAA<br>GGGCCACGACGGCCTCTACCAGGGCTTAAGCACAGCTACAAAGGACACCTA<br>CGACGCCCTGCACATGCAGGCCCTGCCCCCTAGATGATTAATTAAatcgat |
| 282 | ggtaccCCCGGgCCCATGGCTCTTCCTGTGACAGCTCTTCTGCTGCCCCTGGCCC<br>TGCTTCTGCATGCTGCTAGACCTCAGGTTCAGTTACAAGAGAGCGGACCTGG<br>CTTAGTGAAGCCCAGCGAAACCCTGTCCCTCACCTGCACCGTTTCTGGCGGA<br>AGCATCAGCTCTCCCGACCATTACTGGGGATGGATCAGGCAGCCCCCTGGCA<br>AGGGTTTGGAATGGATCGGCAGCATCTACGCCAGCGGCAGCACATTCTACAA<br>CCCCTCGCTCAAAAGCAGGGTTACTATTTCTGTGGACACAAGCAAAAATCAG<br>TTCAGCCTGAAGCTGAGCTCTGTGACTGCCGCCGACACAGCTGTGTACTACT<br>GTGCCAGAGAGACAGACTACTCCAGCGGGATGGGCTACGGCATGGATGTGT<br>GGGGACAAGGAACCACCGTTACTGTGAGCAGCGGCTCCACAAGCGGCTCAG<br>GCAAGCCTGGCTCAGGAGAAGGAAGCACCAAGGGGGACATTCAAATGACCC<br>AAAGCCCCTCCAGCCTGTCCGCCAGCGTTGGCGATAGGGTTACCATTACCTG<br>CAGGGCCAGCCAAAGCATCAACTCCTACCTAAATTGGTATCAACAGAAGCC<br>AGGCAAGGCCCCCAAACTACTCATTTACGCCGCCAGCAGCTTACAGAGCGG<br>GGTTCCCTCTAGATTCTCCGGCAGCGGTTCTGGAACAGATTTCACTCTCACAA<br>TATCTTCGCTGCAGCCCGAGGATTTCGCTACCTACTATTGCCAGCAATCCCTG<br>GCCGACCCCTTCACATTCGGCGGAGGCACAAAGGTTGAGATCAAGGCTGCTG<br>CATTGGATAATGAAAAATCGAACGGCACAATCATTCATGTGAAGGGCAAAC<br>ACCTGTGTCCCAGCCCCTTGTTCCCAGGACCTAGCAAGCCTTTTTGGGTTCTC<br>GTGGTGGTGGGCGGCGTTCTGGCTTGCTACTCTCTACTTGTAACTGTCGCATT<br>TATTATATTCTGGGTTAGATTCAGCGTTGTGAAGAGAGGCCGGAAGAAGCTG<br>CTGTACATCTTCAAGCAGCCCTTCATGAGACCTGTGCAGACCACACAGGAGG<br>AAGACGGCTGCAGCTGTAGATTCCCCGAGGAAGAGGAGGGCGGCTGTGAGC<br>TGAGAGTTAAGTTCAGCAGGAGCGCCGACGCCCCTGCCTACCAGCAAGGAC<br>AGAATCAACTGTACAACGAGCTGAACCTGGGCAGACGGGAGGAATACGATG<br>TGCTGGACAAGAGGAGAGGCAGAGACCCCGAGATGGGCGGCAAACCTAGA<br>AGAAAGAACCCCCAGGAGGGCCTGTATAACGAGCTCCAGAAGGACAAGATG<br>GCCGAGGCCTACAGCGAGATCGGCATGAAGGGCGAAAGAAGAAGAGGCAA<br>GGGCCACGACGGCCTCTACCAGGGCTTAAGCACAGCTACAAAGGACACCTA<br>CGACGCCCTGCACATGCAGGCCCTGCCCCCTAGATGATTAATTAAatcgat |
| 283 | ggtaccCCCGGgCCCATGGCTCTTCCTGTGACAGCTCTTCTGCTGCCCCTGGCCC<br>TGCTTCTGCATGCTGCTAGACCTCAGATCACATTAAAAGAGAGCGGACCTAC<br>ACTGGTGAAGCCCACCCAAACGCTTACCCTCACCTGCACCTTTAGCGGGTTC<br>AGCCTGGACACAGAGGGCGTTGGCGTTGGATGGATCAGGCAGCCTCCTGGC<br>AAAGCCCTCGAATGGCTTGCCCTCATCTACTTCAACGACCAGAAGAGATACA<br>GCCCCTCCTTAAAAATCTCGGCTCACAATCACCAAAGACACAAGCAAAAATCA<br>GGTTGTGCTCACCATGACCAACATGGACCCTGTGGACACCGCTGTGTACTAC<br>TGTGCCAGAGACACCGGCTACAGCAGATGGTACTACGGGATGGACGTTTGG<br>GGCCAAGGCACCACTGTGACCGTTTCCAGCGGCTCTACAAGCGGCAGCGGG |

TABLE 68-continued

Exemplary nucleotide sequences encoding a binding motif, hinge, and 41BB costimulatory domain

| SEQ ID NO | Sequence |
|---|---|
| | AAACCTGGTTCTGGAGAGGGCAGCACAAAGGGCGACATCCAGATGACGCAA<br>TCCCCCAGCTCTGTGAGCGCCTCTGTGGGAGACAGAGTTACAATCACATGCC<br>GGGCCTCCCAGGGCATCAGCTCTTGGCTGGCATGGTATCAACAGAAGCCTGG<br>CAAGGCTCCCAAGCTGCTCATCTATGCCGCCTCCTCCTTACAATCTGGAGTTC<br>CCTCCAGGTTCAGCGGGAGCGGCTCAGGAACAGACTTCACCCTTACCATCTC<br>TAGCCTGCAACCCGAGGACTTCGCTACTTATTACTGTCAGCAGGCCTACGCC<br>TACCCCATCACATTCGGCGGAGGAACAAAGGTTGAGATCAAGGCTGCTGCAT<br>TGGATAATGAAAAATCGAACGGCACAATCATTCATGTGAAGGGCAAACACC<br>TGTGTCCCAGCCCCTTGTTCCCAGGACCTAGCAAGCCTTTTTGGGTTCTCGTG<br>GTGGTGGGCGGCGTTCTGGCTTGCTACTCTCTACTTGTAACTGTCGCATTTAT<br>TATATTCTGGGTTAGATTCAGCGTTGTGAAGAGAGGCCGGAAGAAGCTGCTG<br>TACATCTTCAAGCAGCCCTTCATGAGACCTGTGCAGACCACACAGGAGGAAG<br>ACGGCTGCAGCTGTAGATTCCCCGAGGAAGAGGAGGGCGGCTGTGAGCTGA<br>GAGTTAAGTTCAGCAGGAGCGCCGACGCCCCTGCCTACCAGCAAGGACAGA<br>ATCAACTGTACAACGAGCTGAACCTGGGCAGACGGGAGGAATACGATGTGC<br>TGGACAAGAGGAGAGGCAGAGACCCCGAGATGGGCGGCAAACCTAGAAGA<br>AAGAACCCCCAGGAGGGCCTGTATAACGAGCTCCAGAAGGACAAGATGGCC<br>GAGGCCTACAGCGAGATCGGCATGAAGGGCGAAAGAAGAAGAGGCAAGGG<br>CCACGACGGCCTCTACCAGGGCTTAAGCACAGCTACAAAGGACACCTACGA<br>CGCCCTGCACATGCAGGCCCTGCCCCCTAGATGATTAATTAAatcgat |
| 284 | ggtaccCCCGGgCCCATGGCTCTTCCTGTGACAGCTCTTCTGCTGCCCCTGGCCC<br>TGCTTCTGCATGCTGCTAGACCTCAGGTTCAGTTACAACAATGGGGAGCTGG<br>CCTGTTAAAGCCCAGCGAAACCCTGTCCCTCACCTGCGCTGTGTATGGCGGA<br>AGCTTCCAGAAATACTACTGGAGCTGGATCCGGCAGCCTCCCGGCAAAGGCT<br>TAGAATGGATCGGAGAGATAGACACCAGCGGCTTCACCAACTACAACCCCA<br>GCCTGAAATCTAGGGTTACAATCTCTGTGGACACAAGCAAGAATCAGTTCTC<br>CCTGAAGCTGAGCAGCGTTACTGCCGCCGACACAGCTGTGTACTATTGCGCC<br>AGAGTTGGCAGATACAGCTACGGCTACTACATCACCGCCTTCGACATTTGGG<br>GCCAAGGCACCACTGTGACCGTTTCCAGCGGAAGCACTAGCGGCAGCGGGA<br>AACCTGGTTCTGGAGAGGGCTCAACCAAGGGCGACATCGTGATGACACAGA<br>GCCCCGACTCTCTGGCTGTGTCCCTGGGAGAGAGAGCCACCATCAACTGCAA<br>GAGCAGCCAGAGCGTTCTGTACAGCAGCAACAACAAGAACTACCTGGCATG<br>GTATCAACAGAAGCCTGGCCAGCCCCTAAGCTGCTCATCTACTGGGCTTCC<br>ACCAGAGAATCAGGCGTTCCAGACAGGTTCTCCGGCTCGGGTTCAGGCACAG<br>ACTTCACCCTTACCATCTCTTCCCTGCAGGCCGAAGATGTGGCCGTTTACTAC<br>TGTCAGCAGCACTACAGCTTCCCTTTCACATTCGGCGGAGGCACCAAGGTTG<br>AGATCAAGGCTGCTGCATTGGATAATGAAAAATCGAACGGCACAATCATTC<br>ATGTGAAGGGCAAACACCTGTGTCCCAGCCCCTTGTTCCCAGGACCTAGCAA<br>GCCTTTTTGGGTTCTCGTGGTGGTGGGCGGCGTTCTGGCTTGCTACTCTCTAC<br>TTGTAACTGTCGCATTTATTATATTCTGGGTTAGATTCAGCGTTGTGAAGAGA<br>GGCCGGAAGAAGCTGCTGTACATCTTCAAGCAGCCCTTCATGAGACCTGTGC<br>AGACCACACAGGAGGAAGACGGCTGCAGCTGTAGATTCCCCGAGGAAGAGG<br>AGGGCGGCTGTGAGCTGAGAGTTAAGTTCAGCAGGAGCGCCGACGCCCCTG<br>CCTACCAGCAAGGACAGAATCAACTGTACAACGAGCTGAACCTGGGCAGAC<br>GGGAGGAATACGATGTGCTGGACAAGAGGAGAGGCAGAGACCCCGAGATG<br>GGCGGCAAACCTAGAAGAAAGAACCCCCAGGAGGGCCTGTATAACGAGCTC<br>CAGAAGGACAAGATGGCCGAGGCCTACAGCGAGATCGGCATGAAGGGCGA<br>AAGAAGAAGAGGCAAGGGCCACGACGGCCTCTACCAGGGCTTAAGCACAGC<br>TACAAAGGACACCTACGACGCCCTGCACATGCAGGCCCTGCCCCCTAGATGA<br>TTAATTAAatcgat |
| 285 | ggtaccCCCGGgCCCATGGCTCTTCCTGTGACAGCTCTTCTGCTGCCCCTGGCCC<br>TGCTTCTGCATGCTGCTAGACCTCAGGTTCAGTTGCAGCAATGGGGAGCTGG<br>CCTGTTAAAGCCCAGCGAAACCCTGTCCCTCACCTGCGCTGTGTATGGCGGA<br>AGCTTCGAGAAATACTACTGGAGCTGGATCCGGCAGCCTCCCGGCAAAGGCT<br>TAGAATGGATCGGCGAGATTTATCACAGCGGGCTCACCAACTACAACCCCAG<br>CCTGAAATCTCGAGTTACAATCTCTGTGGACACAAGCAAGAATCAGTTCTCC<br>CTGAAGCTGAGCAGCGTTACTGCCGCCGACACAGCTGTGTACTATTGCGCCA<br>GAGTTAGATACGACAGCAGCGACAGCTATTACTACAGCTATGACTACGGCAT<br>GGATGTGTGGGGCAGGGCACCACCGTTACTGTCTCCTCTGGATCTACCAGC<br>GGCAGCGGCAAGCCTGGATCTGGCGAAGGAAGCACAAAGGGCGACATTGTG<br>CTCACCCAGAGCCCCGACAGCCTGGCTGTGTCTTTAGGCGAAAGGGCTACCA<br>TCAACTGCAAGAGCAGCCAGAGCGTTCTGTACAGCAGCAACAACAAGAACT<br>ACCTTGCTTGGTATCAACAGAAGCCTGGCCAGCCCCCTAAGCTGCTCATCTA<br>CTGGGCCTCTAGCAGAGAGAGCGGGGTTCCCGATCGGTTTAGCGGCTCCGGC<br>TCAGGAACCGATTTCACCCTCACTATCTCCAGCCTCCAGGCCGAGGATGTGG<br>CTGTCTACTATTGTCAGCAGAGCTATAGCTTCCCCTGGACATTCGGCGGAGG<br>CACCAAGGTTGAGATCAAGGCTGCTGCATTGGATAATGAAAAATCGAACGG<br>CACAATCATTCATGTGAAGGGCAAACACCTGTGTCCCAGCCCCTTGTTCCCA<br>GGACCTAGCAAGCCTTTTTGGGTTCTCGTGGTGGTGGGCGGCGTTCTGGCTT<br>GCTACTCTCTACTTGTAACTGTCGCATTTATTATATTCTGGGTTAGATTCAGC<br>GTTGTGAAGAGAGGCCGGAAGAAGCTGCTGTACATCTTCAAGCAGCCCTTCA<br>TGAGACCTGTGCAGACCACACAGGAGGAAGACGGCTGCAGCTGTAGATTCC |

TABLE 68-continued

Exemplary nucleotide sequences encoding a binding motif, hinge, and 41BB costimulatory domain

| SEQ ID NO | Sequence |
|---|---|
| | CCGAGGAAGAGGAGGGCGGCTGTGAGCTGAGAGTTAAGTTCAGCAGGAGCG<br>CCGACGCCCCTGCCTACCAGCAAGGACAGAATCAACTGTACAACGAGCTGA<br>ACCTGGGCAGACGGGAGGAATACGATGTGCTGGACAAGAGGAGAGGCAGA<br>GACCCCGAGATGGGCGGCAAACCTAGAAGAAGAACCCCCAGGAGGGCCTG<br>TATAACGAGCTCCAGAAGGACAAGATGGCCGAGGCCTACAGCGAGATCGGC<br>ATGAAGGGCGAAAGAAGAAGAGGCAAGGGCCACGACGGCCTCTACCAGGG<br>CTTAAGCACAGCTACAAAGGACACCTACGACGCCCTGCACATGCAGGCCCT<br>GCCCCCTAGATGATTAATTAAatcgat |
| 286 | ggtaccCCCGGgCCCATGGCTCTTCCTGTGACAGCTCTTCTGCTGCCCCTGGCCC<br>TGCTTCTGCATGCTGCTAGACCTCAGGTTCAGTTACAACAATGGGGAGCTGG<br>CCTGTTAAAGCCCAGCGAAACCCTGTCCCTCACCTGCGCTGTGTATGGCGGA<br>AGCTTCAGCCGCTATGTGTGGAGCTGGATCCGGCAGCCTCCTGGCAAAGGCC<br>TTGAATGGATCGGAGAGATAGACAGCAGCGGCAAGACCAACTACAACCCCA<br>GCCTGAAATCACGCGTTACAATCTCTGTGGACACAAGCAAGAATCAGTTCTC<br>CCTGAAGCTGAGCAGCGTTACTGCCGCCGACACAGCTGTGTACTATTGCGCC<br>AGAGTTAGATACGACAGCTCCGACAGCTATTACTACAGCTATGACTACGGCA<br>TGGATGTGTGGGGCAGGGCACCACCGTTACAGTTAGCTCTGGAAGCACCA<br>GCGGCTCCGGCAAGCCTGGATCTGGTGAAGGAAGCACAAAGGGCGACATTG<br>TGCTCACCCAGAGCCCCGACAGCCTGGCTGTGTCTTTAGGCGAAAGGGCTAC<br>CATCAACTGCAAGAGCAGCCAGAGCGTTCTGTACAGCAGCAACAACAAGAA<br>CTACCTTGCATGGTATCAACAGAAGCCTGGCCAGCCTCCCAAGCTGCTCATC<br>TACTGGGCCTCTAGCAGAGAGAGCGGGGTTCCCGATCGCTTTAGCGGCAGCG<br>GTTCTGGCACCGATTTCACTCTTACAATCAGCAGCTTACAGGCCGAGGATGT<br>GGCTGTCTACTATTGTCAGCAGAGCTATAGCTTCCCCTGGACATTCGGCGGA<br>GGCACCAAGGTTGAGATCAAGGCTGCTGCATTGGATAATGAAAAATCGAAC<br>GGCACAATCATTCATGTGAAGGGCAAACACCTGTGTCCCAGCCCCTTGTTCC<br>CAGGACCTAGCAAGCCTTTTTGGGTTCTCGTGGTGGTGGGCGGCGTTCTGGC<br>TTGCTACTCTCTACTTGTAACTGTCGCATTTATTATATTCTGGGTTAGATTCA<br>GCGTTGTGAAGAGAGGCCGGAAGAAGCTGCTGTACATCTTCAAGCAGCCCTT<br>CATGAGACCTGTGCAGACCACACAGGAGGAAGACGGCTGCAGCTGTAGATT<br>CCCCGAGGAAGAGGAGGGCGGCTGTGAGCTGAGAGTTAAGTTCAGCAGGAG<br>CGCCGACGCCCCTGCCTACCAGCAAGGACAGAATCAACTGTACAACGAGCT<br>GAACCTGGGCAGACGGGAGGAATACGATGTGCTGGACAAGAGGAGAGGCA<br>GAGACCCCGAGATGGGCGGCAAACCTAGAAGAAAGAACCCCCAGGAGGGC<br>CTGTATAACGAGCTCCAGAAGGACAAGATGGCCGAGGCCTACAGCGAGATC<br>GGCATGAAGGGCGAAAGAAGAAGAGGCAAGGGCCACGACGGCCTCTACCA<br>GGGCTTAAGCACAGCTACAAAGGACACCTACGACGCCCTGCACATGCAGGC<br>CCTGCCCCCTAGATGATTAATTAAatcgat |
| 287 | ggtaccCCCGGgCCCATGGCTCTTCCTGTGACAGCTCTTCTGCTGCCCCTGGCCC<br>TGCTTCTGCATGCTGCTAGACCTCAGGTTCAGTTACAACAATGGGGAGCTGG<br>CCTGTTAAAGCCCAGCGAAACCCTGTCCCTCACCTGCGCTGTGTATGGCGGA<br>AGCTTCAGCGGCTACGCTTGGAGCTGGATTAGCAGCCTCCTGGCAAAGGAC<br>TAGAATGGATCGGAGAGATCGACCACAGAGGCTTCACCAACTACAACCCCA<br>GCCTGAAATCCAGAGTTACAATCTCTGTGGACACAAGCAAGAATCAGTTCTC<br>CCTGAAGCTGAGCAGCGTTACTGCCGCCGACACAGCTGTGTACTATTGCGCC<br>AGGGTTAGATACGACAGCAGCGACAGCTATTACTACAGCTATGACTACGGC<br>ATGGATGTGTGGGGGCAGGGCACCACCGTTACGGTTAGCTCTGGATCTACCA<br>GCGGCAGCGGCAAGCCTGGCTCAGGAGAAGGAAGCACAAAGGGCGACATTG<br>TGCTCACCCAGAGCCCCGACAGCCTGGCCGTTTCTTTAGGCGAAAGGGCTAC<br>CATCAACTGCAAGAGCAGCCAGAGCGTTCTGTACAGCAGCAACAACAAGAA<br>CTACCTTGCATGGTATCAACAGAAGCCAGGCCAGCCTCCCAAGCTGCTCATC<br>TACTGGGCCTCTAGCAGAGAGAGCGGGGTTCCCGATAGATTTTCGGGATCAG<br>GCTCCGGCACCGATTTCACTCTTACGATCAGCAGCTTACAGGCCGAGGATGT<br>GGCTGTCTACTATTGTCAGCAGAGCTATAGCTTCCCCTGGACATTCGGCGGA<br>GGCACCAAGGTTGAGATCAAGGCTGCTGCATTGGATAATGAAAAATCGAAC<br>GGCACAATCATTCATGTGAAGGGCAAACACCTGTGTCCCAGCCCCTTGTTCC<br>CAGGACCTAGCAAGCCTTTTTGGGTTCTCGTGGTGGTGGGCGGCGTTCTGGC<br>TTGCTACTCTCTACTTGTAACTGTCGCATTTATTATATTCTGGGTTAGATTCA<br>GCGTTGTGAAGAGAGGCCGGAAGAAGCTGCTGTACATCTTCAAGCAGCCCTT<br>CATGAGACCTGTGCAGACCACACAGGAGGAAGACGGCTGCAGCTGTAGATT<br>CCCCGAGGAAGAGGAGGGCGGCTGTGAGCTGAGAGTTAAGTTCAGCAGGAG<br>CGCCGACGCCCCTGCCTACCAGCAAGGACAGAATCAACTGTACAACGAGCT<br>GAACCTGGGCAGACGGGAGGAATACGATGTGCTGGACAAGAGGAGAGGCA<br>GAGACCCCGAGATGGGCGGCAAACCTAGAAGAAAGAACCCCCAGGAGGGC<br>CTGTATAACGAGCTCCAGAAGGACAAGATGGCCGAGGCCTACAGCGAGATC<br>GGCATGAAGGGCGAAAGAAGAAGAGGCAAGGGCCACGACGGCCTCTACCA<br>GGGCTTAAGCACAGCTACAAAGGACACCTACGACGCCCTGCACATGCAGGC<br>CCTGCCCCCTAGATGATTAATTAAatcgat |
| 288 | ggtaccCCCGGgCCCATGGCTCTTCCTGTGACAGCTCTTCTGCTGCCCCTGGCCC<br>TGCTTCTGCATGCTGCTAGACCTCAGGTTCAGTTGCAGCAATGGGGAGCTGG<br>CCTGTTAAAGCCCAGCGAAACCCTGTCCCTCACCTGCGCTGTGTATGGCGGA |

TABLE 68-continued

Exemplary nucleotide sequences encoding a binding motif, hinge, and 41BB costimulatory domain

| SEQ ID NO | Sequence |
|---|---|
| | AGCTTCAGCGGCTATTACTGGAGCTGGATCCGGCAGCCTCCTGGAAAAGGAT
TAGAATGGATCGGCGAGATAGACCACAGCGGGAGCACAAACTACAACCCCA
GCCTGAAATCGCGGGTTACAATCTCTGTGGACACAAGCAAGAATCAGTTCTC
CCTGAAGCTGAGCAGCGTTACTGCCGCCGACACAGCTGTGTACTATTGCGCC
AGAGGCGGAGGCTCCTGGTACAGCAACTGGTTCGATCCTTGGGGCAAGGC
ACCATGGTGACCGTTTCCAGCGGCTCTACAAGCGGCAGCGGGAAACCTGGTT
CTGGAGAGGGCAGCACAAAGGGCGACATCCAGATGACACAGAGCCCCAGCA
CCCTTAGCGCCTCTGTGGGAGATAGGGTTACCATTACCTGCAGGGCTTCCCA
GAGCATCAGCAGCTGGCTGGCATGGTATCAACAGAAGCCTGGCAAGGCTCC
CAAGCTGCTCATCTATGACGCCTCCAGCCTGGAAAGCGGGGTTCCCTCCAGA
TTTAGCGGCTCAGGCTCCGGAACAGAGTTCACCCTTACCATCTCTAGCCTGC
AACCCGACGACTTCGCTACTTATTACTGTCAACAAGACAGAAGCTTGCCCCC
CACATTCGGCGGAGGGACCAAGGTTGAGATCAAGGCTGCTGCATTGGATAA
TGAAAAATCGAACGGCACAATCATTCATGTGAAGGGCAAACACCTGTGTCCC
AGCCCCTTGTTCCCAGGACCTAGCAAGCCTTTTTGGGTTCTCGTGGTGGTGGG
CGGCGTTCTGGCTTGCTACTCTCTACTTGTAACTGTCGCATTTATTATATTCTG
GGTTAGATTCAGCGTTGTGAAGAGAGGCCGGAAGAAGCTGCTGTACATCTTC
AAGCAGCCCTTCATGAGACCTGTGCAGACCACACAGGAGGAAGACGGCTGC
AGCTGTAGATTCCCCGAGGAAGAGGAGGGCGGCTGTGAGCTGAGAGTTAAG
TTCAGCAGGAGCGCCGACGCCCCTGCCTACCAGCAAGGACAGAATCAACTG
TACAACGAGCTGAACCTGGGCAGACGGGAGGAATACGATGTGCTGGACAAG
AGGAGAGGCAGAGACCCCGAGATGGGCGGCAAACCTAGAAGAAAGAACCC
CCAGGAGGGCCTGTATAACGAGCTCCAGAAGGACAAGATGGCCGAGGCCTA
CAGCGAGATCGGCATGAAGGGCGAAAGAAGAAGAGGCAAGGGCCACGACG
GCCTCTACCAGGGCTTAAGCACAGCTACAAAGGACACCTACGACGCCCTGC
ACATGCAGGCCCTGCCCCCTAGATGATTAATTAAatcgat |
| 289 | ggtaccCCCGGgCCCATGGCTCTTCCTGTGACAGCTCTTCTGCTGCCCCTGGCCC
TGCTTCTGCATGCTGCTAGACCTCAGGTTCAGCTTGTGCAGAGCGGAGCTGA
AGTTAAGAAGCCTGGCGCCTCTGTGAAGGTTAGCTGCAAGGCCAGCGGCTAC
ACATTCAAGGAATATGGCATCTCCTGGGTTAGGCAGGCTCCCGGCCAAGGCT
TAGAATGGATGGGCTGGATCTCCGCCTACTCCGGCCACACCTACTACGCCCA
GAAGCTTCAGGGCAGGGTTACCATGACCACCGACACCAGCACCTCTACCGCC
TATATGGAGCTGAGGAGCCTGAGATCGGACGACACAGCTGTGTATTACTGCG
CCAGAGGCCCCCACTACGACGACTGGTCTGGATTTATCATCTGGTTCGACCC
CTGGGGGCAGGGCACCCTGGTCACAGTTTCTTCTGGCTCCACCAGCGGAAGC
GGCAAGCCAGGCTCAGGCGAAGGATCTACAAAAGGCGACATCCAAATGACA
CAGAGCCCCAGCAGCTTGAGCGCCTCCGTTGGCGACAGAGTTACAATCACCT
GCAGGGCCTCTCAGAGCATCAGCAGCTATTTGAATTGGTATCAACAGAAGCC
AGGAAAGGCCCCTAAGCTGCTCATCTACGCTGCCAGCTCGCTCCAATCTGGC
GTTCCTAGCAGATTTAGCGGCTCCGGCAGCGGCACAGACTTTACTCTTACCA
TTAGCTCCCTGCAGCCCGAGGACTTCGCTACCTACTATTGCCAGCAAAGCTA
CAGATTCCCTCCCACCTTTGGCCAGGGCACAAAGGTTGAGATCAAGGCTGCT
GCATTGGATAATGAAAAATCGAACGGCACAATCATTCATGTGAAGGGCAAA
CACCTGTGTCCCAGCCCCTTGTTCCCAGGACCTAGCAAGCCTTTTTGGGTTCT
CGTGGTGGTGGGCGGCGTTCTGGCTTGCTACTCTCTACTTGTAACTGTCGCAT
TTATTATATTCTGGGTTAGATTCAGCGTTGTGAAGAGAGGCCGGAAGAAGCT
GCTGTACATCTTCAAGCAGCCCTTCATGAGACCTGTGCAGACCACACAGGAG
GAAGACGGCTGCAGCTGTAGATTCCCCGAGGAAGAGGAGGGCGGCTGTGAG
CTGAGAGTTAAGTTCAGCAGGAGCGCCGACGCCCCTGCCTACCAGCAAGGA
CAGAATCAACTGTACAACGAGCTGAACCTGGGCAGACGGGAGGAATACGAT
GTGCTGGACAAGAGGAGAGGCAGAGACCCCGAGATGGGCGGCAAACCTAG
AAGAAAGAACCCCCAGGAGGGCCTGTATAACGAGCTCCAGAAGGACAAGAT
GGCCGAGGCCTACAGCGAGATCGGCATGAAGGGCGAAAGAAGAAGAGGCA
AGGGCCACGACGGCCTCTACCAGGGCTTAAGCACAGCTACAAAGGACACCT
ACGACGCCCTGCACATGCAGGCCCTGCCCCCTAGATGATTAATTAAatcgat |
| 290 | ggtaccCCCGGgCCCATGGCTCTTCCTGTGACAGCTCTTCTGCTGCCCCTGGCCC
TGCTTCTGCATGCTGCTAGACCTCAGGTTCAGTTGCAGCAATGGGGAGCTGG
CCTGTTAAAGCCCAGCGAAACCCTGTCCCTCACCTGCGCTGTGTATGGCGGA
AGCTTCAGCGGCATCCACTGGAACTGGATCCGGCAGCCTCCTGGCAAAGGCC
TTGAATGGATCGGCGATATCGACACCAGCGGCTCCACCAACTACAACCCCAG
CCTGAAATCGAGGGTTACAATCTCTGTGGACACAAGCAAGAATCAGTTCTCC
CTGAAGCTGAGCAGCGTTACTGCCGCCGACACAGCTGTGTACTATTGCGCCA
GACTGGGCAGGAAAGCGCTACCTACCTTGGCATGGATGTGTGGGGCAGG
GCACCACCGTTACTGTTAGCTCTGGCTCAACAAGCGGCAGCGGCAAGCCTGG
CTCAGGAGAAGGAAGCACAAAGGGCGACATTGTAATGACTCAGAGCCCCGA
CAGCCTGGCCGTTAGCTTAGGCGAAAGGGCTACAATCAATTGCAAGAGCAG
CCAGAGCGTTCTGTACAGCAGCAACAACAAGAACTACCTCGCATGGTATCAA
CAGAAGCCAGGCCAGCCTCCCAAGCTGCTCATCTACTGGGCTTCCACCAGAG
AGAGCGGGGTTCCCGATAGATTCTCCGGCTCCGGTTCTGGAACAGATTTCAC
GCTCACAATCAGCAGCTTACAGGCCGAGGATGTGGCTGTCTACTATTGTCAG
CAGTTGTACACCTACCCCTTCACATTCGGCGGAGGCACCAAGGTTGAGATCA
AGGCTGCTGCATTGGATAATGAAAAATCGAACGGCACAATCATTCATGTGAA |

TABLE 68-continued

Exemplary nucleotide sequences encoding a binding motif, hinge, and 41BB costimulatory domain

| SEQ ID NO | Sequence |
|---|---|
| | GGGCAAACACCTGTGTCCCAGCCCCTTGTTCCCAGGACCTAGCAAGCCTTTT<br>TGGGTTCTCGTGGTGGTGGGCGGCGTTCTGGCTTGCTACTCTCTACTTGTAAC<br>TGTCGCATTTATTATATTCTGGGTTAGATTCAGCGTTGTGAAGAGAGGCCGG<br>AAGAAGCTGCTGTACATCTTCAAGCAGCCCTTCATGAGACCTGTGCAGACCA<br>CACAGGAGGAAGACGGCTGCAGCTGTAGATTCCCCGAGGAAGAGGAGGGCG<br>GCTGTGAGCTGAGAGTTAAGTTCAGCAGGAGCGCCGACGCCCCTGCCTACCA<br>GCAAGGACAGAATCAACTGTACAACGAGCTGAACCTGGGCAGACGGGAGGA<br>ATACGATGTGCTGGACAAGAGGAGAGGCAGAGACCCCGAGATGGGCGGCAA<br>ACCTAGAAGAAAGAACCCCCAGGAGGGCCTGTATAACGAGCTCCAGAAGGA<br>CAAGATGGCCGAGGCCTACAGCGAGATCGGCATGAAGGGCGAAAGAAGAA<br>GAGGCAAGGGCCACGACGGCCTCTACCAGGGCTTAAGCACAGCTACAAAGG<br>ACACCTACGACGCCCTGCACATGCAGGCCCTGCCCCCTAGATGATTAATTAA<br>atcgat |
| 271 | ggtaccCCCGGgCCCATGGCTCTTCCTGTGACAGCTCTTCTGCTGCCCCTGGCCC<br>TGCTTCTGCATGCTGCTAGACCTCAGCTTCAGCTCCAAGAGAGCGGACCTGG<br>CTTAGTGAAGCCCAGCGAAACCCTGTCCCTCACCTGCACCGTTTCTGGCGGA<br>AGCATCAGCAGCTCCAGCTATTACTGGGGATGGATCAGGCAGCCCCCTGGCA<br>AGGGTTTAGAATGGATCGGCTCGATATATTACTCCGGCAGCACCTACTATAA<br>CCCCAGCTTGAAGAGCCGGGTTACCATTTCTGTGGACACATCAAAGAACCAG<br>TTCAGCCTGAAGCTGAGCTCTGTGACTGCCGCCGACACAGCTGTGTACTACT<br>GTGCCAGAGAGACAGACTACTCCAGCGGCATGGGCTACGGCATGGATGTGT<br>GGGGACAAGGAACCACCGTTACTGTGAGCAGCGGTTCCACCAGCGGCTCAG<br>GCAAGCCTGGCTCAGGAGAAGGAAGCACCAAGGGGGATATACAGATGACAC<br>AGAGCCCCTCCAGCCTGTCCGCCAGCGTTGGCGATCGTGTAACGATCACCTG<br>CCGGGCCTCTCAGAGCATCAACTCCTACCTCAATTGGTATCAACAGAAGCCA<br>GGCAAGGCCCCCAAATTACTCATCTACGCCGCCAGCAGCTTACAGAGCGGG<br>GTTCCCTCTAGATTCTCCGGCTCCGGTTCTGGAACAGATTTCACCCTCACTAT<br>CTCCAGCTTGCAGCCCGAGGATTTCGCCACTTATTACTGTCAGCAGAGCCTG<br>GCCGACCCCTTCACATTCGGCGGAGGCACAAAGGTTGAGATCAAGGCAGCT<br>GCTTTCGTGCCTGTGTTCCTGCCTGCTAAGCCCACCACCACTCCTGCTCCAAG<br>ACCTCCTACCCCCGCTCCTACAATCGCCAGCCAACCTCTGAGCCTGAGACCG<br>GAGGCATGCAGACCTGCGGCAGGGGGAGCAGTTCACACAAGAGGCTTGGAC<br>TTCGCTTGCGACATCTACATCTGGGCCCCTCTGGCCGGCACATGCGGAGTTCT<br>TCTTCTTAGCCTGGTGATCACCCTGTACTGCAACCACAGAAACAGATTCAGC<br>GTTGTGAAGAGAGGCCGGAAGAAGCTGCTGTACATCTTCAAGCAGCCCTTCA<br>TGAGACCTGTGCAGACCACACAGGAGGAAGACGGCTGCAGCTGTAGATTCC<br>CCGAGGAAGAGGAGGGCGGCTGTGAGCTGAGAGTTAAGTTCAGCAGGAGCG<br>CCGACGCCCCTGCCTACCAGCAAGGACAGAATCAACTGTACAACGAGCTGA<br>ACCTGGGCAGACGGGAGGAATACGATGTGCTGGACAAGAGGAGAGGCAGA<br>GACCCCGAGATGGGCGGCAAACCTAGAAGAAAGAACCCCCAGGAGGGCCTG<br>TATAACGAGCTCCAGAAGGACAAGATGGCCGAGGCCTACAGCGAGATCGGC<br>ATGAAGGGCGAAAGAAGAAGAGGCAAGGGCCACGACGGCCTCTACCAGGG<br>CTTAAGCACAGCTACAAAGGACACCTACGACGCCCTGCACATGCAGGCCCT<br>GCCCCCTAGATGATTAATTAAatcgat |
| 272 | ggtaccCCCGGgCCCATGGCTCTTCCTGTGACAGCTCTTCTGCTGCCCCTGGCCC<br>TGCTTCTGCATGCTGCTAGACCTCAGGTTCAGTTACAAGAGAGCGGACCTGG<br>CTTAGTGAAGCCCAGCGAAACCCTGTCCCTCACCTGCACCGTTTCTGGCGGA<br>AGCATCAGCTCTCCCGACCATTACTGGGGATGGATCAGGCAGCCCCCTGGCA<br>AGGGTTTGGAATGGATCGGCAGCATCTACGCCAGCGGCAGCACATTCTACAA<br>CCCCTCGCTCAAAAGCAGGGTTACTATTTCTGTGGACACAAGCAAAAATCAG<br>TTCAGCCTGAAGCTGAGCTCTGTGACTGCCGCCGACACAGCTGTGTACTACT<br>GTGCCAGAGAGACAGACTACTCCAGCGGGATGGGCTACGGCATGGATGTGT<br>GGGGACAAGGAACCACCGTTACTGTGAGCAGCGGCTCCACAAGCGGCTCAG<br>GCAAGCCTGGCTCAGGAGAAGGAAGCACCAAGGGGGACATTCAAATGACCC<br>AAAGCCCCTCCAGCCTGTCCGCCAGCGTTGGCGATAGGGTTACCATTACCTG<br>CAGGGCCAGCCAAAGCATCAACTCCTACCTAAATTGGTATCAACAGAAGCC<br>AGGCAAGGCCCCCAAACTACTCATTTACGCCGCCAGCAGCTTACAGAGCGG<br>GGTTCCCTCTAGATTCTCCGGCAGCGGTTCTGGAACAGATTTCACTCTCACAA<br>TATCTTCGCTGCAGCCCGAGGATTTCGCTACCTACTATTGCCAGCAATCCCTG<br>GCCGACCCCTTCACATTCGGCGGAGGCACAAAGGTTGAGATCAAGGCAGCT<br>GCTTTCGTGCCTGTGTTCCTGCCTGCTAAGCCCACCACCACTCCTGCTCCAAG<br>ACCTCCTACCCCCGCTCCTACAATCGCCAGCCAACCTCTGAGCCTGAGACCG<br>GAGGCATGCAGACCTGCGGCAGGGGGAGCAGTTCACACAAGAGGCTTGGAC<br>TTCGCTTGCGACATCTACATCTGGGCCCCTCTGGCCGGCACATGCGGAGTTCT<br>TCTTCTTAGCCTGGTGATCACCCTGTACTGCAACCACAGAAACAGATTCAGC<br>GTTGTGAAGAGAGGCCGGAAGAAGCTGCTGTACATCTTCAAGCAGCCCTTCA<br>TGAGACCTGTGCAGACCACACAGGAGGAAGACGGCTGCAGCTGTAGATTCC<br>CCGAGGAAGAGGAGGGCGGCTGTGAGCTGAGAGTTAAGTTCAGCAGGAGCG<br>CCGACGCCCCTGCCTACCAGCAAGGACAGAATCAACTGTACAACGAGCTGA<br>ACCTGGGCAGACGGGAGGAATACGATGTGCTGGACAAGAGGAGAGGCAGA<br>GACCCCGAGATGGGCGGCAAACCTAGAAGAAAGAACCCCCAGGAGGGCCTG<br>TATAACGAGCTCCAGAAGGACAAGATGGCCGAGGCCTACAGCGAGATCGGC |

TABLE 68-continued

Exemplary nucleotide sequences encoding a binding motif, hinge, and 41BB costimulatory domain

| SEQ ID NO | Sequence |
|---|---|
|  | ATGAAGGGCGAAAGAAGAAGAGGCAAGGGCCACGACGGCCTCTACCAGGG<br>CTTAAGCACAGCTACAAAGGACACCTACGACGCCCTGCACATGCAGGCCCT<br>GCCCCCTAGATGATTAATTAAatcgat |
| 273 | ggtaccCCCGGgCCCATGGCTCTTCCTGTGACAGCTCTTCTGCTGCCCCTGGCCC<br>TGCTTCTGCATGCTGCTAGACCTCAGATCACATTAAAAGAGAGCGGACCTAC<br>ACTGGTGAAGCCCACCCAAACGCTTACCCTCACCTGCACCTTTAGCGGGTTC<br>AGCCTGGACACAGAGGGCGTTGGCGTTGGATGGATCAGGCAGCCTCCTGGC<br>AAAGCCCTCGAATGGCTTGCCCTCATCTACTTCAACGACCAGAAGAGATACA<br>GCCCCTCCTTAAAATCTCGGCTCACAATCACCAAAGACACAAGCAAAAATCA<br>GGTTGTGCTCACCATGACCAACATGGACCCTGTGGACACCGCTGTGTACTAC<br>TGTGCCAGAGACACCGGCTACAGCAGATGGTACTACGGGATGGACGTTTGG<br>GGCCAAGGCACCACTGTGACCGTTTCCAGCGGCTCTACAAGCGGCAGCGGG<br>AAACCTGGTTCTGGAGAGGGCAGCACAAAGGGCGACATCCAGATGACGCAA<br>TCCCCCAGCTCTGTGAGCGCCTCTGTGGGAGACAGAGTTACAATCACATGCC<br>GGGCCTCCCAGGGCATCAGCTCTTGGCTGGCATGGTATCAACAGAAGCCTGG<br>CAAGGCTCCCAAGCTGCTCATCTATGCCGCCTCCTCCTTACAATCTGGAGTTC<br>CCTCCAGGTTCAGCGGGAGCGGCTCAGGAACAGACTTCACCCTTACCATCTC<br>TAGCCTGCAACCCGAGGACTTCGCTACTTATTACTGTCAGCAGGCCTACGCC<br>TACCCCATCACATTCGGCGGAGGAACAAAGGTTGAGATCAAGGCAGCTGCTT<br>TCGTGCCTGTGTTCCTGCCTGCTAAGCCCACCACCACTCCTGCTCCAAGACCT<br>CCTACCCCCGCTCCTACAATCGCCAGCCAACCTCTGAGCCTGAGACCGGAGG<br>CATGCAGACCTGCGGCAGGGGGAGCAGTTCACACAAGAGGCTTGGACTTCG<br>CTTGCGACATCTACATCTGGGCCCCTCTGGCCGGCACATGCGGAGTTCTTCTT<br>CTTAGCCTGGTGATCACCCTGTACTGCAACCACAGAAACAGATTCAGCGTTG<br>TGAAGAGAGGCCGGAAGAAGCTGCTGTACATCTTCAAGCAGCCCTTCATGA<br>GACCTGTGCAGACCACACAGGAGGAAGACGGCTGCAGCTGTAGATTCCCCG<br>AGGAAGAGGAGGGCGGCTGTGAGCTGAGAGTTAAGTTCAGCAGGAGCGCCG<br>ACGCCCCTGCCTACCAGCAAGGACAGAATCAACTGTACAACGAGCTGAACC<br>TGGGCAGACGGGAGGAATACGATGTGCTGGACAAGAGGAGAGGCAGAGAC<br>CCCGAGATGGGCGGCAAACCTAGAAGAAAGAACCCCCAGGAGGGCCTGTAT<br>AACGAGCTCCAGAAGGACAAGATGGCCGAGGCCTACAGCGAGATCGGCATG<br>AAGGGCGAAAGAAGAAGAGGCAAGGGCCACGACGGCCTCTACCAGGGCTTA<br>AGCACAGCTACAAAGGACACCTACGACGCCCTGCACATGCAGGCCCTGCCC<br>CCTAGATGATTAATTAAatcgat |
| 274 | ggtaccCCCGGgCCCATGGCTCTTCCTGTGACAGCTCTTCTGCTGCCCCTGGCCC<br>TGCTTCTGCATGCTGCTAGACCTCAGGTTCAGTTACAACAATGGGGAGCTGG<br>CCTGTTAAAGCCCAGCGAAACCCTGTCCCTCACCTGCGCTGTGTATGGCGGA<br>AGCTTCCAGAAATACTACTGGAGCTGGATCCGGCAGCCTCCCGGCAAAGGCT<br>TAGAATGGATCGGAGAGATAGACACCAGCGGCTTCACCAACTACAACCCCA<br>GCCTGAAATCTAGGGTTACAATCTCTGTGGACACAAGCAAGAATCAGTTCTC<br>CCTGAAGCTGAGCAGCGTTACTGCCGCCGACACAGCTGTGTACTATTGCGCC<br>AGAGTTGGCAGATACAGCTACGGCTACTACATCACCGCCTTCGACATTTGGG<br>GCCAAGGCACCACTGTGACCGTTTCCAGCGGAAGCACTAGCGGCAGCGGGA<br>AACCTGGTTCTGGAGAGGGCTCAACCAAGGGCGACATCGTGATGACACAGA<br>GCCCCGACTCTCTGGCTGTGTCCCTGGGAGAGAGAGCCACCATCAACTGCAA<br>GAGCAGCCAGAGCGTTCTGTACAGCAGCAACAACAAGAACTACCTGGCATG<br>GTATCAACAGAAGCCTGGCCAGCCCCTAAGCTGCTCATCTACTGGGCTTCC<br>ACCAGAGAATCAGGCGTTCCAGACAGGTTCTCCGGCTCGGGTTCAGGCACAG<br>ACTTCACCCTTACCATCTCTTCCCTGCAGGCCGAAGATGTGGCCGTTTACTAC<br>TGTCAGCAGCACTACAGCTTCCCTTTCACATTCGGCGGAGGCACCAAGGTTG<br>AGATCAAGGCAGCTGCTTTCGTGCCTGTGTTCCTGCCTGCTAAGCCCACCAC<br>CACTCCTGCTCCAAGACCTCCTACCCCCGCTCCTACAATCGCCAGCCAACCT<br>CTGAGCCTGAGACCGGAGGCATGCAGACCTGCGGCAGGGGGAGCAGTTCAC<br>ACAAGAGGCTTGGACTTCGCTTGCGACATCTACATCTGGGCCCCTCTGGCCG<br>GCACATGCGGAGTTCTTCTTCTTAGCCTGGTGATCACCCTGTACTGCAACCAC<br>AGAAACAGATTCAGCGTTGTGAAGAGAGGCCGGAAGAAGCTGCTGTACATC<br>TTCAAGCAGCCCTTCATGAGACCTGTGCAGACCACACAGGAGGAAGACGGC<br>TGCAGCTGTAGATTCCCCGAGGAAGAGGAGGGCGGCTGTGAGCTGAGAGTT<br>AAGTTCAGCAGGAGCGCCGACGCCCCTGCCTACCAGCAAGGACAGAATCAA<br>CTGTACAACGAGCTGAACCTGGGCAGACGGGAGGAATACGATGTGCTGGAC<br>AAGAGGAGAGGCAGAGACCCCGAGATGGGCGGCAAACCTAGAAGAAAGAA<br>CCCCCAGGAGGGCCTGTATAACGAGCTCCAGAAGGACAAGATGGCCGAGGC<br>CTACAGCGAGATCGGCATGAAGGGCGAAAGAAGAAGAGGCAAGGGCCACG<br>ACGGCCTCTACCAGGGCTTAAGCACAGCTACAAAGGACACCTACGACGCCC<br>TGCACATGCAGGCCCTGCCCCCTAGATGATTAATTAAatcgat |

Example 21

TABLE 69

Exemplary anti-CD20/anti-CD19 bicistronic CAR nucleotide and amino acid sequences set forth in SEQ ID NOs: 291 and 292.

| | |
|---|---|
| SEQ ID NO: 291 | ATGCTGCTGCTGGTGACATCTCTGCTGCTTTGCGAGCTGCCCCACCCT GCCTTCCTGCTTATCCCCGACATTCAGATGACCCAGACCACCAGCAGC CTGAGCGCCAGCTTAGGAGATAGAGTTACCATCAGCTGCAGAGCCAG CCAGGACATCAGCAAATACCTGAACTGGTATCAGCAGAAGCCCGACG GCACTGTGAAACTGCTTATTTACCACACCTCCAGACTGCACAGCGGCG TTCCCAGCAGATTCTCTGGCAGCGGATCTGGAACCGACTACAGCCTCA CCATCTCCAACCTGGAGCAGGAGGACATCGCCACCTACTTCTGCCAGC AGGGGCAACACACTGCCCTACACCTTCGGAGGAGGAACCAAGCTGGAG ATCACCGGGGGAGGAGGCTCTGGAGGCGGCGGATCAGGAGGAGGGG GATCTGAGGTTAAGCTGCAGGAGAGCGGCCCTGGCCTGGTGGCTCCT AGCCAATCTTTATCTGTGACCTGCACTGTGTCCGGCGTTAGCCTGCCC GATTATGGCGTTTCCTGGATCAGACAGCCCCCCAGAAAGGGCCTGGA ATGGCTGGGCGTTATCTGGGGCAGCGAGACCACATACTACAACAGCG CCCTGAAGAGCAGACTTACGATTATCAAGGACAACAGCAAGAGCCAG GTTTTCCTGAAGATGAACAGCCTGCAGACCGACGACACCGCCATCTAC TACTGCGCTAAGCACTACTACTACGGCGGCAGCTACGCCATGGACTAC TGGGGCCAGGGAACAAGCGTTACCGTTAGCAGCGCTGCTGCACTGGA CAACGAGAAGAGCAACGGCACCATCATCCACGTTAAGGGCAAGCACC TGTGCCCCAGCCCTCTGTTCCCTGGACCTTCTAAGCCTTTCTGGGTTCT GGTGGTGGTCGGCGGCGTTTTAGCCTGTTACAGCCTTCTGGTGACTGT GGCCTTCATCATCTTTTGGGTTAGAAGCAAGAGAAGCAGACTGCTCCA CAGCGACTACATGAACATGACCCCAGACGGCCTGGCCCCACCAGAA AGCATTACCAGCCCTACGCTCCTCCCAGAGACTTCGCCGCCTACAGGA GCAGAGTTAAATTCAGCAGATCCGCCGATGCCCCCGCTTACCAACAG GGACAAAACCAGCTGTACAATGAGCTCAACCTGGGGAGAAGAGAAG AATACGACGTTCTGGATAAGAGAAGGGGCAGAGATCCCGAAATGGGG GGCAAGCCCAGACGCAAGAACCCTCAGGAGGGGCTTTACAACGAACT GCAGAAGGATAAGATGGCTGAGGCTTACTCGGAGATTGGGATGAAGG GGGAGAGAAGGCGGGGCAAGGGACACGATGGCTTATACCAGGGGCT GAGCACCGCCACCAAGGACACATACGACGCTCTTCATATGCAGGCTC TGCCCCCAAGAAGGGCTAAGAGATCTGGCTCTGGCGAGGGCAGAGGC AGCTTGCTTACATGTGGCGATGTGGAGGAGAACCCCGGGCCCATGGC TCTTCCTGTGACAGCTCTTCTGCTGCCCCTGGCCCTGCTTCTGCATGCT GCTAGACCTCAGCTTCAGCTCCAAGAGAGCGGACCTGGCTTAGTGAA GCCCAGCGAAACCCTGTCCCTCACCTGCACCGTTTCTGGCGGAAGCAT CAGCAGCTCCAGCTATTACTGGGGATGGATCAGGCAGCCCCCTGGCA AGGGTTTAGAATGGATCGGCTCGATATATTACTCCGGCAGCACCTACT ATAACCCCAGCTTGAAGAGCCGGGTTACCATTTCTGTGGACACATCAA AGAACCAGTTCAGCCTGAAGCTGAGCTCTGTGACTGCCGCCGACACA GCTGTGTACTACTGTGCCAGAGAGACAGACTACTCCAGCGGCATGGG CTACGGCATGGATGTGTGGGGACAAGGAACCACCGTTACTGTGAGCA GCGGTTCCACCAGCGGCTCAGGCAAGCCTGGCTCAGGAGAAGGAAGC ACCAAGGGGGATATACAGATGACACAGAGCCCCTCCAGCCTGTCCGC CAGCGTTGGCGATCGTGTAACGATCACCTGCCGGGCCTCTCAGAGCAT CAACTCCTACCTCAATTGGTATCAACAGAAGCCAGGCAAGGCCCCCA AATTACTCATCTACGCCGCCAGCAGCTTACAGAGCGGGGTTCCCTCTA GATTCTCCGGCTCCGGTTCTGGAACAGATTTCACCCTCACTATCTCCA GCTTGCAGCCCGAGGATTTCGCCACTTATTACTGTCAGCAGAGCCTGG CCGACCCCTTCACATTCGGCGGAGGCACAAAGGTTGAGATCAAGGCA GCTGCTTTCGTGCCTGTGTTCCTGCCTGCTAAGCCCACCACCACTCCTG CTCCAAGACCTCCTACCCCCGCTCCTACAATCGCCAGCCAACCTCTGA GCCTGAGACCGGAGGCATGCAGACCTGCGGCAGGGGGAGCAGTTCAC ACAAGAGGCTTGGACTTCGCTTGCAGACATCTACATCTGGGCCCCTCTG GCCGGCACATGCGGAGTTCTTCTTCTTAGCCTGGTGATCACCCTGTAC TGCAACCACAGAAACAGATTCAGCGTTGTGAAGAGAGGCCGGAAGAA GCTGCTGTACATCTTCAAGCAGCCCTTCATGAGACCTGTGCAGACCAC ACAGGAGGAAGACGGCTGCAGCTGTAGATTCCCCGAGGAAGAGGAG GGCGGCTGTGAGCTGAGAGTTAAGTTCAGCAGGAGCGCCGACGCCCC TGCCTACCAGCAAGGACAGAATCAACTGTACAACGAGCTGAACCTGG GCAGACGGGAGGAATACGATGTGCTGGACAAGAGGAGAGGCAGAGA CCCCGAGATGGGCGGCAAACCTAGAAGAAAGAACCCCCAGGAGGGC CTGTATAACGAGCTCCAGAAGGACAAGATGGCCGAGGCCTACAGCGA GATCGGCATGAAGGGCAAAGAAGAAGAGGCAAGGGCCACGACGGC CTCTACCAGGGCTTAAGCACAGCTACAAAGGACACCTACGACGCCCT GCACATGCAGGCCCTGCCCCCTAGATGA |
| SEQ ID NO: 292 | MLLLVTSLLLCELPHPAFLLIPDIQMTQTTSSLSASLGDRVTISCRASQDIS KYLNWYQQKPDGTVKLLIYHTSRLHSGVPSRFSGSGSGTDYSLTISNLEQ EDIATYFCQQGNTLPYTFGGGTKLEITGGGSGGGGSGGGGSEVKLQESG PGLVAPSQSLSVTCTVSGVSLPDYGVSWIRQPPRKGLEWLGVIWGSETTY YNSALKSRLTIIKDNSKSQVFLKMNSLQTDDTAIYYCAKHYYYGGSYAM DYWGQGTSVTVSSAAALDNEKSNGTIIHVKGKHLCPSPLFPGPSKPFWVL VVVGGVLACYSLLVTVAFIIFWVRSKRSRLLHSDYMNMTPRRPGPTRKH YQPYAPPRDFAAYRSRVKFSRSADAPAYQQGQNQLYNELNLGRREEYD |

TABLE 69-continued

Exemplary anti-CD20/anti-CD19 bicistronic CAR nucleotide and amino acid sequences set forth in SEQ ID NOs: 291 and 292.

```
VLDKRRGRDPEMGGKPRRKNPQEGLYNELQKDKMAEAYSEIGMKGERR
RGKGHDGLYQGLSTATKDTYDALHMQALPPRRAKRSGSGEGRGSLLTC
GDVEENPGPMALPVTALLLPLALLLHAARPQLQLQESGPGLVKPSETLSL
TCTVSGGSISSSSYYVVGWIRQPPGKGLEWIGSIYYSGSTYYNPSLKSRVTI
SVDTSKNQFSLKLSSVTAADTAVYYCARETDYSSGMGYGMDVWGQGTT
VTVSSGSTSGSGKPGSGEGSTKGDIQMTQSPSSLSASVGDRVTITCRASQS
INSYLNWYQQKPGKAPKLLIYAASSLQSGVPSRFSGSGSGTDFTLTISSLQ
PEDFATYYCQQSLADPFTFGGGTKVEIKAAAFVPVFLPAKPTTTPAPRPPT
PAPTIASQPLSLRPEACRPAAGGAVHTRGLDFACDIYIWAPLAGTCGVLL
LSLVITLYCNHRNRFSVVKRGRKKLLYIFKQPFMRPVQTTQEEDGCSCRF
PEEEEGGCELRVKFSRSADAPAYQQGQNQLYNELNLGRREEYDVLDKRR
GRDPEMGGKPRRKNPQEGLYNELQKDKMAEAYSEIGMKGERRRGKGH
DGLYQGLSTATKDTYDALHMQALPPR
```

Example 22

TABLE 70

Exemplary anti-CD20/anti-CD19 bispecific CAR and components thereof

| | SEQ ID NO: | Sequence |
|---|---|---|
| Bispecific CAR (nt sequence) | 293 | ATGCTTCTCCTGGTGACAAGCCTTCTGCTCTGTGAGTTAC<br>CACACCCAGCATTCCTCCTGATCCCAGACATCCAGATGA<br>CCCAGTCTCCATCCTCCCTGTCTGCATCTGTAGGAGACAG<br>AGTCACCATCACTTGCCGGGCAAGTCAGAGCATTAACAG<br>CTATTTAAATTGGTATCAGCAGAAACCAGGGAAAGCCCC<br>TAAGCTCCTGATCTATGCTGCATCCAGTTTGCAAAGTGGG<br>GTCCCATCAAGGTTCAGTGGCAGTGGATCTGGGACAGAT<br>TTCACTCTCACCATCAGCAGTCTGCAACCTGAAGATTTTG<br>CAACTTACTACTGCCAGCAAAGCCTCGCCGACCCTTTCAC<br>TTTTGGCGGAGGGACCAAGGTTGAGATCAAAGGGGGGG<br>GTGGAAGTGGGAAGCCTGGCAGCGGCGAGGGCGGCAGT<br>CAGCTGCAGCTGCAGGAGTCGGGCCCAGGACTGGTGAAG<br>CCTTCGGAGACCCTGTCCCTCACCTGCACTGTCTCTGGTG<br>GCTCCATCAGCAGTAGTAGTTACTACTGGGGCTGGATCC<br>GCCAGCCCCAGGGAAGGGGCTGGAGTGGATTGGGAGT<br>ATCTATTATAGTGGGAGCACCTACTACAACCCGTCCCTCA<br>AGAGTCGAGTCACCATATCCGTAGACACGTCCAAGAACC<br>AGTTCTCCCTGAAGCTGAGTTCTGTGACCGCCGCAGACA<br>CGGCCGGTGTACTACTGCGCCAGAGAGACTGACTACAGCA<br>GCGGAATGGGATACGGAATGGACGTATGGGGCCAGGGA<br>ACAACTGTCACCGTCTCCTCAGGCGGTGGCGGCAGTGGG<br>AAGCCTGGCAGCGATATTCAAATGACCCAGTCCCCGTCC<br>TCCCTGAGTGCCTCCGTCGGTGACCGTGTTACGATTACCT<br>GCCGTGCGAGCCAAGACATCTCTAAATACCTGAACTGGT<br>ATCAGCAAAAACCGGATCAGGCACCGAAACTGCTGATCA<br>AACATACCTCACGTCTGCACTCGGGTGTGCCGAGCCGCTT<br>TAGTGGTTCCGGCTCAGGTACCGATTACACCCTGACGATC<br>AGCTCTCTGCAGCCGGAAGACTTTGCCACGTATTACTGCC<br>AGCAAGGTAATACCCTGCCGTATACGTTCGGCCAAGGTA<br>CCAAACTGGAAATCAAAGGGGGGGGTGGAAGTGGGGGC<br>GGTGGCAGCGGCGGTGGCGGCAGTGAAGTGCAGCTGGTT<br>GAAAGCGGTGGTGGTCTGGTTCAACCGGGTCGTTCCCTG<br>CGTCTGTCATGTACGGCGAGTGGTGTCTCCCTGCCGGACT<br>ATGGCGTGTCCTGGATTCGTCAGCCGCCGGGTAAAGGCC<br>TGGAATGGATTGGTGTCATCTGGGGCAGTGAAACCACGT<br>ATTACAACTCGGCCCTGAAAAGCCGTTTCACCATCTCTCG<br>CGATAACAGTAAAAATACGCTGTACCTGCAGATGAATAG<br>CCTGCGCGCGGAAGACACCGCCGTTTACTACTGCGCAAA<br>ACATTACTACTACGGTGGCAGCTATGCTATGGATTACTGG<br>GGTCAAGGCACGCTGGTCACCGTTTCGTCAGCCGCTGCC<br>CTAGACAATGAGAAGAGCAATGGAACCATTATCCATGTG<br>AAAGGGAAACACCTTTGTCCAAGTCCCCTATTTCCCGGA<br>CCTTCTAAGCCCTTTTGGGTGCTGGTGGTGGTTGGGGGAG<br>TCCTGGCTTGCTATAGCTTGCTAGTAACAGTGGCCTTTAT<br>TATTTTCTGGGTGAGGAGTAAGAGGAGCAGGCTCCTGCA<br>CAGTGACTACATGAACATGACTCCCCGCCGCCCCGGGCC<br>CACCCGCAAGCATTACCAGCCCTATGCCCCACCACGCGA<br>CTTCGCAGCCTATCGCTCCAGAGTGAAGTTCAGCAGGAG<br>CGCAGACGCCCCCGCGTACCAGCAGGGCCAGAACCAGCT<br>CTATAACGAGCTCAATCTAGGACGAAGAGAGGAGTACGA |

TABLE 70-continued

Exemplary anti-CD20/anti-CD19 bispecific CAR and components thereof

| | SEQ ID NO: | Sequence |
|---|---|---|
| | | TGTTTTGGACAAGAGACGTGGCCGGGACCCTGAGATGGG GGGAAAGCCGAGAAGGAAGAACCCTCAGGAAGGCCTGT ACAATGAACTGCAGAAAGATAAGATGGCGGAGGCCTAC AGTGAGATTGGGATGAAAGGCGAGCGCCGGAGGGGCAA GGGGCACGATGCCTTTACCAGGGTCTCAGTACAGCCAC CAAGGACACCTACGACGCCCTTCACATGCAGGCCCTGCC CCCTCGATGA |
| Bispecific CAR (AA sequence) | 294 | MLLLVTSLLLCELPHPAFLLIPDIQMTQSPSSLSASVGDRVTI TCRASQSINSYLNWYQQKPGKAPKLLIYAASSLQSGVPSRFS GSGSGTDFTLTISSLQPEDFATYYCQQSLADPFTFGGGTKVE IKGGGGSGKPGSGEGGSQLQLQESGPGLVKPSETLSLTCTVS GGGSISSSSYYWGWIRQPPGKGLEWIGSIYYSGSTYYNPSLKS RVTISVDTSKNQFSLKLSSVTAADTAVYYCARETDYSSGMG YGMDVWGQGTTVTVSSGGGGSGKPGSDIQMTQSPSSLSAS VGDRVTITCRASQDISKYLNWYQQKPDQAPKLLIKHTSRLH SGVPSRFSGSGSGTDYTLTISSLQPEDFATYYCQQGNTLPYT FGQGTKLEIKGGGGSGGGGSGGGGSEVQLVESGGGLVQPG RSLRLSCTASGVSLPDYGVSWIRQPPGKGLEWIGVIWGSETT YYNSALKSRFTISRDNSKNTLYLQMNSLRAEDTAVYYCAK HYYYGGSYAMDYWGQGTLVTVSSAAALDNEKSNGTIIHV KGKHLCPSPLFPGPSKPFWVLVVVGGVLACYSLLVTVAFIIF WVRSKRSRLLHSDYMNMTPRRPGPTRKHYQPYAPPRDFAA YRSRVKFSRSADAPAYQQGQNQLYNELNLGRREEYDVLDK RRGRDPEMGGKPRRKNPQEGLYNELQKDKMAEAYSEIGM KGERRRGKGHDGLYQGLSTATKDTYDALHMQALPPR |
| CSF2RA Signal Peptide | 295 | MLLLVTSLLLCELPHPAFLLIP |
| Ab3 VL | 296 | DIQMTQSPSSLSASVGDRVTITCRASQSINSYLNWYQQKPG KAPKLLIYAASSLQSGVPSRFSGSGSGTDFTLTISSLQPEDFA TYYCQQSLADPFTFGGGTKVEIK |
| KL2 linker | 297 | GGGGSGKPGSGEGGS |
| Ab3 VH | 298 | QLQLQESGPGLVKPSETLSLTCTVSGGSISSSSYYWGWIRQP PGKGLEWIGSIYYSGSTYYNPSLKSRVTISVDTSKNQFSLKL SSVTAADTAVYYCARETDYSSGMGYGMDVWGQGTTVTVS S |
| truncated linker | 299 | GGGGSGKPGS |
| Anti-CD19 VL | 300 | DIQMTQSPSSLSASVGDRVTITCRASQDISKYLNWYQQKPDQAPK LLIKHTSRLHSGVPSRFSGSGSGTDYTLTISSLQPEDFATYYCQQG NTLPYTFGQGTKLEIK |
| G4S linker | 301 | GGGGSGGGGSGGGGS |
| Anti-CD19 VH | 302 | EVQLVESGGGLVQPGRSLRLSCTASGVSLPDYGVSWIRQPPGKGL EWIGVIWGSETTYYNSALKSRFTISRDNSKNTLYLQMNSLRAEDT AVYYCAKHYYYGGSYAMDYWGQGTLVTVSS |
| CD28T extracellular region | 303 | LDNEKSNGTIIHVKGKHLCPSPLFPGPSKP |
| CD28 transmembrane region | 304 | FWVLVVVGGVLACYSLLVTVAFIIFWV |
| CD28 intracellular region | 305 | RSKRSRLLHSDYMNMTPRRPGPTRKHYQPYAPPRDFAAYR S |
| CD3z | 306 | RVKFSRSADAPAYQQGQNQLYNELNLGRREEYDVLDKRRG RDPEMGGKPRRKNPQEGLYNELQKDKMAEAYSEIGMKGE RRRGKGHDGLYQGLSTATKDTYDALHMQALPPR |

Example 23

TABLE 71

Exemplary linkers

| | SEQ ID NO: | Sequence |
|---|---|---|
| G4S (G4Sx1) | 307 | GGGGS |
| G4Sx2 | 308 | GGGGSGGGGS |
| G4Sx3 | 309 | GGGGSGGGGSGGGGS |
| G4Sx4 | 310 | GGGGSGGGGSGGGGSGGGGS |
| IgA | 311 | PSTPPTPSPSTPPTPSPS |
| PAPAP | 312 | PAPAP (optionally comprising 1, 2, 3, 4, 5, 6, 7, 8, 9, or 10 adjacent copies of PAPAP) |
| EAAAK | 313 | EAAAK (optionally comprising 1, 2, 3, 4, 5, 6, 7, 8, 9, or 10 adjacent copies of EAAAK) |

While a number of embodiments have been described, it is apparent that the disclosure and examples may provide other embodiments that utilize or are encompassed by the compositions and methods described herein. Therefore, it will be appreciated that the scope of is to be defined by that which may be understood from the disclosure and the appended claims rather than by the embodiments that have been represented by way of example.

What is claimed is:

1. An antibody or antigen binding fragment thereof that binds CD20, wherein the antibody or antigen binding fragment thereof comprises a heavy chain variable domain (VH) comprising complementarity determining regions HCDR1, HCDR2 and HCDR3, and a light chain variable domain (VL) comprising complementarity determining regions LCDR1, LCDR2 and LCDR3, wherein:

(i) the HCDR1 comprises an amino acid sequence selected from the group consisting of SEQ ID NOs: 3-5; the HCDR2 comprises an amino acid sequence selected from the group consisting of SEQ ID NOs: 6-8; the HCDR3 comprises an amino acid sequence selected from the group consisting of SEQ ID NOs: 9-11; the LCDR1 comprises an amino acid sequence selected from the group consisting of SEQ ID NOs: 14-16; the LCDR2 comprises an amino acid sequence selected from the group consisting of SEQ ID NOs: 17-19; and the LCDR3 comprises an amino acid sequence selected from the group consisting of SEQ ID NOs: 20-22;

(ii) the HCDR1 comprises an amino acid sequence selected from the group consisting of SEQ ID NOs: 25-27; the HCDR2 comprises an amino acid sequence selected from the group consisting of SEQ ID NOs: 28-30; the HCDR3 comprises an amino acid sequence selected from the group consisting of SEQ ID NOs: 31-33; the LCDR1 comprises an amino acid sequence selected from the group consisting of SEQ ID NOs: 36-38; the LCDR2 comprises an amino acid sequence selected from the group consisting of SEQ ID NOs: 39-41; and the LCDR3 comprises an amino acid sequence selected from the group consisting of SEQ ID NOs: 42-44;

(iii) the HCDR1 comprises an amino acid sequence selected from the group consisting of SEQ ID NOs: 47-49; the HCDR2 comprises an amino acid sequence selected from the group consisting of SEQ ID NOs: 50-52; the HCDR3 comprises an amino acid sequence selected from the group consisting of SEQ ID NOs: 53-55; the LCDR1 comprises an amino acid sequence selected from the group consisting of SEQ ID NOs: 58-60; the LCDR2 comprises an amino acid sequence selected from the group consisting of SEQ ID NOs: 61-63; and the LCDR3 comprises an amino acid sequence selected from the group consisting of SEQ ID NOs: 64-66;

(iv) the HCDR1 comprises an amino acid sequence selected from the group consisting of SEQ ID NOs: 69-71; the HCDR2 comprises an amino acid sequence selected from the group consisting of SEQ ID NOs: 72-74; the HCDR3 comprises an amino acid sequence selected from the group consisting of SEQ ID NOs: 75-77; the LCDR1 comprises an amino acid sequence selected from the group consisting of SEQ ID NOs: 80-82; the LCDR2 comprises an amino acid sequence selected from the group consisting of SEQ ID NOs: 83-85; and the LCDR3 comprises an amino acid sequence selected from the group consisting of SEQ ID NOs: 86-88;

(v) the HCDR1 comprises an amino acid sequence selected from the group consisting of SEQ ID NOs: 91-93; the HCDR2 comprises an amino acid sequence selected from the group consisting of SEQ ID NOs: 94-96; the HCDR3 comprises an amino acid sequence selected from the group consisting of SEQ ID NOs: 97-99; the LCDR1 comprises an amino acid sequence selected from the group consisting of SEQ ID NOs: 102-104; the LCDR2 comprises an amino acid sequence selected from the group consisting of SEQ ID NOs: 105-107; and the LCDR3 comprises an amino acid sequence selected from the group consisting of SEQ ID NOs: 108-110;

(vi) the HCDR1 comprises an amino acid sequence selected from the group consisting of SEQ ID NOs: 113-115; the HCDR2 comprises an amino acid sequence selected from the group consisting of SEQ ID NOs: 116-118; the HCDR3 comprises an amino acid sequence selected from the group consisting of SEQ ID NOs: 119-121; the LCDR1 comprises an amino acid sequence selected from the group consisting of SEQ ID NOs: 124-126; the LCDR2 comprises an amino acid sequence selected from the group consisting of SEQ ID NOs: 127-129; and the LCDR3 comprises an amino acid sequence selected from the group consisting of SEQ ID NOs: 130-132;

(vii) the HCDR1 comprises an amino acid sequence selected from the group consisting of SEQ ID NOs: 135-137; the HCDR2 comprises an amino acid sequence selected from the group consisting of SEQ ID NOs: 138-140; the HCDR3 comprises an amino acid sequence selected from the group consisting of SEQ ID NOs: 141-143; the LCDR1 comprises an amino acid sequence selected from the group consisting of SEQ ID NOs: 146-148; the LCDR2 comprises an amino acid sequence selected from the group consisting of SEQ ID NOs: 149-151; and the LCDR3 comprises an amino acid sequence selected from the group consisting of SEQ ID NOs: 152-154;

(viii) the HCDR1 comprises an amino acid sequence selected from the group consisting of SEQ ID NOs: 157-159; the HCDR2 comprises an amino acid sequence selected from the group consisting of SEQ ID NOs: 160-162; the HCDR3 comprises an amino acid sequence selected from the group consisting of SEQ ID NOs: 163-165; the LCDR1 comprises an amino acid sequence selected from the group consisting of SEQ ID NOs: 168-170; the LCDR2 comprises an amino acid sequence selected from the group consisting of SEQ ID NOs: 171-173; and the LCDR3 comprises an amino acid sequence selected from the group consisting of SEQ ID NOs: 174-176;

(ix) the HCDR1 comprises an amino acid sequence selected from the group consisting of SEQ ID NOs: 179-181; the HCDR2 comprises an amino acid sequence selected from the group consisting of SEQ ID NOs: 182-184; the HCDR3 comprises an amino acid sequence selected from the group consisting of SEQ ID NOs: 185-187; the LCDR1 comprises an amino acid sequence selected from the group consisting of SEQ ID NOs: 190-192; the LCDR2 comprises an amino acid sequence selected from the group consisting of SEQ ID NOs: 193-195; and the LCDR3 comprises an amino acid sequence selected from the group consisting of SEQ ID NOs: 196-198; or (x) the HCDR1 comprises an amino acid sequence selected from the group consisting of SEQ ID NOs: 201-203; the HCDR2 comprises an amino acid sequence selected from the group consisting of SEQ ID NOs: 204-206; the HCDR3 comprises an amino acid sequence selected from the group consisting of SEQ ID NOs: 207-209; the LCDR1 comprises an amino acid sequence selected from the group consisting of SEQ ID NOs: 212-214; the LCDR2 comprises an amino acid sequence selected from the group consisting of SEQ ID NOs: 215-217; and the LCDR3 comprises an amino acid sequence selected from the group consisting of SEQ ID NOs: 218-220.

2. The antibody or antigen binding fragment thereof of claim 1, wherein:

(i) the HCDR1 comprises the amino acid of SEQ ID NO: 3; the HCDR2 comprises the amino acid of SEQ ID NO: 6; the HCDR3 comprises the amino acid of SEQ ID NO: 9; the LCDR1 comprises the amino acid of SEQ ID NO: 14; the LCDR2 comprises the amino acid of SEQ ID NO: 17; and the LCDR3 comprises the amino acid of SEQ ID NO: 20;

(ii) the HCDR1 comprises the amino acid of SEQ ID NO: 25; the HCDR2 comprises the amino acid of SEQ ID NO: 28; the HCDR3 comprises the amino acid of SEQ ID NO: 31; the LCDR1 comprises the amino acid of SEQ ID NO: 36; the LCDR2 comprises the amino acid of SEQ ID NO: 39; and the LCDR3 comprises the amino acid of SEQ ID NO: 42;

(iii) the HCDR1 comprises the amino acid of SEQ ID NO: 47; the HCDR2 comprises the amino acid of SEQ ID NO: 50; the HCDR3 comprises the amino acid of SEQ ID NO: 53; the LCDR1 comprises the amino acid of SEQ ID NO: 58; the LCDR2 comprises the amino acid of SEQ ID NO: 61; and the LCDR3 comprises the amino acid of SEQ ID NO: 64;

(iv) the HCDR1 comprises the amino acid of SEQ ID NO: 69; the HCDR2 comprises the amino acid of SEQ ID NO: 72; the HCDR3 comprises the amino acid of SEQ ID NO: 75; the LCDR1 comprises the amino acid of SEQ ID NO: 80; the LCDR2 comprises the amino acid of SEQ ID NO: 83; and the LCDR3 comprises the amino acid of SEQ ID NO: 86;

(v) the HCDR1 comprises the amino acid of SEQ ID NO: 91; the HCDR2 comprises the amino acid of SEQ ID NO: 94; the HCDR3 comprises the amino acid of SEQ ID NO: 97; the LCDR1 comprises the amino acid of SEQ ID NO: 102; the LCDR2 comprises the amino acid of SEQ ID NO: 105; and the LCDR3 comprises the amino acid of SEQ ID NO: 108;

(vi) the HCDR1 comprises the amino acid of SEQ ID NO: 113; the HCDR2 comprises the amino acid of SEQ ID NO: 116; the HCDR3 comprises the amino acid of SEQ ID NO: 119; the LCDR1 comprises the amino acid of SEQ ID NO: 124; the LCDR2 comprises the amino acid of SEQ ID NO: 127; and the LCDR3 comprises the amino acid of SEQ ID NO: 130;

(vii) the HCDR1 comprises the amino acid of SEQ ID NO: 135; the HCDR2 comprises the amino acid of SEQ ID NO: 138; the HCDR3 comprises the amino acid of SEQ ID NO: 141; the LCDR1 comprises the amino acid of SEQ ID NO: 146; the LCDR2 comprises the amino acid of SEQ ID NO: 149; and the LCDR3 comprises the amino acid of SEQ ID NO: 152;

(viii) the HCDR1 comprises the amino acid of SEQ ID NO: 157; the HCDR2 comprises the amino acid of SEQ ID NO: 160; the HCDR3 comprises the amino acid of SEQ ID NO: 163; the LCDR1 comprises the amino acid of SEQ ID NO: 168; the LCDR2 comprises the amino acid of SEQ ID NO: 171; and the LCDR3 comprises the amino acid of SEQ ID NO: 174;

(ix) the HCDR1 comprises the amino acid of SEQ ID NO: 179; the HCDR2 comprises the amino acid of SEQ ID NO: 182; the HCDR3 comprises the amino acid of SEQ ID NO: 185; the LCDR1 comprises the amino acid of SEQ ID NO: 190; the LCDR2 comprises the amino acid of SEQ ID NO: 193; and the LCDR3 comprises the amino acid of SEQ ID NO: 196; or (x) the HCDR1 comprises the amino acid of SEQ ID NO: 201; the HCDR2 comprises the amino acid of SEQ ID NO: 204; the HCDR3 comprises the amino acid of SEQ ID NO: 207; the LCDR1 comprises the amino acid of SEQ ID NO: 212; the LCDR2 comprises the amino acid of SEQ ID NO: 215; and the LCDR3 comprises the amino acid of SEQ ID NO: 218.

3. The antibody or antigen binding fragment thereof of claim 1, wherein:

(i) the HCDR1 comprises the amino acid of SEQ ID NO: 4; the HCDR2 comprises the amino acid of SEQ ID NO: 7; the HCDR3 comprises the amino acid of SEQ ID NO: 10; the LCDR1 comprises the amino acid of SEQ ID NO: 15; the LCDR2 comprises the amino acid of SEQ ID NO: 18; and the LCDR3 comprises the amino acid of SEQ ID NO: 21;

(ii) the HCDR1 comprises the amino acid of SEQ ID NO: 26; the HCDR2 comprises the amino acid of SEQ ID NO: 29; the HCDR3 comprises the amino acid of SEQ ID NO: 32; the LCDR1 comprises the amino acid of SEQ ID NO: 37; the LCDR2 comprises the amino acid of SEQ ID NO: 40; and the LCDR3 comprises the amino acid of SEQ ID NO: 43;

(iii) the HCDR1 comprises the amino acid of SEQ ID NO: 48; the HCDR2 comprises the amino acid of SEQ ID NO: 51; the HCDR3 comprises the amino acid of SEQ ID NO: 54; the LCDR1 comprises the amino acid of SEQ ID NO: 59; the LCDR2 comprises the amino acid of SEQ ID NO: 62; and the LCDR3 comprises the amino acid of SEQ ID NO: 65;

(iv) the HCDR1 comprises the amino acid of SEQ ID NO: 70; the HCDR2 comprises the amino acid of SEQ ID NO: 73; the HCDR3 comprises the amino acid of SEQ ID NO: 76; the LCDR1 comprises the amino acid of SEQ ID NO: 81; the LCDR2 comprises the amino acid of SEQ ID NO: 84; and the LCDR3 comprises the amino acid of SEQ ID NO: 87;

(v) the HCDR1 comprises the amino acid of SEQ ID NO: 92; the HCDR2 comprises the amino acid of SEQ ID NO: 95; the HCDR3 comprises the amino acid of SEQ ID NO: 98; the LCDR1 comprises the amino acid of SEQ ID NO: 103; the LCDR2 comprises the amino acid of SEQ ID NO: 106; and the LCDR3 comprises the amino acid of SEQ ID NO: 109;

(vi) the HCDR1 comprises the amino acid of SEQ ID NO: 114; the HCDR2 comprises the amino acid of SEQ ID NO: 117; the HCDR3 comprises the amino acid of SEQ ID NO: 120; the LCDR1 comprises the amino acid of SEQ ID NO: 125; the LCDR2 comprises the amino acid of SEQ ID NO: 128; and the LCDR3 comprises the amino acid of SEQ ID NO: 131;

(vii) the HCDR1 comprises the amino acid of SEQ ID NO: 136; the HCDR2 comprises the amino acid of SEQ ID NO: 139; the HCDR3 comprises the amino acid of SEQ ID NO: 142; the LCDR1 comprises the amino acid of SEQ ID NO: 147; the LCDR2 comprises the amino acid of SEQ ID NO: 150; and the LCDR3 comprises the amino acid of SEQ ID NO: 153;

(viii) the HCDR1 comprises the amino acid of SEQ ID NO: 158; the HCDR2 comprises the amino acid of SEQ ID NO: 161; the HCDR3 comprises the amino acid of SEQ ID NO: 164; the LCDR1 comprises the amino acid of SEQ ID NO: 169; the LCDR2 comprises the amino acid of SEQ ID NO: 172; and the LCDR3 comprises the amino acid of SEQ ID NO: 175;

(ix) the HCDR1 comprises the amino acid of SEQ ID NO: 180; the HCDR2 comprises the amino acid of SEQ ID NO: 183; the HCDR3 comprises the amino acid of SEQ ID NO: 186; the LCDR1 comprises the amino acid of SEQ ID NO: 191; the LCDR2 comprises the amino acid of SEQ ID NO: 194; and the LCDR3 comprises the amino acid of SEQ ID NO: 197; or (x) the HCDR1 comprises the amino acid of SEQ ID NO: 202; the HCDR2 comprises the amino acid of SEQ ID NO: 205; the HCDR3 comprises the amino acid of SEQ ID NO: 208; the LCDR1 comprises the amino acid of SEQ ID NO: 213; the LCDR2 comprises the amino acid of SEQ ID NO: 216; and the LCDR3 comprises the amino acid of SEQ ID NO: 219.

4. The antibody or antigen binding fragment thereof of claim 1, wherein:

(i) the HCDR1 comprises the amino acid of SEQ ID NO: 5; the HCDR2 comprises the amino acid of SEQ ID NO: 8; the HCDR3 comprises the amino acid of SEQ ID NO: 11; the LCDR1 comprises the amino acid of SEQ ID NO: 16; the LCDR2 comprises the amino acid of SEQ ID NO: 19; and the LCDR3 comprises the amino acid of SEQ ID NO: 22;

(ii) the HCDR1 comprises the amino acid of SEQ ID NO: 27; the HCDR2 comprises the amino acid of SEQ ID NO: 30; the HCDR3 comprises the amino acid of SEQ ID NO: 33; the LCDR1 comprises the amino acid of SEQ ID NO: 38; the LCDR2 comprises the amino acid of SEQ ID NO: 41; and the LCDR3 comprises the amino acid of SEQ ID NO: 44;

(iii) the HCDR1 comprises the amino acid of SEQ ID NO: 49; the HCDR2 comprises the amino acid of SEQ ID NO: 52; the HCDR3 comprises the amino acid of SEQ ID NO: 55; the LCDR1 comprises the amino acid of SEQ ID NO: 60; the LCDR2 comprises the amino acid of SEQ ID NO: 63; and the LCDR3 comprises the amino acid of SEQ ID NO: 66;

(iv) the HCDR1 comprises the amino acid of SEQ ID NO: 71; the HCDR2 comprises the amino acid of SEQ ID NO: 74; the HCDR3 comprises the amino acid of SEQ ID NO: 77; the LCDR1 comprises the amino acid of SEQ ID NO: 82; the LCDR2 comprises the amino acid of SEQ ID NO: 85; and the LCDR3 comprises the amino acid of SEQ ID NO: 88;

(v) the HCDR1 comprises the amino acid of SEQ ID NO: 93; the HCDR2 comprises the amino acid of SEQ ID NO: 96; the HCDR3 comprises the amino acid of SEQ ID NO: 99; the LCDR1 comprises the amino acid of SEQ ID NO: 104; the LCDR2 comprises the amino acid of SEQ ID NO: 107; and the LCDR3 comprises the amino acid of SEQ ID NO: 110;

(vi) the HCDR1 comprises the amino acid of SEQ ID NO: 115; the HCDR2 comprises the amino acid of SEQ ID NO: 118; the HCDR3 comprises the amino acid of SEQ ID NO: 121; the LCDR1 comprises the amino acid of SEQ ID NO: 126; the LCDR2 comprises the amino acid of SEQ ID NO: 129; and the LCDR3 comprises the amino acid of SEQ ID NO: 132;

(vii) the HCDR1 comprises the amino acid of SEQ ID NO: 137; the HCDR2 comprises the amino acid of SEQ ID NO: 140; the HCDR3 comprises the amino acid of SEQ ID NO: 143; the LCDR1 comprises the amino acid of SEQ ID NO: 148; the LCDR2 comprises the amino acid of SEQ ID NO: 151; and the LCDR3 comprises the amino acid of SEQ ID NO: 154;

(viii) the HCDR1 comprises the amino acid of SEQ ID NO: 159; the HCDR2 comprises the amino acid of SEQ ID NO: 162; the HCDR3 comprises the amino acid of SEQ ID NO: 165; the LCDR1 comprises the amino acid of SEQ ID NO: 170; the LCDR2 comprises the amino acid of SEQ ID NO: 173; and the LCDR3 comprises the amino acid of SEQ ID NO: 176;

(ix) the HCDR1 comprises the amino acid of SEQ ID NO: 181; the HCDR2 comprises the amino acid of SEQ ID NO: 184; the HCDR3 comprises the amino acid of SEQ ID NO: 187; the LCDR1 comprises the amino acid of SEQ ID NO: 192; the LCDR2 comprises the amino acid of SEQ ID NO: 195; and the LCDR3 comprises the amino acid of SEQ ID NO: 198; or (x) the HCDR1 comprises the amino acid of SEQ ID NO: 203; the HCDR2 comprises the amino acid of SEQ ID NO: 206; the HCDR3 comprises the amino acid of SEQ ID NO: 209; the LCDR1 comprises the amino acid of SEQ ID NO: 214; the LCDR2 comprises the amino acid of SEQ ID NO: 217; and the LCDR3 comprises the amino acid of SEQ ID NO: 220.

5. The antibody or antigen binding fragment thereof of claim 1, wherein:

(i) the VH comprises the amino acid sequence of SEQ ID NO: 1 and the VL comprises the amino acid sequence of SEQ ID NO: 12;
(ii) the VH comprises the amino acid sequence of SEQ ID NO: 23 and the VL comprises the amino acid sequence of SEQ ID NO: 34;
(iii) the VH comprises the amino acid sequence of SEQ ID NO: 45 and the VL comprises the amino acid sequence of SEQ ID NO: 56;
(iv) the VH comprises the amino acid sequence of SEQ ID NO: 67 and the VL comprises the amino acid sequence of SEQ ID NO: 78;
(v) the VH comprises the amino acid sequence of SEQ ID NO: 89 and the VL comprises the amino acid sequence of SEQ ID NO: 100;
(vi) the VH comprises the amino acid sequence of SEQ ID NO: 111 and the VL comprises the amino acid sequence of SEQ ID NO: 122;
(vii) the VH comprises the amino acid sequence of SEQ ID NO: 133 and the VL comprises the amino acid sequence of SEQ ID NO: 144;
(viii) the VH comprises the amino acid sequence of SEQ ID NO: 155 and the VL comprises the amino acid sequence of SEQ ID NO: 166;
(ix) the VH comprises the amino acid sequence of SEQ ID NO: 177 and the VL comprises the amino acid sequence of SEQ ID NO: 188; or
(x) the VH comprises the amino acid sequence of SEQ ID NO: 199 and the VL comprises the amino acid sequence of SEQ ID NO: 210.

6. The antibody or antigen binding fragment thereof of claim 1, wherein:
(i) the heavy chain variable domain is at least 80% identical to SEQ ID NO: 1 and the light chain variable domain is at least 80% identical to SEQ ID NO: 12;
(ii) the heavy chain variable domain is at least 80% identical to SEQ ID NO: 23 and the light chain variable domain is at least 80% identical to SEQ ID NO: 34;
(iii) the heavy chain variable domain is at least 80% identical to SEQ ID NO: 45 and the light chain variable domain is at least 80% identical to SEQ ID NO: 56;
(iv) the heavy chain variable domain is at least 80% identical to SEQ ID NO: 67 and the light chain variable domain is at least 80% identical to SEQ ID NO: 78;
(v) the heavy chain variable domain is at least 80% identical to SEQ ID NO: 89 and the light chain variable domain is at least 80% identical to SEQ ID NO: 100;
(vi) the heavy chain variable domain is at least 80% identical to SEQ ID NO: 111 and the light chain variable domain is at least 80% identical to SEQ ID NO: 122;
(vii) the heavy chain variable domain is at least 80% identical to SEQ ID NO: 133 and the light chain variable domain is at least 80% identical to SEQ ID NO: 144;
(viii) the heavy chain variable domain is at least 80% identical to SEQ ID NO: 155 and the light chain variable domain is at least 80% identical to SEQ ID NO: 166;
(ix) the heavy chain variable domain is at least 80% identical to SEQ ID NO: 177 and the light chain variable domain is at least 80% identical to SEQ ID NO: 188; or
(x) the heavy chain variable domain is at least 80% identical to SEQ ID NO: 199 and the light chain variable domain is at least 80% identical to SEQ ID NO: 210.

7. The antibody or antigen binding fragment thereof of claim 1, wherein the antigen binding fragment is a single chain fragment (scFv).

8. A cell, comprising (i) the antibody or antigen binding fragment thereof of claim 1, or a chimeric antigen receptor comprising the antibody or antigen binding fragment, and
(ii) a second chimeric antigen receptor, an antibody, or an antigen binding fragment thereof, which comprises a binding motif that specifically binds an antigen selected from the group consisting of 5T4, alpha-fetoprotein, B cell maturation antigen (BCMA), B cell receptor, CA-125, carcinoembryonic antigen, CD19, CD20, CD22, CD23, CD30, CD33, CD40, CD56, CD79, CD78, CD123, CD138, c-Met, CSPG4, IgM, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gp120, IL-11Ralpha, kappa chain, lambda chain, melanoma-associated antigen, mesothelin, MUC-1, mutated p53, mutated ras, prostate-specific antigen, ROR1, VEGFR2, EphA3 (EPH receptor A3), BAFFR (B-cell activating factor receptor), and combinations thereof.

9. The cell of claim 8, wherein the binding motif is an anti-CD19 binding motif.

10. The cell of claim 9, wherein the anti-CD19 binding motif comprises a heavy chain variable domain (VH) comprising complementarity determining regions HCDR1 comprising the amino acid sequence of SEQ ID NO: 224, HCDR2 comprising the amino acid sequence of SEQ ID NO: 227 and HCDR3 comprising the amino acid sequence of SEQ ID NO: 230, and a light chain variable domain (VL) comprising complementarity determining regions LCDR1 comprising the amino acid sequence of SEQ ID NO: 235, LCDR2 comprising the amino acid sequence of SEQ ID NO: 238 and LCDR3 comprising the amino acid sequence of SEQ ID NO: 241.

11. The cell of claim 10, wherein the VH of the anti-CD19 binding motif comprises the amino acid sequence of SEQ ID NO: 221 or an amino acid sequence having at least 80% sequence identity to SEQ ID NO: 221, and the VL of the anti-CD19 binding motif comprises the amino acid sequence of SEQ ID NO: 232 or an amino acid sequence having at least 80% sequence identity to SEQ ID NO: 232.

12. The cell of claim 10, wherein the anti-CD19 binding motif is a single chain fragment (scFv).

13. The cell of claim 10, wherein the second chimeric antigen receptor further comprises a transmembrane domain that is a transmembrane domain of 4-1BB/CD137, an alpha chain of a T cell receptor, a beta chain of a T cell receptor, CD3 epsilon, CD4, CD5, CD8 alpha, CD9, CD16, CD19, CD22, CD28, CD33, CD37, CD45, CD64, CD80, CD86, CD134, CD137, CD154, or a zeta chain of a T cell receptor, or any combination thereof.

14. A nucleic acid encoding the antibody or antigen binding fragment thereof of claim 1.

15. A vector comprising the nucleic acid of claim 14.

16. A method of generating an engineered cell, the method comprising transfecting or transducing a cell with a nucleic acid according to claim 14.

17. A cell expressing the antibody or antigen binding fragment thereof of claim 1.

\* \* \* \* \*